(12) United States Patent
Baumhof et al.

(10) Patent No.: US 11,690,910 B2
(45) Date of Patent: *Jul. 4, 2023

(54) PHARMACEUTICAL COMPOSITION COMPRISING A POLYMERIC CARRIER CARGO COMPLEX AND AT LEAST ONE PROTEIN OR PEPTIDE ANTIGEN

(71) Applicant: CureVac SE, Tübingen (DE)

(72) Inventors: Patrick Baumhof, Dusslingen (DE);
Thomas Kramps, Tübingen (DE);
Söhnke Voss, Neckargemund (DE);
Karl-Josef Kallen, Konigsdorf (DE);
Mariola Fotin-Mleczek, Sindelfingen (DE)

(73) Assignee: CureVac SE, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/555,881

(22) Filed: Aug. 29, 2019

(65) Prior Publication Data
US 2020/0085943 A1    Mar. 19, 2020

Related U.S. Application Data

(63) Continuation of application No. 14/375,215, filed as application No. PCT/EP2013/000291 on Jan. 31, 2013, now abandoned.

(30) Foreign Application Priority Data

Jan. 31, 2012  (WO) ................ PCT/EP2012/000420

(51) Int. Cl.
*A61K 39/385* (2006.01)
*A61K 39/39* (2006.01)
(Continued)

(52) U.S. Cl.
CPC .......... *A61K 39/39* (2013.01); *A61K 39/0011* (2013.01); *A61K 39/00117* (2018.08);
(Continued)

(58) Field of Classification Search
None
See application file for complete search history.

(56) References Cited

U.S. PATENT DOCUMENTS 3,906,092 A   9/1975  Hilleman et al.
4,373,071 A   2/1983  Itakura
(Continued)

FOREIGN PATENT DOCUMENTS

AU    776268     12/2000
CA   2329858      6/2002
(Continued)

OTHER PUBLICATIONS

"Cell-penetrating peptide," *Wikipedia*, located at http://en.wikipedia.org/wiki/Cell-penetrating_peptide, downloaded Dec. 11, 2012.
(Continued)

*Primary Examiner* — M Franco G Salvoza
(74) *Attorney, Agent, or Firm* — Parker Highlander PLLC

(57) ABSTRACT

The present invention is directed to a pharmaceutical composition including (e.g. for use as an adjuvant) a polymeric carrier cargo complex, comprising as a carrier a polymeric carrier formed by disulfide-crosslinked cationic components; and as a cargo at least one nucleic acid molecule, and at least one antigen that is selected from an antigen from a pathogen associated with infectious disease; an antigen associated with allergy or allergic disease; an antigen associated with autoimmune disease; or an antigen associated with a cancer or tumour disease, or in each case a fragment, variant and/or derivative of said antigen. The pharmaceutical composition allows for efficient induction of an adaptive (Continued)

Figure 1:
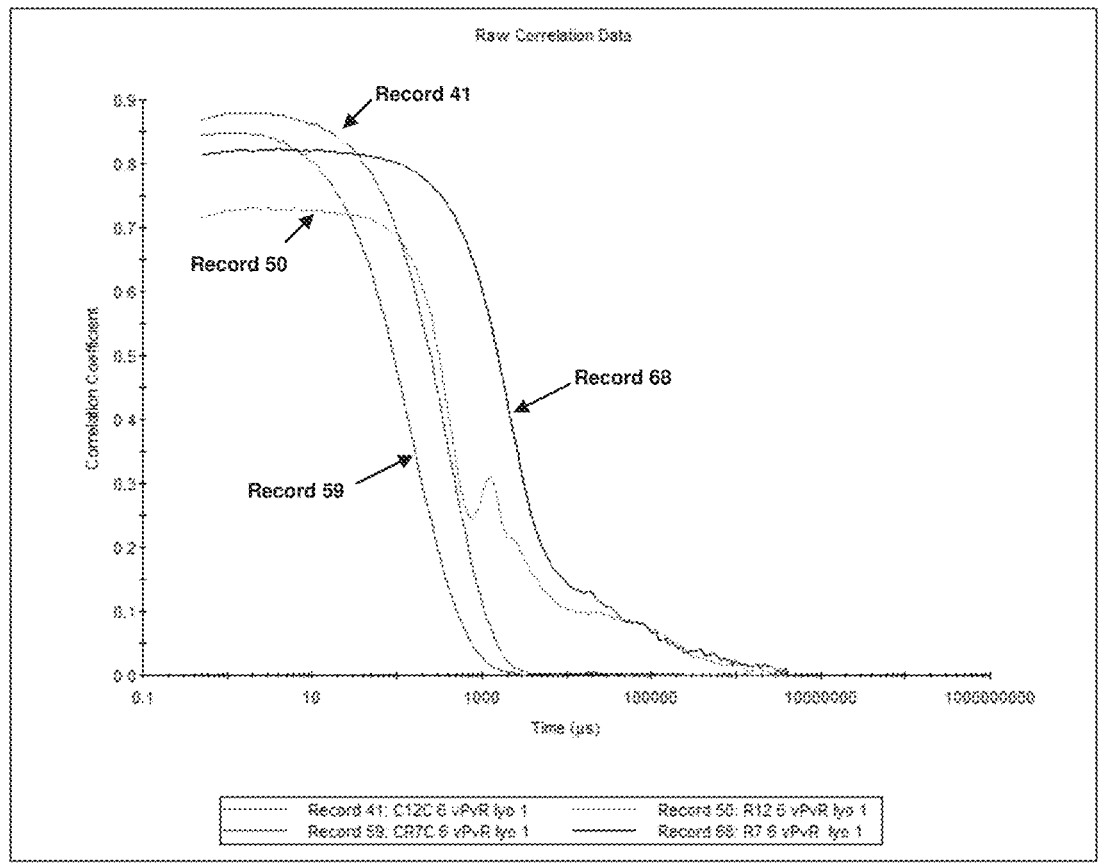

immune response directed against said antigen. The present invention furthermore provides kits, as well as the use of the pharmaceutical composition or the kit as a vaccine, particularly in the treatment of infectious diseases, allergies, autoimmune diseases and tumour or cancer diseases.

20 Claims, 32 Drawing Sheets

Specification includes a Sequence Listing.

(51) Int. Cl.
*A61K 39/12* (2006.01)
*A61K 39/00* (2006.01)
*A61K 47/64* (2017.01)
*A61K 39/145* (2006.01)
*A61K 39/205* (2006.01)
*A61K 39/29* (2006.01)
*A61K 39/35* (2006.01)
*A61K 48/00* (2006.01)
*C12N 7/00* (2006.01)

(52) U.S. Cl.
CPC ............... *A61K 39/001104* (2018.08); *A61K 39/001106* (2018.08); *A61K 39/001109* (2018.08); *A61K 39/001135* (2018.08); *A61K 39/001151* (2018.08); *A61K 39/001153* (2018.08); *A61K 39/001156* (2018.08); *A61K 39/001157* (2018.08); *A61K 39/001164* (2018.08); *A61K 39/001168* (2018.08); *A61K 39/001182* (2018.08); *A61K 39/001186* (2018.08); *A61K 39/001188* (2018.08); *A61K 39/001191* (2018.08); *A61K 39/001192* (2018.08); *A61K 39/001193* (2018.08); *A61K 39/001194* (2018.08); *A61K 39/001195* (2018.08); *A61K 39/12* (2013.01); *A61K 39/145* (2013.01); *A61K 39/205* (2013.01); *A61K 39/29* (2013.01); *A61K 39/35* (2013.01); *A61K 47/645* (2017.08); *A61K 47/646* (2017.08); *A61K 48/0041* (2013.01); *C12N 7/00* (2013.01); *A61K 2039/5252* (2013.01); *A61K 2039/53* (2013.01); *A61K 2039/55511* (2013.01); *A61K 2039/55516* (2013.01); *A61K 2039/55561* (2013.01); *A61K 2039/572* (2013.01); *A61K 2039/575* (2013.01); *A61K 2039/6093* (2013.01); *C12N 2710/20034* (2013.01); *C12N 2710/20071* (2013.01); *C12N 2730/10134* (2013.01); *C12N 2730/10171* (2013.01); *C12N 2760/16134* (2013.01); *C12N 2760/16171* (2013.01); *C12N 2760/20134* (2013.01); *C12N 2760/20171* (2013.01); *Y02A 50/30* (2018.01)

(56) References Cited

U.S. PATENT DOCUMENTS

| | | | |
|---|---|---|---|
| 4,401,796 A | 8/1983 | Itakura | |
| 4,415,732 A | 11/1983 | Caruthers et al. | |
| 4,578,399 A | 3/1986 | Schorlemmer et al. | |
| 5,516,652 A | 5/1996 | Abramovitz et al. | |
| 5,663,153 A | 9/1997 | Hutcherson et al. | |
| 5,663,163 A | 9/1997 | Takaya et al. | |
| 5,844,075 A | 12/1998 | Kawakami et al. | |
| 5,965,720 A | 10/1999 | Gryaznov et al. | |
| 6,096,307 A | 8/2000 | Braswell et al. | |
| 6,218,371 B1 | 4/2001 | Krieg et al. | |
| 6,239,116 B1 | 5/2001 | Krieg et al. | |
| 6,322,967 B1 | 11/2001 | Parkin | |
| 6,406,705 B1 | 6/2002 | Davis et al. | |
| 6,498,148 B1 | 12/2002 | Raz | |
| 6,514,948 B1 | 2/2003 | Raz et al. | |
| 6,552,006 B2 | 4/2003 | Raz et al. | |
| 6,589,940 B1 | 7/2003 | Raz et al. | |
| 6,610,661 B1 | 8/2003 | Carson | |
| 6,689,757 B1 | 2/2004 | Jacob et al. | |
| 6,716,434 B1 | 4/2004 | Ansley et al. | |
| 7,001,890 B1 | 2/2006 | Wagner et al. | |
| 7,208,478 B2 | 4/2007 | Carson et al. | |
| 7,407,944 B2 | 8/2008 | Agrawal et al. | |
| 7,470,674 B2 | 12/2008 | Agrawal et al. | |
| 7,517,862 B2 | 4/2009 | Agrawal et al. | |
| 8,703,906 B2 | 4/2014 | Baumhof et al. | |
| 8,968,746 B2 | 3/2015 | Baumhof et al. | |
| 2003/0133942 A1 | 7/2003 | Segal | |
| 2003/0225016 A1 | 12/2003 | Fearon et al. | |
| 2004/0006010 A1 | 1/2004 | Carson et al. | |
| 2004/0006034 A1 | 1/2004 | Raz et al. | |
| 2004/0019007 A1 | 1/2004 | Monahan et al. | |
| 2004/0047869 A1 | 3/2004 | Garcon et al. | |
| 2004/0052763 A1 | 3/2004 | Mond et al. | |
| 2005/0032730 A1 | 2/2005 | Von Der Mulbe et al. | |
| 2005/0037494 A1 | 2/2005 | Hecker et al. | |
| 2005/0059624 A1 | 3/2005 | Hoerr et al. | |
| 2005/0130918 A1 | 6/2005 | Agrawal et al. | |
| 2005/0215501 A1 | 9/2005 | Lipford et al. | |
| 2005/0250723 A1 | 11/2005 | Hoerr et al. | |
| 2006/0172966 A1 | 8/2006 | Lipford et al. | |
| 2006/0188490 A1 | 8/2006 | Hoerr et al. | |
| 2006/0251623 A1 | 11/2006 | Bachmann et al. | |
| 2007/0280929 A1 | 12/2007 | Hoerr et al. | |
| 2008/0025944 A1 | 1/2008 | Hoerr et al. | |
| 2008/0171711 A1 | 7/2008 | Hoerr et al. | |
| 2008/0248067 A1 | 10/2008 | Frazer | |
| 2008/0267873 A1 | 10/2008 | Hoerr et al. | |
| 2009/0081157 A1 | 3/2009 | Kornbluth et al. | |
| 2009/0111765 A1 | 4/2009 | Harmann et al. | |
| 2009/0123467 A1 | 5/2009 | Bedi et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |
| 2011/0311472 A1 | 12/2011 | Hoerr et al. | |
| 2012/0021043 A1 | 1/2012 | Kramps et al. | |
| 2012/0058153 A1* | 3/2012 | Ilyinskii | A61P 37/04 424/400 |
| 2012/0258046 A1 | 10/2012 | Mutzke | |
| 2013/0142818 A1 | 6/2013 | Baumhof et al. | |

FOREIGN PATENT DOCUMENTS

| | | |
|---|---|---|
| CN | 1668335 | 9/2005 |
| DE | 102004035227 | 2/2002 |
| DE | 10148886 | 4/2003 |
| DE | 69819150 | 7/2004 |
| DE | 102006007433 | 8/2007 |
| EP | 0347501 | 12/1989 |
| EP | 0772619 | 5/1997 |
| EP | 0839912 | 5/1998 |
| EP | 1063232 | 3/2001 |
| EP | 1083232 | 3/2001 |
| EP | 1167379 | 1/2002 |
| EP | 1374894 | 1/2004 |
| EP | 1393745 | 3/2004 |
| EP | 1564291 | 8/2005 |
| EP | 1905844 | 2/2008 |
| JP | 2005-521749 | 7/2005 |
| JP | 2008-542500 | 11/2008 |
| KR | 10-1003622 | 9/2003 |
| KR | 10-1051785 | 1/2005 |
| KR | 10-1032853 | 4/2005 |
| WO | WO 1991/005560 | 5/1991 |
| WO | WO 1994/017093 | 8/1994 |

(56) References Cited

FOREIGN PATENT DOCUMENTS

| | | |
|---|---|---|
| WO | WO 1994/017792 | 8/1994 |
| WO | WO 1998/019710 | 5/1998 |
| WO | WO 1998/047913 | 10/1998 |
| WO | WO 1999/053961 | 10/1999 |
| WO | WO 2000/075304 | 12/2000 |
| WO | WO 2001/004135 | 1/2001 |
| WO | WO 2001/054720 | 8/2001 |
| WO | WO 2001/075164 | 10/2001 |
| WO | WO 2001/093902 | 12/2001 |
| WO | WO 2001/097843 | 12/2001 |
| WO | WO 2002/000594 | 1/2002 |
| WO | WO 2002/000694 | 1/2002 |
| WO | WO 2002/078614 | 10/2002 |
| WO | WO 2002/098443 | 12/2002 |
| WO | WO 2003-000227 | 1/2003 |
| WO | WO 2003/028656 | 4/2003 |
| WO | WO 2003/057822 | 7/2003 |
| WO | WO 2003/059381 | 7/2003 |
| WO | WO 2003/066649 | 8/2003 |
| WO | WO 2003/068942 | 8/2003 |
| WO | WO 2003/086280 | 10/2003 |
| WO | WO 2003/097105 | 11/2003 |
| WO | WO 2004/004743 | 1/2004 |
| WO | WO 2004/058159 | 7/2004 |
| WO | WO 2004/064782 | 8/2004 |
| WO | WO 2004/092329 | 10/2004 |
| WO | WO 2005/001022 | 1/2005 |
| WO | WO 2005/030259 | 4/2005 |
| WO | WO 2005/062947 | 7/2005 |
| WO | WO 2005/097993 | 10/2005 |
| WO | WO 2006/029223 | 3/2006 |
| WO | WO 2006/046978 | 5/2006 |
| WO | WO 2006/080946 | 8/2006 |
| WO | WO 2006/116458 | 11/2006 |
| WO | WO 2007/008300 | 1/2007 |
| WO | WO 2007/031319 | 3/2007 |
| WO | WO 2007/031322 | 3/2007 |
| WO | WO 2007/042554 | 4/2007 |
| WO | WO 2007/051303 | 5/2007 |
| WO | WO 2007/062107 | 5/2007 |
| WO | WO 2007/069068 | 6/2007 |
| WO | WO 2007/124755 | 11/2007 |
| WO | WO 2008/014979 | 2/2008 |
| WO | WO 2008/022046 | 2/2008 |
| WO | WO 2009/030254 | 3/2009 |
| WO | WO 2009/030481 | 3/2009 |
| WO | WO 2009/053700 | 4/2009 |
| WO | WO 2009/086640 | 7/2009 |
| WO | WO 2009/095226 | 8/2009 |
| WO | WO 2010/037408 | 4/2010 |
| WO | WO 2010/037539 | 4/2010 |
| WO | WO 2011/026641 | 3/2011 |
| WO | WO 2012/013326 | 2/2012 |
| WO | WO 2012-113413 | 8/2012 |
| WO | WO 2013/113502 | 8/2013 |
| WO | WO 2013/174409 | 11/2013 |

OTHER PUBLICATIONS

"DOC/Alum Complex," Violin: Vaccine investigation and online information network, located at http://www.violinet.org/vaxjo/vaxjo_detail.php?c_vaxjo_id=49, downloaded on Aug. 28, 2012.
"QS21," Wikipedia, located at http://en.wikipedia.org/wiki/QS21, downloaded on Dec. 11, 2012.
"Ribi vaccine adjuvant," Violin: Vaccine investigation and online information network, located at http://www.violinet.org/vaxjo/vaxjo_detail.php?c_vaxjo_id=21, downloaded on Dec. 17, 2012.
"SPT (Antigen Formulation)," Violin: Vaccine investigation and online information network, located at http://www.violinet.org/vaxjo/vaxjo_detail.php?c_vaxjo_id=72, downloaded on Aug. 21, 2012.
"Virus-like particle," Wikipedia, located at http://en.wikipedia.org/wiki/virus-like_particle, downloaded on Sep. 3, 2012.

Adams et al., "Preparation and hybridization properties of oligonucleotides containing 1-alpha-D-arabinofuranosylthymine", Nucleic Acids Res., 19(13):3647-51, 1991.
Agrawal, "Antisense oligonucleotides: towards clinical trials", Trends Biotechnol., 14(10):376-387, 1996.
Andreu et al., "Formation of disulfide bonds in synthetic peptides and proteins," From Methods in Molecular Biology, Peptide Synthesis Protocols, 35(7):91-169, 1994.
Ara et al., "Zymosan enhances the immune response to DNA vaccine for human immunodeficiency virus type-1 through the activation of complement system", Immunology, 103(1):98-105, 2001.
Bayard et al., "Antiviral activity in L1210 cells of liposome-encapsulated (2'-5')oligo(adenylate)analogues", Eur J Biochem., 151(2):319-326, 1985.
Berzofsky et al., "Progress on new vaccine strategies against chronic viral infections", J Clin Invest., 114(4):450-62, 2004.
Bettinger T. et al., "Peptide-mediated RNA delivery: a novel approach for enhanced transfection of primary and Post-mitotic cells," Nucleic Acids Research, vol. 29, No. 18, pp. 3882-3891, 2001.
Blaxter et al., "The Brugia malayi genome project: expressed sequence tags and gene discovery", Transactions of the Royal Society of Tropical Medicine and Hygiene, 96(1):1-17, 2002.
Bocchia et al., "Antitumor vaccination: where we stand", Heamatologica, 85(11):1172-1206, 2000.
Bolhassani A. et al., "Improvement of different vaccine delivery systems for cancer therapy," Molecular Cancer, vol. 10, No. 1, p. 3, Jan. 7, 2011.
Bot A. et al., "Enhanced protection against influenza virus of mice immunized as newborns with a mixture of plasmids expressing hemagglutinin and nucleoprotein," Vaccine, 16, No. 17, pp. 1675-1682, Oct. 1, 1998.
Bot A. et al., "Genetic immunization of neonates, Microbes and Infection, Institut Pasteur," vol. 4, No. 4, pp. 511-520, Apr. 2002.
Bot A. et al., "Induction of humoral and cellular immunity against influenza virus by immunization of newborn mice with a plasmid bearing a hemagglutinin gene," International Immunology,vol. 9, No. 11, pp. 1641-1650, Dec. 31, 1997.
Brito et al., "Non-viral eNOS gene delivery and transfection with stents for the treatment of restenosis," BioMedical Engineering OnLine, 9:56, 2010.
Burke R.S. et al., "Extracellular barriers to in Vivo PEI and PEGylated PEI polyplex-mediated gene delivery to the liver," Bioconjug Chem. Mar. 2008;19(3):693-704. Epub Feb. 23, 2008.
Buteau et al., "Challenges in the development of effective peptide vaccines for cancer", Mayo Clin Proc., 77:339-349, 2002.
CAPLUS accession No. 190686-49-8; Brugia malayi strain TRS Labs conie RRAMCA1537 EST; Chemical Abstracts Services; Database Caplus; Jun. 2009.
Carralot J-P. et al., "Polarization of immunity induced by direct injection of naked sequence-stabilized mRNA vaccines," CMLS Cellular and Molecular Life Sciences, vo. 61, No. 18, pp. 2418-2424, Sep. 1, 2004.
Casciato et al., Manual of Clinical Oncology, 6$^{th}$ Edition, Lippincott Williams & Wilkins, 2009.
Cooper et al., "CPG 7909 adjuvant improves hepatitis B virus vaccine seroprotection in antiretroviral-treated HIV-infected adults," AIDS, 19:1473-1479, 2005.
Danhier et al., "PLGA-based nanoparticles: An overview of biomedical applications," Journal of Controlled Release, 161:505-522, 2012.
Declaration of Regina Heidenreich Under 37 C.F.R. § 1.132, regarding Lipford et al., submitted in U.S. Appl. No. 14/375,215, executed Jun. 1, 2018.
Declaration of Regina Heidenreich Under 37 C.F.R. § 1.132, regarding Heidenreich et al., submitted in U.S. Appl. No. 14/375,215, executed Jun. 1, 2018.
Deshayes S. et al., "Cell-penetrating peptides: tools for intracellular delivery of therapeutics," Cell Mol Life Sci., 62(16): 1839-49. Review. 2005.
Diebold et al., "Innate antiviral responses by means of TLR7-mediated recognition of single-stranded RNA", Science, 1529-1531, 2004.

(56) References Cited

OTHER PUBLICATIONS

Dmitriev, "Bactenecin 7 peptide fragment as a tool for intracellular delivery of a phosphorescent oxygen sensor," *FEBS Journal*, 277:4651-4661, 2010.
EBI Database accession No. BP836659; *Arabidopsis thaliana* clone RAFL22-17-C17 EST; Database EMBL; Jan. 2005.
EBI Database accession No. CZ193289; PST12107-MICB1 *Mus musculus* genomic clone PST12107-NR; Database EMBL; Feb. 2005.
EBI Database accession No. DN868844; NEIBank analysis of Dog lens; Wistow, G., Database EMBL; Apr. 2005.
Eliyahu et al., "Polymers for DNA delivery," *Molecules*, 10:34-64, 2005.
EMBL accession No. AA430815; Brugia malayi strain TRS Labs clone RRAMCA1537 EST; Database EMBL; May 1997.
Fajac I. et al., "Histidylated polylysine as a synthetic vector for gene transfer into immortalized cystic fibrosis airway surface and airway gland serous cells," *J Gene Med.* 2(5):368-78. Sep.-Oct. 2000.
Feroze-Merzoug et al., "Molecular profiling in prostate cancer", *Cancer and Metastasis Reviews*, 20:165-171, 2001.
Fire et al., "Potent and specific genetic interferences by double-stranded RNA in *Caenorhabditis elegans*", 391:806-811, 1998.
Foerg C. et al., "On the biomedical promise of cell penetrating peptides: limits versus prospects," *J Pharm Sci*. Jan. 2008;97(1):144-62.
Fotin-Mleczek et al., "Messenger RNA-based vaccines with dual activity induce balanced TLR-7 dependent adaptive immune responses and provide antitumor activity", *Journal of Immunotheraphy*, 34(1):1-15, 2011.
Fox, "Squalene emulsions for parenteral vaccine and drug delivery," *Molecules*, 14:3286-3312, 2009.
Fujita T et al., "Calcium enhanced delivery of tetraarginine-PEG-lipid-coated DNA/protamine complexes," *International Journal of Pharmaceutics*, vol. 368, No. 1-2, pp. 186-192, Feb. 23, 2009.
Galbraith et al., "Complement activation and hemodynamic changes following intravenous administration of phosphorothioate oligonucleotides in the monkey", *Antisense Research and Development*, 4:201-206, 1994.
Gao X et al., Nonviral gene delivery: what we know and what is next, AAPS J. 23;9(1):E92-104. Review. Mar. 2007.
Garinot et al., "PEGylated PLGA-based nanoparticles targeting M cells for oral vaccination," *Journal of controlled release*, vol. 120, No. 3, pp. 195-204, Jul. 17, 2007.
GenBank Accession No. JK489756.1, GI; 346421249, publicly available Sep. 2011.
Gerogieva et al., "Comparative study on the changes in photosynthetic activity of the homoiochlorophyllous desiccation-tolerant *Haberlea rhodopensis* and desiccation-sensitive spinach leaves during desiccation and rehydration", *Photosynthesis Research*, 65:191-203, 2005.
Giel-Peitraszuk M. et al., "Database Biosis," DB Acc. No. Prev199800116011, 1997.
Gravekamp et al., "Cancer vaccines in old age," *Experimental Gerontology*, vol. 42, No. 5, pp. 441-450, Apr. 14, 2007.
Gryaznov, "Oligonucleotide N3'-P5' phosphoramidates as potential therapeutic agents", *Biochimica et Biophysica Acta*, 1489:131-140, 1999.
Hamidi M. et al., "Pharmacokinetic consequences of pegylation," *Drug Deliv.*; 13(6) pp. 399-409, 2006.
Hamm et al., "Immunostimulatory RNA is a potent inducer of antigen-specific cytotoxic and humoral immune response in vivo," *International Immunology*, 19(3):297-304, 2007.
Hardy et al., "Synergistic effects of gene delivery—co-formulation of small disulfide-linked dendritic polycations with Lipofectamine 2000", *Organic and Biomolecular Chemistry*, 7(4):789-793, 2009.
Hausch et al., "A novel carboxy-functionalized photocleavable dinucleotide analog for the selection to RNA catalysts", *Tetrahedron Letters*, 39(34):6157-6158, 1998.

Heffernan et al., "Disulfide-crosslinke plyion micelles for delivery of protein therapeutics", *Annals of Biomedical Engineering*, 37(10):1993-2002, 2009.
Heidenreich et al., "A novel RNA-based adjuvant combines strong immunostimulatory capacities with a favorable safety profile," *Int. J. Cancer*, 137(2):372-384, 2015.
Heidenreich et al., "Chemically modified RNA: approaches and applications", *The FASEB Journal*, 7(1):90-6, 1993.
Heil et al., "Species-specific recognition of single-stranded RNA via Toll-like receptor 7 and 8", *Science*, vol. 303, pp. 1526-1529, 2004.
Herbert et al., "Lipid modification of GRN163, an N3'-P5' thio-phosphoramidate oligonucleotide enhances the potency telomerase inhibition", *Oncogene*, 24:5262-5268, 2005.
Herbert et al., *The Dictionary of Immunology*, Academic Press: San Diego, $4^{th}$ ed. 1995. Print.
Heyman, "The immune complex: possible ways of regulating the antibody response", *Immunology Today*, 11(9):310-313, 1990.
Hoerr et al., "In vivo application of RNA leads to induction of specific cytotoxic T lymphocytes and antibodies", *Eur J Immunol.*, 30(1):1-7, 2000.
Huang et al., "Recent development of therapeutics for chronic HCV infection", *Antiviral Res.*, 71:351-362, 2006.
Huget et al., "Adjuvant and suppressor activity of the polycation protamine hydrochloride in the primary immune response of mice", *Z Immunitatsforsch Immunobiol.*, 152(3):190-9, 1976. (English Abstract).
Hwang et al., "A brain-targeted rabies virus glycoprotein-disulfide linked PEI nanocarrier for delivery of neurogenic microRNA," *Biomaterials*, 32:4968-4975, 2011.
Janssens et al., "Role of toll-like receptors in pathogen recognition", *Clinical Microbiology Reviews*, 16(4):637-646, 2003.
Kilk, "Cell-penetrating peptides and bioactive cargoes. Strategies and mechanisms," *Department of Neurochemistry and Neurotoxicology, Stockholm University*, Doctoral dissertation, 2004.
Kim et al., "Bioreducible polymers for gene delivery," *React Funct Polym*, 71(3):344-349, 2011.
Kim et al., "VeGF siRNA delivery system using arginine-grafted bioreducible poly(disulfide amine)", *Molecular Pharmaceutics*, 6(3):718-726, 2009.
Kovarik J. et al., "Optimization of vaccine responses in early life: the role of delivery systems and immunomodulators," *Immunology and Cell Biology*, vol. 76, No. 3, pp. 222-236, Jun. 1998.
Koziel et al., "Hepatitis C virus (HCV)-specific cytotoxic T lymphocytes recognize epitopes in the core and envelope proteins of HCV", *J Virol.*, 67(12):7522-32, 1993.
Kwiatkowski et al., "The 9-(4-Octadecyloxyphenylxanthen)-9-yl-Group. A new Acid-labile Hydroxyl Protective Group and Its Application in the Preparative Reverse-phase Chromatographic Separation of Oligoribonucleotides", *Acta Chemica Scandinavica*, 38b:657-671, 1984.
Kwok KY et al., "Formulation of highly soluble poly(ethylene glycol)-peptide DNA condensates," *J Pharm Sci.*;88(10):996-1003, Oct. 1999.
Lo et al., "An endosomolytic Tat peptide produced by incorporation of histidine and cysteine residues as a nonviral vector for DNA transfection", *Biomaterials*, 29(15):2408-2414, 2008.
Lochmann et al., "Drug delivery of oligonucleotides by peptides," *European Journal of Pharmaceutics and Biopharmaceutics*; vol. 58, No. 2, pp. 237-251, 2004.
Martin M.E. et al., "Peptide-guided gene delivery," *AAPS J.* 9;9(1):E18-29. Review. Feb. 2007.
Mateo et al., "An HLA-A2 polyepitope vaccine for melanoma immunotheraphy", *J Immunol.*, 163:4058-4063, 1999.
Matray and Gryaznov., "Synthesis and properties of RNA analogs-oligoribonucleotide N3'-P5' phosphoramidates", *Nucleic Acids Research*, 27(20):3976-85, 1999.
Mattner et al., "Vaccination with poly-L-arginine as immunostimulant for peptide vaccines: induction of potent and long-lasting T-cell responses against cancer antigens," *Cancer Research*, 62(5):1477-1480, 2002.
McKenzie et al., "A potent new class of reductively activated peptide gene delivery agents", *Journal of Biological Chemistry*, 275(14):9970-9977, 2000.

(56) References Cited

OTHER PUBLICATIONS

McKenzie et al., "Low molecular weight disulfide cross-linking peptides as nonviral gene discovery carriers", *Bioconjugate Chemistry*, 11(6):901-909, 2000.

Milich et al., "The hepatitis B virus core and e antigens elicit different Th cell subsets: antigen structure can affect Th cell phenotype", *J Virol.*, 71(3):2192-201, 1997.

Minks et al., "Structural requirements of double-stranded RNA for the activation of 2',5'-oligo(A)polymerase and protein kinase of interferon-treated HeLa cells", *The Journal of Biological Chemistry*, 254(20):10180-10183, 1979.

Miyata et al., "Block catiomer polyplexes with regulated densities of charge and disulfide cross-linking directed to enhance gene expression", *Journal of the American Chemical Society*, 126(8):2355-2361, 2004.

Nakamura Y et al., "Octaarginine-modified multifunctional envelope-type nano device for siRNA," *J Control Release*. Jun. 22, 2007, 119(3):360-7. Epub Mar. 23, 2007.

Neu Met al., "Recent advances in rational gene transfer vector design based on poly( ethylene imine) and its derivatives," *J Gene Med.*, 7(8):992-1009, Aug. 2005.

Nicholson et al., "Accurate in vitro cleavage by RNase III of phosphorothioate-substituted RNA processing signals in bacteriophage T7 early mRNA", *Nucleic Acids Res.*, 16(4):1577-91, 1988.

Notice of Allowance issued in U.S. Appl. No. 13/378,241, dated Nov. 22, 2013.

Office Action issued in U.S. Appl. No. 13/203,653, dated Jan. 30, 2014.

Office Action issued in U.S. Appl. No. 13/203,653, dated Jul. 17, 2014.

Office Action issued in U.S. Appl. No. 13/378,241, dated Apr. 24, 2013.

Office Action issued in U.S. Appl. No. 13/378,241, dated Jan. 10, 2013.

Office Action issued in U.S. Appl. No. 14/375,215, dated Feb. 4, 2016.

Office Action issued in U.S. Appl. No. 14/375,215, dated Jan. 16, 2018.

Office Action issued in U.S. Appl. No. 14/375,215, dated Jul. 9, 2015.

Office Action issued in U.S. Appl. No. 14/375,215, dated May 30, 2019.

Office Action issued in U.S. Appl. No. 14/375,215, dated Nov. 17, 2016.

Office Action issued in U.S. Appl. No. 14/375,215, dated Oct. 5, 2018.

Oupicky D. et al., "Importance of lateral and steric stabilization of polyelectrolyte gene delivery vectors for extended systemic circulation," *Mol Ther.*, 5(4):463-72, Apr. 2002.

Oupicky D. et al., "Laterally stabilized complexes of DNA with linear reducible polycations: strategy for triggered intracellular activation of DNA delivery vectors," *J Am Chem. Soc.*, 124(1):8-9, Soc., Jan. 9, 2002.

Parker A.L. et al., "Enhanced gene transfer activity of peptide-targeted gene-delivery vectors," *J Drug Target.*, 13(1):39-51, Jan. 2005.

Parkinson et al., "A transcriptomic analysis of the phylum Nematoda", *Nature Genetics*, 36(12):1259-1267, 2004.

Pichon C. et al., "Poly[Lys-(AEDTP)]: a cationic polymer that allows dissociation of pDNA/cationic polymer complexes in a reductive medium and enhances polyfection," *Bioconjug Chem.*, 13(1):76-82, Jan.-Feb. 2002.

Pomroy N.C. et al., "Solubilization of hydrophobic peptides by reversible cysteine PEGylation," Biochem Biophys Res Commun., 245(2):618-21, Apr. 17, 1998.

Racanelli et al., "Presentation of HCV antigens to naive CD8+T cells: why the where, when, what and how are important for virus control and infection outcome", *Clin Immunol.*, 124(1):5-12, 2007.

Radu D.L. et al, "Plasmid expressing the influenza HA gene protects old mice from lethal challenge with influenza viraus," *Viral Immunology*, vol. 12, No. 3, pp. 217-226, 1999.

Ramazeilles et al., "Antisense phosphorothioate oligonucleotides: selective killing of the intracellular parasite *Leishmania amazonensis*", *Proc Natl Acad Sci USA*, 91(17):7859-63, 1994.

Read et al., "Vectors based on reducible polycations facilitate intracellular release of nucleic acids", *The Journal of Gene Medicine*, 5(3):232-245, 2003.

Read M.L. et al., "A versatile reducible polycation-based system for efficient delivery of a broad range of nucleic acids," *Nucleic Acids Res.*, 33(9):e86, May 24, 2005.

Read M.L. et al., "RNA-based therapeutic strategies for cancer," *Expert Opinion on Therapeutic Patents*, vol. 13, No. 5, pp. 627-638, 2003.

Riedl et al., "Priming Th1 immunity to viral core particles is facilitated by trace amounts of RNA bound to its arginine-rich domain", *J Immunol.*, 168(10):4951-9, 2002.

Rittner et al., "New basic membrane-destabilizing peptides for plasmid-based gene delivery in Vitro and in Vivo," *Molecular Therapy*, 5(2)104-114, 2002.

Rollier et al., "Control of heterologous hepatitis C virus infection in chimpanzees is associated with the quality of vaccine-induced peripheral t-helper immune response", *J Virol.*, 78(1):187-196, 2004.

Romagne et al., "Current and future drugs targeting one class of innate immunity receptors: the toll-like receptors", *Drug Discov Today*, 12(1-2):80-7, 2007.

Rozenfeld et al., "Stable assemblies of cationic bilayer fragments and CpG oligonucleotide with enhanced immunoadjuvant activity in vivo", *Journal of Controlled Release*, 160(2):367-373, 2011.

Saenz-Badillos et al., "RNA as a tumor vaccine: a review of the literature", *Exp Dermatol.*, 10(3):143-154, 2001.

Sakae M. et al, "Highly efficient in vivo gene transfection by plasmid/PEI complexes coated by anionic PEG derivatives bearing carboxyl groups and RGD peptide," *Biomedicine and Pharmacotherapy*, vol. 62, No. 7, pp. 448-453, Sep. 1, 2008.

Scheel et al., "Therapeutic anti-tumor immunity triggered by injections of immunostimulating single-stranded RNA," *Eur J Immunol*, vol. 36, No. 10, pp. 2807-2816, 2006.

Scheel et al., "Toll-like receptor-dependent activation of several human blood cell types by protamine-condensed mRNA," *Eur J Immunol*, vol. 35, No. 5, pp. 1557-1566, 2005.

Scheel et al., "Immunostimulating capacities of stabilized RNA molecules", *Eur J Immunol.*, 24:537-547, 2004.

Scheel et al., "mRNA as immunostimulatory molecule", Krebsimmuntherapie Annual Meeting, Oral Presentation May 9, 2003. (Abstract).

Schirrmacher et al., "Intra-pinna anti-tumor vaccinaton with self-replicating infectious RNA or with DNA encoding a model tumor antigen and a cytokine", *Gene Therapy*, 7(13):1137-1147, 2000.

Shea et al., "Synthesis, hybridization properties and antiviral activity of lipid-oligodeoxynucleotide conjugates", *Nucleic Acids Research*, 18(13):3777-3783, 1990.

Shiffman et al., "Protein dissociation from DNA in model systems and chromatin," *Nucleic Acids Res.*, 5(9):3409-3426, 1978.

Shirai et al., "An epitope in hepatitis C virus core region recognized by cytotoxic T cells in mice and humans", *J Virol.*, 68(5):3334-3342, 1994.

Stephens et al., "Sequence analysis of the major outer membrane protein gene from *Chlamydia trachomatis* serovar L2", *Journal of Bacteriology*, 168(3):1277-1282, 1986.

Sun et al., "Advances in saponin-based adjuvants," *Vaccine*, 27:1787-1796, 2009.

Takae S. et al., "PEG-detachable polyplex micelles based on disulfide-linked block catiomers as bioresponsive nonviral gene vectors," *J Am Chem Soc.*, 130(18):6001-9, May 7, 2008. Epub Apr. 9, 2008.

Tan et al., "Strategies for hepatitis C therapeutic intervention: now and next", *Curr Opin in Pharmacology*, 4:465-470, 2004.

Tanaka et al., "Disulfide crosslinked stearoyl carrier peptides containing arginine and histidine enhance siRNA uptake and gene silencing," *International Journal of Pharmaceutics*, 398:219-224, 2010.

(56) References Cited

OTHER PUBLICATIONS

Teplova et al., "Crystal structure and improved antisense properties of 2'-O-(2-methoxyethyl)-RNA", *Nature Structural Biology*, 6(6):535-539, 1999.

Tokunaga et al., "Effect of oligopeptides on gene expression: comparison of DNA/peptide and DNA/peptide/liposome complexes", *International Journal of Pharmaceutics*, 269(1):71-80, 2004.

Tönges L. et al., "Stearylated octaarginine and artificial virus-like particles for transfection of siRNA into primary rat neurons," *RNA*, 12(7):1431-8. Epub May 12, 2006.

Trinchieri et al., "Cooperation of toll-like receptor signals in innate immune defence", *Nature Reviews Immunology*, 7:179-190, 2007.

Tse et al., "Update on toll-like receptor-directed therapies for human disease", *Ann Rheum Dis.*, 66 Suppl 3:iii77-80, 2007.

Unnamalai N. et al., "Cationic oligopeptide-mediated delivery of dsRNA for posttranscriptional gene silencing in plant cells," *FEBS Lett.*, 566(1-3):307-10, May 21, 2004.

Vivès E. et al., "A truncated HIV-1 Tat protein basic domain rapidly translocates through the plasma membrane and accumulates in the cell nucleus," *J Biol Chem.*, 272(25):16010-7, Jun. 20, 1997.

Wang Y.H. et al., "An intracellular delivery method for siRNA by an arginine-rich peptide," *J Biochem Biophys Methods*, 70(4):579-86, Jun. 10, 2007. Epub Jan. 30, 2007.

Weide et al., "Direct injection of protamine-protected mRNA: results of a phase 1/2 vaccination trial in metastatic melanoma patients," *J Immunother.*, 32(5):498-507, 2009.

Wyman et al., "Design, synthesis, and characterization of a cationic peptide that binds to nucleic acids and permeabilizes bilayers," *Biochemistry*, 36:3008-3017, 1997.

Xiong et al., "pH-responsive multi-PEGylated dual cationic nanoparticles enable charge modulations for safe gene delivery," *Chem Med Chem*, 2:1321-1327, 2007.

Yoshitomi et al., "Design of core-shell-type nanoparticles carrying stable radicals in the core," *Biomacromolecules*, 10:596-601, 2009.

Zhang et al., "Delivery of telomerase reverse transcriptase small interfering RNA in complex with positively charged single-walled carbon nanotubes suppresses tumor growth," *Clinical Cancer Research*, 12:4933-4939, 2006.

Zhao et al., "N/P ratio significantly influences the transfection efficiency and cytotoxicity of a polyethylenimine/chitosan/DNA complex," *Biological and Pharmaceutical Bulletin*, 32(4):706-710, 2009.

Zhou et al., "RNA melanoma vaccine: induction of antitumor immunity by human glycoprotein 100 mRNA immunization", *Human Gene Therapy*, 10:2719-2724, 1999.

Zimmermann et al., "Immunostimulatory DNA as adjuvant: efficacay of phosphodiester CpG oligonucleotides is enhanced by 3' sequence modifications", *Vaccine*, 21(9-10):990-5, 2003. (abstract only).

Zohra et al., "Effective delivery with enhanced translational activity synergistically accelerates mRNA-based transfection," *Biochem Biphys Res Commun.*, 358(1):373-378, 2007.

Arnon & Ben-Yedidia, "Old and new vaccine approaches," Int. Immunopharmacol., 3:1195-1204, 2003.

\* cited by examiner

| Cationic component/nucleic acid | Ratio (w/w) | ZP mV |
|---|---|---|
| $CR_{12}C/R722$ | 5:1 | 47,5 |
| $CR_{12}C/R722$ | 4:1 | 19,6 |
| $CR_{12}C/R722$ | 3:1 | 23,8 |
| $CR_{12}C/R722$ | 2:1 | 35 |
| $CR_{12}C/R722$ | 1:1 | -14,5 |
| $CR_{12}C/R722$ | 1:2 | -14 |
| $CR_{12}C/R722$ | 1:3 | -5,16 |
| $CR_{12}C/R722$ | 1:4 | -8,07 |
| $CR_{12}C/R722$ | 1:5 | -12,4 |

A
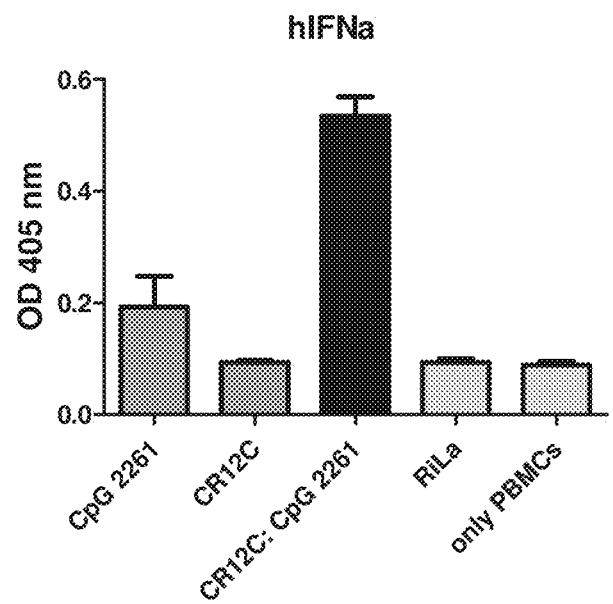
B
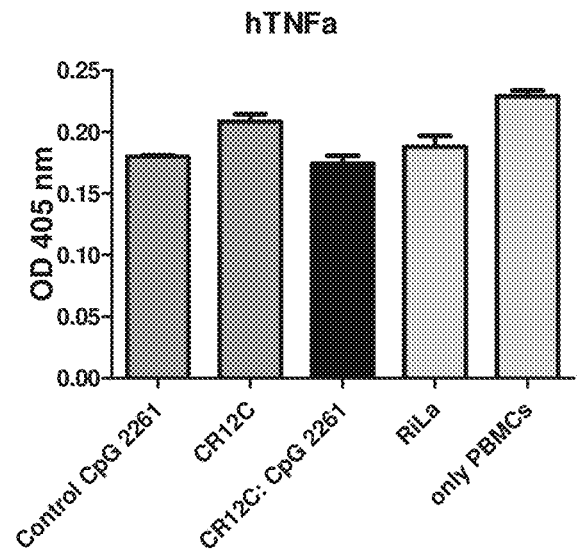
Figs. 3A-B

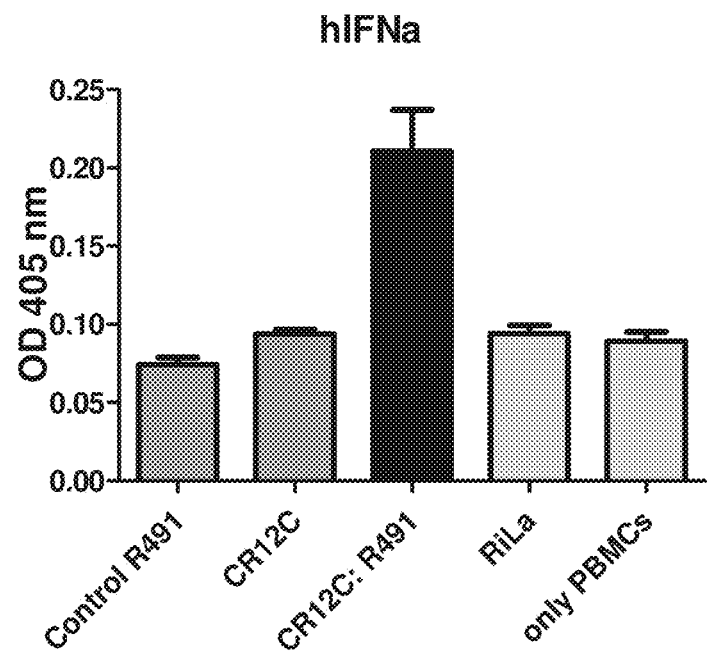
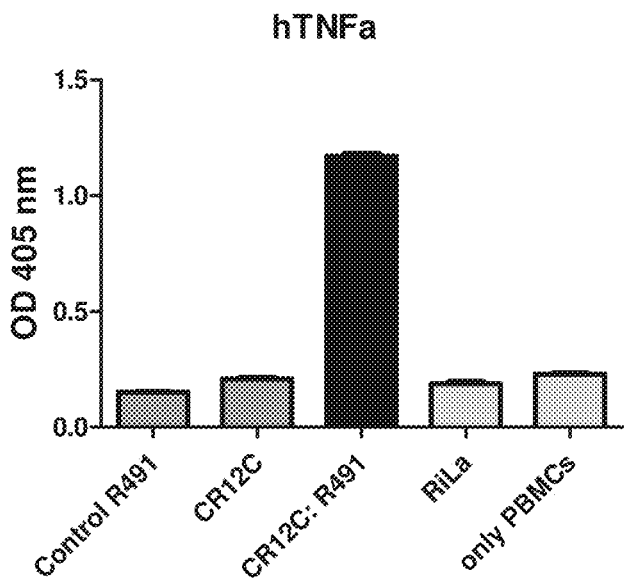
Figs. 4A-B

A
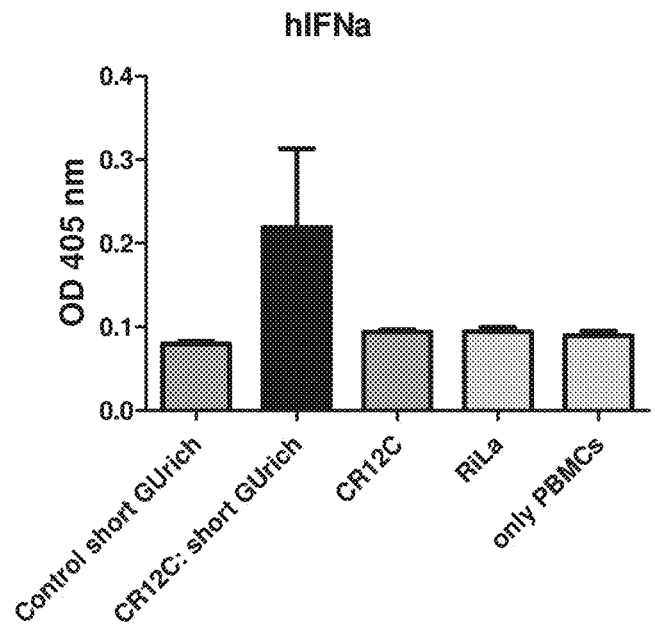
B
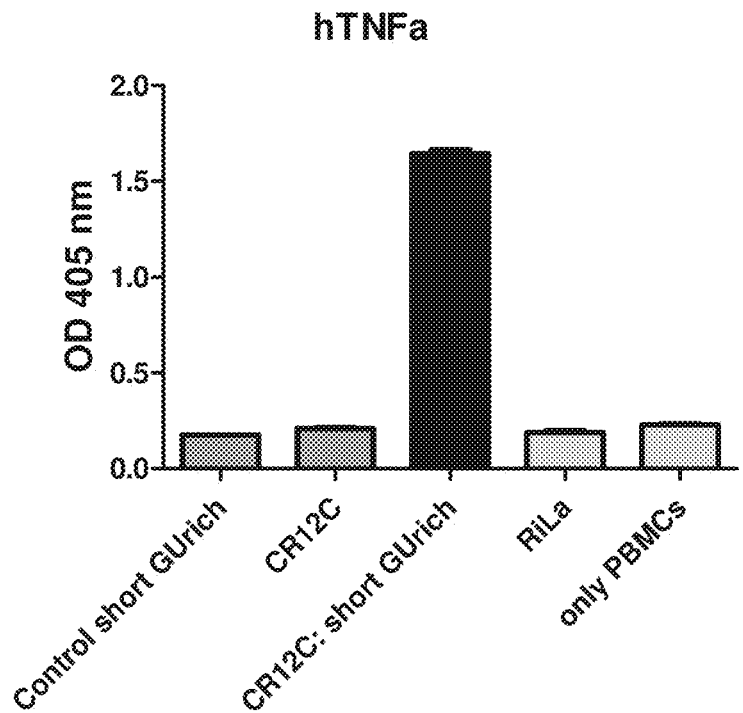
Figs. 5A-B

A
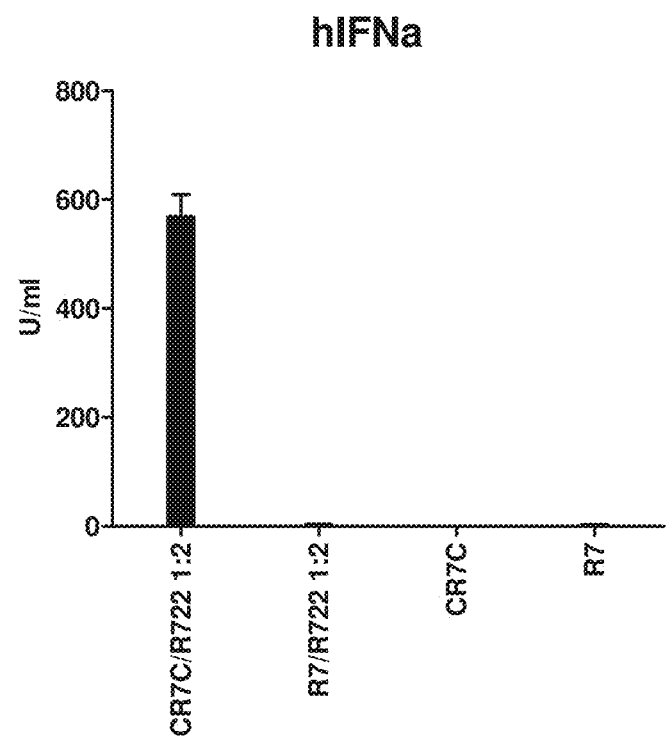
B
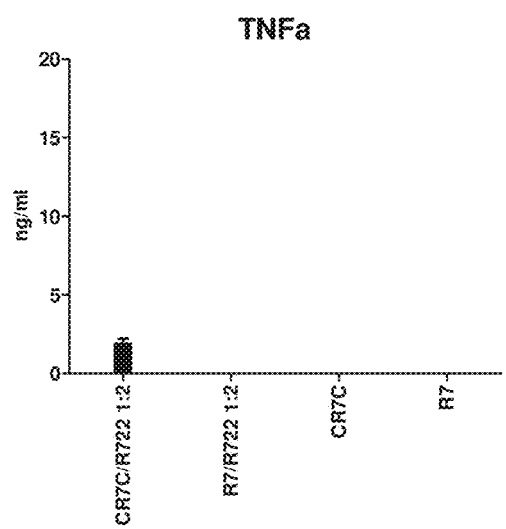
Figs. 6A-B

A
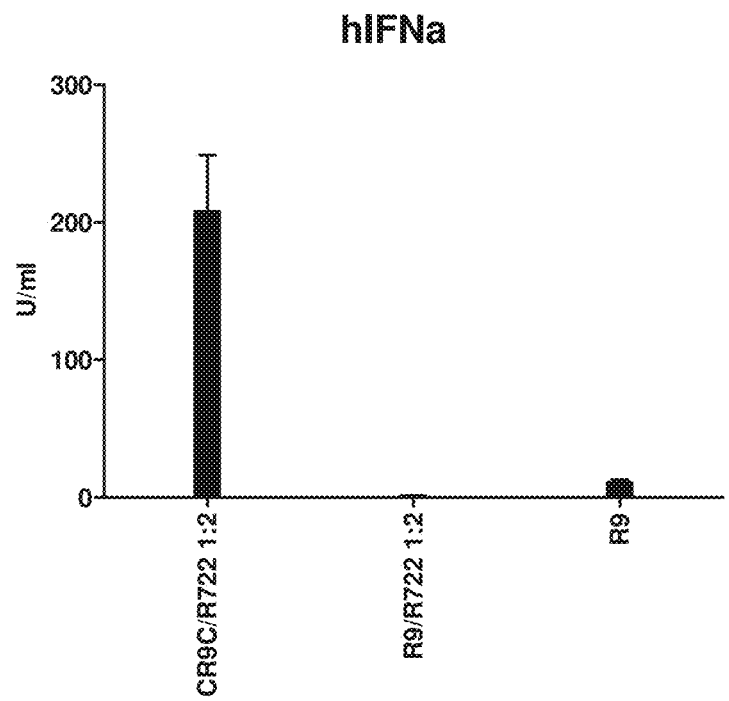
B
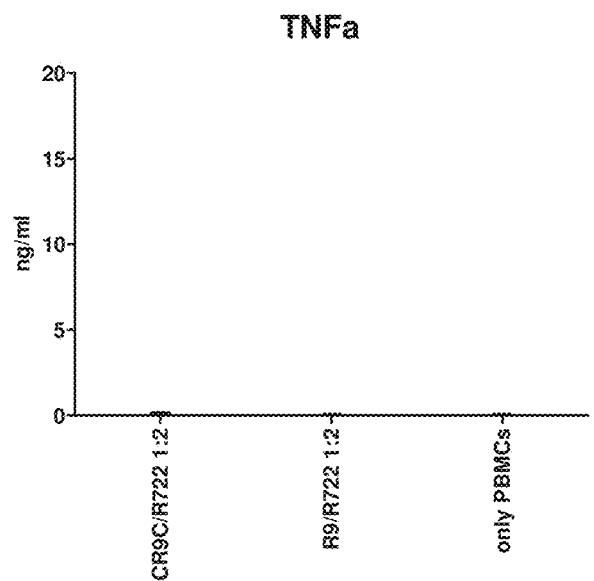
Figs. 7A-B

A
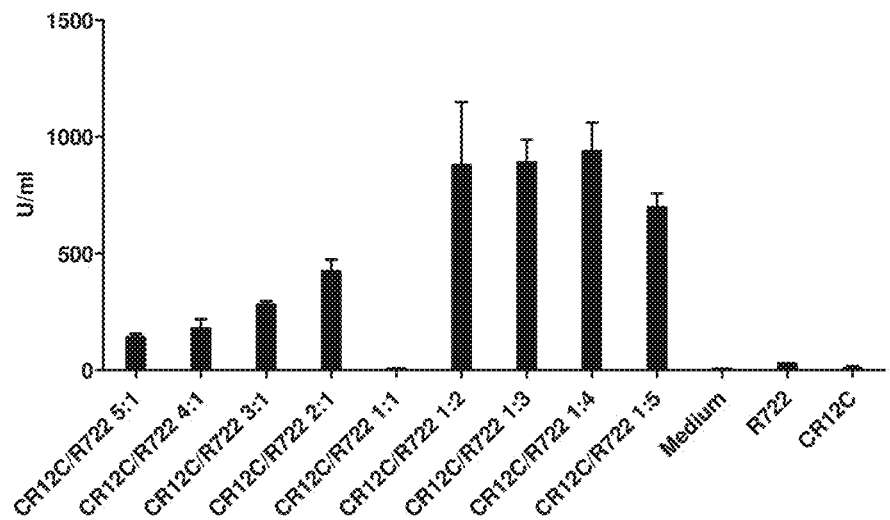
B
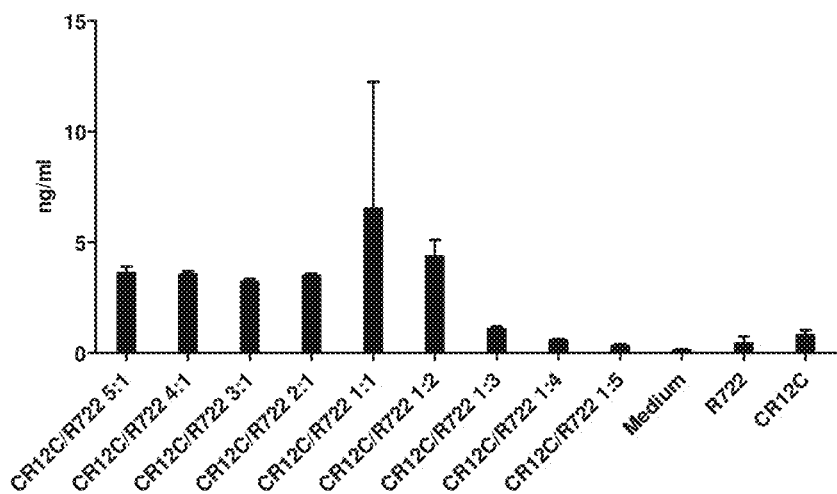
Figs. 8A-B

A
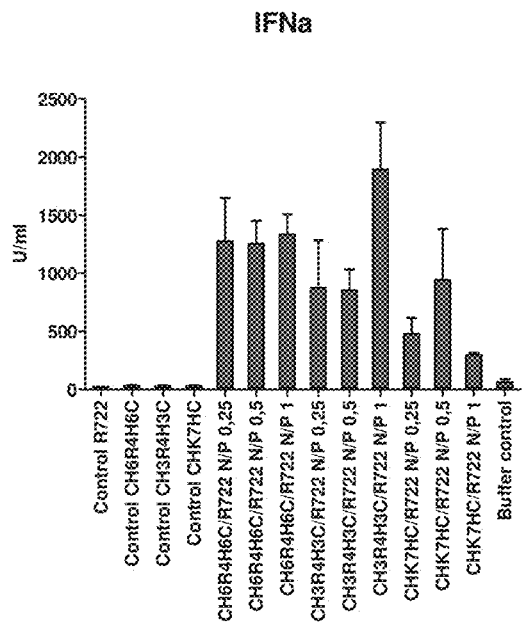
B
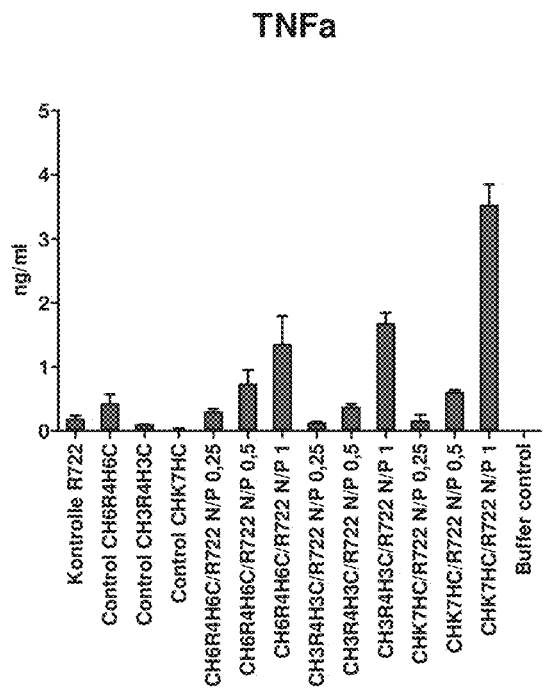
Figs. 9A-B

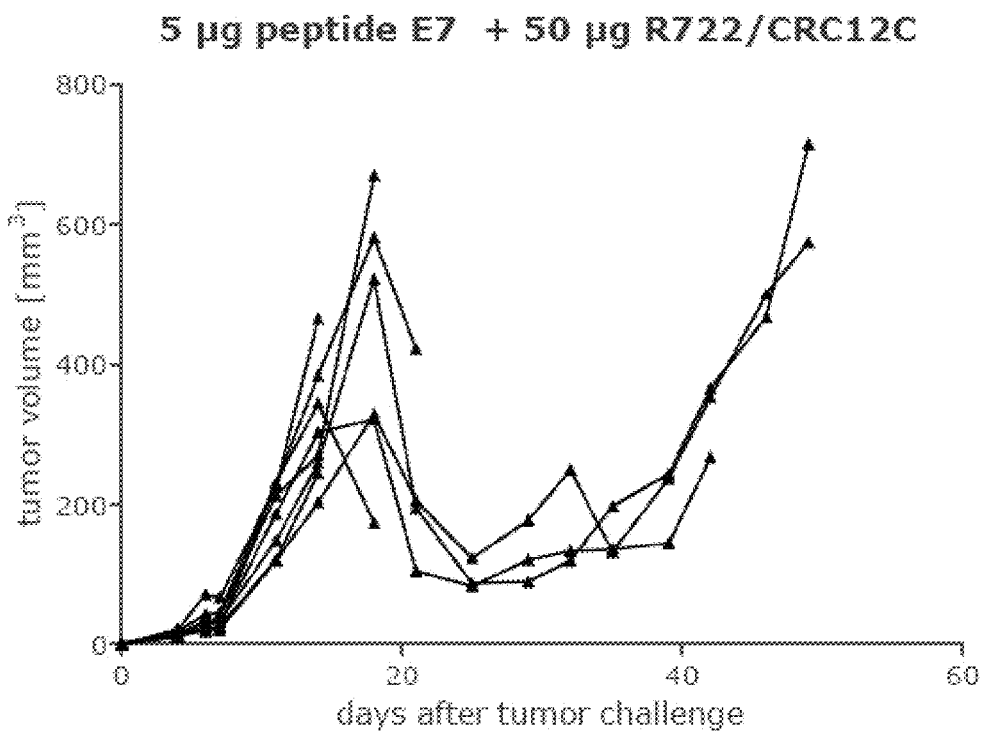
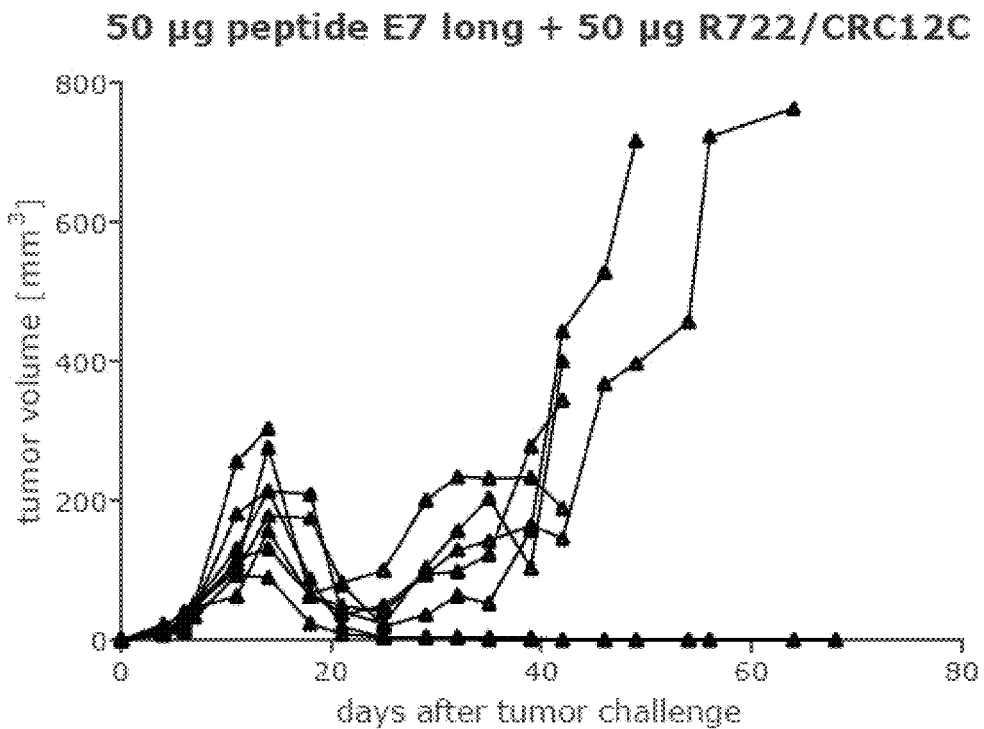
Figs. 25A-B

SEQUENCE LISTING

```
<160> NUMBER OF SEQ ID NOS: 123

<210> SEQ ID NO 1
<211> LENGTH: 9
<212> TYPE: PRT
<213> ORGANISM: artificial
<220> FEATURE:
<223> OTHER INFORMATION: Synthetic peptide

<400> SEQUENCE: 1

Cys Arg Arg Arg Arg Arg Arg Arg Cys
1               5

<210> SEQ ID NO 2
<211> LENGTH: 10
<212> TYPE: PRT
<213> ORGANISM: artificial
<220> FEATURE:
<223> OTHER INFORMATION: Synthetic peptide

<400> SEQUENCE: 2

Cys Arg Arg Arg Arg Arg Arg Arg Arg Cys
1               5                   10

<210> SEQ ID NO 3
<211> LENGTH: 11
<212> TYPE: PRT
<213> ORGANISM: artificial
<220> FEATURE:
<223> OTHER INFORMATION: Synthetic peptide
```

-continued

```
<400> SEQUENCE: 3

Cys Arg Arg Arg Arg Arg Arg Arg Arg Cys
1               5                   10

<210> SEQ ID NO 4
<211> LENGTH: 12
<212> TYPE: PRT
<213> ORGANISM: artificial
<220> FEATURE:
<223> OTHER INFORMATION: Synthetic peptide

<400> SEQUENCE: 4

Cys Arg Arg Arg Arg Arg Arg Arg Arg Arg Cys
1               5                   10

<210> SEQ ID NO 5
<211> LENGTH: 13
<212> TYPE: PRT
<213> ORGANISM: artificial
<220> FEATURE:
<223> OTHER INFORMATION: Synthetic peptide

<400> SEQUENCE: 5

Cys Arg Arg Arg Arg Arg Arg Arg Arg Arg Arg Cys
1               5                   10

<210> SEQ ID NO 6
<211> LENGTH: 14
<212> TYPE: PRT
<213> ORGANISM: artificial
<220> FEATURE:
<223> OTHER INFORMATION: Synthetic peptide

<400> SEQUENCE: 6

Cys Arg Arg Arg Arg Arg Arg Arg Arg Arg Arg Arg Cys
1               5                   10

<210> SEQ ID NO 7
<211> LENGTH: 15
<212> TYPE: PRT
<213> ORGANISM: artificial
<220> FEATURE:
<223> OTHER INFORMATION: Synthetic peptide

<400> SEQUENCE: 7

Cys Arg Arg Arg Arg Arg Arg Arg Arg Arg Arg Arg Arg Cys
1               5                   10                  15

<210> SEQ ID NO 8
<211> LENGTH: 16
<212> TYPE: PRT
<213> ORGANISM: artificial
<220> FEATURE:
<223> OTHER INFORMATION: Synthetic peptide

<400> SEQUENCE: 8

Cys Arg Arg Arg Arg Arg Arg Arg Arg Arg Arg Arg Arg Arg Cys
1               5                   10                  15

<210> SEQ ID NO 9
<211> LENGTH: 17
<212> TYPE: PRT
<213> ORGANISM: artificial
<220> FEATURE:
<223> OTHER INFORMATION: Synthetic peptide
```

-continued

```
<400> SEQUENCE: 9

Cys Arg Arg Arg Arg Arg Arg Arg Arg Arg Arg Arg Arg Arg Arg Arg
1               5                   10                  15

Cys

<210> SEQ ID NO 10
<211> LENGTH: 18
<212> TYPE: PRT
<213> ORGANISM: artificial
<220> FEATURE:
<223> OTHER INFORMATION: Synthetic peptide

<400> SEQUENCE: 10

Cys Arg Arg Arg Arg Arg Arg Arg Arg Arg Arg Arg Arg Arg Arg Arg
1               5                   10                  15

Arg Cys

<210> SEQ ID NO 11
<211> LENGTH: 19
<212> TYPE: PRT
<213> ORGANISM: artificial
<220> FEATURE:
<223> OTHER INFORMATION: Synthetic peptide

<400> SEQUENCE: 11

Cys Arg Arg Arg Arg Arg Arg Arg Arg Arg Arg Arg Arg Arg Arg Arg
1               5                   10                  15

Arg Arg Cys

<210> SEQ ID NO 12
<211> LENGTH: 20
<212> TYPE: PRT
<213> ORGANISM: artificial
<220> FEATURE:
<223> OTHER INFORMATION: Synthetic peptide

<400> SEQUENCE: 12

Cys Arg Arg Arg Arg Arg Arg Arg Arg Arg Arg Arg Arg Arg Arg Arg
1               5                   10                  15

Arg Arg Arg Cys
            20

<210> SEQ ID NO 13
<211> LENGTH: 21
<212> TYPE: PRT
<213> ORGANISM: artificial
<220> FEATURE:
<223> OTHER INFORMATION: Synthetic peptide

<400> SEQUENCE: 13

Cys Arg Arg Arg Arg Arg Arg Arg Arg Arg Arg Arg Arg Arg Arg Arg
1               5                   10                  15

Arg Arg Arg Arg Cys
            20

<210> SEQ ID NO 14
<211> LENGTH: 22
<212> TYPE: PRT
<213> ORGANISM: artificial
<220> FEATURE:
<223> OTHER INFORMATION: Synthetic peptide

<400> SEQUENCE: 14
```

```
Cys Arg Arg Arg Arg Arg Arg Arg Arg Arg Arg Arg Arg Arg Arg Arg
1               5                   10                  15

Arg Arg Arg Arg Arg Cys
            20

<210> SEQ ID NO 15
<211> LENGTH: 20
<212> TYPE: RNA
<213> ORGANISM: artificial
<220> FEATURE:
<223> OTHER INFORMATION: Synthetic oligonucleotide

<400> SEQUENCE: 15
gguuuuuuuu uuuuuuuggg                                                    20

<210> SEQ ID NO 16
<211> LENGTH: 20
<212> TYPE: RNA
<213> ORGANISM: artificial
<220> FEATURE:
<223> OTHER INFORMATION: Synthetic oligonucleotide

<400> SEQUENCE: 16 gggggguuuuu uuuuugggggg                                                   20

<210> SEQ ID NO 17
<211> LENGTH: 40
<212> TYPE: RNA
<213> ORGANISM: artificial
<220> FEATURE:
<223> OTHER INFORMATION: Synthetic oligonucleotide

<400> SEQUENCE: 17
ggggguuuuu uuuuuuuuuu uuuuuuuuuu uuuuugggg                               40

<210> SEQ ID NO 18
<211> LENGTH: 39
<212> TYPE: RNA
<213> ORGANISM: artificial
<220> FEATURE:
<223> OTHER INFORMATION: Synthetic oligonucleotide

<400> SEQUENCE: 18
gugugugugu guuuuuuuuu uuuuuuugug ugugugugu                               39

<210> SEQ ID NO 19
<211> LENGTH: 39
<212> TYPE: RNA
<213> ORGANISM: artificial
<220> FEATURE:
<223> OTHER INFORMATION: Synthetic oligonucleotide

<400> SEQUENCE: 19
gguugguugg uuuuuuuuuu uuuuuuuggu ugguuggu                                39

<210> SEQ ID NO 20
<211> LENGTH: 20
<212> TYPE: RNA
<213> ORGANISM: artificial
<220> FEATURE:
<223> OTHER INFORMATION: Synthetic oligonucleotide

<400> SEQUENCE: 20
gggggggggu uugggggggg                                                    20
```

```
<210> SEQ ID NO 21
<211> LENGTH: 20
<212> TYPE: RNA
<213> ORGANISM: artificial
<220> FEATURE:
<223> OTHER INFORMATION: Synthetic oligonucleotide

<400> SEQUENCE: 21
gggggggguu uugggggggg                                              20

<210> SEQ ID NO 22
<211> LENGTH: 20
<212> TYPE: RNA
<213> ORGANISM: artificial
<220> FEATURE:
<223> OTHER INFORMATION: Synthetic oligonucleotide

<400> SEQUENCE: 22
ggggggguuu uuugggggggg                                             20

<210> SEQ ID NO 23
<211> LENGTH: 20
<212> TYPE: RNA
<213> ORGANISM: artificial
<220> FEATURE:
<223> OTHER INFORMATION: Synthetic oligonucleotide

<400> SEQUENCE: 23
ggggggguuu uuuggggggg                                              20

<210> SEQ ID NO 24
<211> LENGTH: 20
<212> TYPE: RNA
<213> ORGANISM: artificial
<220> FEATURE:
<223> OTHER INFORMATION: Synthetic oligonucleotide

<400> SEQUENCE: 24
gggggguuuu uuugggggg                                               20

<210> SEQ ID NO 25
<211> LENGTH: 20
<212> TYPE: RNA
<213> ORGANISM: artificial
<220> FEATURE:
<223> OTHER INFORMATION: Synthetic oligonucleotide

<400> SEQUENCE: 25
ggggggguuu uuuuggggg                                               20

<210> SEQ ID NO 26
<211> LENGTH: 20
<212> TYPE: RNA
<213> ORGANISM: artificial
<220> FEATURE:
<223> OTHER INFORMATION: Synthetic oligonucleotide

<400> SEQUENCE: 26
gggggguuuu uuuuuggggg                                              20

<210> SEQ ID NO 27
<211> LENGTH: 20
<212> TYPE: RNA
<213> ORGANISM: artificial
<220> FEATURE:
<223> OTHER INFORMATION: Synthetic oligonucleotide
```

<400> SEQUENCE: 27
ggggguuuuu uuuuuuggggg                                              20

<210> SEQ ID NO 28
<211> LENGTH: 20
<212> TYPE: RNA
<213> ORGANISM: artificial
<220> FEATURE:
<223> OTHER INFORMATION: Synthetic oligonucleotide

<400> SEQUENCE: 28
ggggguuuuu uuuuuuuggg                                               20

<210> SEQ ID NO 29
<211> LENGTH: 20
<212> TYPE: RNA
<213> ORGANISM: artificial
<220> FEATURE:
<223> OTHER INFORMATION: Synthetic oligonucleotide

<400> SEQUENCE: 29
gggguuuuuu uuuuuuuggg                                               20

<210> SEQ ID NO 30
<211> LENGTH: 20
<212> TYPE: RNA
<213> ORGANISM: artificial
<220> FEATURE:
<223> OTHER INFORMATION: Synthetic oligonucleotide

<400> SEQUENCE: 30
gggguuuuuu uuuuuuuugg                                               20

<210> SEQ ID NO 31
<211> LENGTH: 20
<212> TYPE: RNA
<213> ORGANISM: artificial
<220> FEATURE:
<223> OTHER INFORMATION: Synthetic oligonucleotide

<400> SEQUENCE: 31
gguuuuuuuu uuuuuuuugg                                               20

<210> SEQ ID NO 32
<211> LENGTH: 20
<212> TYPE: RNA
<213> ORGANISM: artificial
<220> FEATURE:
<223> OTHER INFORMATION: Synthetic oligonucleotide

<400> SEQUENCE: 32
guuuuuuuuu uuuuuuuuug                                               20

<210> SEQ ID NO 33
<211> LENGTH: 22
<212> TYPE: RNA
<213> ORGANISM: artificial
<220> FEATURE:
<223> OTHER INFORMATION: Synthetic oligonucleotide

<400> SEQUENCE: 33
gggggggggg uuugggggggg gg                                           22

<210> SEQ ID NO 34
<211> LENGTH: 22

```
<212> TYPE: RNA
<213> ORGANISM: artificial
<220> FEATURE:
<223> OTHER INFORMATION: Synthetic oligonucleotide

<400> SEQUENCE: 34 ggggggggggu uuggggggggg gg                                               22

<210> SEQ ID NO 35
<211> LENGTH: 22
<212> TYPE: RNA
<213> ORGANISM: artificial
<220> FEATURE:
<223> OTHER INFORMATION: Synthetic oligonucleotide

<400> SEQUENCE: 35 ggggggggguu uuuggggggg gg                                                22

<210> SEQ ID NO 36
<211> LENGTH: 22
<212> TYPE: RNA
<213> ORGANISM: artificial
<220> FEATURE:
<223> OTHER INFORMATION: Synthetic oligonucleotide

<400> SEQUENCE: 36 ggggggggguu uuuuggggggg gg                                               22

<210> SEQ ID NO 37
<211> LENGTH: 22
<212> TYPE: RNA
<213> ORGANISM: artificial
<220> FEATURE:
<223> OTHER INFORMATION: Synthetic oligonucleotide

<400> SEQUENCE: 37 gggggggguuu uuuuggggg gg                                                 22

<210> SEQ ID NO 38
<211> LENGTH: 22
<212> TYPE: RNA
<213> ORGANISM: artificial
<220> FEATURE:
<223> OTHER INFORMATION: Synthetic oligonucleotide

<400> SEQUENCE: 38 gggggggguuu uuuuugggg gg                                                 22

<210> SEQ ID NO 39
<211> LENGTH: 22
<212> TYPE: RNA
<213> ORGANISM: artificial
<220> FEATURE:
<223> OTHER INFORMATION: Synthetic oligonucleotide

<400> SEQUENCE: 39
ggggggguuu uuuuuuggg gg                                                  22

<210> SEQ ID NO 40
<211> LENGTH: 22
<212> TYPE: RNA
<213> ORGANISM: artificial
<220> FEATURE:
<223> OTHER INFORMATION: Synthetic oligonucleotide

<400> SEQUENCE: 40
```

| | |
|---|---|
| gggggguuuu uuuuuuuggg gg | 22 |

<210> SEQ ID NO 41
<211> LENGTH: 22
<212> TYPE: RNA
<213> ORGANISM: artificial
<220> FEATURE:
<223> OTHER INFORMATION: Synthetic oligonucleotide

<400> SEQUENCE: 41

| | |
|---|---|
| ggggggguuuu uuuuuuugg gg | 22 |

<210> SEQ ID NO 42
<211> LENGTH: 22
<212> TYPE: RNA
<213> ORGANISM: artificial
<220> FEATURE:
<223> OTHER INFORMATION: Synthetic oligonucleotide

<400> SEQUENCE: 42

| | |
|---|---|
| gggggguuuu uuuuuuuugg gg | 22 |

<210> SEQ ID NO 43
<211> LENGTH: 22
<212> TYPE: RNA
<213> ORGANISM: artificial
<220> FEATURE:
<223> OTHER INFORMATION: Synthetic oligonucleotide

<400> SEQUENCE: 43

| | |
|---|---|
| gggggguuuu uuuuuuuuug gg | 22 |

<210> SEQ ID NO 44
<211> LENGTH: 22
<212> TYPE: RNA
<213> ORGANISM: artificial
<220> FEATURE:
<223> OTHER INFORMATION: Synthetic oligonucleotide

<400> SEQUENCE: 44

| | |
|---|---|
| gggguuuuuu uuuuuuuuug gg | 22 |

<210> SEQ ID NO 45
<211> LENGTH: 22
<212> TYPE: RNA
<213> ORGANISM: artificial
<220> FEATURE:
<223> OTHER INFORMATION: Synthetic oligonucleotide

<400> SEQUENCE: 45

| | |
|---|---|
| gguuuuuuuu uuuuuuuuuu gg | 22 |

<210> SEQ ID NO 46
<211> LENGTH: 24
<212> TYPE: RNA
<213> ORGANISM: artificial
<220> FEATURE:
<223> OTHER INFORMATION: Synthetic oligonucleotide

<400> SEQUENCE: 46

| | |
|---|---|
| gggggggggg guuugggggg gggg | 24 |

<210> SEQ ID NO 47
<211> LENGTH: 24
<212> TYPE: RNA
<213> ORGANISM: artificial

```
-continued

<220> FEATURE:
<223> OTHER INFORMATION: Synthetic oligonucleotide

<400> SEQUENCE: 47
gggggggggg uuugggggg gggg                                          24

<210> SEQ ID NO 48
<211> LENGTH: 24
<212> TYPE: RNA
<213> ORGANISM: artificial
<220> FEATURE:
<223> OTHER INFORMATION: Synthetic oligonucleotide

<400> SEQUENCE: 48 ggggggggggu uuuuggggg gggg                                         24

<210> SEQ ID NO 49
<211> LENGTH: 24
<212> TYPE: RNA
<213> ORGANISM: artificial
<220> FEATURE:
<223> OTHER INFORMATION: Synthetic oligonucleotide

<400> SEQUENCE: 49 ggggggggggu uuuuugggg gggg                                         24

<210> SEQ ID NO 50
<211> LENGTH: 24
<212> TYPE: RNA
<213> ORGANISM: artificial
<220> FEATURE:
<223> OTHER INFORMATION: Synthetic oligonucleotide

<400> SEQUENCE: 50
gggggggguu uuuuugggg gggg                                          24

<210> SEQ ID NO 51
<211> LENGTH: 24
<212> TYPE: RNA
<213> ORGANISM: artificial
<220> FEATURE:
<223> OTHER INFORMATION: Synthetic oligonucleotide

<400> SEQUENCE: 51
gggggggguu uuuuuuggg gggg                                          24

<210> SEQ ID NO 52
<211> LENGTH: 24
<212> TYPE: RNA
<213> ORGANISM: artificial
<220> FEATURE:
<223> OTHER INFORMATION: Synthetic oligonucleotide

<400> SEQUENCE: 52 ggggggggguu uuuuuuugg gggg                                         24

<210> SEQ ID NO 53
<211> LENGTH: 24
<212> TYPE: RNA
<213> ORGANISM: artificial
<220> FEATURE:
<223> OTHER INFORMATION: Synthetic oligonucleotide

<400> SEQUENCE: 53
ggggggguuu uuuuuuugg gggg                                          24
```

```
<210> SEQ ID NO 54
<211> LENGTH: 24
<212> TYPE: RNA
<213> ORGANISM: artificial
<220> FEATURE:
<223> OTHER INFORMATION: Synthetic oligonucleotide

<400> SEQUENCE: 54 gggggggguuu uuuuuuuug gggg                                          24

<210> SEQ ID NO 55
<211> LENGTH: 23
<212> TYPE: RNA
<213> ORGANISM: artificial
<220> FEATURE:
<223> OTHER INFORMATION: Synthetic oligonucleotide

<400> SEQUENCE: 55 ggggggguuuu uuuuuuuug ggg                                           23

<210> SEQ ID NO 56
<211> LENGTH: 24
<212> TYPE: RNA
<213> ORGANISM: artificial
<220> FEATURE:
<223> OTHER INFORMATION: Synthetic oligonucleotide

<400> SEQUENCE: 56 ggggggguuuu uuuuuuuuu gggg                                          24

<210> SEQ ID NO 57
<211> LENGTH: 24
<212> TYPE: RNA
<213> ORGANISM: artificial
<220> FEATURE:
<223> OTHER INFORMATION: Synthetic oligonucleotide

<400> SEQUENCE: 57
gggguuuuuu uuuuuuuuu gggg                                           24

<210> SEQ ID NO 58
<211> LENGTH: 24
<212> TYPE: RNA
<213> ORGANISM: artificial
<220> FEATURE:
<223> OTHER INFORMATION: Synthetic oligonucleotide

<400> SEQUENCE: 58
ggguuuuuuu uuuuuuuuu uggg                                           24

<210> SEQ ID NO 59
<211> LENGTH: 32
<212> TYPE: RNA
<213> ORGANISM: artificial
<220> FEATURE:
<223> OTHER INFORMATION: Synthetic oligonucleotide

<400> SEQUENCE: 59
guuuuuuuuu uuuuuuuuuu uuuuuuuuuu ug                                 32

<210> SEQ ID NO 60
<211> LENGTH: 34
<212> TYPE: RNA
<213> ORGANISM: artificial
<220> FEATURE:
<223> OTHER INFORMATION: Synthetic oligonucleotide
```

<400> SEQUENCE: 60
gguuuuuuuu uuuuuuuuuu uuuuuuuuuu uugg                            34

<210> SEQ ID NO 61
<211> LENGTH: 36
<212> TYPE: RNA
<213> ORGANISM: artificial
<220> FEATURE:
<223> OTHER INFORMATION: Synthetic oligonucleotide

<400> SEQUENCE: 61
ggguuuuuuu uuuuuuuuuu uuuuuuuuuu uuuggg                          36

<210> SEQ ID NO 62
<211> LENGTH: 37
<212> TYPE: RNA
<213> ORGANISM: artificial
<220> FEATURE:
<223> OTHER INFORMATION: Synthetic oligonucleotide

<400> SEQUENCE: 62
ggdgguuuuu uuuuuuuuuu uuuuuuuuuu uuuuggg                         37

<210> SEQ ID NO 63
<211> LENGTH: 39
<212> TYPE: RNA
<213> ORGANISM: artificial
<220> FEATURE:
<223> OTHER INFORMATION: Synthetic oligonucleotide

<400> SEQUENCE: 63
gggggguuuu uuuuuuuuuu uuuuuuuuuu uuuuugggg                       39

<210> SEQ ID NO 64
<211> LENGTH: 41
<212> TYPE: RNA
<213> ORGANISM: artificial
<220> FEATURE:
<223> OTHER INFORMATION: Synthetic oligonucleotide

<400> SEQUENCE: 64 ggggggguuuu uuuuuuuuuu uuuuuuuuuu uuuuuugggg g                   41

<210> SEQ ID NO 65
<211> LENGTH: 43
<212> TYPE: RNA
<213> ORGANISM: artificial
<220> FEATURE:
<223> OTHER INFORMATION: Synthetic oligonucleotide

<400> SEQUENCE: 65
ggggggguuu uuuuuuuuuu uuuuuuuuuu uuuuuuuggg ggg                  43

<210> SEQ ID NO 66
<211> LENGTH: 45
<212> TYPE: RNA
<213> ORGANISM: artificial
<220> FEATURE:
<223> OTHER INFORMATION: Synthetic oligonucleotide

<400> SEQUENCE: 66
gggggggguu uuuuuuuuuu uuuuuuuuuu uuuuuuuugg ggggg                45

<210> SEQ ID NO 67

```
<211> LENGTH: 47
<212> TYPE: RNA
<213> ORGANISM: artificial
<220> FEATURE:
<223> OTHER INFORMATION: Synthetic oligonucleotide

<400> SEQUENCE: 67
gggggggggu uuuuuuuuu uuuuuuuuuu uuuuuuuug ggggggg                        47

<210> SEQ ID NO 68
<211> LENGTH: 7
<212> TYPE: RNA
<213> ORGANISM: artificial
<220> FEATURE:
<223> OTHER INFORMATION: Synthetic oligonucleotide

<400> SEQUENCE: 68 gguuugg                                                                   7

<210> SEQ ID NO 69
<211> LENGTH: 8
<212> TYPE: RNA
<213> ORGANISM: artificial
<220> FEATURE:
<223> OTHER INFORMATION: Synthetic oligonucleotide

<400> SEQUENCE: 69 gguuuugg                                                                  8

<210> SEQ ID NO 70
<211> LENGTH: 9
<212> TYPE: RNA
<213> ORGANISM: artificial
<220> FEATURE:
<223> OTHER INFORMATION: Synthetic oligonucleotide

<400> SEQUENCE: 70 gguuuuugg                                                                 9

<210> SEQ ID NO 71
<211> LENGTH: 10
<212> TYPE: RNA
<213> ORGANISM: artificial
<220> FEATURE:
<223> OTHER INFORMATION: Synthetic oligonucleotide

<400> SEQUENCE: 71
gguuuuuugg                                                               10

<210> SEQ ID NO 72
<211> LENGTH: 11
<212> TYPE: RNA
<213> ORGANISM: artificial
<220> FEATURE:
<223> OTHER INFORMATION: Synthetic oligonucleotide

<400> SEQUENCE: 72
gguuuuuuug g                                                             11

<210> SEQ ID NO 73
<211> LENGTH: 12
<212> TYPE: RNA
<213> ORGANISM: artificial
<220> FEATURE:
<223> OTHER INFORMATION: Synthetic oligonucleotide

<400> SEQUENCE: 73
```
gguuuuuuuu gg                                                        12

<210> SEQ ID NO 74
<211> LENGTH: 13
<212> TYPE: RNA
<213> ORGANISM: artificial
<220> FEATURE:
<223> OTHER INFORMATION: Synthetic oligonucleotide

<400> SEQUENCE: 74
gguuuuuuuu ugg                                                       13

<210> SEQ ID NO 75
<211> LENGTH: 14
<212> TYPE: RNA
<213> ORGANISM: artificial
<220> FEATURE:
<223> OTHER INFORMATION: Synthetic oligonucleotide

<400> SEQUENCE: 75
gguuuuuuuu uugg                                                      14

<210> SEQ ID NO 76
<211> LENGTH: 15
<212> TYPE: RNA
<213> ORGANISM: artificial
<220> FEATURE:
<223> OTHER INFORMATION: Synthetic oligonucleotide

<400> SEQUENCE: 76
gguuuuuuuu uuugg                                                     15

<210> SEQ ID NO 77
<211> LENGTH: 16
<212> TYPE: RNA
<213> ORGANISM: artificial
<220> FEATURE:
<223> OTHER INFORMATION: Synthetic oligonucleotide

<400> SEQUENCE: 77
gguuuuuuuu uuuugg                                                    16

<210> SEQ ID NO 78
<211> LENGTH: 17
<212> TYPE: RNA
<213> ORGANISM: artificial
<220> FEATURE:
<223> OTHER INFORMATION: Synthetic oligonucleotide

<400> SEQUENCE: 78
gguuuuuuuu uuuuugg                                                   17

<210> SEQ ID NO 79
<211> LENGTH: 18
<212> TYPE: RNA
<213> ORGANISM: artificial
<220> FEATURE:
<223> OTHER INFORMATION: Synthetic oligonucleotide

<400> SEQUENCE: 79
gguuuuuuuu uuuuuugg                                                  18

<210> SEQ ID NO 80
<211> LENGTH: 19
<212> TYPE: RNA

```
<213> ORGANISM: artificial
<220> FEATURE:
<223> OTHER INFORMATION: Synthetic oligonucleotide

<400> SEQUENCE: 80
gguuuuuuuu uuuuuugg                                                  19

<210> SEQ ID NO 81
<211> LENGTH: 9
<212> TYPE: RNA
<213> ORGANISM: artificial
<220> FEATURE:
<223> OTHER INFORMATION: Synthetic oligonucleotide

<400> SEQUENCE: 81 ggguuuggg                                                             9

<210> SEQ ID NO 82
<211> LENGTH: 10
<212> TYPE: RNA
<213> ORGANISM: artificial
<220> FEATURE:
<223> OTHER INFORMATION: Synthetic oligonucleotide

<400> SEQUENCE: 82
ggguuuuggg                                                           10

<210> SEQ ID NO 83
<211> LENGTH: 11
<212> TYPE: RNA
<213> ORGANISM: artificial
<220> FEATURE:
<223> OTHER INFORMATION: Synthetic oligonucleotide

<400> SEQUENCE: 83
ggguuuuugg g                                                         11

<210> SEQ ID NO 84
<211> LENGTH: 12
<212> TYPE: RNA
<213> ORGANISM: artificial
<220> FEATURE:
<223> OTHER INFORMATION: Synthetic oligonucleotide

<400> SEQUENCE: 84
ggguuuuuug gg                                                        12

<210> SEQ ID NO 85
<211> LENGTH: 13
<212> TYPE: RNA
<213> ORGANISM: artificial
<220> FEATURE:
<223> OTHER INFORMATION: Synthetic oligonucleotide

<400> SEQUENCE: 85
ggguuuuuuu ggg                                                       13

<210> SEQ ID NO 86
<211> LENGTH: 14
<212> TYPE: RNA
<213> ORGANISM: artificial
<220> FEATURE:
<223> OTHER INFORMATION: Synthetic oligonucleotide

<400> SEQUENCE: 86
ggguuuuuuu uggg                                                      14
```

<210> SEQ ID NO 87
<211> LENGTH: 15
<212> TYPE: RNA
<213> ORGANISM: artificial
<220> FEATURE:
<223> OTHER INFORMATION: Synthetic oligonucleotide

<400> SEQUENCE: 87
ggguuuuuuu uuggg                                              15

<210> SEQ ID NO 88
<211> LENGTH: 16
<212> TYPE: RNA
<213> ORGANISM: artificial
<220> FEATURE:
<223> OTHER INFORMATION: Synthetic oligonucleotide

<400> SEQUENCE: 88
ggguuuuuuu uuuggg                                             16

<210> SEQ ID NO 89
<211> LENGTH: 17
<212> TYPE: RNA
<213> ORGANISM: artificial
<220> FEATURE:
<223> OTHER INFORMATION: Synthetic oligonucleotide

<400> SEQUENCE: 89
ggguuuuuuu uuuuggg                                            17

<210> SEQ ID NO 90
<211> LENGTH: 18
<212> TYPE: RNA
<213> ORGANISM: artificial
<220> FEATURE:
<223> OTHER INFORMATION: Synthetic oligonucleotide

<400> SEQUENCE: 90
ggguuuuuuu uuuuuggg                                           18

<210> SEQ ID NO 91
<211> LENGTH: 19
<212> TYPE: RNA
<213> ORGANISM: artificial
<220> FEATURE:
<223> OTHER INFORMATION: Synthetic oligonucleotide

<400> SEQUENCE: 91
ggguuuuuuu uuuuuuggg                                          19

<210> SEQ ID NO 92
<211> LENGTH: 57
<212> TYPE: RNA
<213> ORGANISM: artificial
<220> FEATURE:
<223> OTHER INFORMATION: Synthetic oligonucleotide

<400> SEQUENCE: 92
ggguuuuuuu uuuuuuugg guuuuuuuuu uuuuugggu uuuuuuuuu uuuggg    57

<210> SEQ ID NO 93
<211> LENGTH: 42
<212> TYPE: RNA
<213> ORGANISM: artificial
<220> FEATURE:

<223> OTHER INFORMATION: Synthetic oligonucleotide

<400> SEQUENCE: 93
ggguuuuuuu uuuuuuuugg ggguuuuuu uuuuuuuug gg            42

<210> SEQ ID NO 94
<211> LENGTH: 51
<212> TYPE: RNA
<213> ORGANISM: artificial
<220> FEATURE:
<223> OTHER INFORMATION: Synthetic oligonucleotide

<400> SEQUENCE: 94
ggguuugggu uggguuugg guuugggu uggguuug g            51

<210> SEQ ID NO 95
<211> LENGTH: 20
<212> TYPE: RNA
<213> ORGANISM: artificial
<220> FEATURE:
<223> OTHER INFORMATION: Synthetic oligonucleotide

<400> SEQUENCE: 95
gguuuuuuuu uuuuuuuggg            20

<210> SEQ ID NO 96
<211> LENGTH: 57
<212> TYPE: RNA
<213> ORGANISM: artificial
<220> FEATURE:
<223> OTHER INFORMATION: Synthetic oligonucleotide

<400> SEQUENCE: 96
cccuuuuuuu uuuuuuucc cuuuuuuuu uuuuucccu uuuuuuuuu uuucc            57

<210> SEQ ID NO 97
<211> LENGTH: 51
<212> TYPE: RNA
<213> ORGANISM: artificial
<220> FEATURE:
<223> OTHER INFORMATION: Synthetic oligonucleotide

<400> SEQUENCE: 97
cccuuucccu uucccuucc cuuucccuuu cccuuucccu uccuuucc c            51

<210> SEQ ID NO 98
<211> LENGTH: 42
<212> TYPE: RNA
<213> ORGANISM: artificial
<220> FEATURE:
<223> OTHER INFORMATION: Synthetic oligonucleotide

<400> SEQUENCE: 98
cccuuuuuuu uuuuuuucc ccccuuuuuu uuuuuuuuc cc            42

<210> SEQ ID NO 99
<211> LENGTH: 60
<212> TYPE: RNA
<213> ORGANISM: artificial
<220> FEATURE:
<223> OTHER INFORMATION: Synthetic oligonucleotide

<400> SEQUENCE: 99
uagcgaagcu cuuggaccua gguuuuuuu uuuuuuggg ugcguuccua gaaguacacg            60

<210> SEQ ID NO 100
<211> LENGTH: 120
<212> TYPE: RNA
<213> ORGANISM: artificial
<220> FEATURE:
<223> OTHER INFORMATION: Synthetic oligonucleotide

<400> SEQUENCE: 100
uagcgaagcu cuuggaccua gguuuuuuuu uuuuuuggg ugcguuccua gaaguacacg    60
aucgcuucga gaaccuggau ccaaaaaaaa aaaaaaccc acgcaaggau cuucaugugc   120

<210> SEQ ID NO 101
<211> LENGTH: 229
<212> TYPE: RNA
<213> ORGANISM: artificial
<220> FEATURE:
<223> OTHER INFORMATION: Synthetic oligonucleotide

<400> SEQUENCE: 101
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagauc              229

<210> SEQ ID NO 102
<211> LENGTH: 547
<212> TYPE: RNA
<213> ORGANISM: artificial
<220> FEATURE:
<223> OTHER INFORMATION: Synthetic oligonucleotide

<400> SEQUENCE: 102
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240
cuggaaggag caggaguagu guucuugcuc uaaguaccga gugugcccaa uacccgauca   300
gcuuauuaac gaacggcucc uccucuuaga cugcagcgua agugcggaau cugggggauca   360 aauuacugac ugccuggauu acccucggac auauaaccuu guagcacgcu guugcuguau   420
aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuag                                                            547

<210> SEQ ID NO 103
<211> LENGTH: 1083
<212> TYPE: RNA
<213> ORGANISM: artificial
<220> FEATURE:
<223> OTHER INFORMATION: Synthetic oligonucleotide

<400> SEQUENCE: 103
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc uauuagaucu cggauuacag   240

| | |
|---|---|
| cuggaaggag caggaguagu guucuugcuc uaaguaccga gugugcccaa uacccgauca | 300 |
| gcuuauuaac gaacggcucc uccucuuaga cugcagcgua agugcggaau cuggggauca | 360 |
| aauuacugac ugccuggauu acccucggac auauaaccuu guagcacgcu guugcuguau | 420 |
| aggugaccaa cgcccacucg aguagaccag cucucuuagu ccggacaaug auaggaggcg | 480 |
| cggucaaucu acuucuggcu aguuaagaau aggcugcacc gaccucuaua aguagcgugu | 540 |
| ccucuagagc uacgcagguu cgcaauaaaa gcguugauua gugugcauag aacagaccuc | 600 |
| uuauucggug aaacgccaga augcuaaauu ccaauaacuc uucccaaaac gcguacggcc | 660 |
| gaagacgcgc gcuuaucuug guacguucu cgcacaugga agaaucagcg ggcaugguga | 720 |
| uagggcaaua ggggagcugg guagcagcga aaaagggccc cugcgcacgu agcuucgcug | 780 |
| uucgucugaa acaacccggc auccguugua gcgaucccgu uaucagugu auucuugugc | 840 |
| gcacuaagau ucaugguguaa gucgacaaua acagcgucuu ggcagauucu ggucacgugc | 900 |
| ccuaugcccg ggcuugugcc ucucaggugc acagcgauac uuaaagccuu caagguacuc | 960 |
| gacgugggua ccgauucgug acacuuccua agauuauucc acuguguuag ccccgcaccg | 1020 |
| ccgaccuaaa cugguccaau guauacgcau ucgcugagcg gaucgauaau aaaagcuuga | 1080 |
| auu | 1083 |

```
<210> SEQ ID NO 104
<211> LENGTH: 229
<212> TYPE: RNA
<213> ORGANISM: artificial
<220> FEATURE:
<223> OTHER INFORMATION: Synthetic oligonucleotide

<400> SEQUENCE: 104
```

| | |
|---|---|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagauc | 229 |

```
<210> SEQ ID NO 105
<211> LENGTH: 546
<212> TYPE: RNA
<213> ORGANISM: artificial
<220> FEATURE:
<223> OTHER INFORMATION: Synthetic oligonucleotide

<400> SEQUENCE: 105
```

| | |
|---|---|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuuu | 180 |
| uuuuuaguaa augcgucuac ugaauccagc gaugaugcug gcccagaucu ucgaccacaa | 240 |
| gugcauauag uagucaucga gggucgccuu uuuuuuuuuu uuuuuuuuuu uggcccaguu | 300 |
| cugagacuuc gcuagagacu acaguuacag cugcaguagu aaccacugcg gcuauugcag | 360 |
| gaaaucccgu ucagguuuuu uuuuuuuuuu uuuuuccgc ucacuaugau uaagaaccag | 420 |
| guggaguguc acugcucucg aggucucacg agagcgcucg auacaguccu uggaagaauc | 480 |
| uuuuuuuuuu uuuuuuuuuu uugugcgacg aucacagaga acuucuauuc augcaggucu | 540 |
| gcucua | 546 |

<210> SEQ ID NO 106
<211> LENGTH: 1083
<212> TYPE: RNA
<213> ORGANISM: artificial
<220> FEATURE:
<223> OTHER INFORMATION: Synthetic oligonucleotide

<400> SEQUENCE: 106

| | | | | | |
|---|---|---|---|---|---|
| gggagaaagc | ucaagcuuau | ccaaguaggc | uggucaccug | uacaacguag | ccgguauuuu | 60 |
| uuuuuuuuuu | uuuuuuuuga | ccgucucaag | guccaaguua | gucugccuau | aaaggugcgg | 120 |
| auccacagcu | gaugaaagac | uugugcggua | cgguuaaucu | ccccuuuuuu | uuuuuuuuuu | 180 |
| uuuuuaguaa | augcgucuac | ugaauccagc | gaugaugcuc | gcccagaucu | ucgaccacaa | 240 |
| gugcauauag | uagcaucga | gggucgccuu | uuuuuuuuuu | uuuuuuuuuu | uggcccaguu | 300 |
| cugagacuuc | gcuagagacu | acaguuacag | cugcaguagu | aaccacgcg | gcauugcag | 360 |
| gaaaucccgu | ucagguuuuu | uuuuuuuuuu | uuuuuccgc | ucacuaugau | uaagaaccag | 420 |
| guggagguc | acugcucucg | aggucucacg | agagcgcucg | auacaguccu | uggaagaauc | 480 |
| uuuuuuuuuu | uuuuuuuuuu | uugugcgacg | aucacagaga | acuucuauuc | augcaggucu | 540 |
| gcucuagaac | gaacugaccu | gacgccugaa | cuuaugagcg | ugcguauuuu | uuuuuuuuuu | 600 |
| uuuuuuuuuc | cucccaacaa | augucgauca | uaagcugggc | uguuggagac | gcgucagcaa | 660 |
| augccguggc | uccauaggac | guguagacuu | cuauuuuuuu | uuuuuuuuuu | uuucccggg | 720 |
| accacaaaua | auauucuugc | uugguuggc | gcaagggccc | cguaucaggu | cauaaacggg | 780 |
| uacauguugc | acaggcuccu | uuuuuuuuuu | uuuuuuuuuu | uucgcugagu | uauuccgguc | 840 |
| ucaaaagacg | gcagacguca | gucgacaaca | cggucuaaag | cagugcuaca | aucugccgug | 900 |
| uucguguuuu | uuuuuuuuuu | uuuuuuguga | accacacgg | cgugcacugu | aguucgcaau | 960 |
| ucauagggua | ccggcucaga | guuaugccuu | gguugaaaac | ugcccagcau | acuuuuuuuu | 1020 |
| uuuuuuuuuu | uucauauucc | caugcuaagc | aagggaugcc | gcgagucaug | uuaagcuuga | 1080 |
| auu | | | | | | 1083 |

<210> SEQ ID NO 107
<211> LENGTH: 59
<212> TYPE: RNA
<213> ORGANISM: artificial
<220> FEATURE:
<223> OTHER INFORMATION: Synthetic oligonucleotide

<400> SEQUENCE: 107
uagcgaagcu cuuggaccua ccuuuuuuuu uuuuuucccu gcguuccuag aaguacacg    59

<210> SEQ ID NO 108
<211> LENGTH: 120
<212> TYPE: RNA
<213> ORGANISM: artificial
<220> FEATURE:
<223> OTHER INFORMATION: Synthetic oligonucleotide

<400> SEQUENCE: 108

| | | | | | |
|---|---|---|---|---|---|
| uagcgaagcu | cuuggaccua | ccuuuuuuuu | uuuuuucccc | ugcguuccua | gaaguacacg | 60 |
| aucgcuucga | gaaccuggau | ggaaaaaaaa | aaaaaaaggg | acgcaaggau | cuucaugugc | 120 |

<210> SEQ ID NO 109
<211> LENGTH: 7
<212> TYPE: PRT
<213> ORGANISM: artificial
<220> FEATURE:

<223> OTHER INFORMATION: Synthetic peptide

<400> SEQUENCE: 109

Arg Arg Arg Arg Arg Arg Arg
1               5

<210> SEQ ID NO 110
<211> LENGTH: 9
<212> TYPE: PRT
<213> ORGANISM: artificial
<220> FEATURE:
<223> OTHER INFORMATION: Synthetic peptide

<400> SEQUENCE: 110

Arg Arg Arg Arg Arg Arg Arg Arg Arg
1               5

<210> SEQ ID NO 111
<211> LENGTH: 12
<212> TYPE: PRT
<213> ORGANISM: artificial
<220> FEATURE:
<223> OTHER INFORMATION: Synthetic peptide

<400> SEQUENCE: 111

Arg Arg Arg Arg Arg Arg Arg Arg Arg Arg Arg Arg
1               5                   10

<210> SEQ ID NO 112
<211> LENGTH: 1845
<212> TYPE: RNA
<213> ORGANISM: Artificial Sequence
<220> FEATURE:
<223> OTHER INFORMATION: Synthetic oligonucleotide

<400> SEQUENCE: 112
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug ggaucagcc agccgaccgu ggucuucgug agcaagaagg ccugcagaa      420 gauccugaac gugcagaaga gcugcccau cauccagaag aucaucauca uggacagcaa     480
gaccgacuac cagggcuucc agucgaugua cacguucgug accagccacc ucccgccggg     540
cuucaacgag uacgacuucg ucccggagag cuucgaccgg acaagaccc aucgcccugau     600 caugaacagc agcggcagca ccggccugcc gaagggggug gcccugccgc accggaccgc     660
cugcgugcgu uucucgcacg cccgggaccc caucuucggc aaccagauca ucccggacac     720
cgccauccug agcgguggug cguuccacca cggcuucggc auguucacga cccugggcua     780
ccucaucugc ggcuuccggg ugguccugau guaccggguuc gaggaggagc uguuccugcg     840
gagccugcag gacuacaaga uccagagcgc gcugcucgug ccgacccgu ucagcuucuu      900 cgccaagagc acccugaucg acaaguacga ccugucgaac cugcacgaga ucgccagcgg     960
gggcgccccg cugagcaagg agugggcga ggccguggcc aagcgguucc accucccggg    1020
cauccgccag ggcuacggcc ugaccgagac cacgagcgcg auccugauca ccccgagg      1080

| | |
|---|---|
| ggacgacaag ccgggcgccg ugggcaaggu gguccccguuc uucgaggcca aggugguggaa | 1140 |
| ccuggacacc ggcaagaccc ugggcgugaa ccagcggggc gagcugugcg ugcgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggucguc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggccccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaauauu ccccccccccc ccccccccccc ccccccccccc ucuag | 1845 |

<210> SEQ ID NO 113
<211> LENGTH: 1857
<212> TYPE: RNA
<213> ORGANISM: Artificial Sequence
<220> FEATURE:
<223> OTHER INFORMATION: Synthetic oligonucleotide

<400> SEQUENCE: 113

| | |
|---|---|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgcccggc gaacgacauc uacaacgagc gggagcugcu | 360 |
| gaacagcaug gggaucagcc agccgaccgu ggguuucgug agcaagaagg gcugcagaa | 420 |
| gauccugaac gugcagaaga gcugcccau cauccagaag aucaucauca uggacagcaa | 480 |
| gaccgacuac cagggcuucc agucgaugua cacguucgug accagccacc ucccgccggg | 540 |
| cuucaacgag uacgacuucg uccgagag uucgaccgg acaagacca ucgcccugau | 600 |
| caugaacagc agcggcagca ccggccugcc gaaggggggug gccugccgc accgaccgc | 660 |
| cugcgugcgc uucucgcacg cccgggaccc caucuucggc aaccagauca ucccggacac | 720 |
| cgccauccug agcguggugc cguuccacca cggcuucggc auguuacga cccuggggua | 780 |
| ccucaucugc ggcuuccggg ugguccugau guaccgguuc gaggaggagc uguuccugcg | 840 |
| gagccugcag gacuacaaga uccagagcgc gcucucgug ccgacccgu ucagcuucuu | 900 |
| cgccaagagc acccugaucg acaaguacga ccgucgaaac cugcacgaga ucgccagcgg | 960 |
| gggcgccccg cugagcaagg aggugggcga ggccgguggc aagcgguuccu accuccccgg | 1020 |
| cauccgccag ggcuacggcc ugaccgagac cacgagcgcg auccgaucaa cccccgaggg | 1080 |
| ggacgacaag ccgggcgccg ugggcaaggu gguccccguuc uucgaggcca agguggugga | 1140 |
| ccuggacacc ggcaagaccc ugggcgugaa ccagcggggc gagcugugcg ugcgggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |

```
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cguggucuuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaauauu cccccccccc cccccccccc cccccccccc ucuagacaau uggaauu       1857
```

```
<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 114
gggggacgat cgtcggggggg                                                20

<210> SEQ ID NO 115
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 115
gguuuuuuuu uuuuuuuggg                                                 20

<210> SEQ ID NO 116
<211> LENGTH: 8
<212> TYPE: PRT
<213> ORGANISM: artificial
<220> FEATURE:
<223> OTHER INFORMATION: Synthetic peptide

<400> SEQUENCE: 116

Ser Ile Ile Asn Phe Glu Lys Leu
1               5

<210> SEQ ID NO 117
<211> LENGTH: 386
<212> TYPE: PRT
<213> ORGANISM: Gallus gallus

<400> SEQUENCE: 117

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
        50                  55                  60

Gly Phe Gly Asp Ser Ile Glu Ala Gln Cys Gly Thr Ser Val Asn Val
65                  70                  75                  80
```

His Ser Ser Leu Arg Asp Ile Leu Asn Gln Ile Thr Lys Pro Asn Asp
            85                  90                  95

Val Tyr Ser Phe Ser Leu Ala Ser Arg Leu Tyr Ala Glu Glu Arg Tyr
        100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
        130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 118
<211> LENGTH: 35
<212> TYPE: PRT
<213> ORGANISM: artificial
<220> FEATURE:
<223> OTHER INFORMATION: Synthetic peptide

<400> SEQUENCE: 118

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 119
<211> LENGTH: 10
<212> TYPE: PRT
<213> ORGANISM: artificial
<220> FEATURE:
<223> OTHER INFORMATION: Synthetic peptide

<400> SEQUENCE: 119

Asp Arg Ala His Tyr Asn Ile Val Thr Phe
1               5                   10

<210> SEQ ID NO 120
<211> LENGTH: 9
<212> TYPE: PRT
<213> ORGANISM: artificial
<220> FEATURE:
<223> OTHER INFORMATION: Synthetic peptide

<400> SEQUENCE: 120

Arg Ala His Tyr Asn Ile Val Thr Phe
1               5

<210> SEQ ID NO 121
<211> LENGTH: 180
<212> TYPE: PRT
<213> ORGANISM: artificial
<220> FEATURE:
<223> OTHER INFORMATION: Synthetic peptide

<400> SEQUENCE: 121

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 122
<211> LENGTH: 547
<212> TYPE: RNA
<213> ORGANISM: artificial
<220> FEATURE:
<223> OTHER INFORMATION: Synthetic oligonucleotide

```
<400> SEQUENCE: 122
gggagaaagc ucaagcuuau ccaaguaggc uggucaccug uacaacguag ccgguauuuu      60
uuuuuuuuuu uuuuuuuuga ccgucucaag guccaaguua gucugccuau aaaggugcgg     120
auccacagcu gaugaaagac uugugcggua cgguuaaucu ccccuuuuuu uuuuuuuuuu     180
uuuuuaguaa augcgucuac ugaauccagc gaugaugcug gcccagaucu ucgaccacaa     240
gugcauauag uagucaucga gggucgccuu uuuuuuuuuu uuuuuuuuuu uggcccaguu     300
cugagacuuc gcuagagacu acaguuacag cugcaguagu aaccacugcg gcuauugcag     360
gaaaucccgu ucagguuuuu uuuuuuuuuu uuuuuccgc ucacuaugau uaagaaccag      420
guggaguguc acugcucucg aggucucacg agagcgcucg auacaguccu uggaagaauc     480
uuuuuuuuuu uuuuuuuuuu uugugcgacg aucacagaga acuucuauuc augcaggucu     540
gcucuag                                                               547

<210> SEQ ID NO 123
<211> LENGTH: 20
<212> TYPE: DNA
<213> ORGANISM: artificial
<220> FEATURE:
<223> OTHER INFORMATION: Synthetic oligonucleotide

<400> SEQUENCE: 123
tccatgacgt tcctgacgtt                                                  20
```

PHARMACEUTICAL COMPOSITION COMPRISING A POLYMERIC CARRIER CARGO COMPLEX AND AT LEAST ONE PROTEIN OR PEPTIDE ANTIGEN

This application is a continuation of U.S. application Ser. No. 14/375,215, filed Jul. 29, 2014, which is a national phase application under 35 U.S.C. § 371 of International Application No. PCT/EP2013/000291, filed Jan. 31, 2013, which claims priority to International Application No. PCT/EP2012/000420, filed Jan. 31, 2012. The entire text of each of the above referenced disclosures is specifically incorporated herein by reference.

The present invention is directed to a pharmaceutical composition comprising a polymeric carrier cargo complex and at least one antigen. The polymeric carrier cargo complex preferably comprises a carrier and a cargo, wherein the carrier is a disulfide-crosslinked cationic component and the cargo at least one nucleic acid molecule. The at least one antigen is preferably selected from an antigen from a pathogen associated with infectious disease, an antigen associated with allergy or allergic disease, an antigen associated with autoimmune disease, or an antigen associated with a cancer or tumour disease, or in each case a fragment, variant and/or derivative of said antigen. Such an inventive pharmaceutical composition may be, e.g., a vaccine wherein the polymeric carrier cargo complex may serve as an adjuvant to support an immune response to the antigen. Accordingly, such a pharmaceutical composition allows for efficient induction of an adaptive immune response directed against the at least one antigen comprised therein, particularly of a Th1-shifted immune response.

The present invention furthermore provides kits or kits of parts comprising the components of the inventive pharmaceutical composition, as well as the use of the inventive pharmaceutical composition or the inventive kit or kit of parts as a vaccine, particularly in the treatment of infectious diseases, allergies, autoimmune diseases and tumour or cancer diseases. Furthermore the invention provides: (a) a polymeric carrier cargo complex for use in therapy in combination with at least one antigen or a fragment, variant and/or derivative thereof; and (b) at least one antigen or a fragment, variant and/or derivative thereof for use in therapy in combination with a polymeric carrier cargo complex, in each case (a) and (b), particularly for use in therapy of infectious diseases, allergies, autoimmune diseases and tumour or cancer diseases.

Many diseases today require administration of adjuvants to provide an innate immune response to support an adaptive immune response, particularly in the context of vaccinations. Some but not necessarily all of these diseases additionally or alternatively require administration of peptide-, protein-, and nucleic acid-based drugs, e.g. the transfection of nucleic acids into cells or tissues. These requirements usually represent different aspects in the treatment of such diseases and are typically difficult to address in one approach. As a consequence, the prior art usually handles such aspects via separate approaches.

In the above context, vaccination is generally believed to be one of the most effective and cost-efficient ways to prevent or treat diseases. Nevertheless, several problems in vaccine development have proved difficult to solve: Vaccines are often inefficient for the very young and the very old; many vaccines need to be given several times, and the protection they confer wanes over time, requiring booster administrations, and, for some diseases such as HIV, development of efficient vaccines is urgently needed. As generally accepted, many of these vaccines would be enabled or improved if they could elicit a stronger and more durable immune response.

Accordingly, the development of new efficient and safe pharmaceutical compositions that include adjuvants for vaccination purposes which support induction and maintenance of an adaptive immune response by initiating or boosting a parallel innate immune response represents a main challenging problem.

Adjuvants are usually defined as compounds that can increase and/or modulate the intrinsic immunogenicity of an antigen. To reduce negative side effects, new vaccines have a more defined composition that often leads to lower immunogenicity compared with previous whole-cell or virus-based vaccines. Adjuvants are therefore required to assist new vaccines to induce potent and persistent immune responses, with the additional benefit that less antigen and fewer injections are needed. Now it is clear that the adaptive immune response mainly depends on the level and specificity of the initial danger signals perceived by innate immune cells following infection or vaccination (Guy, B. (2007), Nat Rev Microbiol 5(7): 505-17). In particular for new generation vaccine candidates, which will increasingly comprise highly purified recombinant proteins and, although very safe, are poorly immunogenic, efficient adjuvants will become increasingly necessary.

Unfortunately, only a few licensed adjuvants are available so far. Most prominent is Alum, which is known to be safe, but also represents a very weak adjuvant. Many further adjuvants have been developed, e.g. including the administration of pathogens, CpG-nucleotides, etc. Most of these new or "established" adjuvants, however, still do not satisfy the above requirements, since many new and emerging problems have to be considered and solved. These problems inter alia include new and re-emerging infectious diseases, repeated administrations, threat of pandemic flu, etc.

Furthermore, the new vaccine targets are usually more difficult to develop and—due to their specifically tailored immune responses—require more potent adjuvants to enable success. Moreover, there are still a significant number of important pathogens for which we do not even have effective vaccines at present. This represents a very challenging future target. To enable vaccine development against such targets, more potent pharmaceutical compositions that include adjuvants and such targets will be necessary. Therefore, the new adjuvants in such compositions will need to offer advantages, including more heterologous antibody responses, covering pathogen diversity, induction of potent functional antibody responses, ensuring pathogen killing or neutralization and induction of more effective T cell responses, for direct and indirect pathogen killing, particularly the induction of cytotoxic T cells which are part of a Th1 immune response. In addition, adjuvants may be necessary to achieve more pragmatic effects, including antigen dose reduction and overcoming antigen competition in combination vaccines. Moreover, against the background of an aging population, which is increasingly susceptible to infectious diseases, new adjuvants will be necessary to overcome the natural deterioration of the immune response with age (O'Hagan, D. T. and E. De Gregorio (2009), Drug Discov Today 14(11-12): 541-51).

The review of O'Hagan (2009; supra) summarizes some reasons for the urgent need of new effective adjuvants e.g. the requirement of a lower antigen dose in vaccines, the necessity to increase the breadth of an immune response and the heterologous activity, to enable complex combination vaccines, and to overcome antigenic competition, to overcome limited immune response in some groups of the population, such as the elderly, the young children, and infants, patients with chronic diseases and the immunocompromised, to increase effector T cell response and antibody titers, to induce protective responses more rapidly and also to extend the duration of response by enhancing memory B and T cell responses.

Summarizing the above, new efficient and safe pharmaceutical compositions that include immunostimulating agents or adjuvants are required, which are preferably efficient in inducing an innate immune response, particularly in inducing the anti-viral cytokine IFN-alpha; and which are also efficient in supporting an adaptive immune response; safe, i.e. not associated with any long-term effects; which are well tolerated; which are available via a simple synthetic pathway; which exhibit low cost storage conditions (particularly feasible lyophilisation); which require simple and inexpensive components; which are biodegradable; which are compatible with many different kinds of vaccine antigens; which are capable of codelivery of antigen and immune potentiator, etc.

As already explained above adjuvants or immunostimulating agents usually act via their capability to induce an innate immune response. The innate immune system forms the dominant system of host defense in most organisms and comprises barriers such as humoral and chemical barriers including, e.g., inflammation, the complement system and cellular barriers. The innate immune system is typically based on a small number of receptors, called pattern recognition receptors. They recognize conserved molecular patterns that distinguish foreign organisms, like viruses, bacteria, fungi and parasites, from cells of the host. Such pathogen-associated molecular patterns (PAMP) include viral nucleic acids, components of bacterial and fungal walls, flagellar proteins, and more. The first family of pattern recognition receptors (PAMP receptors) studied in detail was the Toll-like receptor (TLR) family. TLRs are transmembrane proteins which recognize ligands of the extracellular milieu or of the lumen of endosomes. Following ligand-binding they transduce the signal via cytoplasmic adaptor proteins which leads to triggering of a host-defence response and entailing production of antimicrobial peptides, proinflammatory chemokines and cytokines, antiviral cytokines, etc. (see e.g. Meylan, E., J. Tschopp, et al. (2006), Nature 442(7098): 39-44). Further relevant components of the immune system include e.g. the endosomal TLRs, cytoplasmic receptors, Type I interferons and cytoplasmic receptors. Therefore, the immunostimulating agents or adjuvants are defined herein preferably as inducers of an innate immune response, which activate pattern recognition receptors (PAMP receptors). Hereby, a cascade of signals is elicited, which e.g. may result in the release of cytokines (e.g. IFN-alpha) supporting the innate immune response. Accordingly, it is preferably a feature of an immunostimulating agent or adjuvant to bind to such receptors and activate such PAMP receptors. Ideally, such as an agent or adjuvant additionally supports the adaptive immune response by e.g. shifting the immune response such that the preferred class of Th cells is activated. Depending on the disease or disorder to be treated a shift to a Th1-based immune response may be preferred or, in other cases, a shift to a Th2 immune response may be preferred.

In the prior art there are some promising adjuvant candidates which fulfil at least some, but not all, of the above defined required characteristics.

As an example, among the above developed new adjuvants, some nucleic acids like CpG DNA oligonucleotides or isRNA (immunostimulating RNA) turned out to be promising candidates for new immunostimulating agents or adjuvants as they allow the therapeutic or prophylactic induction of an innate immune response. Comprehensibly, such nucleic acid based adjuvants usually have to be delivered effectively to the site of action to allow induction of an effective innate immune response without unnecessary loss of adjuvant activity and, in some cases, without the necessity to increase the administered volume above systemically tolerated levels.

One approach to solve this issue may be the transfection of cells which are part of the innate immune system (e.g. dendritic cells, plasmacytoid dendritic cells (pDCs)) with immunostimulatory nucleic acids, which are ligands of PAMP receptors, (e.g. Toll-like receptors (TLRs)), and thus may lead to immunostimulation by the nucleic acid ligand. Further approaches may be the direct transfection of nucleic acid based adjuvants. All of these approaches, however, are typically impaired by inefficient delivery of the nucleic acid and consequently diminished adjuvant activity, in particular when administered locally.

However, one main disadvantage of such nucleic acid based adjuvant approaches until today is their limited ability to cross the plasma membrane of mammalian cells, resulting in poor cellular access and inadequate therapeutic efficacy. Until today this hurdle represents a major challenge for nucleic acid transfection based applications, e.g. biomedical developments and accordingly the commercial success of many biopharmaceuticals (see e.g. Foerg, C. & Merkle, H. P., *J Pharm Sci* 97, 144-62 (2008).

Transfection of nucleic acids or genes into cells or tissues has been investigated up to date in the context of in vitro transfection purposes and in the context of gene therapeutic approaches. However, no adjuvants are available so far which are based on such gene delivery techniques which are efficient and safe, in particular no licensed adjuvants. This is presumably due to the complex requirements of adjuvants in general in combination with stability issues to be solved in the case of nucleic acid based adjuvants.

Nevertheless, transfection of nucleic acids or genes into cells or tissues for eliciting an (innate and/or adaptive) immune response appears to provide a promising approach to provide new adjuvants.

However, many of these approaches utilize transfection of nucleic acids or genes into cells or tissues without the purpose to induce an innate immune response. There are even some gene therapeutic therapies, which have to strictly avoid induction of an innate immune response. Even in the rare cases, where vaccination is carried out to induce an adaptive antigen-specific immune response using administration of nucleic acids, e.g. in tumour vaccinations using DNA or mRNA encoded antigens, induction of an adaptive immune response is typically carried out as an active immunization against the encoded antigen but not as an accompanying adjuvant therapy and thus may require additional administration of a separate adjuvant to induce an innate immune response.

Even if a lot of transfection methods are known in the art, transfer or insertion of nucleic acids or genes into an individual's cells still represents a major challenge today and is not yet solved satisfactorily. To address this complex issue a variety of methods were developed in the last decade. These include transfection by calcium phosphate, cationic lipids, cationic polymers, and liposomes. Further methods for transfection are electroporation and viral transduction.

However, as known to a skilled person, systems for transfer or insertion of nucleic acids or genes have to fulfil several requirements for in vivo applications which include efficient nucleic acid delivery into an individual's cells with high functionality, protection of the nucleic acid against ubiquitously occurring nucleases, release of the nucleic acid in the cell, no safety concerns, feasible manufacturing in a commercially acceptable form amenable to scale-up and storage stability under low cost conditions (e.g feasible lyophilisation). These requirements are to be added to the complex requirements of an adjuvant particularly if it is in the form of a nucleic acid as outlined above.

Some successful strategies for the transfer or insertion of nucleic acids or genes available today rely on the use of viral vectors, such as adenoviruses, adeno-associated viruses, retroviruses, and herpes viruses. Viral vectors are able to mediate gene transfer with high efficiency and the possibility of long-term gene expression. However, the acute immune response ("cytokine storm"), immunogenicity, and insertion mutagenesis uncovered in gene therapy clinical trials have raised serious safety concerns about some commonly used viral vectors.

Another solution to the problem of transfer or insertion of nucleic acids or genes may be found in the use of non-viral vectors. Although non-viral vectors are not as efficient as viral vectors, many non-viral vectors have been developed to provide a safer alternative. Methods of non-viral nucleic acid delivery have been explored using physical (carrier-free nucleic acid delivery) and chemical approaches (synthetic vector-based nucleic acid delivery). Physical approaches usually include needle injection, electroporation, gene gun, ultrasound, and hydrodynamic delivery, employ a physical force that permeates the cell membrane and facilitates intracellular gene transfer. The chemical approaches typically use synthetic or naturally occurring compounds (e.g. cationic lipids, cationic polymers, lipid-polymer hybrid systems) as carriers to deliver the nucleic acid into the cells. Although significant progress has been made in the basic science and applications of various nonviral nucleic acid delivery systems, the majority of non-viral approaches are still much less efficient than viral vectors, especially for in vivo gene delivery (see e.g. Gao, X., Kim, K. & Liu, D., *AAPS J* 9, E92-104 (2007)).

Such transfection agents as defined above typically have been used successfully solely in in vitro reactions. For application of nucleic acids in vivo, however, further requirements have to be fulfilled. For example, complexes between nucleic acids and transfection agents have to be stable in physiological salt solutions with respect to agglomerisation. Furthermore, such complexes typically must not interact with parts of the complement system of the host and thus must not be immunogenic itself as the carrier itself shall not induce an adaptive immune response in the individual. Additionally, the complex shall protect the nucleic acid from early extracellular degradation by ubiquitously occurring nucleases.

In the art many transfection reagents are available, especially cationic lipids, which show excellent transfection activity in cell culture. However, most of these transfection reagents do not perform well in the presence of serum, and only a few are active in vivo. A dramatic change in size, surface charge, and lipid composition occurs when lipoplexes are exposed to the overwhelming amount of negatively charged and often amphipathic proteins and polysaccharides that are present in blood, mucus, epithelial lining fluid, or tissue matrix. Once administered in vivo, lipoplexes tend to interact with negatively charged blood components and form large aggregates that could be absorbed onto the surface of circulating red blood cells, trapped in a thick mucus layer, or embolized in microvasculatures, preventing them from reaching the intended target cells in the distal location. Some even undergo dissolution after they are introduced to the blood circulation (see e.g. Gao, X., Kim, K. & Liu, D., *AAPS J* 9, E92-104 (2007)).

One more promising approach utilizes cationic polymers. Cationic polymers turned out to be efficient in transfection of nucleic acids, as they can tightly complex and condense a negatively charged nucleic acid. Thus, a number of cationic polymers have been explored as carriers for in vitro and in vivo gene delivery. These include polyethylenimine (PEI), polyamidoamine and polypropylamine dendrimers, polyallylamine, cationic dextran, chitosan, cationic proteins and cationic peptides. Although most cationic polymers share the function of condensing DNA into small particles and facilitate cellular uptake via endocytosis through charge-charge interaction with anionic sites on cell surfaces, their transfection activity and toxicity differs dramatically.

Only in one approach in the art, the immunostimulatory effect of RNA complexed to short cationic peptides was demonstrated by Fotin-Mleczek et al. (WO 2009/030481). These formulations appear to efficiently induce the cytokine production in immunocompetent cells. Unfortunately Fotin-Mleczek et al. did not assess the induction of the preferable anti-viral cytokine IFN-α by these complexes. Additionally, these complexes turned out to be unstable during lyophilisation.

In the above context, cationic polymers exhibit better transfection efficiency with rising molecular weight. However, a rising molecular weight also leads to a rising toxicity of the cationic polymer. In this above context, (high molecular weight) PEI is perhaps the most active and most studied polymer for transfection of nucleic acids, in particular for gene delivery purposes. Unfortunately, it exhibits the same drawback due to its non-biodegradable nature and toxicity. Furthermore, even though polyplexes formed by high molecular weight polymers exhibit improved stability under physiological conditions, data have indicated that such polymers can hinder vector unpacking. To overcome this negative impact, Read et al. (see Read, M. L. et al., *J Gene Med*. 5, 232-245 (2003); and Read, M. L. et al., Nucleic Acids Res 33, e86 (2005)) developed a new type of synthetic vector based on a linear reducible polycation (RPC) prepared by oxidative polycondensation of the peptide Cys-Lys$_{10}$-Cys. This peptide Cys-Lys$_{10}$-Cys can be cleaved by the intracellular environment to facilitate release of nucleic acids. In this context, Read et al. (2003, supra) could show that polyplexes formed by these RPCs are destabilised by reducing conditions enabling efficient release of DNA and mRNA. However, examining the transfection efficiency in vitro Read et al. (2003, supra) also observed that N/P (nitrogen to phosphor atoms) ratios of 2 were unsatisfying and higher N/P ratios were necessary to improve transfection efficiency. Additionally, Read et al. (2003, supra) observed that chloroquine or the cationic lipid DOTAP was additionally necessary to enhance transfection efficiency to adequate levels. As a consequence, Read et al. (2005, supra) included histidine residues into the RPCs which have a known endosomal buffering capacity and showed that such histidine-rich RPCs can be cleaved by the intracellular reducing environment. This approach enabled efficient cytoplasmic delivery of a broad range of nucleic acids, including plasmid DNA, mRNA and siRNA molecules without the requirement for the endosomolytic agent chloroquine.

Unfortunately, neither Read et al. (2003, supra) nor Read et al. (2005, supra) did assess as to whether RPCs can be directly used for in vivo applications. In their study in 2005, transfections were performed in the absence of serum to avoid masking the ability of histidine residues to enhance gene transfer that may have arisen from binding of serum proteins to polyplexes restricting cellular uptake. Preliminary experiments, however, indicated that the transfection properties of histidine-rich RPC polyplexes can be affected by the presence of serum proteins with a 50% decrease in GFP-positive cells observed in 10% FCS. For in vivo application Read et al. (2005, supra) proposed modifications with the hydrophilic polymer poly-[N-(2hydroxy-propyl) methacrylamide]. Unfortunately, they could not prevent aggregation of polyplexes and binding of polycationic complexes to serum proteins. Furthermore, strong cationic charged complexes are formed (positive zeta potential) when complexing the nucleic acid due to the large excess of cationic polymer, which is characterized by the high N/P ratio. Accordingly, such complexes are only of limited use in vivo due to their strong tendency of salt induced agglomeration and interactions with serum contents (opsonization). Additionally, these (positively charged) complexes may excite complement activation, when used for purposes of gene therapy. It has also turned out that these positively charged RPC based complexes showed poor translation of the nucleic acid cargo subsequent to local administration into the dermis.

In an approach similar to Read et al. McKenzie et al. (McKenzie, D. L., K. Y. Kwok, et al. (2000), J Biol Chem 275(14): 9970-7 and McKenzie, D. L., E. Smiley, et al. (2000), Bioconjug Chem 11(6): 901-9) developed cross-linking peptides as gene delivery agents by inserting multiple cysteines into short synthetic peptides. In their studies they examined the optimal complex formation with DNA and as a result they could show that an N/P ratio of at least 2 is necessary for fully formed peptide DNA condensates. Therefore only positively charged complexes appeared to show optimal DNA condensation. In contrast to these data they proposed the development of negatively charged complexes for in vivo gene delivery, since it was shown in previous studies that intravenous application of electropositive DNA condensates leads to rapid opsonisation and nonspecific biodistribution to lung and liver (Collard, W. T., Evers, D. L., McKenzie, D. L., and Rice, K. G. (2000), Carbohydr. Res. 323, 176-184). Therefore, McKenzie et al. (2000; supra) proposed the derivatization of the carriers with polyethylene glycol and targeting ligands. To be noted, the approach of McKenzie et al. (2000, supra) is additionally subject of a patent (U.S. Pat. No. 6,770,740 B1), which particularly discloses the transfection of coding nucleic acids, antisense nucleic acids and ribozymes.

Thus, in vivo application of nucleic acids appears to be still one of the most challenging problems because plasma proteins with anionic charges may non-specifically bind to positively charged complexes and rapidly remove them e.g. via the reticulo-endothelial system. Opsonization and activation of the complement system by cationic complexes are additional physiological phenomena that can participate in lowering the efficacy of in vivo administered cationic complexes. This particularly applies to administration of nucleic acid-based drugs, e.g. the transfection of nucleic acids into cells or tissues, particularly if the expression of an encoded protein or peptide or transcription of an RNA of the transfected nucleic acid is intended.

Summarizing the above, the prior art does not provide feasible means or methods, which allow to establish efficient and safe pharmaceutical compositions that include adjuvants for vaccination purposes, particularly if a Th1-shifted immune response is desired.

Accordingly, it is the object of the present invention to provide such means or methods, which address one or more of these problems.

The object underlying the present invention is solved by the subject matter of the present invention, preferably by the subject matter of the attached claims.

For the sake of clarity and readability the following definitions are provided. Any technical features disclosed thereby can be part of each and every embodiment of the invention. Additional definitions and explanations can be provided in the context of this disclosure.

Nucleic acid: The term nucleic acid means typically any DNA- or RNA-molecule and is used synonymous with polynucleotide. Furthermore, modifications or derivatives of the nucleic acid as defined herein are explicitly included in the general term "nucleic acid". For example, PNA is also included in the term "nucleic acid".

Monocistronic RNA: A monocistronic RNA may typically be a RNA, preferably a mRNA, that encodes only one open reading frame. An open reading frame in this context is a sequence of several nucleotide triplets (codons) that can be translated into a peptide or protein.

Bi-/multicistronic RNA: RNA, preferably a mRNA, that typically may have two (bicistronic) or more (multicistronic) open reading frames (ORF). An open reading frame in this context is a sequence of several nucleotide triplets (codons) that can be translated into a peptide or protein.

5'-Cap structure: A 5' Cap is typically a modified nucleotide, particularly a guanine nucleotide, added to the 5'-end of a RNA-molecule. Preferably, the 5'-Cap is added using a 5'-5'-triphosphate linkage.

Poly(C) sequence: A poly(C) sequence is typically a long sequence of cytosine nucleotides, typically about 10 to about 200 cytidine nucleotides, preferably about 10 to about 100 cytidine nucleotides, more preferably about 10 to about 70 cytidine nucleotides or even more preferably about 20 to about 50 or even about 20 to about 30 cytidine nucleotides. A poly(C) sequence may preferably be located 3' of the coding region comprised by a nucleic acid.

Poly(A) tail: A poly(A) tail also called "3'-poly(A) tail" is typically a long sequence of adenine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3'-end of a RNA.

Stabilized nucleic acid: A stabilized nucleic acid, typically, may be essentially resistant to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of mRNA can, e.g., be achieved by providing a 5'-Cap structure, a Poly(A) tail, a poly (C) tail, or any other UTR modification. It can also be achieved by backbone modification or modification of the G/C-content of the nucleic acid. Various other methods are conceivable in the context of the invention.

Modification of a nucleic acid (modified nucleic acid): Modification of a nucleic acid molecule typically may contain backbone modifications, sugar modifications or base modifications. A backbone modification in connection with the present invention is, typically, a modification in which phosphates of the backbone of the nucleotides contained in the nucleic acid molecule may be chemically modified. A sugar modification in connection with the present invention, typically, may be a chemical modification of the sugar of the nucleotides of the nucleic acid. Furthermore, a base modification in connection with the present invention, typically, may be a chemical modification of the base moiety of the nucleotides of the nucleic acid molecule. Therefore a modified nucleic acid may also be defined herein as a nucleic acid molecule which may include nucleotide analogues. Furthermore a modification of a nucleic acid molecule may contain a lipid modification. Such a lipid-modified nucleic acid typically may comprise a nucleic acid as defined herein. Such a lipid-modified nucleic acid molecule typically may further comprise at least one linker covalently linked with that nucleic acid molecule, and at least one lipid covalently linked with the respective linker. Alternatively, the lipid-modified nucleic acid molecule may comprise at least one nucleic acid molecule as defined herein and at least one (bifunctional) lipid covalently linked (without a linker) with that nucleic acid molecule. According to a third alternative, the lipid-modified nucleic acid molecule may comprise a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule.

A modification of a nucleic acid may also comprise the modification of the G/C content of the coding region of a nucleic acid molecule, especially if the nucleic acid molecule is in the form of an mRNA. In this context it is particularly preferred that the G/C content of the coding region of the nucleic acid molecule is increased, compared to the G/C content of the coding region of its particular wild type coding sequence, i.e. the unmodified mRNA. The encoded amino acid sequence of the nucleic acid sequence is preferably not modified compared to the coded amino acid sequence of the particular wild type mRNA. The modification of the G/C-content of the nucleic acid molecule, especially if the nucleic acid molecule is in the form of an mRNA or codes for an mRNA, is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. Therefore, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Preferably, the G/C content of the coding region of the nucleic acid molecule, especially if the nucleic acid is in the form of an mRNA or codes for an mRNA, is increased by at least 7%, more preferably by at least 15%, particularly preferably by at least 20%, compared to the G/C content of the coded region of the wild type mRNA. According to a specific embodiment, at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment, variant and/or derivative thereof or the whole sequence of the wild type mRNA sequence or coding sequence are substituted, thereby increasing the G/C content of said sequence. In this context, it is particularly preferable to increase the G/C content of the nucleic acid molecule, especially if the nucleic acid is in the form of an mRNA or codes for an mRNA, to the maximum (i.e. 100% of the substitutable codons), in particular in the region coding for a protein, compared to the wild type sequence. Furthermore, a modification of the nucleic acid, especially if the nucleic acid is in the form of an mRNA or codes for an mRNA, is based on the finding that the translation efficiency is also determined by a different frequency in the occurrence of tRNAs in cells. The frequency in the occurrence of tRNAs in a cell, and thus the codon usage in said cell, is dependent on the species the cell is derived from. Accordingly, a yeast cell generally exhibits a different codon usage than a mammalian cell, such as a human cell. Thus, if so-called "rare codons" are present in the nucleic acid molecule (with respect to the respective expression system), especially if the nucleic acid is in the form of an mRNA or codes for an mRNA, to an increased extent, the corresponding modified nucleic acid molecule is translated to a significantly poorer degree than in the case where codons coding for relatively "frequent" tRNAs are present. Therefore, especially if the modified nucleic acid molecule is in the form of an mRNA or codes for an mRNA, the coding region of the modified nucleic acid is preferably modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the nucleic acid molecule, especially if the nucleic acid is in the form of an mRNA or codes for an mRNA, is modified such that codons for which frequently occurring tRNAs are available are inserted. In other words, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. It is particularly preferred that a nucleic acid sequence coding for a protein used in the present invention is codon optimized for the human codon usage. The codons which use for the particular amino acid the tRNA which occurs the most frequently, e.g. the Gly codon, which uses the tRNA which occurs the most frequently in the (human) cell, are particularly preferred. In this context, it is particularly preferable to link the sequential G/C content which is increased, in particular maximized, in the modified nucleic acid molecule, especially if the nucleic acid is in the form of an mRNA or codes for an mRNA, with the "frequent" codons without modifying the amino acid sequence of the protein encoded by the coding region of the nucleic acid molecule. This preferred embodiment allows provision of a particularly efficiently translated and stabilized (modified) nucleic acid, especially if the nucleic acid is in the form of an mRNA or codes for an mRNA.

Derivative of a nucleic acid molecule: A derivative of a nucleic acid molecule may typically be understood herein as a modified nucleic acid, as defined above.

Nucleotide analogues: Nucleotide analogues, typically, are nucleotides structurally similar (analogue) to naturally occurring nucleotides which include phosphate backbone modifications, sugar modifications, or modifications of the nucleobase.

UTR modification: A UTR modification is, typically, a modification of the 5' and/or 3' region of a nucleic acid molecule, particularly a coding nucleic acid molecule. Therein, "UTR" typically means "untranslated region". An UTR may, e.g., contain, comprise or consist of a stabilizing sequence (UTR modification). These stabilizing sequences in the 5' and/or 3' untranslated regions may have the effect of increasing the half-life of the nucleic acid in the cytosol. These stabilizing sequences may have 100% sequence identity to naturally occurring sequences which occur in viruses, bacteria and eukaryotes, but may also be partly or completely synthetic. The untranslated sequences (UTR) of the (alpha-)globin gene, e.g. from *Homo sapiens* or *Xenopus laevis* may be mentioned as an example of stabilizing sequences which may be used for a stabilized nucleic acid. Another example of a stabilizing sequence has the general formula (C/U)CCAN$_x$CCC(U/A)Py$_x$UC(C/U)CC which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. In the context of the present invention, a UTR modification preferably means a modification of a coding nucleic acid, such as a gene or mRNA, by adding or exchanging a 5'- and/or 3'-UTR, preferably by adding or exchanging for a stabilizing 5'- and/or 3'-UTR, e.g., as specified above.

Nucleic acid synthesis: Nucleic acid molecules used according to the invention as defined herein may be prepared using any method known in the art, including synthetic methods such as e.g. solid phase synthesis, as well as in vitro methods, such as in vitro transcription reactions.

For preparation of a nucleic acid molecule, especially if the nucleic acid is in the form of an mRNA, a corresponding DNA molecule may, e.g., be transcribed in vitro. This DNA matrix preferably comprises a suitable promoter, e.g. a T7 or SP6 promoter, for in vitro transcription, which is followed by the desired nucleotide sequence coding for the nucleic acid molecule, e.g. mRNA, to be prepared, and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), PGEM® series, e.g. PGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

Protein: A protein typically consists of one or more polypeptides folded into 3-dimensional form, facilitating a biological function.

Peptide: A peptide is typically a short polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units, more specifically between 50 and 300 monomeric units. Furthermore a "peptide" is defined herein also to include any peptidyl molecule, including peptide analogues.

Peptide analogues: A peptide analogue may, typically, comprise naturally or non-naturally occurring amino acids which may be used for the purpose of the invention. For example they can comprise amino acids selected from an isostere or a chiral analog (D-amino acid or L-amino acid) of an amino acid. Additionally, the analog may comprise one or more amino acids, preferably selected from hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid [beta]-2-thienylalanine, methionine sulfoxide, homoarginine, N-acetyl lysine, 2,4-diamino butyric acid, p-aminophenylalanine, N-methylvaline, homocysteine, homoserine, ε-amino hexanoic acid, δ-amino valeric acid, 2,3-diaminobutyric acid. A peptide analogue as defined herein may further contain modified peptides. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including Ψ[CH2S], Ψ[CH2NH], Ψ[CSNH2], Ψ[NHCO], Ψ[COCH2], and Ψ[(E) or (Z) CH=CH]. In the nomenclature used above, Ψ indicates the absence of an amide bond. The structure that replaces the amide group is specified within the brackets. Other modifications include, for example, an N-alkyl (or aryl) substitution (Ψ[CONR]), or backbone crosslinking to construct lactams and other cyclic structures, C-terminal hydroxymethyl modifications, O-modified modifications (e.g., C-terminal hydroxymethyl benzyl ether), N-terminal modifications including substituted amides such as alkylaniides and hydrazides.

Peptide synthesis: A peptide, a peptide analogue, or a derivative thereof is preferably synthesized using a chemical method known to the skilled artisan. For example, synthetic peptides are prepared using known techniques of solid phase, liquid phase, or peptide condensation, or any combination thereof, and can include natural and/or unnatural amino acids. Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. These methods are suitable for synthesis of a peptide used for the purpose of the present invention (such as a peptide analogue) or derivative thereof. Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (BzI); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Recombinant peptide or protein production: A peptide or protein or derivative thereof may be produced using recombinant protein or peptide production. To facilitate the production of a recombinant peptide or protein, at least one nucleic acid encoding the same is preferably isolated or synthesized. Typically, the nucleic acid encoding the recombinant protein or peptide is isolated using a known method, such as, for example, amplification (e.g., using PCR) or isolated from nucleic acid from an organism using one or more restriction enzymes or isolated from a library of nucleic acids. For expressing a protein or peptide by recombinant means, a protein/peptide-encoding nucleic acid is placed in operable connection with a promoter or other regulatory sequence capable of regulating expression in a cell-free system or cellular system. For example, nucleic acid comprising a sequence that encodes a peptide or protein is placed in operable connection with a suitable promoter and maintained in a suitable cell for a time and under conditions sufficient for expression to occur. Typical expression vectors for in vitro expression, cell-free expression or cell-based expression have been described and are well known for the skilled person. In this context cell-free expression systems may include E. coli S30 fraction, rabbit reticulocyte lysate and wheat germ extract and a cellular system may be selected from bacterial (e.g. E. coli), insect, plant, or mammalian cells (e.g., 293, COS, CHO, 1OT cells, 293T cells).

Secretory signal peptide: Such signal peptides are sequences, which typically exhibit a length of about 15 to 30 amino acids and are preferably located at the N-terminus of the encoded peptide, without being limited thereto. Signal peptides as defined herein preferably allow the transport of the protein or peptide into a defined cellular compartment, preferably the cell surface, the endoplasmic reticulum (ER) or the endosomal-lysosomal compartment.

Carrier/polymeric carrier: A carrier in the context of the invention may typically be a compound that facilitates transport and/or complexation of another compound. A polymeric carrier is typically a carrier that is formed of a polymer. A carrier, in the context of the present invention, is preferably suitable as carrier for nucleic acid molecules, e.g. for mediating dissolution in physiological acceptable liquids, transport and cellular uptake of the nucleic acid molecules or a vector. Accordingly, a carrier, in the context of the present invention, may be a component which may be suitable for depot and delivery of a nucleic acid molecule or vector. Such carriers may be, for example, cationic or polycationic carriers or compounds which may serve as transfection or complexation agent. Particularly preferred carriers or polymeric carriers in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from Drosophila antennapedia), pAntp, pIsl, FGF, Lactoferrin, Transportan, Buforin-2, Bac715-24, SynB, SynB(1), pVEC, hCT-derived peptides, SAP, or histones. In the context of the present invention, such cationic or polycationic carriers are preferably cationic or polycationic peptides or proteins, which preferably comprise or are additionally modified to comprise at least one moiety, which is capable of forming a disulfide bond, preferably an —SH moiety.

Cationic component: The term "cationic component" typically refers to a charged molecule, which is positively charged (cation) at a pH value of about typically 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein contains a larger number of cationic amino acids, e.g. a larger number of Arg, His, Lys or Orn, than negatively charged or neutral amino acids. In a preferred embodiment, a cationic peptide or protein in the context of the present invention contains a larger number of cationic amino acids, e.g. a larger number of Arg, His, Lys or Orn, than other residues. The definition "cationic" may also refer to "polycationic" components.

The charge of a compound, complex or component, such as the cationic component or the polymeric carrier cargo complex (A) as defined herein is preferably determined or assessed under physiological conditions, e.g. at a pH of between about 5.5 and 7.5, preferably at a pH of between about 6.0 and 7.4, such as about 7.0, at a temperature of between about 25° C. and 40° C., preferably at a temperature of about 35 and 38° C., such as about 37° C., at a physiological salt concentration of, e.g. between about 130 and 160 mM, preferably between about 137 mM and 150 mM, such as at about 137 mM. Particularly preferred conditions for determining or assessing the charge of a compound, complex or component as defined herein are the conditions found in a 100% Ringer lactate solution at 25° C.

Zetapotential: The "zetapotential" is a widely used parameter for the electrical surface charge of a particle. It is typically determined by moving the charged particle through an electrical field. In the context of the present invention, the zetapotential is the preferred parameter for characterizing the charge of a particle, e.g. of complex (A) of the pharmaceutical compositions according to the present invention. Thus, in the context of the present invention, the charge of a particle is preferably determined by determining the zetapotential by the laser Doppler electrophoresis method using a Zetasizer Nano instrument (Malvern Instruments, Malvern, UK) at 25° C. and a scattering angle of 173°. The surface charge of a given particle also depends on the ionic strength of the utilized matrix (e.g. salt containing buffer) and the pH of the solution. Therefore, the actual zetapotential of a given complex (A) at a charge ratio (N/P) may differ slightly between different buffers used for injection. For the measurement, the particles, such as complex (A) of the pharmaceutical compositions according to the present invention are preferably suspended in Ringer Lactate solution. The present invention claims therefore the use of a negatively charged complex (A) under the conditions of a given injection buffer, preferably under the conditions of a Ringer lactate solution, assessed by its Zetapotential. A Ringer lactate solution according to the present invention preferably contains 130 mmol/L sodium ions, 109 mmol/L chloride ions, 28 mmol/L lactate, 4 mmol/L potassium ions and 1.5 mmol/L calcium ion. The sodium, chloride, potassium and lactate typically come from NaCl (sodium chloride), $NaC_3H_5O_3$ (sodium lactate), $CaCl_2$ (calcium chloride), and KCl (potassium chloride). The osmolarity of the Ringer lactate solution is 273 mOsm/L and the pH is adjusted to 6.5.

Pharmaceutically effective amount: A pharmaceutically effective amount in the context of the invention is typically understood to be an amount that is sufficient to induce an immune response.

Immune system: The immune system may protect organisms, for example, from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune response: An immune response may typically either be a specific reaction of the adaptive immune system to a particular antigen (so called specific or adaptive immune response) or an unspecific reaction of the innate immune system (so called unspecific or innate immune response). In essence, the invention is associated with specific reactions (adaptive immune responses) of the adaptive immune system. However, this specific response can be supported by an additional unspecific reaction (innate immune response). Therefore, the invention also relates to a compound or composition for simultaneous stimulation of the innate and the adaptive immune system to evoke an efficient adaptive immune response.

Adaptive immune response: The adaptive immune response is typically understood to be antigen-specific. Antigen specificity allows for the generation of responses that are tailored to specific antigens, antigen-expressing cells, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Adaptive immune system: The adaptive immune system is, typically, composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Innate immune system: Typically, the innate immune system, also known as non-specific immune system, is understood to comprise the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Cellular immunity/cellular immune response: Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Humoral immunity/humoral immune response: Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Antigen: According to the present invention, the term "antigen" refers typically to a substance which may be recognized by the immune system and may be capable of triggering an antigen-specific immune response, e.g. by formation of antibodies or antigen-specific T-cells as part of an adaptive immune response. Typically, an antigen is a protein or peptide, but may also be a sugar, lipid, nucleic acid etc. structure. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. $CD4^+$ T cells bind to a MHC class II molecule and $CD8^+$ T cells to a MHC class I molecule. MHC class I and MHC class II molecules have distinct distributions among cells that reflect the different effector functions of the T cells that recognize them. MHC class I molecules present peptides from pathogens, commonly viruses to $CD8^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. Thereby MHC class I molecules on the surface of cells infected with viruses or other cytosolic pathogens display peptides from these pathogen. The $CD8^+$ T cells that recognize MHC class I:peptide complexes are specialized to kill any cells displaying foreign peptides and so rid the body of cells infected with viruses and other cytosolic pathogens. The main function of $CD4^+$ T cells ($CD4^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodes such as IgG1 and IgG3 (mouse) and IgG2 and IgG4 (human) as well as IgA and IgE (mouse and human).

Vaccine: A vaccine is typically understood to be a prophylactic or therapeutic material providing at least one antigen or antigenic function. The antigen or antigenic function may stimulate the body's adaptive immune system to provide an adaptive immune response.

Immunostimulating agent: The term "immunostimulating agent" is typically understood not to include agents as e.g. antigens (of whatever chemical structure), which elicit an adaptive/cytotoxic immune response, e.g. a "humoral" or "cellular" immune response, in other words elicit immune reponses (and confer immunity by themselves) which are characterized by a specific response to structural properties of an antigen recognized to be foreign by immune competent cells. Rather, by "immunostimulating agent", it is typically understood to mean agents/compounds/complexes which do not trigger any adaptive/cytotoxic immune response by themselves, but which may exclusively enhance such an adaptive/cytotoxic immune response in an unspecific way, by e.g. activating "PAMP" receptors and thereby triggering the release of cytokines which support the actual adaptive/cytotoxic immune response. Accordingly, any immunostimulation by agents (e.g. antigens) which evoke an adaptive and/or cytotoxic immune response by themselves (conferring immunity by themselves directly or indirectly) is typically disclaimed by the phrase "immunostimulating agent".

Adjuvant: The term "adjuvant" is typically understood not to comprise agents which confer immunity by themselves. Accordingly, adjuvants may, typically, not confer immunity by themselves, but assist the immune system in various ways to enhance the antigen-specific immune response by e.g. promoting presentation of an antigen to the immune system. Hereby, an adjuvant may preferably e.g. modulate the antigen-specific immune response by e.g. shifting the dominating Th1-based antigen specific response to a more Th2-based antigen specific response or vice versa. Accordingly, the terms "immunostimulating agent" and "adjuvant" in the context of the present invention are typically understood to mean agents, compounds or complexes which do not confer immunity by themselves, but exclusively support the immune response in an unspecific way (in contrast to an antigen-specific immune response) by effects, which modulate the antigen-specific (adaptive cellular and/or humoral immune response) by unspecific measures, e.g. cytokine expression/secretion, improved antigen presentation, shifting the nature of the arms of the immune response etc. Accordingly, any agents evoking by themselves immunity are typically disclaimed by the terms "adjuvant" or "immunostimulating agent".

Immunostimulatory RNA: An immunostimulatory RNA (isRNA) in the context of the invention may typically be a RNA that is able to induce an innate immune response itself. It usually does not have an open reading frame and thus does not provide a peptide-antigen but elicits an innate immune response e.g. by binding to a specific kind of pathogen-associated molecular patterns (PAMP) receptors (e.g. Toll-like-receptor (TLR) or other suitable receptors). However, of course also mRNAs having an open reading frame and coding for a peptide/protein (e.g. an antigenic function) may induce an innate immune response.

Fragment of a sequence: a fragment of a sequence is typically a shorter portion of a full-length sequence of e.g. a nucleic acid sequence or an amino acid sequence. Accordingly, a fragment of a sequence, typically, consists of a sequence that is identical to the corresponding stretch or corresponding stretches within the full-length sequence. A preferred fragment of a sequence in the context of the present invention, consists of a continuous stretch of entities, such as nucleotides or amino acids, corresponding to a continuous stretch of entities in the molecule the fragment is derived from, which represents at least 5%, preferably at least 20%, preferably at least 30%, more preferably at least 40%, more preferably at least 50%, even more preferably at least 60%, even more preferably at least 70%, and most preferably at least 80% of the total (i.e. full-length) molecule from which the fragment is derived. Thus, for example, a fragment of a protein or peptide antigen preferably corresponds to a continuous stretch of entities in the protein or peptide antigen the fragment is derived from, which represents at least 5%, preferably at least 20%, preferably at least 30%, more preferably at least 40%, more preferably at least 50%, even more preferably at least 60%, even more preferably at least 70%, and most preferably at least 80% of the total (i.e. full-length) protein or peptide antigen. It is particularly preferred that the fragment of a sequence is a functional fragment, i.e. that the fragment fulfills one or more of the functions fulfilled by the sequence the fragment is derived from. For example, a fragment of a protein or peptide antigen preferably exhibits at least one antigenic function (e.g. is capable of eliciting a specific immune reaction against at least one antigen determinant in said protein or peptide antigen) of the protein or peptide antigen the fragment is derived from.

Fragments of proteins: "Fragments" of proteins or peptides, i.e., fragments of amino acid sequences, in the context of the present invention may, typically, comprise a sequence of a protein or peptide as defined herein, which is, with regard to its amino acid sequence (or its encoding nucleic acid molecule), N-terminally, C-terminally and/or intrasequentially truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

Likewise, "fragments" of nucleic acid sequences in the context of the present invention may comprise a sequence of a nucleic acid as defined herein, which is, with regard to its nucleic acid molecule 5'-, 3'- and/or intrasequentially truncated compared to the nucleic acid molecule of the original (native) nucleic acid molecule. A sequence identity with respect to such a fragment as defined herein may therefore preferably refer to the entire nucleic acid as defined herein.

Preferred fragments of proteins or peptides in the context of the present invention may furthermore comprise a sequence of a protein or peptide as defined herein, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These preferred fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore, also domains of a protein, like the extracellular domain, the intracellular domain or the transmembrane domain and shortened or truncated versions of a protein may be understood to comprise a fragment of a protein.

Epitope: (also called "antigen determinant"): T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Variant: A variant of an entity, such as a variant of a sequence, e.g. of a nucleotide or amino acid sequence, refers to a modified entity, such as a modified sequence, e.g. a modified nucleotide or amino acid sequence. For example, a variant of a sequence may exhibit one or more nucleotide or amino acid deletions, insertions, additions and/or substitutions compared to the sequence the variant is derived from. Preferably, a variant of a sequence in the context of the present invention is at least 40%, preferably at least 50%, more preferably at least 60%, more preferably at least 70%, even more preferably at least 80%, even more preferably at least 90%, most preferably at least 95% identical to the sequence the variant is derived from. Accordingly, a variant of a peptide or protein antigen in the context of the present invention is preferably at least 40%, preferably at least 50%, more preferably at least 60%, more preferably at least 70%, even more preferably at least 80%, even more preferably at least 90%, most preferably at least 95% identical to the sequence of the protein or peptide antigen the variant is derived from. Preferably, the variant is a functional variant, i.e. that the variant fulfills one or more of the functions fulfilled by the sequence the variant is derived from. For example, a variant of a protein or peptide antigen preferably exhibits at least one antigenic function (e.g. is capable of eliciting a specific immune reaction against at least one antigen determinant in said protein or peptide antigen) of the protein or peptide antigen the variant is derived from.

"Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may, e.g., comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Additionally variants of proteins or peptides may comprise peptide analogues as defined herein. Furthermore, variants of proteins or peptides as defined herein, which may be encoded by a nucleic acid molecule, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Sequence identity: In order to determine the percentage to which two sequences are identical, e.g. nucleic acid sequences or amino acid sequences as defined herein, such as the amino acid sequences encoded by a nucleic acid sequence of the polymeric carrier cargo complex or a nucleic acid sequence or amino acid sequence of an antigen as defined herein, the cargo nucleic acid sequence or the amino acid sequences themselves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program. A "variant" of a protein or peptide may have, e.g., at least 70%, 75%, 80%, 85%, 90%, 95%, 98% or 99% amino acid identity over a stretch of 10, 20, 30, 50, 75 or 100 amino acids, preferably over the full length sequence, of such protein or peptide. Analogously, a "variant" of a nucleic acid sequence may have, e.g., at least 70%, 75%, 80%, 85%, 90%, 95%, 98% or 99% nucleotide identity over a stretch of 10, 20, 30, 50, 75 or 100 nucleotides, preferably over the full length sequence, of such nucleic acid sequence.

Derivative of a protein or peptide: A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope or an HA epitope. For example, the epitope is a FLAG epitope. Such a tag is useful for, for example, purifying the fusion protein. The term "derivative" of a peptide or protein also encompasses a derivatised peptide or protein, such as, for example, a peptide or protein modified to contain one or more-chemical moieties other than an amino acid. The chemical moiety may be linked covalently to the peptide or protein e.g., via an amino terminal amino acid residue, a carboxyl terminal amino acid residue, or at an internal amino acid residue. Such modifications include the addition of a protective or capping group on a reactive moiety in the peptide or protein, addition of a detectable label, and other changes that do not adversely destroy the activity of the peptide or protein compound. For example, a derivative may comprise a PEG moiety, radionuclide, coloured latex, etc. A derivative generally possesses or exhibits an improved characteristic relative to a e.g., enhanced protease resistance and/or longer half-life and/or enhanced transportability between cells or tissues of the human or animal body and/or reduced adverse effect(s) and/or enhanced affinity or immunogenicity. WO 2010/003193 describes various methodologies to provide peptide or protein derivatives which may be employed separately or in combination using standard procedures known to the person of ordinary skill, including derivatisation of a protein or peptide by e.g. PEGylation, HESylation, or glycosylation.

According to a first aspect, one or more objects underlying the present invention are solved by a pharmaceutical composition including:

(A) a polymeric carrier cargo complex, comprising:
  a) a polymeric carrier comprising disulfide-crosslinked cationic components, preferably formed by disulfide-crosslinked cationic components; and
  b) at least one nucleic acid molecule, and
(B) at least one antigen that is selected from the group consisting of:
  (i) an antigen from a pathogen associated with infectious disease;
  (ii) an antigen associated with allergy or allergic disease;
  (iii) an antigen associated with autoimmune disease; and
  (iv) an antigen associated with a cancer or tumour disease,
  or a fragment, variant and/or derivative of said antigen.

Preferably, component (B) is not covalently linked, in particular not by a disulfide bond, with component (A). Thus, component (B) is preferably not covalently linked, such as by a disulfide bond, to the polymeric carrier and/or the at least one nucleic acid molecule. Preferably, the at least one antigen is not covalently linked to the polymeric carrier cargo complex, in particular not to the polymeric carrier of the polymeric carrier cargo complex. For example, preferably, the at least one antigen, such as a protein or peptide antigen, is not covalently linked to the polymeric carrier cargo complex, such as to the polymeric carrier, by a disulfide bond. However, in an embodiment, wherein component (A) and component (B) are linked via disulfide bonds, such linkage is preferably not realized via a crosslinker, such as via a 3,6-Dioxa-1,8-octanedithiol (DODT) crosslinker. Furthermore, in an embodiment, wherein component (A) and component (B) are linked via disulfide bonds, component (B) is preferably not ovalbumine or a fragment of ovalbumine.

The advantage of component (B), e.g. a protein antigen, not being covalently linked to the polymeric carrier is that the structure of the antigen, e.g. the protein antigen, will not be disturbed and its immunogenicity will be preserved. If the antigen, e.g. the protein antigen, is covalently linked to the polymeric carrier, e.g. by disulfide bonds, the tertiary structure of the antigen may be changed, or even denatured, which may destroy the structure of conformational epitopes and may render the protein less immunogenic or non-immunogenic. Epitopes that are recognized by the immune system may be linear epitopes consisting of a continuous stretch of amino acids, or conformational epitopes that have a specific three-dimensional shape consisting of amino acids from distinct parts of the protein.

Furthermore, preferably, the polymeric carrier, in particular the cationic components of the polymeric carrier, and the at least one nucleic acid molecule of the polymeric carrier cargo complex are not covalently linked, but are preferably associated via other bonds than covalent bonds, such as by ionic bonds and/or van der Waals bonds. Thus, it is preferred that, in the polymeric carrier cargo complex, only the cationic components are covalently linked with each other, but that the nucleic acid molecules are associated non-covalently with the polymeric carrier.

Moreover, in a preferred embodiment, components (A) and (B) do not form a micelle structure together, in particular, the polmeric carrier preferably does not form a micelle structure.

In certain embodiments of all aspects of the invention, the polymeric carrier cargo complex is for use as an adjuvant. For example, it is used as an adjuvant, and/or has adjuvant properties, as may be readily determined by the person of ordinary skill using routine methodologies, and including methodologies as described herein.

As a first ingredient the inventive pharmaceutical composition includes (e.g. as an adjuvant) at least one polymeric carrier cargo complex, comprising
  a) (as a carrier) a polymeric carrier comprising disulfide-crosslinked cationic components, preferably formed by disulfide-crosslinked cationic components, and
  b) (as a cargo) at least one nucleic acid molecule.

The polymeric carrier cargo complex comprised in the inventive pharmaceutical composition allows provision of a more efficient and/or safer adjuvant for vaccination purposes. Advantageously, the polymeric carrier cargo complex is suited for in vivo delivery of nucleic acids, in particular for compacting and stabilizing a nucleic acid for the purposes of nucleic acid transfection, such as exhibiting one or more reduced negative side effects of high-molecular weight polymers as discussed above, such as poor biodegradability or high toxicity, agglomeration, low transfection activity in vivo, etc. The polymeric carrier cargo complex also provides for improved nucleic acid transfer in vivo particularly via intradermal or intramuscular routes, including serum stability, salt stability, efficiency of uptake, reduced complement activation, nucleic acid release, etc. Such a polymeric carrier cargo complex, furthermore may support induction and maintenance of an adaptive immune response by initiating or boosting a parallel innate immune response. Additionally, the polymeric carrier cargo complex may exhibit improved storage stability, particularly during lyophilisation.

The polymeric carrier cargo complex as defined above comprises as one component a polymeric carrier formed by disulfide-crosslinked cationic components. The term "cationic component" typically refers to a charged molecule, which is positively charged (cation) at a pH value of about 1 to 9, preferably of a pH value of or below 9, of or below 8, of or below 7, most preferably at physiological pH values, e.g. about 7.3 to 7.4. Accordingly, a cationic peptide, protein or polymer according to the present invention is positively charged under physiological conditions, particularly under physiological salt conditions of the cell in vivo. The definition "cationic" may also refer to "polycationic" components.

In this context, the cationic components, which form basis for the polymeric carrier of the polymeric carrier cargo complex by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer is preferably a linear molecule, however, branched cationic or polycationic peptides, proteins or polymers may also be used.

Each cationic or polycationic protein, peptide or polymer of the polymeric carrier contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

Each cationic or polycationic protein, peptide or polymer or any further component of the polymeric carrier is preferably linked to its neighbouring component(s) (cationic proteins, peptides, polymers or other components) via disulfide-crosslinking. Preferably, the disulfide-crosslinking is a (reversible) disulfide bond (—S—S—) between at least one cationic or polycationic protein, peptide or polymer and at least one further cationic or polycationic protein, peptide or polymer or other component of the polymeric carrier. The disulfide-crosslinking is typically formed by condensation of —SH-moieties of the components of the polymeric carrier particularly of the cationic components. Such an —SH-moiety may be part of the structure of the cationic or polycationic protein, peptide or polymer or any further component of the polymeric carrier prior to disulfide-crosslinking or may be added prior to disulfide-crosslinking by a modification as defined below. In this context, the sulphurs adjacent to one component of the polymeric carrier, necessary for providing a disulfide bond, may be provided by the component itself, e.g. by a —SH moiety as defined herein or may be provided by modifying the component accordingly to exhibit a —SH moiety. These —SH-moieties are typically provided by each of the component, e.g. via a cysteine or any further (modified) amino acid or compound of the component, which carries a —SH moiety. In the case that the cationic component or any further component of the polymeric carrier is a peptide or protein it is preferred that the —SH moiety is provided by at least one cysteine residue. Alternatively, the component of the polymeric carrier may be modified accordingly with a —SH moiety, preferably via a chemical reaction with a compound carrying a —SH moiety, such that each of the components of the polymeric carrier carries at least one such —SH moiety. Such a compound carrying a —SH moiety may be e.g. an (additional) cysteine or any further (modified) amino acid or compound of the component of the polymeric carrier, which carries a —SH moiety. Such a compound may also be any non-amino compound or moiety, such as a non amino acid compound or moiety, which contains or allows to introduce a —SH moiety into the component as defined herein. Such non-amino compounds, e.g. non amino acid compounds, may be attached to the component of the polymeric carrier according to the present invention via chemical reactions or binding of compounds, e.g. by binding of a 3-thio propionic acid or 2-iminothiolane (Traut's reagent), by amide formation (e.g. carboxylic acids, sulphonic acids, amines, etc.), by Michael addition (e.g maleinimide moieties, α,β unsatured carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. In some cases, the —SH moiety may be masked by protecting groups during chemical attachment to the component. Such protecting groups are known in the art and may be removed after chemical coupling. In each case, the —SH moiety, e.g. of a cysteine or of any further (modified) amino acid or compound, may be present at the terminal ends or internally at any position of the component of the polymeric carrier. As defined herein, each of the components of the polymeric carrier, preferably each of the cationic components of the polymeric carrier, typically exhibits at least one —SH-moiety, but may also contain two, three, four, five, or even more —SH-moieties.

In a preferred embodiment, the polymeric carrier, the cargo nucleic acid molecule and/or the antigen, such as the protein or peptide antigen, are not modified by introducing new coupling sites for forming disulfide bonds, such as by introducing new —SH-moieties, in particular the polymeric carrier, the cargo nucleic acid molecule and/or the antigen, such as the protein or peptide antigen, are preferably not modified by dithiopyridine. Thus, in a particular preferred embodiment, the polymeric carrier, the cargo nucleic acid molecule and/or the antigen do not comprise dithiopyridine.

In a further preferred embodiment, the polymeric carrier does not comprise a polyethylene glycol (PEG) moiety, in particular preferably the cationic components of the polymeric carrier preferably do not comprise a PEG moiety. However, if the polymeric carrier comprises a PEG moiety, the cationic component is preferably not poly-L-lysine.

Additionally to binding of cationic components a —SH moiety may be used to attach further components to the polymeric carrier as defined herein, particularly an amino acid component, e.g. antigen epitopes, antigens, antibodies, cell penetrating peptides (e.g. TAT), ligands, etc. If the polymeric carrier comprises further components in addition to the cationic components, it is preferred that the additional component is not ovalbumin or a fragment of ovalbumin, in particular, if the additional component is an amino acid component.

As defined above, the polymeric carrier of the polymeric carrier cargo complex is formed by disulfide-crosslinked cationic (or polycationic) components.

According to one first alternative, at least one cationic (or polycationic) component of the polymeric carrier may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10; 5 to 20; 5 to 15; 8 to 15, 16 or 17; 10 to 15, 16, 17, 18, 19, or 20; or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa. In this context also analogues and derivatives of proteins or peptides as defined herein are explicitly encompassed.

In the specific case that the cationic component of the polymeric carrier comprises or consists of a cationic or polycationic peptide or protein, the cationic properties of the cationic or polycationic peptide or protein or of the entire polymeric carrier, if the polymeric carrier is composed of cationic or polycationic peptides or proteins, may be determined based on its content of cationic amino acids, in particular based on its content of cationic amino acids in excess over anionic or neutral amino acids, and thus, based on its net positive charge. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20%, 30%, 40% or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

In this context, cationic amino acids are preferably the naturally occurring amino acids Arg (Arginine), Lys (Lysine), His (Histidine), and Orn (Ornithin). However, in a broader sense any (non-natural) amino acid carrying a cationic charge on its side chain may also be envisaged to carry out the invention. However, those cationic amino acids are preferred which comprise side chains which are positively charged under physiological pH conditions. In a more preferred embodiment, these amino acids are Arg, Lys, and Orn.

Preferably, such cationic or polycationic peptides or proteins of the polymeric carrier, which comprise or are additionally modified to comprise at least one —SH moeity, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from Drosophila antennapedia), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moeity, are selected from, without being restricted thereto, following cationic peptides having the following sum formula (I):

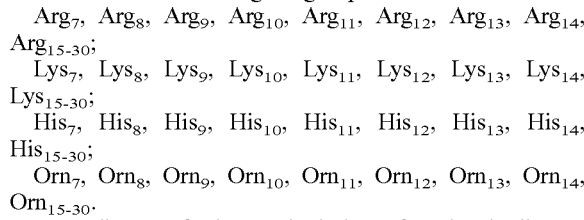

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3Arg_9$, $Arg_9His_3$, $His_3Arg_9His_3$, $His_6Arg_9His_6$, $His_3Arg_4His_3$, $His_6Arg_4His_6$, $TyrSer_2Arg_9Ser_2Tyr$, $(Arg-LysHis)_4$, $Tyr(ArgLysHis)_2Arg$, etc.

According to a particular preferred embodiment, such cationic or polycationic peptides or proteins of the polymeric carrier having the empirical sum formula (I) as shown above, may, without being restricted thereto, comprise at least one of the following subgroup of formulae:

$Arg_7$, $Arg_8$, $Arg_9$, $Arg_{10}$, $Arg_{11}$, $Arg_{12}$, $Arg_{13}$, $Arg_{14}$, $Arg_{15-30}$;

$Lys_7$, $Lys_8$, $Lys_9$, $Lys_{10}$, $Lys_{11}$, $Lys_{12}$, $Lys_{13}$, $Lys_{14}$, $Lys_{15-30}$;

$His_7$, $His_8$, $His_9$, $His_{10}$, $His_{11}$, $His_{12}$, $His_{13}$, $His_{14}$, $His_{15-30}$;

$Orn_7$, $Orn_8$, $Orn_9$, $Orn_{10}$, $Orn_{11}$, $Orn_{12}$, $Orn_{13}$, $Orn_{14}$, $Orn_{15-30}$.

According to a further particularly preferred embodiment, cationic or polycationic peptides or proteins of the polymeric carrier, having the empirical sum formula (I) as shown above and which comprise or are additionally modified to comprise at least one —SH moeity, may be preferably selected from, without being restricted thereto, at least one of the following subgroup of formulae. The following formulae (as with empirical formula (I)) do not specify any amino acid order, but are intended to reflect empirical formulae by exclusively specifying the (number of) amino acids as components of the respective peptide. Accordingly, as an example, empirical formula $Arg_{(7-29)}Lys_1$ is intended to mean that peptides falling under this formula contain 7 to 19 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$,
$Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$,
$Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$,
$Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;
$Arg_{(2-27)}Lys_2His_1$, $Arg_{(2-27)}Lys_1His_2$, $Arg_{(2-27)}Lys_2Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}$, $Arg_2His_{(2-27)}Orn_1$, $Arg_1His_{(2-27)}Orn_2$, $Lys_2His_{(2-27)}Orn_1$, $Lys_1His_{(2-27)}Orn_2$;
$Arg_{(1-26)}Lys_3His_1$, $Arg_{(1-26)}Lys_2His_2$, $Arg_{(1-26)}Lys_1His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;
$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;
$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_1His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$;

According to a further particular preferred embodiment, cationic or polycationic peptides or proteins of the polymeric carrier, having the empirical sum formula (I) as shown above and which comprise or are additionally modified to comprise at least one —SH moeity, may be, without being restricted thereto, selected from the subgroup consisting of generic formulas $Arg_7$ (also termed as $R_7$), $Arg_9$ (also termed $R_9$), $Arg_{12}$ (also termed as $R_{12}$).

According to a one further particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (I)) as shown above and which comprise or are additionally modified to comprise at least one —SH moeity, may be, without being restricted thereto, selected from subformula (Ia):

$$\{(Arg)_l;(Lys)_m;(His)_n;(Orn)_o;(Xaa')_x;(Cys)_y\} \quad \text{formula (Ia)}$$

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_l;(Lys)_m;(His)_n;(Orn)_o;(Xaa)_x$(formula (I)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (I)) as shown above, may be, without being restricted thereto, selected from subformula (Ib):

$$Cys_1\{(Arg)_l;(Lys)_m;(His)_n;(Orn)_o;(Xaa)_x\}Cys_2 \quad \text{(formula (Ib))}$$

wherein empirical formula $\{(Arg)_l;(Lys)_m;(His)_n;(Orn)_o;(Xaa)_x\}$ (formula (I)) is as defined herein and forms a core of an amino acid sequence according to (semiempirical) formula (I) and wherein $Cys_1$ and $Cys_2$ are Cysteines proximal to, or terminal to $(Arg)_l;(Lys)_m;(His)_n;(Orn)_o;(Xaa)_x$. Exemplary examples may comprise any of the above sequences flanked by two Cys and following sequences:

(SEQ ID NOs: 1-14):
$Cys(Arg_7)Cys$, $Cys(Arg_8)Cys$, $Cys(Arg_9)Cys$, $Cys(Arg_{10})Cys$, $Cys(Arg_{11})Cys$, $Cys(Arg_{12})Cys$, $Cys(Arg_{13})Cys$, $Cys(Arg_{14})Cys$, $Cys(Arg_{15})Cys$, $Cys(Arg_{16})Cys$, $Cys(Arg_{17})Cys$, $Cys(Arg_{18})Cys$, $Cys(Arg_{19})Cys$, $Cys(Arg_{20})Cys$ $CysArg_7Cys$
(SEQ ID NO. 1)
Cys-Arg-Arg-Arg-Arg-Arg-Arg-Arg-Cys $CysArg_8Cys$
(SEQ ID NO. 2)
Cys-Arg-Arg-Arg-Arg-Arg-Arg-Arg-Arg-Cys $CysArg_9Cys$:
(SEQ ID NO. 3)
Cys-Arg-Arg-Arg-Arg-Arg-Arg-Arg-Arg-Arg-Cys $CysArg_{10}Cys$
(SEQ ID NO. 4)
Cys-Arg-Arg-Arg-Arg-Arg-Arg-Arg-Arg-Arg-Arg-Cys $CysArg_{11}Cys$
(SEQ ID NO. 5)
Cys-Arg-Arg-Arg-Arg-Arg-Arg-Arg-Arg-Arg-Arg-Arg-Cys $CysArg_{12}Cys$:
(SEQ ID NO. 6)
Cys-Arg-Arg-Arg-Arg-Arg-Arg-Arg-Arg-Arg-Arg-Arg-Arg-Cys $CysArg_{13}Cys$:
(SEQ ID NO. 7)
Cys-Arg-Arg-Arg-Arg-Arg-Arg-Arg-Arg-Arg-Arg-Arg-Arg-Cys $CysArg_{14}Cys$:
(SEQ ID NO. 8)
Cys-Arg-Arg-Arg-Arg-Arg-Arg-Arg-Arg-Arg-Arg-Arg-Arg-Arg-Cys $CysArg_{15}Cys$:
(SEQ ID NO. 9)
Cys-Arg-Arg-Arg-Arg-Arg-Arg-Arg-Arg-Arg-Arg-Arg-Arg-Arg-Arg-Cys

-continued

CysArg₁₆Cys:
(SEQ ID NO. 10)
Cys-Arg-Arg-Arg-Arg-Arg-Arg-Arg-Arg-Arg-Arg-

Arg-Arg-Arg-Arg-Arg-Cys

CysArg₁₇Cys:
(SEQ ID NO. 11)
Cys-Arg-Arg-Arg-Arg-Arg-Arg-Arg-Arg-Arg-Arg-

Arg-Arg-Arg-Arg-Arg-Arg-Cys

CysArg₁₈Cys:
(SEQ ID NO. 12)
Cys-Arg-Arg-Arg-Arg-Arg-Arg-Arg-Arg-Arg-Arg-

Arg-Arg-Arg-Arg-Arg-Arg-Arg-Cys

CysArg₁₉Cys:
(SEQ ID NO. 13)
Cys-Arg-Arg-Arg-Arg-Arg-Arg-Arg-Arg-Arg-Arg-

Arg-Arg-Arg-Arg-Arg-Arg-Arg-Cys

CysArg₂₀Cys:
(SEQ ID NO. 14)
Cys-Arg-Arg-Arg-Arg-Arg-Arg-Arg-Arg-Arg-Arg-

Arg-Arg-Arg-Arg-Arg-Arg-Arg-Arg Cys

This embodiment may apply to situations, wherein the cationic or polycationic peptide or protein of the polymeric carrier, e.g. when defined according to empirical formula $(Arg)_l;(Lys)_m;(His)_n;(Orn)_o;(Xaa)_x$ (formula (I)) as shown above, has been modified with at least two cysteines as —SH moieties in the above meaning such that the cationic or polycationic peptide of the polymeric carrier cargo complex as cationic component carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (non-peptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges, preferably the net cationic charges (i.e. upon subtraction of anionic and neutral charges), in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

Said cationic or polycationic peptides or proteins may be prepared by all methods known to a person of ordinary skill or by recombinant peptide or protein production or by peptide synthesis as described herein.

In the above context, the (non-peptidic) cationic component of the polymeric carrier may be selected from acrylates, modified acrylates, such as pDMAEMA (poly(dimethylaminoethyl methylacrylate)), chitosanes, aziridines or 2-ethyl-2-oxazoline (forming oligo ethylenimines or modifed oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

In the context of the polymeric carrier, the cationic components, which form basis for the polymeric carrier by disulfide-crosslinkage, may be the same or different from each other. It is also particularly preferred that the polymeric carrier of the present invention comprises mixtures of cationic peptides, proteins or polymers and optionally further components as defined herein, which are crosslinked by disulfide bonds as described herein. Particularly preferred cationic components of the polymeric carrier in the context of the present invention are cationic peptides or proteins.

In this context, the polymeric carrier cargo complex due to its variable polymeric carrier advantageously allows to combine desired properties of different (short) cationic or polycationic peptides, proteins or polymers or other components. The polymeric carrier, e.g., allows to efficiently compact nucleic acids for the purpose of efficient transfection of nucleic acids, for adjuvant therapy, for the purposes of gene therapy, for gene knock-down or others strategies without loss of activity, particularly exhibiting an efficient transfection of a nucleic acid into different cell lines in vitro but particularly transfection in vivo. The polymeric carrier and thus the polymeric carrier cargo complex is furthermore not toxic to cells, provides for efficient release of its nucleic acid cargo, is stable during lyophilization and is applicable as immunostimulating agent or adjuvant. Preferably, the polymer carrier cargo complex may induce the anti-viral cytokine IFN-alpha.

In particular, the polymeric carrier formed by disulfide-linked cationic components allows considerably to vary its peptide or polymeric content and thus to modulate its biophysical/biochemical properties, particularly the cationic properties of the polymeric carrier, quite easily and fast, e.g. by incorporating as cationic components the same or different cationic peptide(s) or polymer(s) and optionally adding other components into the polymeric carrier. Even though consisting of quite small non-toxic monomer units the polymeric carrier forms a long cationic binding sequence providing a strong condensation of the nucleic acid cargo and complex stability. Under the reducing conditions of the cytosole (e.g. cytosolic GSH), the complex is rapidly degraded into its (cationic) components, which are further degraded (e.g. oligopeptides). This supports deliberation of the nucleic acid cargo in the cytosol. Due to degradation into small oligopeptides or polymers in the cytosol, no toxicity is observed as known for high-molecular oligopeptides or polymers, e.g. from high-molecular polyarginine.

Accordingly, the polymeric carrier of the polymeric carrier cargo complex may comprise different (short) cationic or polycationic peptides, proteins or polymers selected from cationic or polycationic peptides, proteins or (non-peptidic) polymers as defined above, optionally together with further components as defined herein.

Additionally, the polymeric carrier of the polymeric carrier cargo complex as defined above, more preferably at least one of the different (short) cationic or polycationic peptides or (non-peptidic) polymers forming basis for the polymeric carrier via disulfide-crosslinking, may be, preferably prior to the disulfide-crosslinking, modified with at least one further component. Alternatively, the polymeric carrier as such may be modified with at least one further component. It may also optionally comprise at least one further component, which typically forms the polymeric carrier disulfide together with the other (short) cationic or polycationic peptides as defined above via disulfide crosslinking.

To allow modification of a cationic or polycationic peptide or a (non-peptidic) polymer as defined above, each of the components of the polymeric carrier may (preferably already prior to disulfide-crosslinking) also contain at least one further functional moiety, which allows attaching such further components as defined herein. Such functional moieties may be selected from functionalities which allow the attachment of further components, e.g. functionalities as defined herein, e.g. by amide formation (e.g. carboxylic acids, sulphonic acids, amines, etc.), by Michael addition (e.g maleinimide moieties, $\alpha,\beta$ unsaturated carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

According to a particularly preferred embodiment, the further component, which may be contained in the polymeric carrier or which may be used to modify the different (short) cationic or polycationic peptides or (non-peptidic) polymers forming basis for the polymeric carrier of the polymeric carrier cargo complex is an amino acid component (AA), which may e.g. modify the biophysical/biochemical properties of the polymeric carrier as defined herein. According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents Cysteine and provides for the necessary —SH-moiety for a disulfide bond. The —SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two cationic polymers). In this case, one —SH moiety is preferably protected in a first step using a protecting group as known in the art, leading to an amino acid component (AA) of formula HS-(AA)-S-protecting group. Then, the amino acid component (AA) may be bound to a further component of the polymeric carrier, to form a first disulfide bond via the non-protected —SH moiety. The protected-SH-moiety is then typically deprotected and bound to a further free —SH-moiety of a further component of the polymeric carrier to form a second disulfide bond.

Alternatively, the amino acid component (AA) may be provided with other functionalities as already described above for the other components of the polymeric carrier, which allow binding of the amino acid component (AA) to any of components of the polymeric carrier.

In embodiments, wherein the amino acid component (AA) is linked via disulfide bonds to the polymeric carrier, it is preferred that the disulfide linkage is not realized via a crosslinker, such as a 3,6-Dioxa-1,8-octanedithiol (DODT) crosslinker.

Thus, the amino acid component (AA) may be bound to further components of the polymeric carrier with or without using a disulfide linkage. Binding without using a disulfide linkage may be accomplished by any of the reactions described above, preferably by binding the amino acid component (AA) to the other component of the polymeric carrier using an amid-chemistry as defined herein. If desired or necessary, the other terminus of the amino acid component (AA), e.g. the N- or C-terminus, may be used to couple another component, e.g. a ligand L. For this purpose, the other terminus of the amino acid component (AA) preferably comprises or is modified to comprise a further functionality, e.g. an alkyn-species (see above), which may be used to add the other component via e.g. click-chemistry. If the ligand is bound via an acid-labile bond, the bond is preferably cleaved off in the endosome and the polymeric carrier presents amino acid component (AA) at its surface.

The amino acid component (AA) may occur as a further component of the polymeric carrier as defined above, e.g. as a linker between cationic components e.g. as a linker between one cationic peptide and a further cationic peptide, as a linker between one cationic polymer and a further cationic polymer, as a linker between one cationic peptide and a cationic polymer, all preferably as defined herein, or as an additional component of the polymeric carrier, e.g. by binding the amino acid component (AA) to the polymeric carrier or a component thereof, e.g. via side chains, SH-moieties or via further moieties as defined herein, wherein the amino acid component (AA) is preferably accordingly modified.

According to a further and particularly preferred alternative, the amino acid component (AA), may be used to modify the polymeric carrier, particularly the content of cationic components in the polymeric carrier as defined above.

In this context it is preferable, that the content of cationic components in the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 30% to 100%, more preferably in the range of about 50% to 100%, even preferably in the range of about 70% to 100%, e.g. 70, 80, 90 or 100%, or in a range formed by any two of the afore mentioned values, provided, that the content of all components in the polymeric carrier is 100%.

In the context of the present invention, the amino acid component (AA) may be selected from the following alternatives.

According to a first alternative, the amino acid component (AA) may be an aromatic amino acid component (AA). The incorporation of aromatic amino acids or sequences as amino aromatic acid component (AA) into the polymeric carrier of the present invention enables a different (second) binding of the polymeric carrier to the nucleic acid due to interactions of the aromatic amino acids with the bases of the nucleic acid cargo in contrast to the binding thereof by cationic charged sequences of the polymeric carrier molecule to the phosphate backbone. This interaction may occur e.g. by intercalations or by minor or major groove binding. This kind of interaction is not prone to decompaction by anionic complexing partners (e.g. Heparin, Hyaluronic acids) which are found mainly in the extracellular matrix in vivo and is also less susceptible to salt effects.

For this purpose, the amino acids in the aromatic amino acid component (AA) may be selected from either the same or different aromatic amino acids e.g. selected from Trp, Tyr or Phe.

Additionally, the aromatic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine.

Additionally, the aromatic amino acid component (AA) may contain or represent at least one proline, which may serve as a structure breaker of longer sequences of Trp, Tyr and Phe in the aromatic amino acid component (AA), preferably two, three or more prolines.

According to a second alternative, the amino acid component (AA) may be a hydrophilic (and preferably non charged polar) amino acid component (AA). The incorporation of hydrophilic (and preferably non charged polar) amino acids or sequences as amino hydrophilic (and preferably non charged polar) acid component (AA) into the polymeric carrier of the present invention enables a more flexible binding to the nucleic acid cargo. This leads to a more effective compaction of the nucleic acid cargo and hence to a better protection against nucleases and unwanted decompaction. It also allows provision of a (long) polymeric carrier which exhibits a reduced cationic charge over the entire carrier and in this context to better adjusted binding properties, if desired or necessary.

For this purpose, the amino acids in the hydrophilic (and preferably non charged polar) amino acid component (AA) may be selected from either the same or different hydrophilic (and preferably non charged polar) amino acids e.g. selected from Thr, Ser, Asn or Gln.

Additionally, the hydrophilic (and preferably non-charged polar) amino acid component (AA) may contain or may be flanked by a —SH containing moiety, which allows introducing this component via a disulfide bond as a further part of generic formula (I) above, e.g. as a linker. Such a —SH containing moiety may be any moiety as defined herein suitable to couple one component as defined herein to a further component as defined herein. As an example, such a —SH containing moiety may be a cysteine.

Additionally, the hydrophilic (and preferably non-charged polar) amino acid component (AA) may contain at least one proline, which may serve as a structure breaker of longer sequences of Ser, Thr and Asn in the hydrophilic (and preferably non charged polar) amino acid component (AA), preferably two, three or more prolines.

According to a third alternative, the amino acid component (AA) may be a lipohilic amino acid component (AA). The incorporation of lipohilic amino acids or sequences as amino lipohilic acid component (AA) into the polymeric carrier of the present invention enables a stronger compaction of the nucleic acid cargo and/or the polymeric carrier and its nucleic acid cargo when forming a complex. This is particularly due to interactions of one or more polymer strands of the polymeric carrier, particularly of lipophilic sections of lipohilic amino acid component (AA) and the nucleic acid cargo. This interaction will preferably add an additional stability to the complex between the polymeric carrier and its nucleic acid cargo. This stabilization may somehow be compared to a sort of non covalent crosslinking between different polymer strands. Especially in aqueous environment this interaction is typically strong and provides a significant effect.

For this purpose, the amino acids in the lipophilic amino acid component (AA) may be selected from either the same or different lipophilic amino acids e.g. selected from Leu, Val, Ile, Ala, Met.

Additionally, the lipophilic amino acid component (AA) may contain or may be flanked by a —SH containing moiety, which allows introducing this component via a disulfide bond as a further part of the polymeric carrier above, e.g. as a linker. Such a —SH containing moiety may be any moiety as defined herein suitable to couple one component as defined herein to a further component as defined herein. As an example, such a —SH containing moiety may be a cysteine.

Additionally, the lipophilic amino acid component (AA) may contain at least one proline, which may serve as a structure breaker of longer sequences of Leu, Val, Ile, Ala and Met in the lipophilic amino acid component (AA), preferably two, three or more prolines.

Finally, according to a fourth alternative, the amino acid component (AA) may be a weak basic amino acid component (AA). The incorporation of weak basic amino acids or sequences as weak basic amino acid component (AA) into the polymeric carrier of the present invention may serve as a proton sponge and facilitates endosomal escape (also called endosomal release) (proton sponge effect). Incorporation of such a weak basic amino acid component (AA) preferably enhances transfection efficiency.

For this purpose, the amino acids in the weak basic amino acid component (AA) may be selected from either the same or different weak amino acids e.g. selected from histidine or aspartate (aspartic acid).

Additionally, the weak basic amino acid component (AA) may contain or may be flanked by a —SH containing moiety, which allows introducing this component via a disulfide bond as a further part of generic formula (I) above, e.g. as a linker. Such a —SH containing moiety may be any moiety as defined herein suitable to couple one component as defined herein to a further component as defined herein.

Additionally, the weak basic amino acid component (AA) may contain at least one proline, which may serve as a structure breaker of longer sequences of histidine or aspartate (aspartic acid) in the weak basic amino acid component (AA), preferably two, three or more prolines.

According to a fifth alternative, the amino acid component (AA) may be a signal peptide or signal sequence, a localization signal or sequence, a nuclear localization signal or sequence (NLS), an antibody, a cell penetrating peptide, (e.g. TAT), etc. Preferably such an amino acid component (AA) is bound to the polymeric carrier or to another component of the polymeric carrier via a (reversible) disulfide bond. In this context, the signal peptide or signal sequence, a localization signal or sequence, a nuclear localization signal or sequence (NLS), an antibody, a cell penetrating peptide, (e.g. TAT), etc. additionally comprises at least one —SH-moiety. In this context, a signal peptide, a localization signal or sequence or a nuclear localization signal or sequence (NLS), may be used to direct the inventive polymeric carrier cargo complex to specific target cells (e.g. hepatocytes or antigen-presenting cells) and preferably allows a translocalization of the polymeric carrier to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytosceleton, etc. Such signal peptide, a localization signal or sequence or a nuclear localization signal may be used for the transport of any of the herein defined nucleic acids, preferably an RNA or a DNA, more preferably an shRNA or a pDNA, e.g. into the nucleus. Without being limited thereto, such a signal peptide, a localization signal or sequence or a nuclear localization signal may comprise, e.g., localisation sequences for the endoplasmic reticulum. Examples of secretory signal peptides as defined herein include, without being limited thereto, signal peptides of classical or non-classical MHC-molecules (e.g. signal sequences of MHC I and II molecules, e.g. of the MHC class I molecule HLA-A*0201), signal peptides of cytokines or immunoglobulins as defined herein, signal peptides of the invariant chain of immunoglobulins or antibodies as defined herein, signal peptides of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal peptides of MHC class I molecule HLA-A*0201 may be used according to the present invention. Such an additional component may be bound e.g. to a cationic polymer or to any other component of the polymeric carrier as defined herein. Preferably this signal peptide, localization signal or sequence or nuclear localization signal or sequence (NLS), is bound to the polymeric carrier or to another component of the polymeric carrier via a (reversible) disulfide bond. For this purpose the (AA) component additionally comprises at least one —SH moiety as defined herein. The binding to any of components of the polymeric carrier may also be accomplished using an acid-labile bond, preferably via a side chain of any of components of the polymeric carrier, which allows to detach or release the additional component at lower pH-values, e.g. at physiological pH-values as defined herein.

Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined below as therapeutically active proteins. According to one alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the polymeric carrier (in complex with a nucleic acid) from the endosome by insertion into the lipid layer of the liposome. These cell penetrating peptides (CPPs) or cationic peptides for transportation, may include, without being limited thereto protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc. Such an amino acid component (AA) may also be bound to any component of the polymeric carrier as defined herein. Preferably it is bound to the polymeric carrier or to another component of the polymeric carrier via a (reversible) disulfide bond. For the above purpose, the amino acid component (AA) preferably comprises at least one —SH moiety as defined herein. The binding to any of the components of the polymeric carrier may also be accomplished using an SH-moiety or an acid-labile bond, preferably via a side chain of any of components of the polymeric carrier which allows to detach or release the additional component at lower pH-values, e.g. at physiological pH-values as defined herein.

According to a last alternative, the amino acid component (AA) may consist of any peptide or protein which can execute any favourable function in the cell. Particularly preferred are peptides or proteins selected from therapeutically active proteins or peptides, from antigens, e.g. tumour antigens, pathogenic antigens (animal antigens, viral antigens, protozoan antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application as defined below for coding nucleic acids. Particularly preferred are peptide epitopes from the at least one antigen (an antigen from a pathogen associated with infectious disease; an antigen associated with allergy or allergic disease; an antigen associated with autoimmune disease; or an antigen associated with a cancer or tumour disease) as defined herein.

In the event, the amino acid component (AA) is covalently attached to the polymeric carrier cargo complex, in particular to the polymeric carrier, the amino acid component (AA) is preferably not ovalbumin or a fragment of ovalbumin. Preferably, the amino acid component is not ovalbumin or a fragment of ovalbumin.

Due to the peptidic nature of the amino acid component also the definition of peptide, protein, or fragment, variant and derivative thereof applies accordingly and are explicitly encompassed.

Furthermore, said (AA) components may be prepared by all methods known to a person of ordinary skill or by recombinant peptide or protein production or by peptide synthesis as described herein.

The polymeric carrier may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

According to another embodiment the polymeric carrier of the polymeric carrier cargo complex or single components thereof, e.g. of the above mentioned cationic or polycationic peptides, proteins or polymers or further components, e.g. (AA), may be further modified with a ligand, preferably a carbohydrate, more preferably a sugar, even more preferably mannose. Preferably this ligand is bound to the polymeric carrier or to a component of the polymeric carrier via a (reversible) disulfide bond or via Michael addition. In the case that the ligand is bound by a disulfide bond the ligand additionally comprises at least one —SH— moiety. These ligands may be used to direct the polymeric carrier cargo complex to specific target cells (e.g. hepatocytes or antigen-presenting cells). In this context mannose is particular preferred as ligand in the case that dendritic cells are the target especially for vaccination or adjuvant purposes.

According to a further embodiment of the invention, the polymeric carrier cargo complex may comprise (AA) components as defined above which do not comprise —SH moieties. These (AA) components can be added before or during the complexation reaction of the at least one nucleic acid molecule. Thereby, the (AA) component(s) is/are (non-covalently) incorporated into the polymeric carrier cargo complex without inclusion of the (AA) component(s) in the polymeric carrier itself by (covalent) polymerization.

According to one specific embodiment, the entire polymeric carrier cargo complex may be formed by a polymerization condensation (of at least one) of the above mentioned cationic or polycationic peptides, proteins or polymers or further components, e.g. (AA), via their —SH-moieties in a first step and complexing the nucleic acid to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific embodiment, the polymeric carrier cargo complex is formed by carrying out the polymerization condensation of at least one of the above mentioned cationic or polycationic peptides, proteins or polymers or further components, e.g. (AA), via their —SH-moieties simultaneously to complexing the nucleic acid cargo to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

The polymeric carrier cargo complex additionally comprises as a cargo at least one nucleic acid (molecule). In the context of the present invention, such a nucleic acid molecule may be any suitable nucleic acid, selected e.g. from any (single-stranded or double-stranded) DNA, preferably, without being limited thereto, e.g. genomic DNA, single-stranded DNA molecules, double-stranded DNA molecules, coding DNA, DNA primers, DNA probes, immunostimulatory DNA, a (short) DNA oligonucleotide ((short) oligodesoxyribonucleotides), or may be selected e.g. from any PNA (peptide nucleic acid) or may be selected e.g. from any (single-stranded or double-stranded) RNA, preferably, without being limited thereto, a (short) RNA oligonucleotide ((short) oligoribonucleotide), a coding RNA, a messenger RNA (mRNA), an immunostimulatory RNA, a small interfering RNA (siRNA), an antisense RNA, a micro RNA, a small nuclear RNA (snRNA), a small-hairpin (sh) RNA or riboswitches, ribozymes or aptamers; etc. The nucleic acid molecule of the polymeric carrier cargo complex may also be a ribosomal RNA (rRNA), a transfer RNA (tRNA), a messenger RNA (mRNA), or a viral RNA (vRNA). Preferably, the nucleic acid molecule of the polymeric carrier cargo complex is an RNA. More preferably, the nucleic acid molecule of the polymeric carrier cargo complex is a (linear) single-stranded RNA, even more preferably an mRNA or an immunostimulatory RNA. In the context of the present invention, an mRNA is typically an RNA, which is composed of several structural elements, e.g. an optional 5'-CAP structure, an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. a RNA which carries the coding sequences of one, two or more proteins or peptides. Such coding sequences in di-, or even multicistronic mRNA may be separated by at least one IRES sequence, e.g. as defined herein.

Furthermore, the nucleic acid of the polymeric carrier cargo complex may be a single- or a double-stranded nucleic acid (molecule) (which may also be regarded as a nucleic acid (molecule) due to non-covalent association of two single-stranded nucleic acid(s) (molecules)) or a partially double-stranded or partially single stranded nucleic acid, which are at least partially self complementary (both of these partially double-stranded or partially single stranded nucleic acid molecules are typically formed by a longer and a shorter single-stranded nucleic acid molecule or by two single stranded nucleic acid molecules, which are about equal in length, wherein one single-stranded nucleic acid molecule is in part complementary to the other single-stranded nucleic acid molecule and both thus form a double-stranded nucleic acid molecule in this region, i.e. a partially double-stranded or partially single stranded nucleic acid (molecule). Preferably, the nucleic acid (molecule) may be a single-stranded nucleic acid molecule. Furthermore, the nucleic acid (molecule) may be a circular or linear nucleic acid molecule, preferably a linear nucleic acid molecule.

According to one alternative, the nucleic acid molecule of the polymeric carrier cargo complex may be a coding nucleic acid, e.g. a DNA or RNA. Such a coding DNA or RNA may be any DNA or RNA as defined herein. Preferably, such a coding DNA or RNA may be a single- or a double-stranded DNA or RNA, more preferably a single-stranded DNA or RNA, and/or a circular or linear DNA or RNA, more preferably a linear DNA or RNA. Even more preferably, the coding DNA or RNA may be a (linear) single-stranded DNA or RNA. Most preferably, the nucleic acid molecule according to the present invention may be a ((linear) single-stranded) messenger RNA (mRNA). Such an mRNA may occur as a mono-, di-, or even multicistronic RNA, i.e. an RNA which carries the coding sequences of one, two or more proteins or peptides. Such coding sequences in di-, or even multicistronic mRNA may be separated by at least one IRES sequence, e.g. as defined herein.

Coding Nucleic Acids:

The nucleic acid molecule of the polymeric carrier cargo complex may encode a protein or a peptide, which may be selected, without being restricted thereto, e.g. from therapeutically active proteins or peptides, including adjuvant proteins, from antigens, e.g. tumour antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, or from any other protein or peptide suitable for a specific (therapeutic) application, wherein the coding nucleic acid may be transported into a cell, a tissue or an organism and the protein may be expressed subsequently in this cell, tissue or organism. In this context, the coding nucleic acid may additionally code for a signal peptide as defined herein.

a) Therapeutically Active Proteins

In the context of the present invention, therapeutically active proteins or peptides may be encoded by the nucleic acid molecule of the herein defined polymeric carrier cargo complex. Therapeutically active proteins are defined herein as proteins which have an effect on healing, prevent prophylactically or treat therapeutically a disease, preferably as defined herein, or are proteins of which an individual is in need of. These may be selected from any naturally or synthetically designed occurring recombinant or isolated protein known to a skilled person from the prior art. Without being restricted thereto therapeutically active proteins may comprise proteins, capable of stimulating or inhibiting the signal transduction in the cell, e.g. cytokines, lymphokines, monokines, growth factors, receptors, signal transduction molecules, transcription factors, etc; anticoagulants; antithrombins; antiallergic proteins; apoptotic factors or apoptosis related proteins, therapeutic active enzymes and any protein or peptide connected with any acquired disease or any hereditary disease or favourable for the treatment of any acquired disease or any hereditary disease.

A therapeutically active protein, which may be encoded by the nucleic acid molecule of the herein defined polymeric carrier cargo complex, may also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. More preferably, the adjuvant protein is selected from human adjuvant proteins or from pathogenic adjuvant proteins, selected from the group consisting of, without being limited thereto, bacterial proteins, protozoan proteins, viral proteins, or fungal proteins, animal proteins, in particular from bacterial adjuvant proteins. In addition, nucleic acids encoding human proteins involved in adjuvant effects (e.g. ligands of pattern recognition receptors, pattern recognition receptors, proteins of the signal transduction pathways, transcription factors or cytokines) may be used as well.

b) Antigens

The nucleic acid molecule of the herein defined polymeric carrier cargo complex may alternatively encode an antigen. In the context of the present invention, antigens as encoded by the nucleic acid molecule of the herein defined polymeric carrier cargo complex typically comprise any antigen, antigenic epitope or antigenic peptide, falling under the above definition, more preferably protein and peptide antigens, e.g. tumour antigens, allergenic antigens, auto-immune self-antigens, pathogenic antigens, etc. In particular antigens as encoded by the nucleic acid molecule of the herein defined polymeric carrier cargo complex may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens, allergenic antigens, etc. Allergenic antigens (allergy antigens) are typically antigens, which cause an allergy in a human and may be derived from either a human or other sources. Additionally, antigens as encoded by the nucleic acid molecule of the herein defined polymeric carrier cargo complex may be furthermore antigens generated inside the cell, the tissue or the body. Such antigens include antigens derived from the host organism (e.g. a human) itself, e.g. tumour antigens, self-antigens or auto-antigens, such as auto-immune self-antigens, etc., but also (non-self) antigens as defined herein, which have been originally been derived from host cells outside the host organism, but which are fragmented or degraded inside the body, tissue or cell, e.g. by (protease) degradation, metabolism, etc. In this context, an antigen as encoded by the nucleic acid cargo comprised in the polymeric carrier cargo complex is defined as described below for the at least one antigen, the second ingredient of the inventive pharmaceutical composition.

Particularly preferred in this context is, that the antigen or a fragment, variant and/or derivative thereof encoded by the nucleic acid cargo is the same antigen as the at least one antigen as defined herein as comprised in the inventive pharmaceutical composition as second ingredient. In alternative embodiments however, the antigen or a fragment, variant and/or derivative thereof encoded by the nucleic acid cargo is a different antigen as the at least one antigen as defined herein as comprised in the inventive pharmaceutical composition as second ingredient. In the specific case that an antigen is encoded by the nucleic acid cargo, the nucleic acid molecule together with the polymeric carrier serves as adjuvant or imunostimulating agent to induce an unspecific innate immune response, whereas the encoded protein or peptide antigen which is expressed by the nucleic acid cargo serves as antigen to induce an antigen-specific adaptive immune response.

c) Antibodies

According to a further alternative, the nucleic acid molecule of the herein defined polymeric carrier cargo complex may encode an antibody or an antibody fragment. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, the term "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ und $C_H3$.

In the context of the present invention, antibodies as encoded by the nucleic acid molecule of the herein defined polymeric carrier cargo complex may preferably comprise full-length antibodies, i.e. antibodies composed of the full heavy and full light chains, as described above. However, derivatives of antibodies such as antibody fragments, variants or adducts may also be encoded by the nucleic acid molecule of the herein defined polymeric carrier cargo complex. Antibody fragments are preferably selected from Fab, Fab', F(ab')$_2$, Fc, Facb, pFc', Fd and Fv fragments of the aforementioned (full-length) antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

In the present context it is preferable that the different chains of the antibody or antibody fragment are encoded by a multicistronic nucleic acid molecule. Alternatively, the different strains of the antibody or antibody fragment are encoded by several monocistronic nucleic acid(s) (sequences).

siRNA:

According to a further alternative, the nucleic acid molecule of the herein defined polymeric carrier cargo complex may be in the form of dsRNA, preferably siRNA. A dsRNA, or a siRNA, is of interest particularly in connection with the phenomenon of RNA interference. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498).

The nucleic acid molecule of the herein defined polymeric carrier cargo complex may thus be a double-stranded RNA (dsRNA) having a length of from 17 to 29, preferably from 19 to 25, and preferably is at least 90%, more preferably 95% and especially 100% (of the nucleotides of a dsRNA) complementary to a section of the nucleic acid molecule of a (therapeutically relevant) protein or antigen described (as active ingredient) hereinbefore or of any further protein as described herein, either a coding or a non-coding section, preferably a coding section. Such a (section of the) nucleic acid molecule may be termed herein a "target sequence" and may be any nucleic acid molecule as defined herein, preferably a genomic DNA, a cDNA, a RNA, e.g. an mRNA, etc. 90% complementary means that with a length of a dsRNA described herein of, for example, 20 nucleotides, the dsRNA contains not more than 2 nucleotides showing no complementarity with the corresponding section of the target sequence. The sequence of the double-stranded RNA used according to the invention is, however, preferably wholly complementary in its general structure with a section of the target sequence. In this context the nucleic acid molecule of the polymeric carrier cargo complex may be a dsRNA having the general structure 5'-(N$_{17-29}$)-3', preferably having the general structure 5'-(N$_{19-25}$)-3', more preferably having the general structure 5'-(N$_{19-24}$)-3', or yet more preferably having the general structure 5'-(N$_{21-23}$)-3', wherein for each general structure each N is a (preferably different) nucleotide of a section of the target sequence, preferably being selected from a continuous number of 17 to 29 nucleotides of a section of the target sequence, and being present in the general structure 5'-(N$_{17-29}$)-3' in their natural order. In principle, all the sections having a length of from 17 to 29, preferably from 19 to 25, base pairs that occur in the target sequence can serve for preparation of a dsRNA as defined herein. Equally, dsRNAs used as nucleic acid molecule of the polymeric carrier cargo complex can also be directed against nucleotide sequences of a (therapeutically relevant) protein or antigen described (as active ingredient) hereinbefore that do not lie in the coding region, in particular in the 5' non-coding region of the target sequence, for example, therefore, against non-coding regions of the target sequence having a regulatory function. The target sequence of the dsRNA used as nucleic acid molecule of the polymeric carrier cargo complex can therefore lie in the translated and untranslated region of the target sequence and/or in the region of the control elements of a protein or antigen described hereinbefore. The target sequence for a dsRNA used as the nucleic acid molecule of the polymeric carrier cargo complex can also lie in the overlapping region of untranslated and translated sequence; in particular, the target sequence can comprise at least one nucleotide upstream of the start triplet of the coding region, e.g. of a genomic DNA, a cDNA, a RNA, or an mRNA, etc.

Immunostimulatory Nucleic Acids:

a) Immunostimulatory CpG Nucleic Acids:

According to another alternative, the nucleic acid molecule of the herein defined polymeric carrier cargo complex may be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated. In a preferred embodiment, the CpG nucleic acid is not a CpG-DNA consisting of the sequence 5'TCCATGACGTTCCTGACGTT-3' (SEQ ID NO: 123), in particular if the protein or peptide antigen is ovalbumin or a fragment of ovalbumin. In a further preferred embodiment, the CpG nucleic acid is not a sequence comprising SEQ ID NO: 123. Preferably, the CpG nucleic acid is not a CpG-DNA. In some embodiments of the present invention, the polymeric carrier cargo complex does not comprise a CpG-DNA, preferably does not comprise a CpG nucleic acid. In some embodiments of the present invention, the pharmaceutical composition does not comprise a CpG-DNA, preferably does not comprise a CpG nucleic acid.

b) Immunostimulatory RNA (isRNA):

Likewise, according to a further alternative, the (immunostimulatory) nucleic acid molecule of the polymeric carrier cargo complex may be in the form of an immunostimulatory RNA (isRNA), which preferably elicits an innate immune response. Such an immunostimulatory RNA may be any (double-stranded or single-stranded) RNA, e.g. a coding RNA, as defined herein. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response, may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl Acad Sci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc. E.g. Lipford et al. determined certain G,U-containing oligoribonucleotides as immunostimulatory by acting via TLR7 and TLR8 (see WO 03/086280). The immunostimulatory G,U-containing oligoribonucleotides described by Lipford et al. were believed to be derivable from RNA sources including ribosomal RNA, transfer RNA, messenger RNA, and viral RNA.

The immunostimulatory RNA (isRNA) used as the nucleic acid molecule of the herein defined polymeric carrier cargo complex may thus comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules, used as the nucleic acid molecule of the polymeric carrier cargo complex may include any other RNA capable of eliciting an innate immune response. Without being limited thereto, such an immunostimulatory RNA may include ribosomal RNA (rRNA), transfer RNA (tRNA), messenger RNA (mRNA), and viral RNA (vRNA), preferably the immunostimulatory RNA is a non-coding RNA. Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, such immunostimulatory nucleic acid sequence is preferably RNA preferably consisting of or comprising a nucleic acid sequence of formula (II) or (III):

$$G_l X_m G_n, \quad \text{(formula (II))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
wherein
when l=1 G is guanosine or an analogue thereof,
when l>1 at least 50% of the nucleotides are guanosine or an analogue thereof;

m is an integer and is at least 3;
wherein
when m=3 X is uracil or an analogue thereof,
when m>3 at least 3 successive uracils or analogues of uracil occur;
n is an integer from 1 to 40,
wherein
when n=1 G is guanosine or an analogue thereof,
when n>1 at least 50% of the nucleotides are guanosine or an analogue thereof.

$$C_l X_m C_n,\quad \text{(formula (III))}$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
wherein
when l=1 C is cytosine or an analogue thereof,
when l>1 at least 50% of the nucleotides are cytosine or an analogue thereof;
m is an integer and is at least 3;
wherein
when m=3 X is uracil or an analogue thereof,
when m>3 at least 3 successive uracils or analogues of uracil occur;
n is an integer from 1 to 40,
wherein
when n=1 C is cytosine or an analogue thereof,
when n>1 at least 50% of the nucleotides are cytosine or an analogue thereof.

The nucleic acids of formula (II) or (III), which may be used the nucleic acid cargo of the polymeric carrier cargo complex may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of the nucleic acid cargo complex has a maximum length of e.g. 100 nucleotides, m will typically be $\leq 98$. The number of nucleotides G in the nucleic acid of formula (II) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_1$ or $G_n$ can be, for example, a GUGU, GGUU, UGUG, UUGG, GUUG, GGGU, GGUG, GUGG, UGGG or GGGG, etc.; when l or n=5 $G_1$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (II) according to the invention is preferably not a uracil. Similarly, the number of nucleotides C in the nucleic acid of formula (III) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_1$ or $C_n$ can be, for example, a CUCU, CCUU, UCUC, UUCC, CUUC, CCCU, CCUC, CUCC, UCCC or CCCC, etc.; when l or n=5 $C_1$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (V) according to the invention is preferably not a uracil. Preferably, for formula (II), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_1$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (III).

According to a particularly preferred embodiment, a nucleic acid according to any of formulas (II) or (III) above, which may be used as nucleic acid of the polymeric carrier cargo complex, may be selected from a sequence consisting of or comprising any of the following sequences:

GGUUUUUUUUUUUUUUGGG;  (SEQ ID NO: 15)

GGGGGUUUUUUUUUGGGGG;  (SEQ ID NO: 16)

GGGGGUUUUUUUUUUUUUUUUUUUUUUUUGGGGG;  (SEQ ID NO: 17)

GUGUGUGUGUGUUUUUUUUUUUUUUGUGUGUGUGU;  (SEQ ID NO: 18)

GGUUGGUUGGUUUUUUUUUUUUUUGGUUGGUUGGUU;  (SEQ ID NO: 19)

GGGGGGGGGUUGGGGGGGG;  (SEQ ID NO: 20)

GGGGGGGGUUUGGGGGGGG;  (SEQ ID NO: 21)

GGGGGGGUUUUUGGGGGGG;  (SEQ ID NO: 22)

GGGGGGGUUUUUUGGGGGG;  (SEQ ID NO: 23)

GGGGGGUUUUUUUGGGGGG;  (SEQ ID NO: 24)

GGGGGGUUUUUUUUGGGGG;  (SEQ ID NO: 25)

GGGGGGUUUUUUUUUGGGG;  (SEQ ID NO: 26)

GGGGGUUUUUUUUUUGGGG;  (SEQ ID NO: 27)

GGGGGUUUUUUUUUUUGGG;  (SEQ ID NO: 28)

GGGGUUUUUUUUUUUUGGG;  (SEQ ID NO: 29)

GGGGUUUUUUUUUUUUUGG;  (SEQ ID NO: 30)

GGUUUUUUUUUUUUUUUGG;  (SEQ ID NO: 31)

GUUUUUUUUUUUUUUUUUG;
(SEQ ID NO: 32)

GGGGGGGGGGUUUGGGGGGGGG;
(SEQ ID NO: 33)

GGGGGGGGGUUUUGGGGGGGG;
(SEQ ID NO: 34)

GGGGGGGGUUUUUGGGGGGGG;
(SEQ ID NO: 35)

GGGGGGGGUUUUUUGGGGGGG;
(SEQ ID NO: 36)

GGGGGGGUUUUUUUGGGGGGG;
(SEQ ID NO: 37)

GGGGGGGUUUUUUUUGGGGGG;
(SEQ ID NO: 38)

GGGGGGGUUUUUUUUUGGGGG;
(SEQ ID NO: 39)

GGGGGGUUUUUUUUUUGGGGG;
(SEQ ID NO: 40)

GGGGGGUUUUUUUUUUUGGGG;
(SEQ ID NO: 41)

GGGGGUUUUUUUUUUUUGGGG;
(SEQ ID NO: 42)

GGGGGUUUUUUUUUUUUUGGG;
(SEQ ID NO: 43)

GGGUUUUUUUUUUUUUUUGGG;
(SEQ ID NO: 44)

GGUUUUUUUUUUUUUUUUUGG;
(SEQ ID NO: 45)

GGGGGGGGGGGUUUGGGGGGGGGG;
(SEQ ID NO: 46)

GGGGGGGGGGUUUUGGGGGGGGGG;
(SEQ ID NO: 47)

GGGGGGGGGGUUUUUGGGGGGGGG;
(SEQ ID NO: 48)

GGGGGGGGGGUUUUUUGGGGGGGG;
(SEQ ID NO: 49)

GGGGGGGGGUUUUUUUGGGGGGGG;
(SEQ ID NO: 50)

GGGGGGGGGUUUUUUUUGGGGGGG;
(SEQ ID NO: 51)

GGGGGGGGGUUUUUUUUUGGGGGG;
(SEQ ID NO: 52)

GGGGGGGUUUUUUUUUUGGGGGGG;
(SEQ ID NO: 53)

GGGGGGGUUUUUUUUUUUGGGGGG;
(SEQ ID NO: 54)

GGGGGGUUUUUUUUUUUUGGGGGG;
(SEQ ID NO: 55)

GGGGGGUUUUUUUUUUUUUGGGGG;
(SEQ ID NO: 56)

GGGGGUUUUUUUUUUUUUUGGGGG;
(SEQ ID NO: 57)

GGGUUUUUUUUUUUUUUUUUGGG;
(SEQ ID NO: 58)

GUUUUUUUUUUUUUUUUUUUUUUG;
(SEQ ID NO: 59)

GGUUUUUUUUUUUUUUUUUUUUUGG;
(SEQ ID NO: 60)

GGGUUUUUUUUUUUUUUUUUUUUUGGG;
(SEQ ID NO: 61)

GGGGUUUUUUUUUUUUUUUUUUUUUGGG;
(SEQ ID NO: 62)

GGGGGUUUUUUUUUUUUUUUUUUUUUGGGG;
(SEQ ID NO: 63)

GGGGGGUUUUUUUUUUUUUUUUUUUUUGGGGG;
(SEQ ID NO: 64)

GGGGGGGUUUUUUUUUUUUUUUUUUUUUGGGGG;
(SEQ ID NO: 65)

GGGGGGGGUUUUUUUUUUUUUUUUUUUUUGGGGGG;
(SEQ ID NO: 66)

GGGGGGGGGUUUUUUUUUUUUUUUUUUUUUGGGGGGG;
(SEQ ID NO: 67)

GGUUUGG;
(SEQ ID NO: 68)

GGUUUUGG;
(SEQ ID NO: 69)

GGUUUUUGG;
(SEQ ID NO: 70)

GGUUUUUUGG;
(SEQ ID NO: 71)

GGUUUUUUUGG;
(SEQ ID NO: 72)

GGUUUUUUUUGG;
(SEQ ID NO: 73)

GGUUUUUUUUUGG;
(SEQ ID NO: 74)

GGUUUUUUUUUUGG;
(SEQ ID NO: 75)

GGUUUUUUUUUUUGG;
(SEQ ID NO: 76)

GGUUUUUUUUUUUUGG;
(SEQ ID NO: 77)

GGUUUUUUUUUUUUUGG;
(SEQ ID NO: 78)

GGUUUUUUUUUUUUUUGG;
(SEQ ID NO: 79)

GGUUUUUUUUUUUUUUUGG;
(SEQ ID NO: 80)

GGGUUUGGG;
(SEQ ID NO: 81)

GGGUUUUGGG;
(SEQ ID NO: 82)

GGGUUUUUGGG;
(SEQ ID NO: 83)

GGGUUUUUUGGG;
(SEQ ID NO: 84)

GGGUUUUUUUGGG;
(SEQ ID NO: 85)

-continued

GGGUUUUUUUUGGG;  (SEQ ID NO: 86)

GGGUUUUUUUUUGGG;  (SEQ ID NO: 87)

GGGUUUUUUUUUUGGG;  (SEQ ID NO: 88)

GGGUUUUUUUUUUUGGG;  (SEQ ID NO: 89)

GGGUUUUUUUUUUUUGGG;  (SEQ ID NO: 90)

GGGUUUUUUUUUUUUUGGG;  (SEQ ID NO: 91)

(SEQ ID NO: 92)
GGGUUUUUUUUUUUUUUGGGUUUUUUUUUUUUUUGGGUUUUUUUU
UUUUUUGGG;

(SEQ ID NO: 93)
GGGUUUUUUUUUUUUUUGGGGGUUUUUUUUUUUUUUUGGG;

(SEQ ID NO: 94)
GGGUUUGGGUUUGGGUUUGGGUUUGGGUUUGGGUUUGGGUUUGGGU
UUGGG;

(shortGU-rich, SEQ ID NO: 95)
GGUUUUUUUUUUUUUUUUGGG or (SEQ ID NO: 96)
CCCUUUUUUUUUUUUUUUCCCUUUUUUUUUUUUUUUCCCUUUUUUUU
UUUUUUCCC (SEQ ID NO: 97)
CCCUUCCCUUUCCCUUUCCCUUUCCCUUUCCCUUUCCCUUUCCCUUU
CCC (SEQ ID NO: 98)
CCCUUUUUUUUUUUUUUUCCCCCCUUUUUUUUUUUUUUUCCC or from a sequence having at least 60%, 70%, 80%, 90%, or even 95% sequence identity with any of these sequences.

According to a further particularly preferred embodiment, such immunostimulatory nucleic acid sequences, particularly isRNA, consist of or comprise a nucleic acid of formula (IV) or (V):

$$(N_u G_l X_m G_n N_v)_a,$$ (formula (IV))

wherein:
G is guanosine (guanine), uridine (uracil) or an analogue of guanosine (guanine) or uridine (uracil), preferably guanosine (guanine) or an analogue thereof;
X is guanosine (guanine), uridine (uracil), adenosine (adenine), thymidine (thymine), cytidine (cytosine), or an analogue of these nucleotides (nucleosides), preferably uridine (uracil) or an analogue thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, G is guanosine (guanine) or an analogue thereof,
  when l>1, at least 50% of these nucleotides (nucleosides) are guanosine (guanine) or an analogue thereof;
m is an integer and is at least 3;
  wherein when m=3, X is uridine (uracil) or an analogue thereof, and
  when m>3, at least 3 successive uridines (uracils) or analogues of uridine (uracil) occur;
n is an integer from 1 to 40,
  wherein when n=1, G is guanosine (guanine) or an analogue thereof,
  when n>1, at least 50% of these nucleotides (nucleosides) are guanosine (guanine) or an analogue thereof;
u,v may be independently from each other an integer from 0 to 50,
  preferably wherein when u=0, v≥1, or
  when v=0, u≥1;
wherein the nucleic acid molecule of formula (IV) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a,$$ (formula (V))

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
  wherein when l=1, C is cytidine (cytosine) or an analogue thereof,
  when l>1, at least 50% of these nucleotides (nucleosides) are cytidine (cytosine) or an analogue thereof;
m is an integer and is at least 3;
  wherein when m=3, X is uridine (uracil) or an analogue thereof,
  when m>3, at least 3 successive uridines (uracils) or analogues of uridine (uracil) occur;
n is an integer from 1 to 40,
  wherein when n=1, C is cytidine (cytosine) or an analogue thereof,
  when n>1, at least 50% of these nucleotides (nucleosides) are cytidine (cytosine) or an analogue thereof.
u, v may be independently from each other an integer from 0 to 50,
  preferably wherein when u=0, v≥1, or
  when v=0, u≥1;
wherein the nucleic acid molecule of formula (V) according to the invention has a length of at least 50 nucleotides, preferably of at least 100 nucleotides, more preferably of at least 150 nucleotides, even more preferably of at least 200 nucleotides and most preferably of at least 250 nucleotides.

For formula (V), any of the definitions given above for elements N (i.e. $N_u$ and $N_v$) and X ($X_m$), particularly the core structure as defined above, as well as for integers a, l, m, n, u and v, similarly apply to elements of formula (IV) correspondingly, wherein in formula (V) the core structure is defined by $C_lX_mC_n$. The definition of bordering elements $N_u$ and $N_v$ is identical to the definitions given above for $N_u$ and $N_v$.

According to a very particularly preferred embodiment, the nucleic acid molecule according to formula (IV) comprises, preferably consists of, e.g. any of the following sequences:

(SEQ ID NO: 99)
UAGCGAAGCUCUUGGACCUAGGUUUUUUUUUUUUUUGGGUGCGUUCCUA
GAAGUACACG (SEQ ID NO: 100)
UAGCGAAGCUCUUGGACCUAGGUUUUUUUUUUUUUUGGGUGCGUUCCUA
GAAGUACACGAUCGCUUCGAGAACCUGGAUCCAAAAAAAAAAAAAACCC
ACGCAAGGAUCUUCAUGUGC (SEQ ID NO: 101
GGGAGAAAGCUCAAGCUUGGAGCAAUGCCCGCACAUUGAGGAAACCGAGU
UGCAUAUCUCAGAGUAUUGGCCCCCGUGUAGGUUAUUCUUGACAGACAGU
GGAGCUUAUUCACUCCCAGGAUCCGAGUCGCAUACUACGGUACUGGUGAC
AGACCUAGGUCGUCAGUUGACCAGUCCGCCACUAGACGUGAGUCCGUCAA
AGCAGUUAGAUGUUACACUCUAUUAGAUC (SEQ ID NO: 102)
GGGAGAAAGCUCAAGCUUGGAGCAAUGCCCGCACAUUGAGGAAACCGAGU
UGCAUAUCUCAGAGUAUUGGCCCCCGUGUAGGUUAUUCUUGACAGACAGU
GGAGCUUAUUCACUCCCAGGAUCCGAGUCGCAUACUACGGUACUGGUGAC
AGACCUAGGUCGUCAGUUGACCAGUCCGCCACUAGACGUGAGUCCGUCAA
AGCAGUUAGAUGUUACACUCUAUUAGAUCUCGGAUUACAGCUGGAAGGAG
CAGGAGUAGUGUUCUUGCUCUAAGUACCGAGUGUGCCCAAUACCCGAUCA
GCUUAUUAACGAACGGCUCCUCCUCUUAGACUGCAGCGUAAGUGCGGAAU
CUGGGGAUCAAAUUACUGACUGCCUGGAUUACCCUCGGACAUAUAACCUU
GUAGCACGCUGUUGCUGUAUAGGUGACCAACGCCCACUCGAGUAGACCAG
CUCUCUUAGUCCGGACAAUGAUAGGAGGCGCGGUCAAUCUACUUCGGCU
AGUUAAGAAUAGGCUGCACCGACCUCUAUAAGUAGCGUGUCCUCUAG (SEQ ID NO: 103)
GGGAGAAAGCUCAAGCUUGGAGCAAUGCCCGCACAUUGAGGAAACCGAGU
UGCAUAUCUCAGAGUAUUGGCCCCCGUGUAGGUUAUUCUUGACAGACAGU
GGAGCUUAUUCACUCCCAGGAUCCGAGUCGCAUACUACGGUACUGGUGAC
AGACCUAGGUCGUCAGUUGACCAGUCCGCCACUAGACGUGAGUCCGUCAA
AGCAGUUAGAUGUUACACUCUAUUAGAUCUCGGAUUACAGCUGGAAGGAG
CAGGAGUAGUGUUCUUGCUCUAAGUACCGAGUGUGCCCAAUACCCGAUCA
GCUUAUUAACGAACGGCUCCUCCUCUUAGACUGCAGCGUAAGUGCGGAAU
CUGGGGAUCAAAUUACUGACUGCCUGGAUUACCCUCGGACAUAUAACCUU
GUAGCACGCUGUUGCUGUAUAGGUGACCAACGCCCACUCGAGUAGACCAG
CUCUCUUAGUCCGGACAAUGAUAGGAGGCGCGGUCAAUCUACUUCGGCU
AGUUAAGAAUAGGCUGCACCGACCUCUAUAAGUAGCGUGUCCUCUAGAGC
UACGCAGGUUCGCAAUAAAAGCGUUGAUUAGUGUGCAUAGAACAGACCUC
UUAUUCGGUGAAACGCCAGAAUGCUAAAUUCCAAUAACUCUUCCCAAAAC
GCGUACGGCCGAAGACGCGCGCUUAUCUUGUGUACGUUCUCGCACAUGGA
AGAAUCAGCGGGCAUGGUGGUAGGGCAAUAGGGGAGCUGGGUAGCAGCGA
AAAAGGGCCCCUGCGCACGUAGCUUCGCUGUUCGUCUGAAACAACCCGGC
AUCCGUUGUAGCGAUCCCGUUAUCAGUGUUAUUCUUGUGCGCACUAAGAU
UCAUGGUGUAGUCGACAAUAACAGCGUCUUGGCAGAUUCUGGUCACGUGC
CCUAUGCCCGGGCUUGUGCCUCUCAGGUGCACAGCGAUACUUAAAGCCUU
CAAGGUACUCGACGUGGGUACCGAUUCGUGACACUUCCUAAGAUUAUUCC
ACUGUGUUAGCCCCGCACCGCCGACCUAAACUGGUCCAAUGUAUACGCAU
UCGCUGAGCGGAUCGAUAAUAAAAGCUUGAAUU (SEQ ID NO: 104)
GGGAGAAAGCUCAAGCUUAUCCAAGUAGGCUGGUCACCUGUACAACGUAG
CCGGUAUUUUUUUUUUUUUUUUUUUUUGACCGUCUCAAGGUCCAAGUUA
GUCUGCCUAUAAAGGUGCGGAUCCACAGCUGAUGAAAGACUUGUGCGGUA
CGGUUAAUCUCCCCUUUUUUUUUUUUUUUUUUUUAGUAAAUGCGUCUAC
UGAAUCCAGCGAUGAUGCUGGCCCAGAUC (R722A or isRNA722A; SEQ ID NO: 105)
GGGAGAAAGCUCAAGCUUAUCCAAGUAGGCUGGUCACCUGUACAACGUAG
CCGGUAUUUUUUUUUUUUUUUUUUUUUGACCGUCUCAAGGUCCAAGUUA
GUCUGCCUAUAAAGGUGCGGAUCCACAGCUGAUGAAAGACUUGUGCGGUA
CGGUUAAUCUCCCCUUUUUUUUUUUUUUUUUUUUAGUAAAUGCGUCUAC
UGAAUCCAGCGAUGAUGCUGGCCCAGAUCUUCGACCACAAGUGCAUAUAG
UAGUCAUCGAGGGUCGCCUUUUUUUUUUUUUUUUUUUUUGGCCCAGUU
CUGAGACUUCGCUAGAGACUACAGUUACAGCUGCAGUAGUAACCACUGCG
GCUAUUGCAGGAAAUCCCGUUCAGGUUUUUUUUUUUUUUUUUUUCCGC
UCACUAUGAUUAAGAACCAGGUGGAGUGUCACUGCUCUCGAGGUCUCACG
AGAGCGCUCGAUACAGUCCUUGGAAGAAUCUUUUUUUUUUUUUUUUUUU
UUGUGCGACGAUCACAGAGAACUUCUAUUCAUGCAGGUCUGCUCUA.

(R722B or isRNA722B; SEQ ID NO: 122)
GGGAGAAAGCUCAAGCUUAUCCAAGUAGGCUGGUCACCUGUACAACGUAG
CCGGUAUUUUUUUUUUUUUUUUUUUUUGACCGUCUCAAGGUCCAAGUUA
GUCUGCCUAUAAAGGUGCGGAUCCACAGCUGAUGAAAGACUUGUGCGGUA
CGGUUAAUCUCCCCUUUUUUUUUUUUUUUUUUUUAGUAAAUGCGUCUAC
UGAAUCCAGCGAUGAUGCUGGCCCAGAUCUUCGACCACAAGUGCAUAUAG
UAGUCAUCGAGGGUCGCCUUUUUUUUUUUUUUUUUUUUUGGCCCAGUU
CUGAGACUUCGCUAGAGACUACAGUUACAGCUGCAGUAGUAACCACUGCG
GCUAUUGCAGGAAAUCCCGUUCAGGUUUUUUUUUUUUUUUUUUUCCGC
UCACUAUGAUUAAGAACCAGGUGGAGUGUCACUGCUCUCGAGGUCUCACG

-continued

```
AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUAG (SEQ ID NO: 106)
GGGAGAAAGCUCAAGCUUAUCCAAGUAGGCUGGUCACCUGUACAACGUAG

CCGGUAUUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUAGAAC

GAACUGACCUGACGCCUGAACUUAUGAGCGUGCGUAUUUUUUUUUUUUU

UUUUUUUUUCCUCCCAACAAAUGUCGAUCAAUAGCUGGGCUGUUGGAGAC

GCGUCAGCAAAUGCCGUGGCUCCAUAGGACGUGUAGACUUCUAUUUUUUU

UUUUUUUUUUUUUUCCCGGGACCACAAAUAAUAUUCUUGCUUGGUUGGGC

GCAAGGGCCCCGUAUCAGGUCAUAAACGGGUACAUGUUGCACAGGCUCCU

UUUUUUUUUUUUUUUUUUUCGCUGAGUUAUUCCGGUCUCAAAAGACG

GCAGACGUCAGUCGACAACACGGUCUAAAGCAGUGCUACAAUCUGCCGUG

UUCGUGUUUUUUUUUUUUUUUUUGUGAACCUACACGGCGUGCACUGU

AGUUCGCAAUUCAUAGGGUACCGGCUCAGAGUUAUGCCUUGGUUGAAAAC

UGCCCAGCAUACUUUUUUUUUUUUUUUUUUUCAUAUUCCCAUGCUAAGC

AAGGGAUGCCGCGAGUCAUGUUAAGCUUGAAUU
``` or a nucleic acid sequence having at least 60%, preferably at least 70%, preferably at least 80%, more preferably at least 90%, and most preferably at least 95% identity to any of the above defined sequences.

According to another very particularly preferred embodiment, the nucleic acid molecule according to formula (V) comprises, preferably consists of, e.g. any of the following sequences:

```
                                          (SEQ ID NO: 107)
UAGCGAAGCUCUUGGACCUACCUUUUUUUUUUUUUUCCCUGCGUUCCUAG

AAGUACACG
``` or

```
                                          (SEQ ID NO: 108)
UAGCGAAGCUCUUGGACCUACCUUUUUUUUUUUUUUUCCCUGCGUUCCUA

GAAGUACACGAUCGCUUCGAGAACCUGGAUGGAAAAAAAAAAAAAAGGG

ACGCAAGGAUCUUCAUGUGC
``` or a nucleic acid sequence having at least 60%, preferably at least 70%, preferably at least 80%, more preferably at least 90%, and most preferably at least 95% identity to any of the above defined sequences.

In a further preferred embodiment, the nucleic acid molecule of the herein defined polymeric carrier cargo complex may also occur in the form of a modified nucleic acid.

According to a first embodiment, the nucleic acid molecule of the herein defined polymeric carrier cargo complex may be provided as a "stabilized nucleic acid", preferably as a stabilized RNA or DNA, more preferably as a RNA that is essentially resistant to in vivo degradation (e.g. by an exo- or endo-nuclease) as defined above.

According to another embodiment, the nucleic acid cargo of the herein defined polymeric carrier cargo complex may be modified as defined herein, and/or stabilized, especially if the nucleic acid molecule is in the form of a coding nucleic acid e.g. an mRNA, by modifying the G/C content of the nucleic acid molecule, particularly an mRNA, preferably of the coding region thereof as defined herein.

Nucleic acid molecules used herein as cargo comprised in the polymeric carrier cargo complex as defined herein may be prepared using any method known in the art, including the methods for nucleic acid synthesis as defined herein.

Furthermore, the present invention explicitly encloses variants and fragments of nucleic acid molecules as defined herein comprised as nucleic acid cargo in the polymeric carrier cargo complex.

Particularly preferred nucleic acid cargo molecules in the context of the present invention are nucleic acid molecules comprising, preferably consisting of, a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122.

In the polymeric carrier cargo complex, the cationic component of the polymeric carrier as defined herein and the nucleic acid cargo are typically provided in a molar ratio of about 1 to 10000, preferably in a molar ratio of about 5 to 5000, more preferably in a molar ratio of about 10 to 2500, even more preferably in a molar ratio of about 25 to 2000, and most preferably in a molar ratio of about 25 to 1000 of polymeric carrier to nucleic acid.

Furthermore, in the polymeric carrier cargo complex, the cationic component of the polymeric carrier as defined herein and the nucleic acid cargo are preferably provided in an N/P-ratio of at least 0.1, 0.2, 0.3, 0.4, 0.5, 0.75, 1, 1.5 or 2. Preferably, the N/P-ratio lies within a range of about 0.1, 0.3, 0.4, 0.5, 0.75, 1.0, 1.5 or 2 to 20, preferably in a range of about 0.2 (0.5 or 0.75 or 1.0) to 12, more preferably in an N/P-ratio of about 0.4 (0.75 or 1.0) to 10, and even more preferably in an N/P ratio of about 0.4 (0.75 or 1.0) to 5. Most preferably the N/P ratio lies in a ratio between 0.1 and 0.9. In this context, the N/P ratio is a measure of the ionic charge of the cationic (side chain) component of the polymeric carrier or of the polymeric carrier as such. In particular, if the cationic properties of the cationic component are generated by nitrogens (e.g. of the amino acid side chains), the N/P ratio expresses the ratio of basic nitrogen atoms to phosphate residues in the nucleotide backbone, considering that (side chain) nitrogen atoms in the cationic component of the polymeric carrier contribute to positive charges and phosphate of the phosphate backbone of the nucleic acid contribute to the negative charge. Generally, one phosphate provides one negative charge, e.g. one nucleotide in the cargo nucleic acid molecule provides one negative charge. A formula is given in the Examples. The N/P-ratio is defined as the nitrogen/phosphate ratio (N/P-ratio) of the entire inventive polymeric carrier cargo complex. This is typically illustrative for the content/amount of cationic components, in the polymeric carrier and characteristic for the content/ amount of nucleic acids bound or complexed in the inventive polymeric carrier cargo complex. It may be calculated on the basis that, for example, 1 μg RNA typically contains about 3 nmol phosphate residues, provided that RNA exhibits a statistical distribution of bases. Additionally, 1 nmol peptide typically contains about x nmol nitrogen residues, dependent on the molecular weight and the number of its (cationic) amino acids.

In this context, it is preferable that in the polymeric carrier cargo complex, the cationic component of the polymeric carrier as defined herein and the nucleic acid cargo are provided in an N/P-ratio of at least about 1 or, preferably, of a range of about 1 to 20 for in vitro applications (e.g. in the case cells extracted from the patient would be treated in vitro with the inventive pharmaceutical composition and subsequently administered to the patient).

For in vivo applications of the inventive pharmaceutical composition, an N/P ratio of at least 0.1 (0.2, 0.3, 0.4, 0.5, 0.6), preferably of a range of about 0.1 (0.2, 0.3, 0.4, 0.5, or 0.6) to 1.5 is preferred. Even more preferred is an N/P ratio range of 0.1 or 0.2 to 0.9 or an N/P ratio range of 0.5 to 0.9.

In the specific case that the induction of IFN-α is intended, an N/P ratio of at least 0.1 (0.2, 0.3, 0.4, 0.5, or 0.6) or an N/P ratio range of 0.1 to 1 is preferred or more preferred is an N/P ratio range of 0.1 or 0.2 to 0.9 or an N/P ratio range of 0.5 to 0.9. Otherwise, if the induction of TNFα would be intended, an N/P ratio of 1 to 20 is particularly preferred.

The N/P ratio significantly influences the surface charge of the resulting polymeric carrier cargo complex. Thus, it is preferable that the resulting polymeric carrier cargo complex is positively charged for in vitro applications and negatively or neutrally charged for in vivo applications. The surface charge of the resulting polymeric carrier cargo complex can be indicated as Zetapotential which may be measured by Doppler electrophoresis method using a Zetasizer Nano (Malvern Instruments, Malvern, UK). Generally, an N/P ratio of below 1 results in a negative Zetapotential, and an N/P ratio of above 1 results in a positive Zetapotential (within the scope of typical measurement errors).

In some embodiments, the surface charge of the polymeric carrier cargo complex, preferably the Zetapotential, is positive, i.e. above 0 mV, such as above 1 mV, above 2 mV, above 4 mV, above 5 mV, or above 10 mV. In alternative embodiments, the surface charge of the polymeric carrier cargo complex, preferably the Zetapotential, is negative, i.e. below 0 mV, such as below −1 mV, below −2 mV, below −4 mV, below −5 mV, or below −10 mV, such as between about −1 mV and −50 mV, between about −2 mV and −40 mV, or between about −5 mV and −30 mV.

The polymeric carrier cargo complex as used in the present invention, such as for use as an adjuvant, is preferably capable of triggering a non-antigen-specific, (innate) immune reaction (as provided by the innate immune system), preferably in an immunostimulating manner. An immune reaction can generally be brought about in various ways. An important factor for a suitable immune response is the stimulation of different T-cell sub-populations. T-lymphocytes typically differentiate into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of effector proteins (cytokines) produced by them. Thus, Th1 cells assist the cellular immune response by activation of macrophages and cytotoxic T-cells. Th2 cells, on the other hand, promote the humoral immune response by stimulation of B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the immune-stimulating agent, in particular the polymeric carrier cargo complex, in the direction towards the cellular response, that is to say the Th1 response, and a predominantly cellular immune response is thereby induced. As described above, the polymeric carrier cargo complex can induce an unspecific innate immune response, which may allow the support of a specific adaptive immune response elicited by the antigen.

Determination of the (Innate) Immunostimulatory or Adjuvant Capacity of a Component in the Inventive Pharmaceutical Composition:

For the determination of the immunostimulatory capacity of an immunostimulating agent or adjuvant (in particular of a polymeric carrier cargo complex as used in the present invention) several methods are known in the art and may be used. E.g., in vitro methods are advantageous to utilise for compounds as to their capacity to induce cytokines, which are (exclusively or at least typically) part of the innate immune system and thereby (as an additional arm of the immune system) typically improve the induction of an antigen-specific immune response caused by an antigen. For this purpose, e.g. PBMCs may be isolated from blood samples and stimulated with the particular immunostimulating agent or adjuvant. After incubation, secretion of the desired cytokines (e.g. as a reaction of an activation of the PAMP receptors) being typically part of the innate immune system (and not of the antigen-specific immune system) is determined by ELISA. These selected cytokines may be used in the art as determinants of the induction of an innate immune response in the body. In this context, the secretion of TNF-alpha and IFN-alpha is preferably measured to determine the unspecific (innate immune response) evoked by a compound or complex. Especially, IFN-alpha plays an important role in the induction of an unspecific immune response after viral infection and can be used as an indicators of induction of a Th1-shifted adaptive immune response, which is particularly preferred in the context of the treatment of cancer or tumour diseases. Accordingly, it is particularly preferred that the the immunostimulatory compound or complex tested in the screening assay, induces the secretion of e.g. IFN-alpha. Such a compound or complex may then be applied e.g. for the use as an immunotimualting agent (triggering the unspecific (innate) immune response) in vaccination therapies.

IFN-alpha is part of the family of type I interferons. Type I interferons (IFN) are pleiotropic cytokines that are essential for supporting anti-viral immune responses. They induce apoptosis of virus-infected cells and cellular resistance to viral infection, in addition to activating natural killer (NK) and T cells. Type I interferons have effects on a large set of cytokines and chemokines that i.a. influence immunocyte maturation, homing, effector functions and apoptosis. Typically, a major role of IFN-alpha is the induction of a priming state affecting the production and regulation of other mediators, including cytokines. For example, IFN-alphaβ signaling upregulates IFN-alphaγ production by dendritic cells (DCs) and T cells and thereby favours the induction and maintenance of Th1 cells. Shifting of an immune response in direction of a Th1 immune response may become particularly important, once protein or peptide vaccines are used, because these vaccines usually induce a Th2-based immune response which consequently prevents or decreases the induction of cytotoxic T cells.

Therefore, it is preferred that a compound or complex to be used as an adjuvant in the context of the present invention may preferably have the property of shifting an antigen-specific immune response caused by a antigen to a Th1-based immune response. The direction of an immune response induced by an antigen is usually measured by determination of the induction of several subtypes of antigen-specific antibodies and the induction of antigen-specific cytotoxic $CD8^+$ T cells. In this context, the subtype antibody IgG1 represents the induction of a Th2-based immune response and the induction of the subtype antibody IgG2a and the induction of cytotoxic T cells represent the induction of a Th1-based immune response. The induction of antigen-specific antibodies is typically determined by measurement of the antibody titer in the blood of the vaccine by ELISA. The induction of antigen-specific cytotoxic T cells is typically determined by measurement of IFN-gamma secretion in splenocytes after stimulation with antigen-specific peptides by ELISPOT. In this context, the induction of IFN-gamma secretion provides evidence that antigen-specific cytotoxic T cells are present in the spleen and which can specifically attack cells that present epitopes of the antigen on MHC I molecules on their surface.

For the determination of beneficial properties of an adjuvant, in vivo vaccinations are typically performed. Therewith, it is possible to investigate if the adjuvant or immunostimulatory compound or complex improves an antigen-specific immune response caused by the vaccine and, furthermore, if it can shift an antigen-specific immune response in the desired direction to display adjuvant properties. Particularly, in the induction of an anti-tumoral immune response the induction of a Th1-shifted immune response, especially the induction of cytotoxic T cells is believed to play a major role, because the induction of antigen-specific cytotoxic T cells are believed to represent an indispensable prerequisite for the successful combat of a tumour.

Accordingly, the methods to screen for, test and/or investigate compound or complexes which exhibit properties as adjuvants are well known in the art and may readily be applied e.g. by ELISA tests measuring the immune response elicited by the tested compounds/complexes.

In another aspect, the present invention relates to a method of preparing a pharmaceutical composition of the invention, said method comprising the steps of: (i) providing at least one polymeric carrier cargo complex as defined anywhere herein; (ii) providing an antigen as defined anywhere herein; and (iii) combining said polymeric carrier cargo complex and said antigen. The combining step of (iii) may occur briefly before administration to a patient (such as about 1, 5, 15, 30 or 60 minutes prior to, up to 72 hours before, said administration), or may occur during manufacture of said pharmaceutical composition. The respective person of ordinary skill (e.g. a doctor or health professional, or a manufacturer) will be aware of the routine methodologies suitable for such combining step.

In the context of the present invention, a method of preparing the polymeric carrier cargo complex as defined herein may comprise the following steps:

a) providing at least one cationic protein or peptide as defined herein and/or at least one cationic or polycationic polymer and optionally at least one amino acid component (AA) as defined herein, each comprising at least one —SH moiety, b) providing at least one nucleic acid molecule as defined herein, preferably in the above mentioned ratios, c) mixing the components provided in steps a) and b), preferably in a basic or neutral milieu as defined herein, preferably in the presence of oxygen or a further starter as defined herein, preferably at a pH, at a temperature and at time as defined herein, and thereby condensing and thus polymerizing the cationic components provided in step a) with each other via disulfide bonds (in a polymerization condensation or polycondensation) to obtain the polymeric carrier and complexing the nucleic acid molecule provided in step b) with the cationic components provided in step a), d) optionally purifying the polymeric carrier cargo complex obtained according to step c), preferably using a method as defined herein, e) optionally lyophilization of the polymeric carrier cargo complex obtained according to step c) or d).

The method of preparing the polymeric carrier cargo complex as described herein may comprise a multi-step condensation polymerization or polycondensation reaction via —SH moieties of the educts e.g. cationic peptides or polymers as defined herein and optionally further amino acid components (AA) in step c). The condensation polymerization or polycondensation reaction which occurs simultaneously to the complexation or electrostatic binding of the nucleic acid molecule preferably leads to the polymeric carrier cargo complex wherein the polymeric carrier is a condensation polymer, wherein the single components are linked by disulfide bonds.

As described herein in a step a) of the method of preparing the polymeric carrier cargo complex, at least one cationic or polycationic protein or peptide as defined herein and/or at least one cationic or polycationic polymer as defined herein are provided, preferably in the ratios indicated above. These components are mixed in step c) with the nucleic acid molecule provided in step b), preferably in a basic or neutral milieu as defined herein, preferably in the presence of oxygen or a further starter as defined herein, preferably at a pH, and at a temperature and at a time as defined herein, and thereby condensing and thus polymerizing these components with each other via disulfide bonds (in a polymerization condensation or polycondensation) to obtain a polymeric carrier complexed to the nucleic acid molecule as defined herein.

According to an alternative, in step a) of the method of preparing the polymeric carrier cargo complex at least one cationic or polycationic protein or peptide and/or at least one cationic or polycationic polymer are provided as defined herein, and optionally at least one amino acid component (AA), are provided in step a) as defined herein, and are used for a polymerization condensation or polycondensation and complexation reaction prior to adding the nucleic acid of step b) but using the same polymerization conditions outlined for step c). The polymerized polymeric carrier and the nucleic acid of step b) are then mixed in step c). Preferably, the components are all provided in the ratios indicated above and mixed, preferably in a basic or neutral milieu as defined herein, preferably in the presence of oxygen or a further starter as defined herein, preferably at a pH, at a temperature and at time as defined herein. Upon mixing and starting the reaction, the components are condensed and thus polymerized with each other via disulfide bonds (in a polymerization condensation or polycondensation) to obtain a polymeric carrier complexed to the nucleic acid molecule as defined herein.

In both of the above alternatives, different polymeric carriers, particularly different peptides and/or different polymers, may be selected in the condensation polymerization as indicated above. In this context, the selection of different component(s) of the polymeric carrier is typically dependent upon the desired properties of the final polymeric carrier and the desired cationic strength of the final polymeric carrier. Accordingly, the content of cationic components, may furthermore be "diluted" or modified in the above alternative of step a) e.g. by introducing an amino acid component (AA) as defined herein, preferably in the above defined ratios. Thereby, a modified polymeric carrier may be obtained, wherein the cationic character of the unmodified polymeric carrier typically remains in the limitations as defined herein. The properties of the final polymeric carrier may thus be adjusted as desired with properties of components (AA) by inserting amino acid component (AA) as defined herein in steps a).

In step c), the at least one cationic or polycationic protein or peptide as defined herein and/or at least one cationic or polycationic polymer as defined herein, and optionally at least one amino acid component (AA) and the at least one nucleic acid as defined herein, are preferably contained in a basic or neutral milieu in the step a) of the inventive method of preparing the inventive polymeric carrier cargo complex. Such a basic or neutral milieu typically exhibits a pH range of about 5 to about 10, preferably a pH range of about 6 to about 9, more preferably a pH range of about 7 to about 8, e.g. about 6.5, 7, 7.5, 8, 8.5, or 9 or any range selected from any two of these or the aforementioned values.

Furthermore, the temperature of the solution in step c) is preferably in a range of about 5° C. to about 60° C., more preferably in a range of about 15° C. to about 40° C., even more preferably in a range of about 20° C. to about 30° C., and most preferably in a range of about 20° C. to about 25° C., e.g. about 25° C.

In step c) of the method of preparing the polymeric carrier cargo complex as described herein, buffers may be used as suitable. Preferred buffers may comprise, but are not limited to, preferably are selected from carbonate buffers, borate buffers, Bicine buffer, CHES buffer, CAPS buffer, Ethanolamine containing buffers, HEPES, MOPS buffer, Phosphate buffer, PIPES buffer, Tris buffer, Tricine buffer, TAPS buffer, and/or TES buffer as buffering agents. Particularly preferred is a carbonate buffer.

Upon mixing the components, preferably in the presence of oxygen, preferably in the presence of a basic or neutral mileu as defined herein, the condensation polymerization or polycondensation reaction and the complexation of the at least one nucleic acid molecule is started. For this purpose, the mixture in step c) is preferably exposed to oxygen or may be started using a further starter, e.g. a catalytic amount of an oxidizing agent, e.g. DMSO, etc. Upon start of the condensation polymerization or polycondensation reaction of the at least one cationic or polycationic protein or peptide and/or at least one cationic or polycationic polymer and optionally at least one amino acid component (AA) as defined herein, are condensed and thus polymerized with each other via disulfide bonds (polymerization condensation or polycondensation). In this reaction step a) preferably linear polymers are created using monomers with at least one reactive —SH moiety, i.e. at least one cationic or polycationic protein or peptide and/or at least one cationic or polycationic polymer and optionally at least one amino acid component (AA) as defined herein, each component exhibiting at least one free —SH-moieties as defined herein, e.g. at their terminal ends. However, components with more than one, preferably two free —SH-moieties may be used, which may lead to branched polymers. Simultaneously to the polymerization reaction the cationic polymers bind to the at least one nucleic acid molecule and thereby complexing it.

According to one alternative, the polymeric carrier cargo complex additionally may be modified with a component (AA) as defined herein.

According to a first example, a component (AA) (e.g. a ligand) is attached to the cationic component prior to providing the cationic component in step a) via any functionality as defined herein, e.g. a —SH moiety. This component (AA) or (e.g. a ligand) is preferably attached to the cationic component at one terminus of these components. If the attachment is carried out via —SH bonds, the cationic components are preferably provided with two (or even more) —SH-moieties. The component (AA) or (e.g. a ligand) preferably carries only one —SH moiety. In this case, one —SH moiety of the cationic component is preferably protected in a first step using a protecting group as known in the art. Then, the cationic component may be bound to a component L to form a first disulfide bond via the non-protected —SH moiety. The protected —SH-moiety of the cationic component is then typically deprotected for further reactions.

Alternatively, the above mentioned component (AA) or (e.g. a ligand) may be used in step c) to be coupled with the cationic components provided in step a) above, e.g. via disulfide bonds without blocking the free —SH moieties. But in this context all methods known to a skilled person or defined herein may be used to attach the component (AA) to the cationic component or to the polymeric carrier.

Alternatively, a component (AA) or (e.g. a ligand) can be bound to the polymeric carrier cargo complex after step c) via any functionality as defined herein, e.g. a —SH moiety. In this context it is preferable that the component (AA) (e.g. a ligand) is bound via free —SH moieties of the polymeric carrier components.

According to step c) of the method of preparing the polymeric carrier cargo complex as described herein, at least one nucleic acid molecule as defined herein is mixed with the cationic components provided in step b), preferably in the above mentioned ratios. Typically, in the polymeric carrier cargo complex, the cationic components as defined herein, and the at least one nucleic acid molecule are provided in a molar ratio of about 5 to 10000, preferably in a molar ratio of about 5 to 5000, more preferably in a molar ratio of about 10 to 2500, even more preferably in a molar ratio of about 10 to 1000 cationic polymer to nucleic acid. The N/P ratios are preferably as indicated above. In this context, it is particularly preferred that the N/P ratios are selected thereby avoiding agglomeration and toxicity in vivo.

In a specific embodiment, (AA) components as defined above which do not comprise —SH moieties can be added in step c) which are thereby incorporated into the polymeric carrier cargo complex without polymerization by (terminal) —SH moieties. Thereby these (AA) components are typically not covalently linked and included non-covalently in the complex as a further component. Particularly preferred in this context is the incorporation of the at least one antigen or a fragment, variant and/or derivative thereof, provided as protein or peptide in the polymeric carrier cargo complex as (AA) component. This embodiment is particularly preferred if AA is ovalbumin or a fragment of ovalbumin. Thus, in a particularly preferred embodiment, if AA is ovalbumin or a fragment thereof, AA is not covalently linked to the polymeric carrier cargo complex, for example, AA is not covalently linked to the polymeric carrier cargo complex by disulfide bonds.

According to a further step d) of the method of preparing the polymeric carrier cargo complex as described herein, the polymeric carrier cargo complex obtained according to step c) is optionally purified. Purification may occur by using chromatographic methods, such as HPLC, FPLC, GPS, dialysis, etc.

According to a further step e) of the method of preparing the polymeric carrier cargo complex as described herein, the polymeric carrier cargo complex obtained according to step c) or d) is optionally lyophilized. For this purpose any suitable cryoprotectant or lyoprotectant may be added to the polymeric carrier cargo complex obtained in step c) or d).

The method of preparing the polymeric carrier cargo complex as defined herein is particularly suitable to adapt the chemical properties of the desired polymeric carrier cargo complex due to specific selection of its components of the polymeric carrier thereby avoiding agglomeration and toxicity in vivo.

As a second ingredient the inventive pharmaceutical composition comprises at least one antigen selected from an antigen from a pathogen associated with infectious disease; an antigen associated with allergy or allergic disease; an antigen associated with autoimmune disease; or an antigen associated with a cancer or tumour disease, or in each case a fragment, variant and/or derivative of said antigen.

This at least one antigen can be provided as protein or peptide, as nucleic acid coding for the at least one antigen, or as antigenic cells, antigenic cellular fragments, cellular fractions; cell wall components modified, attenuated or inactivated (e.g. chemically or by irradiation) pathogens (virus, bacteria etc.) comprising the at least one antigen.

In certain embodiments, the antigen included as a second ingredient in the pharmaceutical composition is a peptide or protein antigen, or a fragment, variant and/or derivative of said peptide or protein antigen.

a) Antigens from a Pathogen Associated with Infectious Disease:

Antigens from a pathogen associated with infectious disease are derived from a pathogen which is associated with the induction of an infectious disease. In certain embodiments, said antigen is a peptide or protein antigen, or a fragment, variant and/or derivative of said peptide or protein antigen, and/or is comprised in, provided as and/or derived from (e.g. a preparation of) inactivated or attenuated said pathogen, (e.g. a virus such as any one described herein). In this context, the (e.g. peptide or protein) antigen may be comprised in provided as and/or derived from (e.g. a preparation of) an attenuated or inactivated pathogen (e.g. a virus such as any one described herein) associated with infectious disease.

In alternative embodiments of all aspects of the invention, an antigen (e.g. a peptide or protein antigen) used in the present invention is not one comprised in (e.g. a preparation of) inactivated or attenuated virus (such as any one described herein, or any pathogen described herein); and/or is one that is not provided as (e.g. a preparation of) inactivated or attenuated said virus or pathogen; and/or is one that is not derived from (e.g. a preparation of) inactivated or attenuated said virus or pathogen. For example, the antigen used in any aspect of the present invention may be, or may be provided as, an isolated and/or purified protein or peptide antigen. As will be understood by the person of ordinary skill, an isolated (and/or purified) antigen includes such antigens that are present (or provided) in a (starting) composition that has less than about 40%, 30%, 20%, 10%, 5%, 2% or 1% non-desired or specified other components such as other proteins/peptides or impurities.

In particular embodiments, the (e.g. protein or peptide) antigen used in the present invention is a recombinant antigen, for example one that is prepared using recombinant production, such as using those methodologies described herein. In alternative embodiments, the (e.g. protein or peptide) antigen used in the present invention is a synthetic antigen, for example one that is prepared using peptide synthesis, such as using those methodologies described herein.

Antigens from a pathogen associated with infectious disease are selected from antigens from the pathogens *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae, *Babesia* genus, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia* genus, *Borrelia* spp, *Brucella* genus, *Brugia malayi*, Bunyaviridae family, *Burkholderia cepacia* and other *Burkholderia* species, *Burkholderia mallei*, *Burkholderia pseudomallei*, Caliciviridae family, *Campylobacter* genus, *Candida albicans*, *Candida* spp, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium* spp, *Clostridium tetani*, *Coccidioides* spp, coronaviruses, *Corynebacterium diphtheriae*, *Coxiella burnetii*, Crimean-Congo hemorrhagic fever virus, *Cryptococcus neoformans*, *Cryptosporidium* genus, Cytomegalovirus, Dengue viruses (DEN-1, DEN-2, DEN-3 and DEN-4), *Dientamoeba fragilis*, Ebolavirus (EBOV), *Echinococcus* genus, *Ehrlichia chaffeensis*, *Ehrlichia ewingii*, *Ehrlichia* genus, *Entamoeba histolytica*, *Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium* genus, *Geotrichum candidum*, *Giardia intestinalis*, *Gnathostoma* spp, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus, Hepatitis C Virus, Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, Kingella kingae, *Klebsiella granulomatis*, Kuru prion, Lassa virus, *Legionella pneumophila*, *Leishmania* genus, Leptospira genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia* spp, *Onchocerca volvulus*, *Orientia tsutsugamushi*, Orthomyxoviridae family, *Paracoccidioides brasiliensis*,

*Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari*, *Rickettsia* genus, *Rickettsia prowazekii*, *Rickettsia rickettsii*, *Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii*, *Staphylococcus* genus, *Staphylococcus* genus, *Streptococcus agalactiae*, *Streptococcus pneumoniae*, *Streptococcus pyogenes*, *Strongyloides stercoralis*, *Taenia* genus, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton* spp, *Trichuris trichiura*, *Trypanosoma brucei*, *Trypanosoma cruzi*, *Ureaplasma urealyticum*, Varicella zoster virus (VZV), Varicella zoster virus (VZV), *Variola major* or *Variola minor*, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In this context particularly preferred are antigens from the pathogens selected from Rabies virus, Hepatitis B virus, human Papilloma virus (hPV), *Bacillus anthracis*, respiratory syncytial virus (RSV), herpes simplex virus (HSV), Influenza virus and *Mycobacterium tuberculosis*.

Furthermore, the antigen from a pathogen associated with infectious disease may be selected from the following antigens: Outer membrane protein A OmpA, biofilm associated protein Bap, transport protein MucK (*Acinetobacter baumannii*, *Acinetobacter* infections)); variable surface glycoprotein VSG, microtubule-associated protein MAPP15, trans-sialidase TSA (*Trypanosoma brucei*, African sleeping sickness (African trypanosomiasis)); HIV p24 antigen, HIV Eenvelope proteins (Gpl20, Gp41, Gp160), polyprotein GAG, negative factor protein Nef, trans-activator of transcription Tat (HIV (Human immunodeficiency virus), AIDS (Acquired immunodeficiency syndrome)); galactose-inhibitable adherence protein GIAP, 29 kDa antigen Eh29, Gal/GalNAc lectin, protein CRT, 125 kDa immunodominant antigen, protein M17, adhesin ADH112, protein STIRP (*Entamoeba histolytica*, Amoebiasis); Major surface proteins 1-5 (MSP1a, MSP1b, MSP2, MSP3, MSP4, MSP5), type IV secreotion system proteins (VirB2, VirB7, VirB11, VirD4) (*Anaplasma* genus, Anaplasmosis); protective Antigen PA, edema factor EF, lethal facotor LF, the S-layer homology proteins SLH (*Bacillus anthracis*, Anthrax); acranolysin, phospholipase D, collagen-binding protein CbpA (*Arcanobacterium haemolyticum*, *Arcanobacterium haemolyticum* infection); nucleocapsid protein NP, glycoprotein precursor GPC, glycoprotein GP1, glycoprotein GP2 (Junin virus, Argentine hemorrhagic fever); chitin-protein layer proteins, 14 kDa suarface antigen A14, major sperm protein MSP, MSP polymerization-organizing protein MPOP, MSP fiber protein 2 MFP2, MSP polymerization-activating kinase MPAK, ABA-1-like protein ALB, protein ABA-1, cuticulin CUT-1 (*Ascaris lumbricoides*, Ascariasis); 41 kDa allergen Asp v13, allergen Asp f3, major conidial surface protein rodlet A, protease Peplp, GPI-anchored protein Gellp, GPI-anchored protein Crflp (*Aspergillus* genus, Aspergillosis); family VP26 protein, VP29 protein (Astroviridae, Astrovirus infection); Rhoptry-associated protein 1 RAP-1, merozoite surface antigens MSA-1, MSA-2 (a1, a2, b, c), 12D3, 11C5, 21B4, P29, variant erythrocyte surface antigen VESA1, Apical Membrane Antigen 1 AMA-1 (*Babesia* genus, Babesiosis); hemolysin, enterotoxin C, PXO1-51, glycolate oxidase, ABC-transporter, penicillin-bingdn protein, zinc transporter family protein, pseudouridine synthase Rsu, plasmid replication protein RepX, oligoendopeptidase F, prophage membrane protein, protein HemK, flagellar antigen H, 28.5-kDa cell surface antigen (*Bacillus cereus*, *Bacillus cereus* infection); large T antigen LT, small T antigen, capsid protein VP1, capsid protein VP2 (BK virus, BK virus infection); 29 kDa-protein, caspase-3-like antigens, glycoproteins (*Blastocystis hominis*, *Blastocystis hominis* infection); yeast surface adhesin WI-1 (*Blastomyces dermatitidis*, Blastomycosis); nucleoprotein N, polymerase L, matrix protein Z, glycoprotein GP (Machupo virus, Bolivian hemorrhagic fever); outer surface protein A OspA, outer surface protein OspB, outer surface protein OspC, decorin binding protein A DbpA, decorin binding protein B DbpB, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); Botulinum neurotoxins BoNT/A1, BoNT/A2, BoNT/A3, BoNT/B, BoNT/C, BoNT/D, BoNT/E, BoNT/F, BoNT/G, recombinant botulinum toxin F He domain FHc (*Clostridium botulinum*, Botulism (and Infant botulism)); nucleocapsid, glycoprotein precursor (Sabia virus, Brazilian hemorrhagic fever); copper/Zinc superoxide dismutase SodC, bacterioferritin Bfr, 50S ribosomal protein RplL, OmpA-like transmembrane domain-containing protein Omp31, immunogenic 39-kDa protein M5 P39, zinc ABC transporter periplasmic zinc-bnding protein znuA, periplasmic immunogenic protein Bp26, 30S ribosomal protein S12 RpsL, glyceraldehyde-3-phosphate dehydrogenase Gap, 25 kDa outer-membrane immunogenic protein precursor Omp25, invasion protein B lalB, trigger factor Tig, molecular chaperone DnaK, putative peptidyl-prolyl cis-trans isomerase SurA, lipoprotein Omp19, outer membrane protein MotY Omp16, conserved outer membrane protein D15, malate dehydrogenase Mdh, component of the Type-IV secretion system (T4SS) VirJ, lipoprotein of unknown function BAB1_0187 (*Brucella* genus, Brucellosis); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein (*Burkholderia cepacia* and other *Burkholderia* species, *Burkholderia* infection); mycolyl-transferase Ag85A, heat-shock protein Hsp65, protein TB10.4, 19 kDa antigen, protein PstS3, heat-shock protein Hsp70 (*Mycobacterium ulcerans*, Buruli ulcer); norovirus major and minor viral capsid proteins VP1 and VP2, genome polyprotein, Sapoviurus capsid protein VP1, protein Vp3, geome polyprotein (Caliciviridae family, Calicivirus infection (Norovirus and Sapovirus)); major outer membrane protein PorA, flagellin FlaA, surface antigen CjaA, fibronectin binding protein CadF, aspartate/glutamate-binding ABC transporter protein PeblA, protein FspA1, protein FspA2 (*Campylobacter* genus, Campylobacteriosis); glycolytic enzyme enolase, secreted aspartyl proteinases SAP1-10, glycophosphatidylinositol (GPI)-linked cell wall protein, protein Hyrl, complement receptor 3-related protein CR3-RP, adhesin Als3p, heat shock protein 90 kDa hsp90, cell surface hydrophobicity protein CSH (usually *Candida albicans* and other *Candida* species, Candidiasis); 17-kDa antigen, protein P26, trimeric autotransporter adhesins TAAs, *Bartonella* adhesin A BadA, variably expressed outer-membrane proteins Vomps, protein Pap3, protein HbpA, envelope-associated protease HtrA, protein OMP89, protein GroEL, protein LalB, protein OMP43, dihydrolipoamide succinyltransferase SucB (*Bartonella henselae*, Cat-scratch disease); amastigote surface protein-2, amastigote-specific surface protein SSP4, cruzipain, trans-sialidase TS, trypomastigote surface glycoprotein TSA-1, complement regulatory protein CRP-10, protein G4, protein G2, paraxonemal rod protein PAR2, paraflagellar rod component Parl, mucin-Associated Surface Proteins MPSP (*Trypanosoma cruzi*, Chagas Disease (American trypanosomiasis)); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB, heat shock proteins Hsp60 HSP10, protein IncA, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (*Chlamydia trachomatis, Chlamydia*); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila pneumoniae, Chlamydophila pneumoniae* infection); cholera toxin B CTB, toxin coregulated pilin A TcpA, toxin coregulated pilin TcpF, toxin co-regulated pilus biosynthesis ptrotein F TcpF, cholera enterotoxin subunit A, cholera enterotoxin subunit B, Heat-stable enterotoxin ST, mannose-sensitive hemagglutinin MSHA, outer membrane protein U Porin ompU, Poring B protein, polymorphic membrane protein-D (*Vibrio cholerae*, Cholera); propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31.8 kDa TP31.8, lysophosphatidic acid phosphatase LPAP, (*Clonorchis sinensis*, Clonorchiasis); surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD (*Clostridium difficile, Clostridium difficile* infection); rhinoviruses: capsid proteins VP1, VP2, VP3, VP4; coronaviruses: sprike proteins S, envelope proteins E, membrane proteins M, nucleocapsid proteins N (usually rhinoviruses and coronaviruses, Common cold (Acute viral rhinopharyngitis; Acute coryza)); prion protein Prp (CJD prion, Creutzfeldt-Jakob disease (CJD)); envelope protein Gc, envelope protein Gn, nucleocapsid proteins (Crimean-Congo hemorrhagic fever virus, Crimean-Congo hemorrhagic fever (CCHF)); virulence-associated DEAD-box RNA helicase VAD1, galactoxylomannan-protein GalXM, glucuronoxylomannan GXM, mannoprotein MP (*Cryptococcus neoformans*, Cryptococcosis); acidic ribosomal protein P2 CpP2, mucin antigens Muc1, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, adult-specific secreted factor Xa serine protease inhibitor anticoagulant AP, cathepsin D-like aspartic protease ARR-1 (usually *Ancylostoma braziliense*; multiple other parasites, Cutaneous larva migrans (CLM)); cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia solium*, Cysticercosis); pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 (Cytomegalovirus, Cytomegalovirus infection); capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 (Dengue viruses (DEN-1, DEN-2, DEN-3 and DEN-4)-Flaviviruses, Dengue fever); 39 kDa protein (*Dientamoeba fragilis*, Dientamoebiasis); diphtheria toxin precursor Tox, diphteria toxin DT, pilin-specific sortase SrtA, shaft pilin protein SpaA, tip pilin protein SpaC, minor pilin protein SpaB, surface-associated protein DIP1281 (*Corynebacterium diphtheriae*, Diphtheria); glycoprotein GP, nucleoprotein NP, minor matrix protein VP24, major matrix protein VP40, transcription activator VP30, polymerase cofactor VP35, RNA polymerase L (Ebolavirus (EBOV), Ebola hemorrhagic fever); prion protein (vCJD prion, Variant Creutzfeldt-Jakob disease (vCJD, nvCJD)); UvrABC system protein B, protein Flp1, protein Flp2, protein Flp3, protein TadA, hemoglobin receptor HgbA, outer membrane protein TdhA, protein CpsRA, regulator CpxR, protein SapA, 18 kDa antigen, outer membrane protein NcaA, protein LspA, protein LspA1, protein LspA2, protein LspB, outer membrane component DsrA, lectin DltA, lipoprotein Hlp, major outer membrane protein OMP, outer membrane protein OmpA2 (*Haemophilus ducreyi*, Chancroid); aspartyl protease 1 Pep1, phospholipase B PLB, alpha-mannosidase 1 AMN1, glucanosyltransferase GEL1, urease URE, peroxisomal matrix protein Pmp1, proline-rich antigen Pra, humal T-cell reative protein TcrP (*Coccidioides immitis* and *Coccidioides posadasii*, Coccidioidomycosis); allergen Tri r 2, heat shock protein 60 Hsp60, fungal actin Act, antigen Tri r2, antigen Tri r4, antigen Tri t1, protein IV, glycerol-3-phosphate dehydrogenase Gpdl, osmosensor HwSholA, osmosensor HwSholB, histidine kinase HwHhk7B, allergen *Mala* s 1, allergen *Mala* s 11, thioredoxin Trx *Mala* s 13, allergen *Mala* f, allergen *Mala* s (usually *Trichophyton* spp, *Epidermophyton* spp., *Malassezia* spp., *Hortaea werneckii*, Dermatophytosis); protein EG95, protein EG10, protein EG18, protein EgA31, protein EM18, antigen EPC1, antigen B, antigen 5, protein P29, protein 14-3-3, 8-kDa protein, myophilin, heat shock protein 20 HSP20, glycoprotein GP-89, fatty acid binding protein FAPB (*Echinococcus* genus, Echinococcosis); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia* genus, Ehrlichiosis); secreted antigen SagA, sagA-like proteins SalA and SalB, collagen adhesin Scm, surface proteins Fms1 (EbpA(fm), Fms5 (EbpB(fm), Fms9 (EpbC(fm) and Fms10, protein EbpC(fm), 96 kDa immunoprotective glycoprotein G1 (*Enterococcus* genus, *Enterococcus* infection); genome polyprotein, polymerase 3D, viral capsid protein VP1, viral capsid protein VP2, viral capsid protein VP3, viral capsid protein VP4, protease 2A, protease 3C (Enterovirus genus, Enterovirus infection); outer membrane proteins OM, 60 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein Adr1 (RP827), cell surface protein Adr2 (RP828), cell surface protein SCA1, Invasion protein invA, cell division protein fts, secretion proteins sec Ofamily, virulence proteins virB, tlyA, tlyC, parvulin-like protein Plp, preprotein translocase SecA, 120-kDa surface protein antigen SPA, 138 kD complex antigen, major 100-kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gp110, glycoprotein gp42, glycoprotein gHgL, glycoprotein gB (Epstein-Barr Virus (EBV), Epstein-Barr Virus Infectious Mononucleosis); cpasid protein VP2, capsid protein VP1, major protein NS1 (Parvovirus B19, Erythema infectiosum (Fifth disease)); pp65 antigen, glycoprotein 105, major capsid protein, envelope glycoprotein H, protein U51 (Human herpesvirus 6 (HHV-6) and Human herpesvirus 7 (HHV-7), Exanthem subitum); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin 1 cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathepsin L5, cathepsin Llg and cathepsin B, fatty acid binding protein FABP, leucine aminopeptidases LAP (*Fasciola hepatica* and *Fasciola gigantica*, Fasciolosis); prion protein (FFI prion, Fatal familial insomnia (FFI)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (Filarioidea superfamily, Filariasis); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (*Clostridium perfringens*, Food poisoning by *Clostridium perfringens*); leukotoxin lktA, adhesion FadA, outer membrane protein RadD, high-molecular weight arginine-binding protein (*Fusobacterium* genus, *Fusobacterium* infection); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (usually *Clostridium perfringens*; other *Clostridium* species, Gas gangrene (Clostridial myonecrosis)); lipase A, lipase B, peroxidase Dec1 (*Geotrichum candidum*, Geotrichosis); prion protein (GSS prion, Gerstmann-Sträussler-Scheinker syndrome (GSS)); cyst wall proteins CWP1, CWP2, CWP3, variant surface protein VSP, VSP1, VSP2, VSP3, VSP4, VSP5, VSP6, 56 kDa antigen, pyruvate ferredoxin oxidoreductase PFOR, alcohol dehydrogenase E ADHE, alpha-giardin, alpha8-giardin, alpha1-guiardin, beta-giardin, cystein proteases, glutathione-S-transferase GST, arginine deiminase ADI, fructose-1,6-bisphosphat aldolase FBA, *Giardia* trophozoite antigens GTA (GTA1, GTA2), ornithine carboxyl transferase OCT, striated fiber-asseblin-like protein SALP, uridine phosphoryl-like protein UPL, alpha-tubulin, beta-tubulin (*Giardia intestinalis*, Giardiasis); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein (*Burkholderia mallei*, Glanders); cyclophilin CyP, 24 kDa third-stage larvae protien GS24, excretion-secretion products ESPs (40, 80, 120 and 208 kDa) (*Gnathostoma spinigerum* and *Gnathostoma hispidum*, Gnathostomiasis); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb, fibronectin/fibrinogen-binding protein FBP54, fibronectin-binding protein FbaA, M protein type 1 Emm1, M protein type 6 Emm6, immunoglobulin-binding protein 35 Sib35, Surface protein R28 Spr28, superoxide dismutase SOD, C5a peptidase ScpA, antigen I/II Ag/II, adhesin AspA, G-related alpha2-macroglobulin-binding protein GRAB, surface fibrillar protein M5 (*Streptococcus pyogenes*, Group A streptococcal infection); C protein β antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALP surface antigen delta, alpha-like protein ALP2, alpha-like protein ALP3, alpha-like protein ALP4, Cbeta protein Bac (*Streptococcus agalactiae*, Group B streptococcal infection); transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein P1, outer membrane protein P2, outer membrane lipoprotein Pcp, Lipoprotein E, outer membrane protein P4, fuculokinase FucK, [Cu,Zn]-superoxide dismutase SodC, protease HtrA, protein 0145, alpha-galactosylceramide (*Haemophilus influenzae, Haemophilus influenzae* infection); polymerase 3D, viral capsid protein VP1, viral capsid protein VP2, viral capsid protein VP3, viral capsid protein VP4, protease 2A, protease 3C (Enteroviruses, mainly Coxsackie A virus and Enterovirus 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M (Sin Nombre virus, Hantavirus, Hantavirus Pulmonary Syndrome (HPS)); heat shock protein HspA, heat shock protein HspB, citrate synthase GltA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein Hsp10, protein MopB, cytotoxicity-associated 10 kDa protein CAG, 36 kDa antigen, beta-lactamase HcpA, Beta-lactamase HcpB (*Helicobacter pylori, Helicobacter pylori* infection); integral membrane proteins, aggregation-prone proteins, 0-antigen, toxin-antigens Stx2B, toxin-antigen StxlB, adhesion-antigen fragment Int28, protein EspA, protein EspB, Intimin, protein Tir, protein IntC300, protein Eae (*Escherichia coli* O157:H7, O111 and O104:H$_4$, Hemolytic-uremic syndrome (HUS)); RNA polymerase L, protein L, glycoprotein Gn, glycoprotein Gc, nucleocapsid protein S, envelope glycoprotein G1, nucleoprotein NP, protein N, polyprotein M (Bunyaviridae family, Hemorrhagic fever with renal syndrome (HFRS)); glycoprotein G, matrix protein M, nucleoprotein N, fusion protein F, polymerase L, protein W, proteinC, phosphoprotein p, non-structural protein V (Henipavirus (Hendra virus Nipah virus), Henipavirus infections); polyprotein, glycoproten Gp2, hepatitis A surface antigen HBAg, protein 2A, virus protein VP1, virus protein VP2, virus protein VP3, virus protein VP4, protein P1B, protein P2A, protein P3AB, protein P3D (Hepatitis A Virus, Hepatitis A); hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (Hepatitis B Virus, Hepatitis B); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NS5A, (Hepatitis C Virus, Hepatitis C); virus protein VP1, virus protein VP2, virus protein VP3, virus protein VP4, large hepaptitis delta antigen, small hepaptitis delta antigen (Hepatitis D Virus, Hepatitis D); virus protein VP1, virus protein VP2, virus protein VP3, virus protein VP4, capsid protein E2 (Hepatitis E Virus, Hepatitis E); glycoprotein L UL1, uracil-DNA glycosylase UL2, protein UL3, protein UL4, DNA replication protein UL5, portal protein UL6, virion maturation protein UL7, DNA helicase UL8, replication origin-binding protein UL9, glycoprotein M UL10, protein UL11, alkaline exonuclease UL12, serine-threonine protein kinase UL13, tegument protein UL14, terminase UL15, tegument protein UL16, protein UL17, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), gGlycoprotein B (UL27), ICP18.5 protein (UL28), major DNA-binding protein ICP8 (UL29), DNA polymerase UL30, nuclear matrix protein UL31, envelope glycoprotein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP11/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein IE63 (ICP27, UL54), protein UL55, protein UL56, viral replication protein ICP22 (IE68, US 1), protein US2, serine/threonine-protein kinase US3, glycoprotein G (US4), gGlycoprotein J (US5), glycoprotein D (US6), glycoprotein I (US7), glycoprotein E (US8), tegument protein US9, capsid/tegument protein US10, Vmw21 protein (US11), ICP47 protein (IE12, US12), major transcriptional activator ICP4 (IE175, RS1), E3 ubiquitin ligase ICP0 (IE110), latency-related protein 1 LRP1, latency-related protein 2 LRP2, neurovirulence factor RL1 (ICP34.5), latency-associated transcript LAT (Herpes simplex virus 1 and 2 (HSV-1 and HSV-2), Herpes simplex); heat shock protein Hsp60, cell surface protein $H_1C$, dipeptidyl peptidase type IV DppIV, M antigen, 70 kDa protein, 17 kDa histone-like protein (*Histoplasma capsulatum*, Histoplasmosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE (*Ancylostoma duodenale* and *Necator americanus*, Hookworm infection); protein NS1, protein NP1, protein VP1, protein VP2, protein VP3 (Human bocavirus (HBoV), Human bocavirus infection); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia ewingii, Human ewingii* ehrlichiosis); major surface proteins 1-5 (MSP1a, MSP1b, MSP2, MSP3, MSP4, MSP5), type IV secreotion system proteins VirB2, VirB7, VirB11, VirD4 (*Anaplasma phagocytophilum*, Human granulocytic anaplasmosis (HGA)); protein NS1, small hydrophobic protein NS2, SH protein, fusion protein F, glycoprotein G, matrix protein M, matrix protein M2-1, matrix protein M2-2, phosphoprotein P, nucleoprotein N, polymerase L (Human metapneumovirus (hMPV), Human metapneumovirus infection); major surface protein 2 MSP2, major surface protein 4 MSP4, MSP variant SGV1, MSP variant SGV2, outer membrane protein OMP, outer membrande protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia chaffeensis*, Human monocytic ehrlichiosis); replication protein E1, regulatory protein E2, protein E3, protein E4, protein E5, protein E6, protein E7, protein E8, major capsid protein L1, minor capsid protein L2 (Human papillomavirus (HPV), Human papillomavirus (HPV) infection); fusion protein F, hemagglutinin-neuramidase HN, glycoprotein G, matrix protein M, phosphoprotein P, nucleoprotein N, polymerase L (Human parainfluenza viruses (HPIV), Human parainfluenza virus infection); "hemagglutinin HA, neuraminidase NA, nucleoprotein NP, matrix protein M1, matrix protein M2, protein NS1, polymerase complex PA, PB1, PB2, nuclear export protein NEP;" (Orthomyxoviridae family, Influenza (flu)); genome polyprotein, protein E, protein M, capsid protein C (Japanese encephalitis virus, Japanese encephalitis); RTX toxin, type IV pili, major pilus subunit PilA, regulatory transcription factors PilS and PilR, protein sigma54, outer membrane proteins (Kingella kingae, Kingella kingae infection); prion protein (Kuru prion, Kuru); nucleoprotein N, polymerase L, matrix protein Z, glycoprotein GP (Lassa virus, Lassa fever); peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP (*Legionella pneumophila*, Legionellosis (Legionnaires' disease, Pontiac fever)); P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase F1, beta-tubulin, heat shock protein 70 Hsp70, KMP-11, glycoprotein GP63, protein BT1, nucleoside hydrolase NH, cell surface protein B1, ribosomal protein P1-like protein P1, sterol 24-c-methyltransferase SMT, LACK protein, histone $H_1$, SPB1 protein, thiol specific antioxidant TSA, protein antigen STl1, signal peptidase SP, histone $H_2B$, suface antigen PSA-2, cystein proteinase b Cpb (*Leishmania* genus, Leishmaniasis); major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycP1 or ML0041 coding protein, htrA2 or ML0176 coding protein, htrA4 or ML2659 coding protein, gcp or ML0379 coding protein, clpC or ML0235 coding protein (*Mycobacterium leprae* and *Mycobacterium* lepromatosis, Leprosy); outer membrane protein LipL32, membrane protein LIC10258, membrane protein LP30, membrane protein LIC12238, Ompa-like protein Lsa66, surface protein LigA, surface protein LigB, major outer membrane protein OmpL1, outer membrane protein LipL41, protein LigAni, surface protein LcpA, adhesion protein LipL53, outer membrane protein UpL32, surface protein Lsa63, flagellin FlaB1, membran lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acyltransferase LpxA (Leptospira genus, Leptospirosis); listeriolysin O precursor Hly (LLO), invasion-associated protein lap (P60), Listeriolysin regulatory protein PrfA, Zinc metalloproteinase Mpl, Phosphatidylinositol-specific phospholipase C PLC (PlcA, PlcB), O-acetyltransferase Oat, ABC-transporter permease Im.G_1771, adhesion protein LAP, LAP receptor Hsp60, adhesin LapB, haemolysin listeriolysin O LLO, protein ActA, Internalin A InlA, protein lnlB (*Listeria monocytogenes*, Listeriosis); outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vlsE (usually *Borrelia burgdorferi* and other *Borrelia* species, Lyme disease (Lyme borreliosis)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (*Wuchereria bancrofti* and *Brugia malayi*, Lymphatic filariasis (Elephantiasis)); glycoprotein GP, matrix protein Z, polymerase L, nucleoprotein N (Lymphocytic choriomeningitis virus (LCMV), Lymphocytic choriomeningitis); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-175, serine repeat antigen 5 SERA-5, circumsporozoite protein CS, merozoite surface protein 3 MSP3, merozoite surface protein 8 MSP8, enolase PF10, hepatocyte erythrocyte protein 17 kDa HEP17, erythrocyte membrane protein 1 EMP1, protein Kbetamerozoite surface protein 4/5 MSP 4/5heat shock protein Hsp90, glutamate-rich protein GLURP, merozoite surface protein 4 MSP-4, protein STARP, circumsporozoite protein-related antigen precursor CRA (*Plasmodium* genus, Malaria); nucleoprotein N, membrane-associated protein VP24, minor nucleoprotein VP30, polymerase cofactor VP35, polymerase L, matrix protein VP40, envelope glycoprotein GP (Marburg virus, Marburg hemorrhagic fever (MHF)); protein C, matrix protein M, phosphoprotein P, non-structural protein V, hemagglutinin glycoprotein H, polymerase L, nucleoprotein N, fusion protein F (Measles virus, Measles); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein (*Burkholderia pseudomallei*, Melioidosis (Whitmore's disease)); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR (*Neisseria meningitidis*, Meningococcal disease); 66 kDa protein, 22 kDa protein (usually *Metagonimus* yokagawai, Metagonimiasis); polar tube proteins (34, 75, and 170 kDa in Glugea, 35, 55 and 150 kDa in Encephalitozoon), kinesin-related protein, RNA polymerase II largest subunit, similar ot integral membrane protein YIPA, anti-silencing protein 1, heat shock transcription factor HSF, protein kinase, thymidine kinase, NOP-2 like nucleolar protein (Microsporidia phylum, Microsporidiosis); CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase G1-type, nucleoside triphosphatase I NPH1, replication protein A28-like MC134L, RNA polymease 7 kDa subunit RPO7 (Molluscum contagiosum virus (MCV), Molluscum contagiosum (MC)); matrix protein M, phosphoprotein P/V, small hydrophobic protein SH, nucleoprotein N, protein V, fusion glycoprotein F, hemagglutinin-neuraminidase HN, RNA polymerase L (Mumps virus, Mumps); Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA (*Rickettsia typhi*, Murine typhus (Endemic typhus)); adhesin P1, adhesion P30, protein p116, protein P40, cytoskeletal protein HMW1, cytoskeletal protein HMW2, cytoskeletal protein HMW3, MPN152 coding protein, MPN426 coding protein, MPN456 coding protein, MPN-500coding protein (*Mycoplasma pneumoniae, Mycoplasma* pneumonia); NocA, Iron dependent regulatory protein, VapA, VapD, VapF, VapG, caseinolytic protease, filament tip-associated 43-kDa protein, protein P24, protein P61, 15-kDa protein, 56-kDa protein (usually *Nocardia asteroides* and other *Nocardia* species, Nocardiosis); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (*Onchocerca volvulus*, Onchocerciasis (River blindness)); 43 kDa secreted glycoprotein, glycoprotein gpO, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 (*Paracoccidioides brasiliensis*, Paracoccidioidomycosis (South American blastomycosis)); 28-kDa cruzipain-like cystein protease Pw28CCP (usually *Paragonimus westermani* and other *Paragonimus* species, Paragonimiasis); outer membrane protein OmpH, outer membrane protein Omp28, protein PM1539, protein PM0355, protein PM1417, repair protein MutL, protein BcbC, prtein PM0305, formate dehydrogenase-N, protein PM0698, protein PM1422, DNA gyrase, lipoprotein PlpE, adhesive protein Cp39, heme aquisition system receptor HasR, 39 kDa capsular protein, iron-regulated OMP IROMP, outer membrane protein OmpA87, fimbrial protein Ptf, fimbrial subunit protein PtfA, transferrin binding protein Tbpl, esterase enzyme MesA, *Pasteurella multocida* toxin PMT, adhesive protein Cp39 (*Pasteurella* genus, Pasteurellosis); "filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3; "(*Bordetella pertussis*, Pertussis (Whooping cough)); "F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YPO0612, heat shock protein 90 HtpG, putative sulfatase protein YdeN, outer-membrane lipoprotein carrier protein LolA, secretion chaperone YerA, putative lipoprotein YP00420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor Pla; "(*Yersinia pestis*, Plague); protein PhpA, surface adhesin PsaA, pneumolysin Ply, ATP-dependent protease Clp, lipoate-protein ligase LplA, cell wall surface anchored protein psrP, sortase SrtA, glutamyl-tRNA synthetase GltX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 (*Streptococcus pneumoniae*, Pneumococcal infection); major surface protein B, kexin-like protease KEX1, protein A12, 55 kDa antigen P55, major surface glycoprotein Msg (*Pneumocystis jirovecii*, Pneumocystis pneumonia (PCP)); genome polyprotein, polymerase 3D, viral capsid protein VP1, viral capsid protein VP2, viral capsid protein VP3, viral capsid protein VP4, protease 2A, protease 3C (Poliovirus, Poliomyelitis); protein Nfal, exendin-3, secretory lipase, cathepsin B-like protease, cysteine protease, cathepsin, peroxiredoxin, protein CrylAc (usually *Naegleria fowleri*, Primary amoebic meningoencephalitis (PAM)); agnoprotein, large T antigen, small T antigen, major capsid protein VP1, minor capsid protein Vp2 (JC virus, Progressive multifocal leukoencephalopathy); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila psittaci*, Psittacosis); outer membrane protein P1, heat shock protein B HspB, peptide ABC transporter, GTP-binding protein, protein IcmB, ribonuclease R, phosphatas SixA, protein DsbD, outer membrane protein TolC, DNA-binding protein PhoB, ATPase DotB, heat shock protein B HspB, membrane protein ComI, 28 kDa protein, DNA-3-methyladenine glycosidase I, pouter membrane protein OmpH, outer membrane protein AdaA, glycine cleavage system T-protein (*Coxiella burnetii*, Q fever); nucleoprotein N, large structural protein L, phophoprotein P, matrix protein M, glycoprotein G (Rabies virus, Rabies); fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 (Respiratory syncytial virus (RSV), Respiratory syncytial virus infection); genome polyprotein, polymerase 3D, viral capsid protein VP1, viral capsid protein VP2, viral capsid protein VP3, viral capsid protein VP4, protease 2A, protease 3C (Rhinovirus, Rhinovirus infection); outer membrane proteins OM, cell surface antigen OmpA, cell surface antigen OmpB (sca5), cell surface protein SCA4, cell surface protein SCA1, protein PS120, intracytoplasmic protein D, protective surface protein antigen SPA (*Rickettsia* genus, Rickettsial infection); outer membrane proteins OM, cell surface antigen OmpA, cell surface antigen OmpB (sca5), cell surface protein SCA4, cell surface protein SCA1, intracytoplasmic protein D (*Rickettsia akari*, Rickettsialpox); envelope glycoprotein GP, polymerase L, nucleoprotein N, non-structural protein NSS (Rift Valley fever virus, Rift Valley fever (RVF)); outer membrane proteins OM, cell surface antigen OmpA, cell surface antigen OmpB (sca5), cell surface protein SCA4, cell surface protein SCA1, intracytoplasmic protein D (*Rickettsia rickettsii*, Rocky mountain spotted fever (RMSF)); "non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NS5, outer capsid glycoprotein VP7, non-structural glycoprotein 4 NS4, outer capsid protein VP4; "(Rotavirus, Rotavirus infection); polyprotein P200, glycoprotein E1, glycoprotein E2, protein NS2, capsid protein C (Rubella virus, Rubella); chaperonin GroEL (MopA), inositol phosphate phosphatase SopB, heat shock protein HslU, chaperone protein DnaJ, protein TviB, protein IroN, flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA, transferase WgaP, effector proteins SifA, SteC, SseL, SseJ and SseF (*Salmonella* genus, *Salmonellosis*); "protein 14, non-structural protein NS7b, non-structural protein NS8a, protein 9b, protein 3a, nucleoprotein N, non-structural protein NS3b, non-structural protein NS6, protein 7a, non-structural protein NS8b, membrane protein M, envelope small membrane protein EsM, replicase polyprotein 1a, spike glycoprotein S, replicase polyprotein lab; "(SARS coronavirus, SARS (Severe Acute Respiratory Syndrome)); serin protease, Atypical *Sarcoptes* Antigen 1 ASA1, glutathione S-transferases GST, cystein protease, serine protease, apolipoprotein (*Sarcoptes scabiei*, Scabies); glutathione S-transferases GST, paramyosin, hemoglbinase SM32, major egg antigen, 14 kDa fatty acid-binding protein Sm14, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin (*Schistosoma* genus, Schistosomiasis (Bilharziosis)); 60 kDa chaperonin, 56 kDa type-specific antigen, pyruvate phosphate dikinase, 4-hydroxybenzoate octaprenyltransferase (*Orientia tsutsugamushi*, Scrub typhus); dehydrogenase GuaB, invasion protein Spa32, invasin IpaA, invasin IpaB, invasin IpaC, invasin IpaD, invasin IpaH, invasin IpaJ (*Shigella* genus, Shigellosis (Bacillary dysentery)); protein P53, virion protein US10 homolog, transcriptional regulator IE63, transcriptional transactivator IE62, protease P33, alpha trans-inducing factor 74 kDa protein, deoxyuridine 5'-triphosphate nucleotidohydrolase, transcriptional transactivator IE4, membrane protein UL43 homolog, nuclear phosphoprotein UL3 homolog, nuclear protein UL4 homolog, replication origin-binding protein, membrane protein 2, phosphoprotein 32, protein 57, DNA polymerase processivity factor, portal protein 54, DNA primase, tegument protein UL14 homolog, tegument protein UL21 homolog, tegument protein UL55 homolog, tripartite terminase subunit UL33 homolog, tripartite terminase subunit UL15 homolog, capsid-binding protein 44, virion-packaging protein 43 (Varicella zoster virus (VZV), Shingles (Herpes zoster)); truncated 3-beta hydroxy-5-ene steroid dehydrogenase homolog, virion membrane protein A13, protein A19, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F11, protein F14, protein F15, protein F16 (Variola major or Variola minor, Smallpox (Variola)); adhesin/glycoprotein gp70, proteases (*Sporothrix schenckii*, Sporotrichosis); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal food poisoning); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal infection); antigen Ss-IR, antigen NIE, strongylastacin, Na+-K+ ATPase Sseat-6, tropomysin SsTmy-1, protein LEC-5, 41 kDa aantigen P5, 41-kDa larval protein, 31-kDa larval protein, 28-kDa larval protein (*Strongyloides stercoralis*, Strongyloidiasis); glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I TprI, repeat protein J TprJ, repeat protein K TprK, treponemal membrane protein A TmpA, lipoprotein, 15 kDa Tpp15, 47 kDa membrane antigen, miniferritin TpF1, adhesin Tp0751, lipoprotein TP0136, protein TpN17, protein TpN47, outer membrane protein TP0136, outer membrane protein TP0155, outer membrane protein TP0326, outer membrane protein TP0483, outer membrane protein TP0956 (*Treponema pallidum*, Syphilis); Cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia* genus, Taeniasis); tetanus toxin TetX, tetanus toxin C TTC, 140 kDa S layer protein, flavoprotein beta-subunit CT3, phospholipase (lecithinase), phosphocarrier protein HPr (*Clostridium tetani*, Tetanus (Lockjaw)); genome polyprotein, protein E, protein M, capsid protein C (Tick-borne encephalitis virus (TBEV), Tick-borne encephalitis); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cpl-1, 26-kDa protein (*Toxocara canis* or *Toxocara cati*, Toxocariasis (Ocular Larva Migrans (OLM) and Visceral Larva Migrans (VLM))); microneme proteins (MIC1, MIC2, MIC3, MIC4, MIC5, MIC6, MIC7, MIC8), rhoptry protein Rop2, rhoptry proteins (Rop1, Rop2, Rop3, Rop4, Rop5, Rop6, Rop7, Rop16, Rjop17), protein SR1, surface antigen P22, major antigen p24, major surface antigen p30, dense granule proteins (GRA1, GRA2, GRA3, GRA4, GRA5, GRA6, GRA7, GRA8, GRA9, GRA10), 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 (*Toxoplasma gondii*, Toxoplasmosis); 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45-kDa glycoprotein Gp45 (*Trichinella spiralis*, Trichinellosis); Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Enol, cysteine proteinase CP30, heat shock proteins (Hsp70, Hsp60), immunogenic protein P270, (*Trichomonas vaginalis*, Trichomoniasis); beta-tubulin, 47-kDa protein, secretory leucocyte-like proteinase-1 SLP-1, 50-kDa protein TT50, 17 kDa antigen, 43/47 kDa protein (*Trichuris trichiura*, Trichuriasis (Whipworm infection)); protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S (usually *Mycobacterium tuberculosis*, Tuberculosis); outer membrane protein FobA, outer membrane protein FobB, intracellular growth locus IglC1, intracellular growth locus IglC2, aminotransferase Wbtl, chaperonin GroEL, 17 kDa major membrane protein TUL4, lipoprotein LpnA, chitinase family 18 protein, isocitrate dehydrogenase, Nif3 family protein, type IV pili glycosylation protein, outer membrane protein tolC, FAD binding family protein, type IV pilin multimeric outer membrane protein, two component sensor protein KdpD, chaperone protein DnaK, protein TolQ (*Francisella tularensis*, Tularemia); "MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen; "(*Ureaplasma urealyticum*, *Ureaplasma urealyticum* infection); non-structural polyprotein, structural polyprotein, capsid protein CP, protein E1, protein E2, protein E3, protease P1, protease P2, protease P3 (Venezuelan equine encephalitis virus, Venezuelan equine encephalitis); glycoprotein GP, matrix protein Z, polymerase L, nucleoprotein N (Guanarito virus, Venezuelan hemorrhagic fever); polyprotein, protein E, protein M, capsid protein C, protease NS3, protein NS1, protein NS2A, protein AS2B, brotein NS4A, protein NS4B, protein NS5 (West Nile virus, West Nile Fever); cpasid protein CP, protein E1, protein E2, protein E3, protease P2 (Western equine encephalitis virus, Western equine encephalitis); genome polyprotein, protein E, protein M, capsid protein C, protease NS3, protein NS1, protein NS2A, protein AS2B, protein NS4A, protein NS4B, protein NS5 (Yellow fever virus, Yellow fever); putative Yop targeting protein YobB, effector protein YopD, effector protein YopE, protein YopH, effector protein YopJ, protein translocation protein YopK, effector protein YopT, protein YpkA, flagellar biosyntheses protein FlhA, peptidase M48, potassium efflux system KefA, transcriptional regulatoer RovA, adhesin Ifp, translocator portein LcrV, protein PcrV, invasin Inv, outer membrane protein OmpF-like porin, adhesin YadA, protein kinase C, phospholipase C1, protein PsaA, mannosyltransferase-like protein WbyK, protein YscU, antigen YPMa (*Yersinia pseudotuberculosis, Yersinia pseudotuberculosis* infection); effector protein YopB, 60 kDa chaperonin, protein WbcP, tyrosin-protein phosphatase YopH, protein YopQ, enterotoxin, Galactoside permease, reductaase NrdE, protein YasN, Invasin Inv, adhesin YadA, outer membrane porin F OmpF, protein UspAl, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease ClpP, protein MyfA, protein FilA, and protein PsaA (*Yersinia enterocolitica*, Yersiniosis).

(in brackets are the particular pathogen of which the antigen(s) is/are derived and the infectious disease with which the antigen is associated)

In specific embodiments according to the present invention, following antigens of pathogens associated with infectious disease are particularly preferred:

The nucleoprotein (N), the phosphoprotein (P), the matrix protein (M), the glycoprotein (G), and the viral RNA polymerase (L), in each case of Rabies virus;

the Hepatitis B surface antigen (HBsAg), the Hepatitis B core antigen (HbcAg), the Hepatitis B virus DNA polymerase, the HBx protein, the preS2 middle surface protein, the large S protein, the virus protein VP1, the virus protein VP2, the virus protein VP3, and the virus protein VP4, in each case of Hepatitis B virus;

the E1 protein, the E2 protein, the E3 protein, the E4 protein, the E5 protein, the E6 protein, the E7 protein, the E8 protein, the L1 protein, and the L2 protein, in each case of human Papilloma virus (hPV);

the protective antigen (PA), the edema factor (EF), the lethal factor (LF), and the S-layer homology proteins (SLH), in each case of *Bacillus anthracis;* the Fusion (F) protein, the nucleocapsid (N) protein, the phosphoprotein (P), the matrix (M) protein, the glycoprotein (G), the large protein (L; RNA polymerase), the non-structural protein 1 (NS1), the non-structural protein 2 (NS2), the small hydrophobic (SH) protein, the elongation factor M2-1, and the transcription regulation protein M2-2, in each case of respiratory syncytial virus (RSV);

the Glycoprotein L (UL1), the Uracil-DNA glycosylase UL2, the UL3 protein, the UL4 protein, the DNA replication protein UL5, the Portal protein UL6, the Virion maturation protein UL7, the DNA helicase UL8, the Replication origin-binding protein UL9, the Glycoprotein M (UL10), the UL11 protein, the Alkaline exonuclease UL12, the Serine-threonine protein kinase UL13, the Tegument protein UL14, the Terminase (UL15), the Tegument protein UL16, the UL17 protein, the Capsid protein VP23 (UL18), the Major capsid protein VP5 (UL19), the Membrane protein UL20, the Tegument protein UL21, the Glycoprotein H (UL22), the Thymidine Kinase UL23, the UL24 protein, the UL25 protein, the Capsid protein P40 (UL26, VP24, VP22A), the Glycoprotein B (UL27), the ICP18.5 protein (UL28), the Major DNA-binding protein ICP8 (UL29), the DNA polymerase UL30, the Nuclear matrix protein UL31, the Envelope glycoprotein UL32, the UL33 protein, the Inner nuclear membrane protein UL34, the Capsid protein VP26 (UL35), the Large tegument protein UL36, the Capsid assembly protein UL37, the VP19C protein (UL38), the Ribonucleotide reductase (Large subunit) UL39, the Ribonucleotide reductase (Small subunit) UL40, the Tegument protein/Virion host shutoff VHS protein (UL41), the DNA polymerase processivity factor UL42, the Membrane protein UL43, the Glycoprotein C (UL44), the Membrane protein UL45, the Tegument proteins VP11/12 (UL46), the Tegument protein VP13/14 (UL47), the Virion maturation protein VP16 (UL48, Alpha-TIF), the Envelope protein UL49, the dUTP diphosphatase UL50, the Tegument protein UL51, the DNA helicase/primase complex protein UL52, the Glycoprotein K (UL53), the Transcriptional regulation protein IE63 (ICP27, UL54), the UL55 protein, the UL56 protein, the Viral replication protein ICP22 (IE68, US1), the US2 protein, the Serine/threonine-protein kinase US3, the Glycoprotein G (US4), the Glycoprotein J (US5), the Glycoprotein D (US6), the Glycoprotein I (US7), the Glycoprotein E (US8), the Tegument protein US9, the Capsid/Tegument protein US10, the Vmw21 protein (US11), the ICP47 protein (IE12, US12), the Major transcriptional activator ICP4 (IE175, RS1), the E3 ubiquitin ligase ICP0 (IE110), the Latency-related protein 1 (LRP1), the Latency-related protein 2 (LRP2), the Neurovirulence factor RL1 (ICP34.5), and the Latency-associated transcript (LAT), in each case of Herpes simplex virus (HSV); or the ESAT-6 protein, the ESX-1 protein, the CFP10 protein, the TB10.4 protein, the MPT63 protein, the MPT64 protein, the MPT83 protein, the MTB12 protein, the MTB8 protein, the AG85A protein, the AG85B protein, the Rpf-like proteins, the KATG protein, the PPE18 protein, the MTB32 protein, the MTB39 protein, the Crystallin, the HSP65 protein, the PST-S protein, and the HBHA protein, the 10 kDa filtrate antigen EsxB, the serine protease PepA, the fibronectin-binding protein D FbpD, the secreted protein MPT51, the periplasmic phosphate-binding lipoprotein PSTS1 (PBP-1), the periplasmic phosphate-binding lipoprotein PSTS3 (PBP-3, Phos-1), the PPE family protein PPE14, the PPE family protein PPE68, the protein MTB72F, the molecular chaperone DnaK, the cell surface lipoprotein MPT83, the lipoprotein P23, the Phosphate transport system permease protein PstA, the 14 kDa antigen, the fibronectin-binding protein C FbpC1, the Alanine dehydrogenase TB43, and the Glutamine synthetase 1, in each case of *Mycobacterium tuberculosis*.

b) Antigens Associated with Allergy or Allergic Disease (Allergenic Antigens or Allergens):

According to another alternative, one further class of antigens comprises allergenic antigens. Such allergenic antigens may be selected from antigens derived from different sources, e.g. from animals, plants, fungi, bacteria, etc. Sources of allergens in this context include e.g. grasses, pollens, molds, drugs, or numerous environmental triggers, etc. Allergenic antigens typically belong to different classes of compounds, such as nucleic acids and their fragments, proteins or peptides and their fragments, carbohydrates, polysaccharides, sugars, lipids, phospholipids, etc. Of particular interest in the context of the present invention are protein or peptide antigens and their fragments or epitopes, or nucleic acids and their fragments, particularly nucleic acids and their fragments, encoding such protein or peptide antigens and their fragments or epitopes.

In alternative embodiments, said antigen is a peptide or protein antigen, or a fragment, variant and/or derivative of said peptide or protein antigen, such as a peptide or protein antigen comprised in a preparation extracted from said source. In alternative embodiments, a peptide or protein antigen used in the present invention is not one comprised in a preparation extracted from said source, and/or is one that is not obtained from a preparation extracted from said source.

Antigens associated with allergy or allergic disease (allergens) are preferably derived from a source selected from the list consisting of:

*Acarus* spp (Aca s 1, Aca s 10, Aca s 10.0101, Aca s 13, Aca s 13.0101, Aca s 2, Aca s 3, Aca s 7, Aca s 8), *Acanthocybium* spp (Aca so 1), *Acanthocheilonema* spp (Aca v 3, Aca v 3.0101), *Acetes* spp (Ace ja 1), *Actinidia* spp (Act a 1, Act c 1, Act c 10, Act c 10.0101, Act c 2, Act c 4, Act c 5, Act c 5.0101, Act c 8, Act c 8.0101, Act c Chitinase, Act d 1, Act d 1.0101, Act d 10, Act d 10.0101, Act d 10.0201, Act d 11, Act d 11.0101, Act d 2, Act d 2.0101, Act d 3, Act d 3.0101, Act d 3.02, Act d 4, Act d 4.0101, Act d 5, Act d 5.0101, Act d 6, Act d 6.0101, Act d 7, Act d 7.0101, Act d 8, Act d 8.0101, Act d 9, Act d 9.0101, Act d Chitinase, Act e 1, Act e 5), *Acyrthosiphon* spp (Acy pi 7, Acy pi 7.0101, Acy pi 7.0102), *Adenia* spp (Ade v RIP), *Aedes* spp (Aed a 1, Aed a 1.0101, Aed a 2, Aed a 2.0101, Aed a 3, Aed a 3.0101, Aed a 4, Aed a 7, Aed a 7.0101, Aed a 7.0102, Aed a 7.0103, Aed a 7.0104, Aed a 7.0105, Aed a 7.0106, Aed a 7.0107, Aed a 7.0108, Aed a 7.0109, Aed a 7.0110, Aed a 7.0111, Aed al 1, Aed al 3, Aed al 37 kD, Aed v 37 kD, Aed v 63 kD), *Aegilops* spp (Aeg ta 28, Aeg ta alpha_Gliadin, Aeg um 28, Aeg un 28), *Aethaloperca* spp (Aet ro 1), *Agropyron* spp (Agr c 7), *Agrostis* spp (Agr ca 1, Agr ca 5, Agr g 1, Agr g 4, Agr s 5), *Agrobacterium* spp (Agr sp CP4 EPSPS), *Ailuropoda* spp (Ail me Phosvitin, Ail me TCTP), *Aix* spp (Aix ga 1, Aix sp 1), *Aleuroglyphus* spp (Ale o 1, Ale o 10, Ale o 10.0101, Ale o 10.0102, Ale o 13, Ale o 14, Ale o 2, Ale o 20, Ale o 3, Ale o 5, Ale o 7, Ale o 8, Ale o 9), *Allium* spp (All a 3, All a Alliin lyase, All c 3, All c 30 kD, All c 4, All c Alliin lyase, All p Alliin lyase, All s Alliin lyase), *Alnus* spp (Aln g 1, Aln g 1.0101, Aln g 1/Bet v 1/Cor a 1 TPC7, Aln g 1/Bet v 1/Cor a 1 TPC9, Aln g 2, Aln g 4, Aln g 4.0101), *Alopochen* spp (Alo ae 1), *Alopecurus* spp (Alo p 1, Alo p 5), *Alternaria* spp (Alt a 1, Alt a 1.0101, Alt a 1.0102, Alt a 10, Alt a 10.0101, Alt a 12, Alt a 12.0101, Alt a 13, Alt a 13.0101, Alt a 2, Alt a 3, Alt a 3.0101, Alt a 4, Alt a 4.0101, Alt a 5, Alt a 5.0101, Alt a 6, Alt a 6.0101, Alt a 7, Alt a 7.0101, Alt a 70 kD, Alt a 8, Alt a 8.0101, Alt a 9, Alt a MnSOD, Alt a NTF2, Alt a TCTP, Alt ar 1, Alt arg 1, Alt b 1, Alt bl 1, Alt br 1, Alt c 1, Alt ca 1, Alt ce 1, Alt ch 1, Alt ci 1, Alt co 1, Alt cr 1, Alt ct 1, Alt cu 1, Alt cy 1, Alt d 1, Alt du 1, Alt e 1, Alt et 1, Alt eu 1, Alt ga 1, Alt gr 1, Alt j 1, Alt l 1, Alt lo 1, Alt m 1, Alt me 1, Alt mi 1, Alt mo 1, Alto 1, Alt p 1, Alt ph 1, Alt po 1, Alt ps 1, Alt r 1, Alt s 1, Alt se 1, Alt sm 1, Alt so 1, Alt su 1, Alt t 1, Alt te 1, Alt to 1), *Amaranthus* spp (Ama r 2, Ama r 2.0101, Ama v 2, Ama v 2.0101, Ama v 2.0201), *Ambrosia* spp (Amb a 1, Amb a 1.0101, Amb a 1.0201, Amb a 1.0202, Amb a 1.0301, Amb a 1.0302, Amb a 1.0303, Amb a 1.0304, Amb a 1.0305, Amb a 1.0401, Amb a 1.0402, Amb a 1.0501, Amb a 1.0502, Amb a 10, Amb a 10.0101, Amb a 3, Amb a 3.0101, Amb a 4, Amb a 4.0101, Amb a 5, Amb a 5.0101, Amb a 6, Amb a 6.0101, Amb a 7, Amb a 7.0101, Amb a 8, Amb a 8.0101, Amb a 8.0102, Amb a 9, Amb a 9.0101, Amb a 9.0102, Amb a CPI, Amb p 1, Amb p 5, Amb p 5.0101, Amb p 5.0201, Amb t 5, Amb t 5.0101, Amb t 8), *Ammothea* spp (Amm h 7, Amm h 7.0101), *Anadara* spp (Ana br 1), *Ananas* spp (Ana c 1, Ana c 1.0101, Ana c 2, Ana c 2.0101, Ana c 2.0101 (MUXF3)), *Anas* spp (Ana ca 1), *Anarhichas* spp (Ana l 1), *Anacardium* spp (Ana o 1, Ana o 1.0101, Ana o 1.0102, Ana o 2, Ana o 2.0101, Ana o 3, Ana o 3.0101), *Anas* spp (Ana p 1, Ana p 2, Ana p 3), *Anguilla* spp (Ang a 1, Ang j 1), *Anisakis* spp (Ani s 1, Ani s 1.0101, Ani s 10, Ani s 10.0101, Ani s 11, Ani s 11.0101, Ani s 12, Ani s 12.0101, Ani s 2, Ani s 2.0101, Ani s 24 kD, Ani s 3, Ani s 3.0101, Ani s 4, Ani s 4.0101, Ani s 5, Ani s 5.0101, Ani s 6, Ani s 6.0101, Ani s 7, Ani s 7.0101, Ani s 8, Ani s 8.0101, Ani s 9, Ani s 9.0101, Ani s CCOS3, Ani s Cytochrome B, Ani s FBPP, Ani s NADHDS4L, Ani s NARaS, Ani s PEPB, Ani s Troponin), *Annona* spp (Ann c Chitinase), *Anopheles* spp (Ano da 17, Ano da 17.0101, Ano da 27, Ano da 27.0101, Ano da 7, Ano da 7.0101, Ano g 7, Ano g 7.0101), *Anser* spp (Ans a 1, Ans a 2, Ans a 3, Ans in 1), *Anthoxanthum* spp (Ant o 1, Ant o 1.0101, Ant o 12, Ant o 13, Ant o 2, Ant o 4, Ant o 5, Ant o 6, Ant o 7), *Apis* spp (Api c 1, Api c 1.0101, Api c 10, Api c 2, Api c 4, Api d 1, Api d 1.0101, Api d 4, Api fl 4), *Apium* spp (Api g 1, Api g 1.0101, Api g 1.0201, Api g 2, Api g 2.0101, Api g 3, Api g 3.0101, Api g 4, Api g 4.0101, Api g 5, Api g 5.0101, Api g 6, Api g 6.0101), *Apis* spp (Api m 1, Api m 1.0101, Api m 10, Api m 10.0101, Api m 11, Api m 11.0101, Api m 11.0201, Api m 13 kD, Api m 2, Api m 2.0101, Api m 3, Api m 3.0101, Api m 4, Api m 4.0101, Api m 5, Api m 5.0101, Api m 6, Api m 6.0101, Api m 7, Api m 7.0101, Api m 8, Api m 8.0101, Api m 9, Api m 9.0101, Api m A1-A2, Api m A1-A2-A3, Api m Apalbumin 1, Api m Apalbumin 2, Api me 1, Api me 4), *Arachis* spp (Ara d 2, Ara d 6, Ara f 3, Ara f 4, Ara h 1, Ara h 1.0101, Ara h 10, Ara h 10.0101, Ara h 10.0102, Ara h 11, Ara h 11.0101, Ara h 2, Ara h 2.0101, Ara h 2.0102, Ara h 2.0201, Ara h 2.0202, Ara h 3, Ara h 3.0101, Ara h 4, Ara h 4.0101, Ara h 5, Ara h 5.0101, Ara h 6, Ara h 6.0101, Ara h 7, Ara h 7.0101, Ara h 7.0201, Ara h 7.0202, Ara h 8, Ara h 8.0101, Ara h 8.0201, Ara h 9, Ara h 9.0101, Ara h 9.0201, Ara h Agglutinin, Ara h Oleosin 18 kD, Ara i 2, Ara i 6), *Arabidopsis* spp (Ara t 3, Ara t 8, Ara t GLP), *Archosargus* spp (Arc pr 1), *Archaeopotamobius* spp (Arc s 8, Arc s 8.0101), *Aequipecten* spp (Arg i 1), *Argas* spp (Arg r 1, Arg r 1.0101), *Ariopsis* spp (Ari fe 1), *Armoracia* spp (Arm r HRP), *Arrhenatherum* spp (Arr e 1, Arr e 5), *Artemisia* spp (Art a 1, Art ap 1), *Artemia* spp (Art fr 1, Art fr 1.0101, Art fr 5, Art fr 5.0101), *Arthrobacter* spp (Art gl CO), *Achorion* spp (Art gy 7), *Artocarpus* spp (Art h 17 kD, Art h 4), *Arthrospira* spp (Art pl beta_Phycocyanin), *Artemisia* spp (Art v 1, Art v 1.0101, Art v 1.0102, Art v 1.0103, Art v 1.0104, Art v 1.0105, Art v 1.0106, Art v 1.0107, Art v 2, Art v 2.0101, Art v 3, Art v 3.0101, Art v 3.0201, Art v 3.0202, Art v 3.0301, Art v 4, Art v 4.0101, Art v 4.0201, Art v 47 kD, Art v 5, Art v 5.0101, Art v 6, Art v 6.0101, Art v 60 kD), *Arthroderma* spp (Art va 4), *Ascaris* spp (Asc l 3, Asc l 3.0101, Asc l 3.0102, Asc l 34 kD, Asc s 1, Asc s 1.0101, Asc s 3, Asc s 3.0101, Asc s GST), *Aspergillus* spp (Asp aw Glucoamylase, Asp c 22, Asp f 1, Asp f 1.0101, Asp f 10, Asp f 10.0101, Asp f 11, Asp f 11.0101, Asp f 12, Asp f 12.0101, Asp f 13, Asp f 13.0101, Asp f 15, Asp f 15.0101, Asp f 16, Asp f 16.0101, Asp f 17, Asp f 17.0101, Asp f 18, Asp f 18.0101, Asp f 2, Asp f 2.0101, Asp f 22, Asp f 22.0101, Asp f 23, Asp f 23.0101, Asp f 27, Asp f 27.0101, Asp f 28, Asp f 28.0101, Asp f 29, Asp f 29.0101, Asp f 3, Asp f 3.0101, Asp f 34, Asp f 34.0101, Asp f 4, Asp f 4.0101, Asp f 5, Asp f 5.0101, Asp f 56 kD, Asp f 6, Asp f 6.0101, Asp f 7, Asp f 7.0101, Asp f 8, Asp f 8.0101, Asp f 9, Asp f 9.0101, Asp f AfCalAp, Asp f AT_V, Asp f Catalase, Asp f Chitosanase, Asp f CP, Asp f DPPV, Asp f FDH, Asp f gamma_Actin, Asp f Glucosidase, Asp f GPI, Asp f GST, Asp f GT, Asp f IAO, Asp f IPMI, Asp f LPL1, Asp f LPL3, Asp f Mannosidase, Asp f MDH, Asp f PL, Asp f PUP, Asp f RPS3, Asp f SXR, Asp fl 13, Asp fl 13.0101, Asp fl 18, Asp fl 2, Asp fl 21, Asp fl 3, Asp fl 4, Asp fl 7, Asp fl 8, Asp fl 9, Asp me Seaprose, Asp n 14, Asp n 14.0101, Asp n 18, Asp n 18.0101, Asp n 25, Asp n 25.0101, Asp n 30, Asp n Glucoamylase, Asp n Hemicellulase, Asp n Pectinase, Asp o 13, Asp o 13.0101, Asp o 21, Asp o 21.0101, Asp o 3, Asp o 4, Asp o 7, Asp o 8, Asp o Lactase, Asp o Lipase, Asp oc 13, Asp r 1, Asp sa AP, Asp sp Glucoamylase, Asp sp Glucoseoxidase, Asp sp PL, Asp sp PME, Asp sy 13, Asp v 13, Asp v 13.0101, Asp v Catalase A, Asp v Enolase, Asp v GAPDH, Asp v MDH, Asp v SXR), *Asparagus* spp (Aspa o 1, Aspa o 1.01, Aspa o 1.02, Aspa o 17 kD, Aspa o 4), *Aspergillus* spp (Aspe ni 2, Aspe ni 3, Aspe ni 4, Aspe ni 7, Aspe ni 8, Aspe ni 9), *Avena* spp (Ave s 1, Ave s 12, Ave s 13, Ave s 2, Ave s 4, Ave s 5, Ave s 7), *Babylonia* spp (Bab ja 1), *Bacillus* spp (Bac al Subtilisin, Bac cl Subtilisin, Bac l Subtilisin, Bac ii aA, Bac ii Subtilisin), *Bactrocera* spp (Bac ol 27, Bac ol 27.0101), *Bacillus* spp (Bac sp aA1, Bac sp aA3, Bac sp Decarboxylase, Bac st amyM, Bac su Subtilisin, Bac t CrylAb, Bac t CrylFa, Bac t Cry3Bbl, Bac t Cry9c), *Bagre* spp (Bag ma 1), *Balistes* spp (Bal ca 1), *Balanus* spp (Bal r 1, Bal r 1.0101), *Beauveria* spp (Bea b Ald, Bea b Enol, Bea b f2, Bea b Hex), *Bertholletia* spp (Ber e 1, Ber e 1.0101, Ber e 2, Ber e 2.0101), *Beryx* spp (Ber sp 1), *Betula* spp (Bet ab 1, Bet al 1, Bet ch 1, Bet co 1, Bet da 1, Bet gr 1, Bet hu 1, Bet le 1, Bet me 1, Bet n 1, Bet p 1, Bet pa 1, Bet po 1, Bet pu 1, Bet pu 2, Bet pu 4, Bet pu 6, Bet pu 7, Bet sc 1, Bet ut 1, Bet v 1, Bet v 1 B1-B1-B1, Bet v 1 fv Mal 4x, Bet v 1.0101, Bet v 1.0102, Bet v 1.0103, Bet v 1.0201, Bet v 1.0301, Bet v 1.0401, Bet v 1.0402, Bet v 1.0501, Bet v 1.0601, Bet v 1.0602, Bet v 1.0701, Bet v 1.0801, Bet v 1.0901, Bet v 1.1001, Bet v 1.1101, Bet v 1.1201, Bet v 1.1301, Bet v 1.1401, Bet v 1.1402, Bet v 1.1501, Bet v 1.1502, Bet v 1.1601, Bet v 1.1701, Bet v 1.1801, Bet v 1.1901, Bet v 1.2001, Bet v 1.2101, Bet v 1.2201, Bet v 1.2301, Bet v 1.2401, Bet v 1.2501, Bet v 1.2601, Bet v 1.2701, Bet v 1.2801, Bet v 1.2901, Bet v 1.3001, Bet v 1.3101, Bet v 2, Bet v 2.0101, Bet v 3, Bet v 3.0101, Bet v 4, Bet v 4.0101, Bet v 6, Bet v 6.0101, Bet v 6.0102, Bet v 7, Bet v 7.0101, Bet v 8, Bet v Glucanase), *Beta* spp (Beta v 1, Beta v 1.0101, Beta v 2, Beta v 2.0101),

*Blattella* spp (Bla g 1, Bla g 1.0101, Bla g 1.0102, Bla g 1.0103, Bla g 1.0201, Bla g 1.0202, Bla g 2, Bla g 2.0101, Bla g 2.0201, Bla g 36 kD, Bla g 4, Bla g 4.0101, Bla g 4.0201, Bla g 5, Bla g 5.0101, Bla g 5.0201, Bla g 6, Bla g 6.0101, Bla g 6.0201, Bla g 6.0301, Bla g 7, Bla g 7.0101, Bla g 8, Bla g 8.0101, Bla g 9, Bla g Enolase, Bla g GSTD1, Bla g RACK1, Bla g TPI, Bla g Trypsin, Bla g Vitellogenin), *Blatta* spp (Bla o 1, Bla o 7), *Blomia* spp (Blo t 1, Blo t 1.0101, Blo t 1.0201, Blo t 10, Blo t 10.0101, Blo t 10.0102, Blo t 11, Blo t 11.0101, Blo t 12, Blo t 12.0101, Blo t 12.0102, Blo t 13, Blo t 13.0101, Blo t 14, Blo t 15, Blo t 18, Blo t 19, Blo t 19.0101, Blo t 2, Blo t 2.0101, Blo t 2.0102, Blo t 2.0103, Blo t 20, Blo t 21, Blo t 21.0101, Blo t 3, Blo t 3.0101, Blo t 4, Blo t 4.0101, Blo t 5, Blo t 5.0101, Blo t 6, Blo t 6.0101, Blo t 7, Blo t 8, Blo t 9, Blo t HSP70), *Bombus* spp (Bom ar 4, Bom hy 4, Bom p 1, Bom p 1.0101, Bom p 2, Bom p 3, Bom p 4, Bom p 4.0101, Bom t 1, Bom t 1.0101, Bom t 4, Bom t 4.0101), *Bombyx* spp (Bomb m 1, Bomb m 1.0101, Bomb m 7, Bomb m 7.0101, Bomb m 7.0102, Bomb m 7.0103, Bomb m 7.0104, Bomb m 7.0105, Bomb m 7.0106), *Boophilus* spp (Boo m 1, Boo m 7, Boo m 7.0101), *Bos* spp (Bos d 2, Bos d 2.0101, Bos d 2.0102, Bos d 2.0103, Bos d 3, Bos d 3.0101, Bos d 4, Bos d 4.0101, Bos d 5, Bos d 5.0101, Bos d 5.0102, Bos d 6, Bos d 6 (MDA), Bos d 6.0101, Bos d 7, Bos d 7.0101, Bos d 8, Bos d 8 alphaS1, Bos d 8 alphaS2, Bos d 8 beta, Bos d 8 kappa, Bos d alpha2I, Bos d alpha2I.0101, Bos d Chymosin, Bos d Fibrin, Bos d Gelatin, Bos d HG, Bos d Insulin, Bos d Lactoferrin, Bos d Lactoperoxidase, Bos d Myoglobin, Bos d OBP, Bos d OSCP, Bos d Phosvitin, Bos d PLA2, Bos d PRVB, Bos d Thrombin, Bos d TI, Bos gr ALA, Bos gr Myoglobin), *Bothrops* spp (Bot as 1, Bot at 1), *Bouteloua* spp (Bou g 1), *Biting* spp (Bov ov 1), *Brama* spp (Bra du 1), *Brassica* spp (Bra j 1, Bra j 1.0101, Bra n 1, Bra n 1.0101, Bra n 4, Bra n 7, Bra n 8, Bra n PG, Bra ni 8, Bra o 3, Bra o 3.0101, Bra r 1, Bra r 1.0101, Bra r 2, Bra r 2.0101, Bra r 3, Bra r 4, Bra r 7), *Bromus* spp (Bro a 1, Bro a 4), *Brosme* spp (Bro br 1), *Bromus* spp (Bro i 1, Bro i 5, Bro i 7), *Brugia* spp (Bru m 3, Bru m 3.0101, Bru m Bm33), *Bubalus* spp (Bub b ALA, Bub b BLG, Bub b Casein, Bub b Casein alphaS1, Bub b Casein alphaS2, Bub b Casein beta, Bub b Casein kappa), *Caenorhabditis* spp (Cae b 3, Cae b 3.0101, Cae br 3, Cae br 3.0101, Cae e 3, Cae e 3.0101, Cae e 3.0102, Cae re 13, Cae re 13.0101), *Cajanus* spp (Caj c 1), *Caligus* spp (Cal cl 1, Cal cl 1.0101, Cal cl 1.0102), *Calamus* spp (Cal le 1), *Callinectes* spp (Cal s 2), *Camelus* spp (Cam d ALA, Cam d Casein, Cam d Casein alphaS1, Cam d Casein alphaS2, Cam d Casein beta, Cam d Casein kappa), *Camponotus* spp (Cam fl 7, Cam fl 7.0101), *Canis* spp (Can f 1, Can f 1.0101, Can f 2, Can f 2.0101, Can f 3, Can f 3.0101, Can f 4, Can f 4.0101, Can f 5, Can f 5.0101, Can f 6, Can f 6.0101, Can f Feldl-like, Can f Homs2-like, Can f Phosvitin, Can f TCTP), *Canthidermis* spp (Can ma 1), *Cancer* spp (Can mg 2, Can p 1), *Cannabis* spp (Can s 3), *Candida* spp (Cand a 1, Cand a 1.0101, Cand a 3, Cand a 3.0101, Cand a CAAP, Cand a CyP, Cand a Enolase, Cand a FPA, Cand a MnSOD, Cand a PGK, Cand b 2, Cand b 2.0101, Cand b FDH, Cand r Lipase), *Capsicum* spp (Cap a 1, Cap a 1.0101, Cap a 17 kD, Cap a 2, Cap a 2.0101, Cap a 30 kD, Cap a Glucanase, Cap ch 17 kD), *Caprella* spp (Cap e 1), *Capra* spp (Cap h ALA, Cap h BLG, Cap h Casein, Cap h Casein alphaS1, Cap h Casein alphaS2, Cap h Casein beta, Cap h Casein kappa, Cap h GSA), *Capitulum* spp (Cap m 1), *Carassius* spp (Car au 1), *Carpinus* spp (Car b 1, Car b 1.0101, Car b 1.0102, Car b 1.0103, Car b 1.0104, Car b 1.0105, Car b 1.0106, Car b 1.0107, Car b 1.0108, Car b 1.0109, Car b 1.0110, Car b 1.0111, Car b 1.0112, Car b 1.0113, Car b 1.0201, Car b 1.0301, Car b 1.0302, Car b 2, Car b 4), *Caranx* spp (Car cr 1), *Carya* spp (Car i 1, Car i 1.0101, Car i 2, Car i 4, Car i 4.0101), *Carcinus* spp (Car ma 2), *Caryota* spp (Car mi 2), *Carica* spp (Car p 1, Car p Chitinase, Car p Chymopapain, Car p Endoproteinase), *Castanea* spp (Cas c 24 kD, Cas s 1, Cas s 1.0101, Cas s 1.0102, Cas s 1.0103, Cas s 2, Cas s 5, Cas s 5.0101, Cas s 8, Cas s 8.0101, Cas s 9, Cas s 9.0101), *Catharanthus* spp (Cat r 1, Cat r 1.0101, Cat r 17 kD, Cat r 2), *Caulolatilus* spp (Cau ch 1), *Cavia* spp (Cav p 1, Cav p 1.0101, Cav p 2, Cav p 2.0101, Cav p 3, Cav p 3.0101, Cav p Gelatin, Cav p GSA), *Centropristis* spp (Cen s 1), *Cephalopholis* spp (Cep so 1), *Charybdis* spp (Cha f 1, Cha f 1.0101), *Chaetodipterus* spp (Cha fa 1), *Chamaecyparis* spp (Cha o 1, Cha o 1.0101, Cha o 2, Cha o 2.0101), *Chenopodium* spp (Che a 1, Che a 1.0101, Che a 2, Che a 2.0101, Che a 3, Che a 3.0101), *Chironomus* spp (Chi k 1, Chi k 10, Chi k 10.0101), *Chinchilla* spp (Chi l 21 kD_a, Chi l 21 kD_b), *Chionoecetes* spp (Chi o 1, Chi o 1.0101, Chi o 2, Chi o 4, Chi o 6, Chi o alpha_Actin, Chi o SERCA), *Chironomus* spp (Chi t 1, Chi t 1.0101, Chi t 1.0201, Chi t 2, Chi t 2.0101, Chi t 2.0102, Chi t 3, Chi t 3.0101, Chi t 4, Chi t 4.0101, Chi t 5, Chi t 5.0101, Chi t 6, Chi t 6.0101, Chi t 6.0201, Chi t 7, Chi t 7.0101, Chi t 8, Chi t 8.0101, Chi t 9, Chi t 9.0101), *Chlamys* spp (Chl n 1), *Chloephaga* spp (Chl pi 1), Chortoglyphus spp (Cho a 10), *Chrysomela* spp (Chr tr 7, Chr tr 7.0101), *Cicer* spp (Cic a 2S Albumin, Cic a Albumin), *Cichorium* spp (Cic i 1), *Cimex* spp (Cim 1 Nitrophorin), *Citrus* spp (Cit l 1, Cit l 3, Cit l 3.0101), *Citrullus* spp (Cit la 2, Cit la MDH, Cit la TPI), *Citrus* spp (Cit r 3, Cit r 3.0101, Cit s 1, Cit s 1.0101, Cit s 2, Cit s 2.0101, Cit s 3, Cit s 3.0101, Cit s 3.0102, Cit s IFR), *Cladosporium* spp (Cla c 14, Cla c 14.0101, Cla c 9, Cla c 9.0101, Cla h 1, Cla h 10, Cla h 10.0101, Cla h 12, Cla h 12.0101, Cla h 2, Cla h 2.0101, Cla h 42 kD, Cla h 5, Cla h 5.0101, Cla h 6, Cla h 6.0101, Cla h 7, Cla h 7.0101, Cla h 8, Cla h 8 CSP, Cla h 8.0101, Cla h 9, Cla h 9.0101, Cla h abH, Cla h GST, Cla h HChl, Cla h HSP70, Cla h NTF2, Cla h TCTP), *Clostridium* spp (Clo hi Collagenase, Clo t Toxoid), *Clupea* spp (Clu h 1, Clu h 1.0101, Clu h 1.0201, Clu h 1.0301), *Cocos* spp (Coc n 2, Coc n 4, Coc n 5), *Coccidioides* spp (Coc po 8), *Coffea* spp (Cof a 1, Cof a 1.0101), *Columba* spp (Col i PSA), *Coprinus* spp (Cop c 1, Cop c 1.0101, Cop c 2, Cop c 2.0101, Cop c 3, Cop c 3.0101, Cop c 4, Cop c 5, Cop c 5.0101, Cop c 6, Cop c 7, Cop c 7.0101), *Corylus* spp (Cor a 1, Cor a 1.0101, Cor a 1.0102, Cor a 1.0103, Cor a 1.0104, Cor a 1.0201, Cor a 1.0301, Cor a 1.0401, Cor a 1.0402, Cor a 1.0403, Cor a 1.0404, Cor a 10, Cor a 10.0101, Cor a 11, Cor a 11.0101, Cor a 12, Cor a 12.0101, Cor a 13, Cor a 13.0101, Cor a 14, Cor a 14.0101, Cor a 2, Cor a 2.0101, Cor a 2.0102, Cor a 8, Cor a 8.0101, Cor a 9, Cor a 9.0101), *Corynebacterium* spp (Cor d Toxoid), *Corylus* spp (Cor he 1), *Coryphaena* spp (Cor hi 1), *Coriandrum* spp (Cor s 1, Cor s 111 kD, Cor s 2), *Cotoneaster* spp (Cot l 3), *Crangon* spp (Cra c 1, Cra c 1.0101, Cra c 2, Cra c 2.0101, Cra c 4, Cra c 4.0101, Cra c 5, Cra c 5.0101, Cra c 6, Cra c 6.0101, Cra c 8, Cra c 8.0101), *Crassostrea* spp (Cra g 1), *Cricetus* spp (Cri c HSA), *Crivellia* spp (Cri pa 1), *Crocus* spp (Cro s 1, Cro s 1.0101, Cro s 2, Cro s 2.0101, Cro s 3, Cro s 3.01, Cro s 3.02), *Cryptomeria* spp (Cry j 1, Cry j 1.0101, Cry j 1.0102, Cry j 1.0103, Cry j 2, Cry j 2.0101, Cry j 2.0102, Cry j 3, Cry j 3.1, Cry j 3.2, Cry j 3.3, Cry j 3.4, Cry j 3.5, Cry j 3.6, Cry j 3.7, Cry j 3.8, Cry j 4, Cry j AP, Cry j Chitinase, Cry j CPA9, Cry j IFR, Cry j LTP, Cry j P1-P2), *Cryphonectria* spp (Cry p AP), *Ctenocephalides* spp (Cte f 1, Cte f 1.0101, Cte f 2, Cte f 2.0101, Cte f 3, Cte f 3.0101), *Ctenopharyngodon* spp (Cte id 1), *Cucumis* spp (Cuc m 1, Cuc m 1.0101, Cuc m 2, Cuc m 2.0101, Cuc m 3, Cuc m 3.0101, Cuc m Lecl7, Cuc m MDH), *Cucurbita* spp (Cuc ma 18 kD, Cuc ma 2, Cuc p 2, Cuc p AscO), *Cucumis* spp (Cuc s 2), *Culicoides* spp (Cul n 1, Cul n 10, Cul n 11, Cul n 2, Cul n 3, Cul n 4, Cul n 5, Cul n 6, Cul n 7, Cul n 8, Cul n 9, Cul n HSP70), *Culex* spp (Cul q 28 kD, Cul q 35 kD, Cul q 7, Cul q 7.0101, Cul q 7.0102), *Culicoides* spp (Cul so 1), *Cuminum* spp (Cum c 1, Cum c 2), *Cupressus* spp (Cup a 1, Cup a 1.0101, Cup a 1.02, Cup a 2, Cup a 3, Cup a 4, Cup a 4.0101, Cup s 1, Cup s 1.0101, Cup s 1.0102, Cup s 1.0103, Cup s 1.0104, Cup s 1.0105, Cup s 3, Cup s 3.0101, Cup s 3.0102, Cup s 3.0103, Cup s 8), *Cochliobolus* spp (Cur l 1, Cur l 1.0101, Cur l 2, Cur l 2.0101, Cur l 3, Cur l 3.0101, Cur l 4, Cur l 4.0101, Cur l ADH, Cur l GST, Cur l MnSOD, Cur l Oryzin, Cur l Trx, Cur l ZPS1), *Cyanochen* spp (Cya cy 1), *Cynoscion* spp (Cyn ar 1), *Cynosurus* spp (Cyn cr 1, Cyn cr 5), *Cynodon* spp (Cyn d 1, Cyn d 1.0101, Cyn d 1.0102, Cyn d 1.0103, Cyn d 1.0104, Cyn d 1.0105, Cyn d 1.0106, Cyn d 1.0107, Cyn d 1.0201, Cyn d 1.0202, Cyn d 1.0203, Cyn d 1.0204, Cyn d 10, Cyn d 11, Cyn d 12, Cyn d 12.0101, Cyn d 13, Cyn d 15, Cyn d 15.0101, Cyn d 2, Cyn d 22, Cyn d 22.0101, Cyn d 23, Cyn d 23.0101, Cyn d 24, Cyn d 24.0101, Cyn d 4, Cyn d 5, Cyn d 6, Cyn d 7, Cyn d 7.0101), *Cynoscion* spp (Cyn ne 1), *Cynomys* spp (Cyn sp Lipocalin), *Cyprinus* spp (Cyp c 1.01, Cyp c 1.02), *Daboia* spp (Dab ru 1), *Dactylis* spp (Dac g 1, Dac g 1.01, Dac g 1.0101, Dac g 1.02, Dac g 12, Dac g 13, Dac g 2, Dac g 2.0101, Dac g 3, Dac g 3.0101, Dac g 4, Dac g 4.0101, Dac g 5, Dac g 5.0101, Dac g 7), *Dama* spp (Dam d CSA), *Danio* spp (Dan re 1, Dan re 2, Dan re alpha2I, Dan re CK), *Dasyatis* spp (Das ak 1, Das am 1, Das sa 1), *Daucus* spp (Dau c 1, Dau c 1.0101, Dau c 1.0102, Dau c 1.0103, Dau c 1.0104, Dau c 1.0105, Dau c 1.0201, Dau c 1.0301, Dau c 3, Dau c 4, Dau c 4.0101, Dau c CyP), *Decapterus* spp (Dec ru 1), *Dendronephthya* spp (Den n 1, Den n 1.0101), *Dermatophagoides* spp (Der f 1, Der f 1.0101, Der f 1.0102, Der f 1.0103, Der f 1.0104, Der f 1.0105, Der f 1.0106, Der f 1.0107, Der f 1.0108, Der f 1.0109, Der f 1.0110, Der f 10, Der f 10.0101, Der f 10.0102, Der f 11, Der f 11.0101, Der f 13, Der f 13.0101, Der f 14, Der f 14.0101, Der f 15, Der f 15.0101, Der f 16, Der f 16.0101, Der f 17, Der f 17.0101, Der f 18, Der f 18.0101, Der f 2, Der f 2.0101, Der f 2.0102, Der f 2.0103, Der f 2.0104, Der f 2.0105, Der f 2.0106, Der f 2.0107, Der f 2.0108, Der f 2.0109, Der f 2.0110, Der f 2.0111, Der f 2.0112, Der f 2.0113, Der f 2.0114, Der f 2.0115, Der f 2.0116, Der f 2.0117, Der f 20, Der f 21, Der f 22, Der f 22.0101, Der f 3, Der f 3.0101, Der f 4, Der f 5, Der f 6, Der f 6.0101, Der f 7, Der f 7.0101, Der f 8, Der f 9, Der f HSP70), *Dermanyssus* spp (Der g 10, Der g 10.0101), *Dermatophagoides* spp (Der m 1, Der m 1.0101, Der p 1, Der p 1.0101, Der p 1.0102, Der p 1.0103, Der p 1.0104, Der p 1.0105, Der p 1.0106, Der p 1.0107, Der p 1.0108, Der p 1.0109, Der p 1.0110, Der p 1.0111, Der p 1.0112, Der p 1.0113, Der p 1.0114, Der p 1.0115, Der p 1.0116, Der p 1.0117, Der p 1.0118, Der p 1.0119, Der p 1.0120, Der p 1.0121, Der p 1.0122, Der p 1.0123, Der p 1.0124, Der p 10, Der p 10.0101, Der p 10.0102, Der p 10.0103, Der p 11, Der p 11.0101, Der p 13, Der p 14, Der p 14.0101, Der p 15, Der p 18, Der p 2, Der p 2.0101, Der p 2.0102, Der p 2.0103, Der p 2.0104, Der p 2.0105, Der p 2.0106, Der p 2.0107, Der p 2.0108, Der p 2.0109, Der p 2.0110, Der p 2.0111, Der p 2.0112, Der p 2.0113, Der p 2.0114, Der p 2.0115, Der p 20, Der p 20.0101, Der p 21, Der p 21.0101, Der p 23, Der p 23.0101, Der p 3, Der p 3.0101, Der p 4, Der p 4.0101, Der p 5, Der p 5.0101, Der p 5.0102, Der p 6, Der p 6.0101, Der p 7, Der p 7.0101, Der p 8, Der p 8.0101, Der p 9, Der p 9.0101, Der p 9.0102, Der p P1-P2, Der p P2-P1, Der s 1, Der s 2, Der s 3), *Dianthus* spp (Dia c RIP), *Dicranopteris* spp (Dic 1 2S Albumin), *Diospyros* spp (Dio k 17 kD, Dio k 4, Dio k IFR), *Dioscorea* spp (Dio p TSP), *Diplodus* spp (Dip ho 1), *Distichlis* spp (Dis s 1, Dis s 7), *Ditrema* spp (Dit te 1), *Dolichovespula* spp (Dol a 1, Dol a 2, Dol a 5, Dol a 5.0101), *Dolichos* spp (Dol b Agglutinin), *Dolichovespula* spp (Dol m 1, Dol m 1.0101, Dol m 1.02, Dol m 2, Dol m 2.0101, Dol m 5, Dol m 5.0101, Dol m 5.02), *Drosophila* spp (Dro an 7, Dro an 7.0101, Dro er 7, Dro er 7.0101, Dro er 7.0102, Dro gr 7, Dro gr 7.0101, Dro gr 7.0102, Dro m 7, Dro m 7.0101, Dro m 7.0102, Dro m 7.0103, Dro m 7.0104, Dro m 7.0105, Dro m 7.0106, Dro m 7.0107, Dro m 7.0108, Dro m 7.0109, Dro m 7.0110, Dro m 7.0111, Dro m 7.0112, Dro m 7.0113, Dro m 9, Dro m MnSOD, Dro mo 7, Dro mo 7.0101, Dro pp 7, Dro pp 7.0101, Dro se 7, Dro se 7.0101, Dro si 7, Dro si 7.0101, Dro si 7.0102, Dro vi 7, Dro vi 7.0101, Dro wi 7, Dro wi 7.0101, Dro y 7, Dro y 7.0101, Dro y 7.0102, Dro y 7.0103), *Echium* spp (Ech p Cytochrome C), *Elaeis* spp (Ela g 2, Ela g Bd31 kD), *Elops* spp (Elo sa 1), *Embellisia* spp (Emb a 1, Emb i 1, Emb nz 1, Emb t 1), *Engraulis* spp (Eng e 1), *Enteroctopus* spp (Ent d 1), *Epinephelus* spp (Epi bl 1, Epi co 1, Epi fl 1, Epi mc 1, Epi mo 1), *Epicoccum* spp (Epi p 1, Epi p 1.0101, Epi p 12 kD, Epi p GST), *Epinephelus* spp (Epi po 1, Epi un 1), *Equisetum* spp (Equ a 17 kD), *Equus* spp (Equ as 4, Equ as DSA, Equ bu 4, Equ c 1, Equ c 1.0101, Equ c 2, Equ c 2.0101, Equ c 2.0102, Equ c 3, Equ c 3.0101, Equ c 4, Equ c 4.0101, Equ c 5, Equ c 5.0101, Equ c ALA, Equ c BLG, Equ c Casein, Equ c Casein beta, Equ c Casein kappa, Equ c PRVB, Equ he 4, Equ z ZSA), *Erimacrus* spp (Eri i 1, Eri i 1.0101, Eri i 1.0102), *Eriocheir* spp (Eri s 1, Eri s 1.0101, Eri s 2), *Erwinia* spp (Erw ch Asparaginase), *Escherichia* spp (Esc c Asparaginase, Esc c beta GAL), *Esox* spp (Eso l 1), *Euphausia* spp (Eup p 1, Eup p 1.0101), *Euphasia* spp (Eup s 1, Eup s 1.0101), *Euroglyphus* spp (Eur m 1, Eur m 1.0101, Eur m 1.0102, Eur m 1.0103, Eur m 10, Eur m 14, Eur m 14.0101, Eur m 2, Eur m 2.0101, Eur m 2.0102, Eur m 3, Eur m 3.0101, Eur m 4, Eur m 4.0101), *Evynnis* spp (Evy j 1), *Fagopyrum* spp (Fag e 1, Fag e 1.0101, Fag e 10 kD, Fag e 19 kD, Fag e 2, Fag e 2.0101, Fag e TI), *Fagus* spp (Fag s 1, Fag s 1.0101, Fag s 2, Fag s 4), *Fagopyrum* spp (Fag t 1, Fag t 10 kD, Fag t 2, Fag t 2.0101), *Felis* spp (Fel d 1, Fel d 1.0101, Fel d 2, Fel d 2.0101, Fel d 3, Fel d 3.0101, Fel d 4, Fel d 4.0101, Fel d 5, Fel d 5.0101, Fel d 6, Fel d 6.0101, Fel d 7, Fel d 7.0101, Fel d 8, Fel d 8.0101, Fel d IgG), *Fenneropenaeus* spp (Fen c 1, Fen c 2, Fen me 1, Fen me 1.0101), *Festuca* spp (Fes e 1, Fes e 13, Fes e 4, Fes e 5, Fes e 7, Fes p 1, Fes p 13, Fes p 4, Fes p 4.0101, Fes p 5, Fes r 1, Fes r 5), *Ficus* spp (Fic c 17 kD, Fic c 4, Fic c Ficin), *Foeniculum* spp (Foe v 1, Foe v 2), *Forsythia* spp (For s 1), *Forcipomyia* spp (For t 1, For t 1.0101, For t 2, For t 2.0101, For t 7, For t FPA, For t Myosin, For t TPI), *Fragaria* spp (Fra a 1, Fra a 1.0101, Fra a 3, Fra a 3.0101, Fra a 3.0102, Fra a 3.0201, Fra a 3.0202, Fra a 3.0203, Fra a 3.0204, Fra a 3.0301, Fra a 4, Fra a 4.0101, Fra c 1), *Fraxinus* spp (Fra e 1, Fra e 1.0101, Fra e 1.0102, Fra e 1.0201, Fra e 12, Fra e 2, Fra e 3, Fra e 9), *Fragaria* spp (Fra v 1), *Fusarium* spp (Fus c 1, Fus c 1.0101, Fus c 2, Fus c 2.0101, Fus c 3, Fus s 1, Fus s 45 kD, Fus sp Lipase), *Gadus* spp (Gad c 1, Gad c 1.0101, Gad c APDH, Gad m 1, Gad m 1.0101, Gad m 1.0102, Gad m 1.0201, Gad m 1.0202, Gad m 45 kD, Gad m Gelatin, Gad ma 1), *Gallus* spp (Gal d 1, Gal d 1.0101, Gal d 2, Gal d 2.0101, Gal d 3, Gal d 3.0101, Gal d 4, Gal d 4.0101, Gal d 5, Gal d 5.0101, Gal d 6, Gal d 6.0101, Gal d Apo I, Gal d Apo VI, Gal d GPI, Gal d HG, Gal d IgY, Gal d L-PGDS, Gal d Ovomucin, Gal d Phosvitin, Gal d PRVB, Gal la 4), *Galleria* spp (Gal m 18 kD, Gal m 24 kD), *Gallus* spp (Gal so 4), *Gammarus* spp (Gam s TM), *Gelonium* spp (Gel m RIP), *Geothelphusa* spp (Geo de 1), *Glossina* spp (Glo m 5, Glo m 5.0101, Glo m 7, Glo m 7.0101, Glo m 7.0102, Glo m 7.0103), *Glycine* spp (Gly a Bd30K, Gly ar Bd30K, Gly ca Bd30K, Gly cl Bd30K, Gly cu Bd30K, Gly cy Bd30K), *Glycyphagus* spp (Gly d 10, Gly d 10.0101, Gly d 13, Gly d 2, Gly d 2.0101, Gly d 2.0201, Gly d 2.03, Gly d 2/Lep d 2 L1, Gly d 2/Lep d 2 L2, Gly d 2/Lep d 2 L3, Gly d 2/Lep d 2 L4, Gly d 2/Lep d 2 R1, Gly d 2/Lep d 2 R2, Gly d 2/Lep d 2 R3, Gly d 2/Lep d 2 R4, Gly d 2/Lep d 2 R5, Gly d 20, Gly d 3, Gly d 5, Gly d 5.01, Gly d 5.02, Gly d 7, Gly d 8), *Glycine* spp (Gly f Bd30K, Gly 1 Bd30K, Gly m 1, Gly m 1.0101, Gly m 1.0102, Gly m 2, Gly m 2.0101, Gly m 2S Albumin, Gly m 3, Gly m 3.0101, Gly m 3.0102, Gly m 39 kD, Gly m 4, Gly m 4.0101, Gly m 5, Gly m 5.0101, Gly m 5.0201, Gly m 5.0301, Gly m 5.0302, Gly m 50 kD, Gly m 6, Gly m 6.0101, Gly m 6.0201, Gly m 6.0301, Gly m 6.0401, Gly m 6.0501, Gly m 68 kD, Gly m Agglutinin, Gly m Bd28K, Gly m Bd30K, Gly m Bd60K, Gly m CPI, Gly m EAP, Gly m TI, Gly mi Bd30K, Gly s Bd30K, Gly t Bd30K, Gly to Bd30K), *Gossypium* spp (Gos h Vicilin), *Haemophilus* spp (Hae in P6), *Haemaphysalis* spp (Hae 17, Hae 17.0101, Hae q 7, Hae q 7.0101), *Haliotis* spp (Hal a 1, Hal d 1, Hal di 1, Hal di PM, Hal m 1, Hal m 1.0101, Hal r 1, Hal r 49 kD, Hal ru 1), *Harmonia* spp (Har a 1, Har a 1.0101, Har a 2, Har a 2.0101), *Harpegnathos* spp (Har sa 7, Har sa 7.0101, Har sa 7.0102), *Helianthus* spp (Hel a 1, Hel a 1.0101, Hel a 2, Hel a 2.0101, Hel a 2S Albumin, Hel a 3, Hel a 3.0101, Hel a 4), *Helix* spp (Hel ap 1, Hel as 1, Hel as 1.0101), *Heligmosomoides* spp (Hel p 3, Hel p 3.0101), *Helianthus* spp (Hel tu 1), *Hemanthias* spp (Hem le 1), *Hemifusus* spp (Hem t 1), *Heterodera* spp (Het g 3, Het g 3.0101), *Hevea* spp (Hev b 1, Hev b 1.0101, Hev b 10, Hev b 10.0101, Hev b 10.0102, Hev b 10.0103, Hev b 11, Hev b 11.0101, Hev b 11.0102, Hev b 12, Hev b 12.0101, Hev b 13, Hev b 13.0101, Hev b 14, Hev b 14.0101, Hev b 2, Hev b 2.0101, Hev b 3, Hev b 3.0101, Hev b 4, Hev b 4.0101, Hev b 5, Hev b 5.0101, Hev b 6, Hev b 6.01, Hev b 6.02, Hev b 6.0202, Hev b 6.03, Hev b 7, Hev b 7.01, Hev b 7.02, Hev b 7.D2, Hev b 7.S2, Hev b 8, Hev b 8.0101, Hev b 8.0102, Hev b 8.0201, Hev b 8.0202, Hev b 8.0203, Hev b 8.0204, Hev b 9, Hev b 9.0101, Hev b Citrate binding Protein, Hev b GAPDH, Hev b HSP80, Hev b IFR, Hev b Proteasome subunit, Hev b Rotamase, Hev b SPI, Hev b Trx, Hev b UDPGP), *Hexagrammos* spp (Hex ot 1), *Hippoglossus* spp (Hip h 1), *Hippoglossoides* spp (Hip pl 1), *Hippoglossus* spp (Hip st 1), *Hirudo* spp (Hir me Hirudin), *Holcus* spp (Hol l 1, Hol l 1.0101, Hol l 1.0102, Hol l 2, Hol l 4, Hol l 5, Hol l 5.0101, Hol l 5.0201), *Holocnemus* spp (Hol pl 9, Hol pl Hemocyanin), *Homarus* spp (Hom a 1, Hom a 1.0101, Hom a 1.0102, Hom a 1.0103, Hom a 3, Hom a 3.0101, Hom a 4, Hom a 6, Hom a 6.0101, Hom g 1, Hom g 2), *Homo* spp (Hom s 1, Hom s 1.0101, Hom s 2, Hom s 2.0101, Hom s 3, Hom s 3.0101, Hom s 4, Hom s 4.0101, Hom s 5, Hom s 5.0101, Hom s AAT, Hom s ACTH, Hom s Adalimumab, Hom s ALA, Hom s alpha_Actin, Hom s alpha-Galactosidase, Hom s APDH, Hom s Arylsulfatase B, Hom s Casein, Hom s CyP A, Hom s CyP B, Hom s CyP C, Hom s DSF70, Hom s DSG3, Hom s eIF6, Hom s Etanercept, Hom s Factor IX, Hom s Factor VII, Hom s Factor VIII, Hom s G-CSF, Hom s Glucocerebrosidase, Hom s Glucosidase, Hom s HLA-DR-alpha, Hom s HSA, Hom s Iduronidase, Hom s Idursulfase, Hom s IgA, Hom s Insulin, Hom s Lactoferrin, Hom s Laminin gamma_2, Hom s MnSOD, Hom s Oxytocin, Hom s P2, Hom s Phosvitin, Hom s Profilin, Hom s PSA, Hom s RP1, Hom s TCTP, Hom s TL, Hom s TPA, Hom s TPO, Hom s Transaldolase, Hom s Trx, Hom s Tubulin-alpha, Hom s/Mus m Basiliximab, Hom s/Mus m Cetuximab, Hom s/Mus m Cetuximab (Gal-Gal), Hom s/Mus m Infliximab, Hom s/Mus m Natalizumab, Hom s/Mus m Omalizumab, Hom s/Mus m Palivizumab, Hom s/Mus m Rituximab, Hom s/Mus m Tocilizumab, Hom s/Mus m Trastuzumab), *Hoplostethus* spp (Hop a 1), *Hordeum* spp (Hor v 1, Hor v 12, Hor v 12.0101, Hor v 13, Hor v 14, Hor v 15, Hor v 15.0101, Hor v 16, Hor v 16.0101, Hor v 17, Hor v 17.0101, Hor v 18 kD, Hor v 2, Hor v 21, Hor v 21.0101, Hor v 28, Hor v 33, Hor v 4, Hor v 5, Hor v 5.0101, Hor v BDAI, Hor v BTI), *Humicola* spp (Hum in Cellulase), *Humulus* spp (Hum j 1, Hum j 1.0101, Hum j 10 kD, Hum j 2), *Huso* spp (Hus h 1), *Hylocereus* spp (Hyl un LTP), *Hymenocephalus* spp (Hym st 1), *Hyperoglyphe* spp (Hyp by 1), *Hypophthalmichthys* spp (Hyp mo 1), *Hypophthalmichthy* spp (Hyp no 1), *Ictalurus* spp (Ict fu 1, Ict p 1), *Imperata* spp (Imp c 4, Imp c 5, Imp c VIIIel), *Ixodes* spp (Ixo r 2, Ixo sc 7, Ixo sc 7.0101), *Jasus* spp (Jas la 1, Jas la 1.0101, Jas la 1.0102), *Juglans* spp (Jug ca 1, Jug ca 2, Jug ci 1, Jug ci 2, Jug n 1, Jug n 1.0101, Jug n 2, Jug n 2.0101, Jug r 1, Jug r 1.0101, Jug r 2, Jug r 2.0101, Jug r 3, Jug r 3.0101, Jug r 4, Jug r 4.0101, Jug r 5), *Juniperus* spp (Jun a 1, Jun a 1.0101, Jun a 1.0102, Jun a 2, Jun a 2.0101, Jun a 3, Jun a 3.0101, Jun c 1, Jun o 1, Jun o 4, Jun o 4.0101, Jun r 3, Jun r 3.1, Jun r 3.2, Jun v 1, Jun v 1.0101, Jun v 1.0102, Jun v 3, Jun v 3.0101, Jun v 3.0102, Jun v 4), *Katsuwonus* spp (Kat p 1), *Kyphosus* spp (Kyp se 1), *Lachnolaimus* spp (Lac ma 1), *Lachesis* spp (Lac mu 1), *Lactuca* spp (Lac s 1, Lac s 1.0101), *Lagocephalus* spp (Lag la 1), *Larus* spp (Lar a 1, Lar a 2, Lar a 3), *Larimichthys* spp (Lar po 1), *Lates* spp (Lat c 1), *Lateolabrax* spp (Lat ja 1), *Lathyrus* spp (Lat oc Agglutinin), *Leiostomus* spp (Lei xa 1), *Lens* spp (Len c 1, Len c 1.0101, Len c 1.0102, Len c 1.0103, Len c 2, Len c 2.0101, Len c 3, Len c 3.0101, Len c Agglutinin), *Leopardus* spp (Leo p 1), *Lepidoglyphus* spp (Lep d 10, Lep d 10.0101, Lep d 12, Lep d 13, Lep d 13.0101, Lep d 2, Lep d 2.0101, Lep d 2.0102, Lep d 2.0201, Lep d 2.0202, Lep d 3, Lep d 39 kD, Lep d 5, Lep d 5.0101, Lep d 5.0102, Lep d 5.0103, Lep d 7, Lep d 7.0101, Lep d 8, Lep d alpha Tubulin), *Lepomis* spp (Lep gi 1), *Leptomelanosoma* spp (Lep i 1), *Lepomis* spp (Lep ma 1), *Lepisma* spp (Lep s 1, Lep s 1.0101, Lep s 1.0102), *Lepeophtheirus* spp (Lep sa 1, Lep sa 1.0101, Lep sa 1.0102, Lep sa 1.0103), *Leptailurus* spp (Lep se 1), *Lepidorhombus* spp (Lep w 1, Lep w 1.0101), *Lethocerus* spp (Let in 7, Let in 7.0101, Let in 7.0102), *Leuciscus* spp (Leu ce 1), *Lewia* spp (Lew in 1), *Ligustrum* spp (Lig v 1, Lig v 1.0101, Lig v 1.0102, Lig v 2), *Lilium* spp (Lil l 2, Lil 1 PG), *Limanda* spp (Lim fe 1), *Limnonectes* spp (Lim m 1), *Limulus* spp (Lim p 1, Lim p 1.0101, Lim p 2, Lim p LPA), *Liposcelis* spp (Lip b 1, Lip b 1.0101), *Litchi* spp (Lit c 1, Lit c 1.0101, Lit c IFR, Lit c TPI), *Lithobates* spp (Lit ca 1), *Litopenaeus* spp (Lit se 1, Lit v 1, Lit v 1.0101, Lit v 2, Lit v 2.0101, Lit v 3, Lit v 3.0101, Lit v 4, Lit v 4.0101), *Filiaria* spp (Loa lo 3, Loa lo 3.0101), *Lobotes* spp (Lob su 1), *Locusta* spp (Loc m 7, Loc m 7.0101), *Loligo* spp (Lol b 1, Lol e 1), *Lolium* spp (Lol m 2, Lol m 5, Lol p 1, Lol p 1.0101, Lol p 1.0102, Lol p 1.0103, Lol p 10, Lol p 11, Lol p 11.0101, Lol p 12, Lol p 13, Lol p 2, Lol p 2.0101, Lol p 3, Lol p 3.0101, Lol p 4, Lol p 4.0101, Lol p 5, Lol p 5.0101, Lol p 5.0102, Lol p 7, Lol p CyP, Lol p FT, Lol p Legumin), *Lonomia* spp (Lon o 7, Lon o 7.0101), *Lophodytes* spp (Lop cu 1), *Lophonetta* spp (Lop sp 1), *Lupinus* spp (Lup a 1, Lup a alpha_Conglutin, Lup a delta_Conglutin, Lup a gamma_Conglutin, Lup an 1, Lup an 1.0101, Lup an alpha_Conglutin, Lup an delta_Conglutin, Lup an gamma_Conglutin, Lup l 17 kD), *Lutjanus* spp (Lut a 1, Lut c 1, Lut cy 1, Lut gr 1, Lut gu 1, Lut jo 1), *Lutraria* spp (Lut p 1), *Lutjanus* spp (Lut pu 1, Lut sy 1), *Lycopersicon* spp (Lyc e 1, Lyc e 1.0101, Lyc e 11S Globulin, Lyc e 2, Lyc e 2.0101, Lyc e 2.0102, Lyc e 3, Lyc e 3.0101, Lyc e 4, Lyc e 4.0101, Lyc e ARP60S, Lyc e Chitinase, Lyc e Glucanase, Lyc e Peroxidase, Lyc e PG, Lyc e PME, Lyc e PR23, Lyc e Vicilin), *Maconellicoccus* spp (Mac h 7, Mac h 7.0101), *Macruronus* spp (Mac ma 1, Mac n 1), *Maclura* spp (Mac po 17 kD), *Macrobrachium* spp (Mac ro 1, Mac ro 1.0101, Mac ro Hemocyanin), *Macropus* spp (Macr s Gelatin), *Malus* spp (Mal d 1, Mal d 1.0101, Mal d 1.0102, Mal d 1.0103, Mal d 1.0104, Mal d 1.0105, Mal d 1.0106, Mal d 1.0107, Mal d 1.0108, Mal d 1.0109, Mal d 1.0201, Mal d 1.0202, Mal d 1.0203, Mal d 1.0204, Mal d 1.0205, Mal d 1.0206, Mal d 1.0207, Mal d 1.0208, Mal d 1.0301, Mal d 1.0302, Mal d 1.0303, Mal d 1.0304, Mal d 1.0401, Mal d 1.0402, Mal d 1.0403, Mal d 2, Mal d 2.0101, Mal d 3, Mal d 3.0101, Mal d 3.0102, Mal d 3.0201, Mal d 3.0202, Mal d 3.0203, Mal d 4, Mal d 4.0101, Mal d 4.0102, Mal d 4.0201, Mal d 4.0202, Mal d 4.0301, Mal d 4.0302), *Malpighia* spp (Mal g 4, Mal g Hevein), *Malus* spp (Mal p 1), *Malassezia* spp (Mala f 2, Mala f 2.0101, Mala f 3, Mala f 3.0101, Mala f 4, Mala f 4.0101, Mala g 10, Mala s 1, Mala s 1.0101, Mala s 10, Mala s 10.0101, Mala s 11, Mala s 11.0101, Mala s 12, Mala s 12.0101, Mala s 13, Mala s 13.0101, Mala s 5, Mala s 5.0101, Mala s 6, Mala s 6.0101, Mala s 7, Mala s 7.0101, Mala s 8, Mala s 8.0101, Mala s 9, Mala s 9.0101), *Manihot* spp (Man e 5, Man e 5.0101, Man e FPA, Man e GAPDH), *Mangifera* spp (Man i 1, Man i 14 kD, Man i 2, Man i 3, Man i 3.01, Man i 3.02, Man i Chitinase), *Marsupenaeus* spp (Mar j 1, Mar j 1.0101, Mar j 2, Mar j 4), *Matricaria* spp (Mat c 17 kD), *Mecopoda* spp (Mec e 7), *Megalobrama* spp (Meg am 2, Meg am CK), *Megathura* spp (Meg c Hemocyanin), *Megalops* spp (Meg sp 1), *Melanogrammus* spp (Mel a 1), *Meleagris* spp (Mel g 1, Mel g 2, Mel g 3, Mel g PRVB, Mel g TSA), *Melicertus* spp (Mel l 1), *Menticirrhus* spp (Men am 1), *Mercurialis* spp (Mer a 1, Mer a 1.0101), *Merluccius* spp (Mer ap 1, Mer au 1, Mer bi 1, Mer ca 1, Mer ga 1, Mer hu 1), *Merlangius* spp (Mer me 1), *Merluccius* spp (Mer mr 1, Mer pa 1, Mer po 1, Mer pr 1, Mer se 1), *Meriones* spp (Mer un 23 kD), *Metarhizium* spp (Met a 30), *Metapenaeopsis* spp (Met ba 1), *Metapenaeus* spp (Met e 1, Met e 1.0101, Met e 2), *Metasequoia* spp (Met gl 2), *Metapenaeus* spp (Met j 1, Met j 2), *Metanephrops* spp (Met ja 1), *Metapenaeopsis* spp (Met la 1), *Metanephrops* spp (Met t 2), *Micromesistius* spp (Mic po 1), *Micropogonias* spp (Mic un 1), *Mimachlamys* spp (Mim n 1), *Momordica* spp (Mom c RIP), *Morus* spp (Mor a 17 kD, Mor a 4), *Morone* spp (Mor am 1), *Morus* spp (Mor n 3, Mor n 3.0101), *Morone* spp (Mor sa 1, Mor sc 1), *Mugil* spp (Mug c 1), *Muraenolepis* spp (Mur mi 1), *Musa* spp (Mus a 1, Mus a 1.0101, Mus a 2, Mus a 2.0101, Mus a 3, Mus a 3.0101, Mus a 4, Mus a 4.0101, Mus a 5, Mus a 5.0101, Mus a 5.0102), *Mus* spp (Mus m 1, Mus m 1.0101, Mus m 1.0102, Mus m 2, Mus m Gelatin, Mus m IgG, Mus m MSA, Mus m Muromonab, Mus m Phosvitin), *Mustela* spp (Mus p 17 kD), *Musa* spp (Mus xp 1, Mus xp 2, Mus xp 5), *Mycteroperca* spp (Myc bo 1, Myc mi 1, Myc ph 1), *Myceliophthora* spp (Myc sp Laccase), *Myrmecia* spp (Myr p 1, Myr p 1.0101, Myr p 2, Myr p 2.0101, Myr p 2.0102, Myr p 3, Myr p 3.0101), *Mytilus* spp (Myt e 1, Myt g 1, Myt g PM), *Myzus* spp (Myz p 7, Myz p 7.0101), *Nemorhedus* spp (Nae go Hya), *Necator* spp (Nec a Calreticulin), *Nemipterus* spp (Nem vi 1), *Neosartorya* spp (Neo fi 1, Neo fi 22), *Neochen* spp (Neo ju 1), *Neoscona* spp (Neo n 7, Neo n 7.0101), *Nephelium* spp (Nep 1 GAPDH), *Nephrops* spp (Nep n 1, Nep n DF9), *Neptunea* spp (Nep po 1, Nep po 1.0101), *Nicotiana* spp (Nic t 8, Nic t Osmotin, Nic t Villin), *Nimbya* spp (Nim c 1, Nim s 1), *Nippostrongylus* spp (Nip b Agl), *Nycticebus* spp (Nyc c 1), *Octopus* spp (Oct f 1, Oct l 1, Oct v 1, Oct v 1.0101, Oct v PM), *Ocyurus* spp (Ocy ch 1), *Olea* spp (Ole e 1, Ole e 1.0101, Ole e 1.0102, Ole e 1.0103, Ole e 1.0104, Ole e 1.0105, Ole e 1.0106, Ole e 1.0107, Ole e 10, Ole e 10.0101, Ole e 11, Ole e 11.0101, Ole e 11.0102, Ole e 12, Ole e 13, Ole e 2, Ole e 2.0101, Ole e 3, Ole e 3.0101, Ole e 36 kD, Ole e 4, Ole e 4.0101, Ole e 5, Ole e 5.0101, Ole e 6, Ole e 6.0101, Ole e 7, Ole e 7.0101, Ole e 8, Ole e 8.0101, Ole e 9, Ole e 9.0101), *Ommastrephes* spp (Omm b 1, Omm b 1.0101), *Oncorhynchus* spp (Onc ke 1, Onc ke 18 kD, Onc ke alpha2I, Onc ke Vitellogenin, Onc m 1, Onc m 1.0101, Onc m 1.0201, Onc m alpha2I, Onc m Protamine, Onc m Vitellogenin, Onc ma 1, Onc ma FPA, Onc ma FSA, Onc ma TPI, Onc n 1), *Onchocerca* spp (Onc o 3, Onc o 3.0101), *Oncorhynchus* spp (Onc ts 1), *Onchocerca* spp (Onc v 3, Onc v 3.0101), *Oratosquilla* spp (Ora o 1, Ora o 1.0101), *Oreochromis* spp (Ore a 1, Ore mo 1, Ore mo 2, Ore mo FPA, Ore mo SCAF7145, Ore ni 1, Ore ni 18 kD, Ore ni 45 kD), *Ornithonyssus* spp (Orn sy 10, Orn sy 10.0101, Orn sy 10.0102), *Oryctolagus* spp (Ory c 1, Ory c 1.0101, Ory c 2, Ory c Casein, Ory c Phosvitin, Ory c RSA), *Oryza* spp (Ory s 1, Ory s 1.0101, Ory s 11, Ory s 12, Ory s 12.0101, Ory s 13, Ory s 14, Ory s 17 kD, Ory s 19 kD, Ory s 2, Ory s 23, Ory s 3, Ory s 7, Ory s aA_TI, Ory s GLP52, Ory s GLP63, Ory s Glyoxalase I, Ory s NRA), *Ostrya* spp (Ost c 1, Ost c 1.0101), *Ovis* spp (Ovi a ALA, Ovi a BLG, Ovi a Casein, Ovi a Casein alphaS1, Ovi a Casein alphaS2, Ovi a Casein beta, Ovi a Casein kappa, Ovi a Phosvitin, Ovi a SSA), *Pachycondyla* spp (Pac c 3), *Pagrus* spp (Pag m 1, Pag pa 1), *Pampus* spp (Pam ar 1, Pam c 1), *Pandalus* spp (Pan b 1, Pan b 1.0101), *Pangasius* spp (Pan bo 1), *Pandalus* spp (Pan e 1, Pan e 1.0101, Pan e 4), *Panulirus* spp (Pan h 1, Pan hy 1), *Pangasius* spp (Pan hy 18 kD, Pan hy 45 kD), *Panulirus* spp (Pan j 1), *Panthera* spp (Pan l 1, Pan o 1, Pan p 1), *Panulirus* spp (Pan s 1, Pan s 1.0101), *Panthera* spp (Pan t 1), *Pan* spp (Pan tr TCTP), *Papaver* spp (Pap s 17 kD, Pap s 2, Pap s 34 kD), *Papilio* spp (Pap xu 7, Pap xu 7.0101, Pap xu 7.0102), *Paralichthys* spp (Par a 1), *Parasilurus* spp (Par as 1, Par c 1), *Paralithodes* spp (Par c 1.0101, Par c 1.0102, Par f 1), *Parthenium* spp (Par h 1), *Parietaria* spp (Par j 1, Par j 1.0101, Par j 1.0102, Par j 1.0103, Par j 1.0201, Par j 2, Par j 2.0101, Par j 2.0102, Par j 3, Par j 3.0101, Par j 3.0102, Par j 4, Par j 4.0101, Par j J1-J2), *Paralichthys* spp (Par le 1), *Parietaria* spp (Par m 1, Par o 1, Par o 1.0101), *Paralichthys* spp (Par ol 1, Par ol alpha2I), *Parahucho* spp (Par pe Vitellogenin), *Passiflora* spp (Pas e Chitinase, Pas e Hevein), *Paspalum* spp (Pas n 1, Pas n 1.0101, Pas n 13), *Patinopecten* spp (Pat y 1), *Pediculus* spp (Ped h 7, Ped h 7.0101), *Penaeus* spp (Pen a 1, Pen a 1.0101, Pen a 1.0102, Pen a 1.0102 (103-117), Pen a 1.0102 (109-123), Pen a 1.0102 (1-15), Pen a 1.0102 (115-129), Pen a 1.0102 (121-135), Pen a 1.0102 (127-141), Pen a 1.0102 (13-27), Pen a 1.0102 (133-147), Pen a 1.0102 (139-153), Pen a 1.0102 (145-159)), *Farfantepenaeus* spp (Pen a 1.0102 (151-165)), *Penaeus* spp (Pen a 1.0102 (157-171), Pen a 1.0102 (163-177), Pen a 1.0102 (169-183), Pen a 1.0102 (175-189), Pen a 1.0102 (181-195), Pen a 1.0102 (187-201), Pen a 1.0102 (193-207), Pen a 1.0102 (19-33), Pen a 1.0102 (199-213), Pen a 1.0102 (205-219), Pen a 1.0102 (211-225), Pen a 1.0102 (217-231), Pen a 1.0102 (223-237), Pen a 1.0102 (229-243)), *Farfantepenaeus* spp (Pen a 1.0102 (235-249)), *Penaeus* spp (Pen a 1.0102 (241-255), Pen a 1.0102 (247-261), Pen a 1.0102 (253-267), Pen a 1.0102 (25-39), Pen a 1.0102 (259-273), Pen a 1.0102 (265-279), Pen a 1.0102

(270-284), Pen a 1.0102 (31-45), Pen a 1.0102 (37-51), Pen a 1.0102 (43-57), Pen a 1.0102 (49-63)), *Farfantepenaeus* spp (Pen a 1.0102 (55-69)), *Penaeus* spp (Pen a 1.0102 (61-75), Pen a 1.0102 (67-81), Pen a 1.0102 (7-21), Pen a 1.0102 (73-87), Pen a 1.0102 (79-93), Pen a 1.0102 (85-99), Pen a 1.0102 (91-105), Pen a 1.0102 (97-111), Pen a 1.0103), *Penicillium* spp (Pen b 13, Pen b 13.0101, Pen b 26, Pen b 26.0101, Pen c 1, Pen c 13, Pen c 13.0101, Pen c 18, Pen c 19, Pen c 19.0101, Pen c 2, Pen c 22, Pen c 22.0101, Pen c 24, Pen c 24.0101, Pen c 3, Pen c 3.0101, Pen c 30, Pen c 30.0101, Pen c 32, Pen c 32.0101, Pen c MnSOD, Pen ch 13, Pen ch 13.0101, Pen ch 18, Pen ch 18.0101, Pen ch 20, Pen ch 20.0101, Pen ch 31, Pen ch 31.0101, Pen ch 33, Pen ch 33.0101, Pen ch 35, Pen ch 35.0101, Pen ch MnSOD), *Penaeus* spp (Pen i 1, Pen i 1.0101, Pen m 1, Pen m 1.0101, Pen m 1.0102, Pen m 2, Pen m 2.0101, Pen m 3, Pen m 3.0101, Pen m 4, Pen m 4.0101, Pen m 6, Pen m 6.0101), *Penicillium* spp (Pen o 18, Pen o 18.0101), *Penaeus* spp (Pena o 1, Pena o 1.0101), *Periplaneta* spp (Per a 1, Per a 1.0101, Per a 1.0102, Per a 1.0103, Per a 1.0104, Per a 1.0105, Per a 1.0201, Per a 10, Per a 10.0101, Per a 2, Per a 3, Per a 3.0101, Per a 3.0201, Per a 3.0202, Per a 3.0203, Per a 4, Per a 5, Per a 6, Per a 6.0101, Per a 7, Per a 7.0101, Per a 7.0102, Per a 7.0103, Per a 9, Per a 9.0101, Per a Cathepsin, Per a FABP, Per a Trypsin, Per f 1, Per f 7, Per f 7.0101), *Perna* spp (Per v 1), *Persea* spp (Pers a 1, Pers a 1.0101, Pers a 4), *Petroselinum* spp (Pet c 1, Pet c 2, Pet c 3), *Phalaris* spp (Pha a 1, Pha a 1.0101, Pha a 5, Pha a 5.0101, Pha a 5.02, Pha a 5.03, Pha a 5.04), *Phaseolus* spp (Pha v 3, Pha v 3.0101, Pha v 3.0201, Pha v aAI, Pha v aAI.0101, Pha v Chitinase, Pha v PHA, Pha v Phaseolin), *Phleum* spp (Phl p 1, Phl p 1.0101, Phl p 1.0102, Phl p 11, Phl p 11.0101, Phl p 12, Phl p 12.0101, Phl p 12.0102, Phl p 12.0103, Phl p 13, Phl p 13.0101, Phl p 2, Phl p 2.0101, Phl p 3, Phl p 3.0101, Phl p 3.0102, Phl p 4, Phl p 4.0101, Phl p 4.0102, Phl p 4.0201, Phl p 4.0202, Phl p 4.0203, Phl p 4.0204, Phl p 5, Phl p 5.0101, Phl p 5.0102, Phl p 5.0103, Phl p 5.0104, Phl p 5.0105, Phl p 5.0106, Phl p 5.0107, Phl p 5.0108, Phl p 5.0109, Phl p 5.0201, Phl p 5.0202, Phl p 5.0203, Phl p 5.0204, Phl p 5.0205, Phl p 5.0206, Phl p 5.0207, Phl p 6, Phl p 6.0101, Phl p 6.0102, Phl p 7, Phl p 7.0101, Phl p P1-P2-P5-P6, Phl p P2-P6, Phl p P5-P1, Phl p P6-P2), *Phoenix* spp (Pho d 2, Pho d 2.0101, Pho d 40 kD, Pho d 90 kD), *Phodopus* spp (Pho s 21 kD), *Phoma* spp (Pho t 1), *Phragmites* spp (Phr a 1, Phr a 12, Phr a 13, Phr a 4, Phr a 5), *Phytolacca* spp (Phy a RIP), *Pimpinella* spp (Pim a 1, Pim a 2), *Pinna* spp (Pin a 1), *Piper* spp (Pip n 14 kD, Pip n 28 kD), *Pisum* spp (Pis s 1, Pis s 1.0101, Pis s 1.0102, Pis s 2, Pis s 2.0101, Pis s 5, Pis s Agglutinin, Pis s Albumin), *Pistacia* spp (Pis v 1, Pis v 1.0101, Pis v 2, Pis v 2.0101, Pis v 2.0201, Pis v 3, Pis v 3.0101, Pis v 4, Pis v 4.0101, Pis v 5, Pis v 5.0101), *Platanus* spp (Pla a 1, Pla a 1.0101, Pla a 2, Pla a 2.0101, Pla a 3, Pla a 3.0101, Pla a 8), *Platichthys* spp (Pla f 1), *Plantago* spp (Pla l 1, Pla l 1.0101, Pla l 1.0102, Pla l 1.0103, Pla l Cytochrome C), *Platanus* spp (Pla oc 1, Pla or 1, Pla or 1.0101, Pla or 2, Pla or 2.0101, Pla or 3, Pla or 3.0101, Pla or 4, Pla or CyP, Pla r 1), *Plectropomus* spp (Ple ar 1), *Pleospora* spp (Ple h 1), *Plectropomus* spp (Ple le 1), *Plodia* spp (Plo i 1, Plo i 1.0101, Plo i 2, Plo i 2.0101), *Poa* spp (Poa p 1, Poa p 1.0101, Poa p 10, Poa p 12, Poa p 13, Poa p 2, Poa p 4, Poa p 5, Poa p 5.0101, Poa p 6, Poa p 7), *Polistes* spp (Pol a 1, Pol a 1.0101, Pol a 2, Pol a 2.0101, Pol a 5, Pol a 5.0101, Pol d 1, Pol d 1.0101, Pol d 1.0102, Pol d 1.0103, Pol d 1.0104, Pol d 4, Pol d 4.0101, Pol d 5, Pol d 5.0101, Pol e 1, Pol e 1.0101, Pol e 2, Pol e 4, Pol e 4.0101, Pol e 5, Pol e 5.0101, Pol f 5, Pol f 5.0101, Pol g 1, Pol g 1.0101, Pol g 2, Pol g 4, Pol g 5, Pol g 5.0101, Pol he MLT, Pol m 5, Pol m 5.0101), *Polypedilum* spp (Pol n 1), *Pollicipes* spp (Pol po 1), *Pollachius* spp (Pol vi 1), *Polybia* spp (Poly p 1, Poly p 1.0101, Poly p 2, Poly p 5, Poly s 5, Poly s 5.0101), *Pomatomus* spp (Pom sa 1), *Pongo* spp (Pon ab HSA), *Pontastacus* spp (Pon l 4, Pon l 4.0101, Pon l 7, Pon l 7.0101), *Portunus* spp (Por s 1, Por s 1.0101, Por s 1.0102, Por tr 1, Por tr 1.0101), *Protortonia* spp (Pro ca 38 kD), *Procumbarus* spp (Pro cl 1, Pro cl 1.0101, Pro cl 21 kD), *Prosopis* spp (Pro j 20 kD), *Prunus* spp (Pru ar 1, Pru ar 1.0101, Pru ar 3, Pru ar 3.0101, Pru av 1, Pru av 1.0101, Pru av 1.0201, Pru av 1.0202, Pru av 1.0203, Pru av 2, Pru av 2.0101, Pru av 3, Pru av 3.0101, Pru av 4, Pru av 4.0101, Pru c 1, Pru d 1, Pru d 2, Pru d 3, Pru d 3.0101, Pru d 4, Pru du 1, Pru du 2, Pru du 2S Albumin, Pru du 3, Pru du 3.0101, Pru du 4, Pru du 4.0101, Pru du 4.0102, Pru du 5, Pru du 5.0101, Pru du 6, Pru du 6.0101, Pru du 6.0201, Pru du Conglutin, Pru p 1, Pru p 1.0101, Pru p 2, Pru p 2.0101, Pru p 2.0201, Pru p 2.0301, Pru p 3, Pru p 3.0101, Pru p 3.0102, Pru p 4, Pru p 4.0101, Pru p 4.0201, Pru sa 3), *Psilocybe* spp (Psi c 1, Psi c 1.0101, Psi c 2, Psi c 2.0101), *Psoroptes* spp (Pso o 1, Pso o 10, Pso o 10.0101, Pso o 11, Pso o 13, Pso o 14, Pso o 2, Pso o 21, Pso o 3, Pso o 5, Pso o 7), *Puma* spp (Pum c 1), *Punica* spp (Pun g 3), *Pyrus* spp (Pyr c 1, Pyr c 1.0101, Pyr c 3, Pyr c 3.0101, Pyr c 4, Pyr c 4.0101, Pyr c 5, Pyr c 5.0101, Pyr py 2), *Quercus* spp (Que a 1, Que a 1.0101, Que a 1.0201, Que a 1.0301, Que a 1.0401, Que a 2, Que a 4), *Rachycentron* spp (Rac ca 1), *Rana* spp (Ran e 1, Ran e 1.0101, Ran e 2, Ran e 2.0101), *Ranina* spp (Ran ra 1), *Rangifer* spp (Ran t BLG), *Rattus* spp (Rat n 1, Rat n 1.0101, Rat n Casein, Rat n Gelatin, Rat n IgG, Rat n Phosvitin, Rat n RSA, Rat n Transferrin), *Rhizomucor* spp (Rhi m AP), *Rhizopus* spp (Rhi nv Lipase, Rhi o Lipase), *Rhomboplites* spp (Rho au 1), *Rhodotorula* spp (Rho m 1, Rho m 1.0101, Rho m 2, Rho m 2.0101), *Ricinus* spp (Ric c 1, Ric c 1.0101, Ric c 2, Ric c 3, Ric c 8, Ric c RIP), *Rivulus* spp (Riv ma 1), *Robinia* spp (Rob p 2, Rob p 4, Rob p Glucanase), *Rosa* spp (Ros r 3), *Roystonea* spp (Roy e 2), *Rubus* spp (Rub i 1, Rub i 1.0101, Rub i 3, Rub i 3.0101, Rub i Chitinase, Rub i CyP), *Saccharomyces* spp (Sac c Carboxypeptidase Y, Sac c CyP, Sac c Enolase, Sac c Glucosidase, Sac c Invertase, Sac c MnSOD, Sac c P2, Sac c Profilin), *Salvelinus* spp (Sal f 1), *Salsola* spp (Sal k 1, Sal k 1.0101, Sal k 1.0201, Sal k 1.0301, Sal k 1.0302, Sal k 2, Sal k 2.0101, Sal k 3, Sal k 3.0101, Sal k 4, Sal k 4.0101, Sal k 4.0201, Sal k 5, Sal k 5.0101), *Salvelinus* spp (Sal le Vitellogenin), *Salmo* spp (Sal s 1, Sal s 1.0101, Sal s 1.0201, Sal s 2, Sal s 2.0101, Sal s Gelatin), *Sambucus* spp (Sam n 1), *Sander* spp (San lu 1), *Saponaria* spp (Sap o RIP), *Sardinops* spp (Sar m 1), *Sarkidiornis* spp (Sar ml 1), *Sardina* spp (Sar p 1), *Sarcoptes* spp (Sar s 1, Sar s 14, Sar s 3, Sar s GST, Sar s PM), *Sardinops* spp (Sar sa 1, Sar sa 1.0101), *Schistosoma* spp (Schj GST, Schj PM, Schj Sj22, Sch j Sj67, Sch ma Sm20, Sch ma Sm21, Sch ma Sm22, Sch ma Sm31), *Sciaenops* spp (Sci oc 1), *Scomber* spp (Sco a 1), *Scombermorus* spp (Sco ca 1), *Scomberomorus* spp (Sco g 1), *Scomber* spp (Sco j 1, Sco ma 1, Sco s 1), *Scolopendra* spp (Sco y 7, Sco y 7.0101), *Scylla* spp (Scy o 1, Scy o 1.0101, Scy o 2, Scy pa 1, Scy pa 2, Scy s 1, Scy s 1.0101, Scy s 2), *Sebastes* spp (Seb fa 1, Seb in 1, Seb m 1, Seb m 1.0101, Seb m 1.0201), *Secale* spp (Sec c 1, Sec c 12, Sec c 13, Sec c 2, Sec c 20, Sec c 20.0101, Sec c 20.0201, Sec c 28, Sec c 3, Sec c 4, Sec c 4.0101, Sec c 4.0201, Sec c 5, Sec c 5.0101, Sec c aA_TI, Sec c aA_TI.0101), *Senecio* spp (Sen j MDH, Sen j PL), *Sepia* spp (Sep e 1, Sep e 1.0101), *Sepioteuthis* spp (Sep l 1, Sep l 1.0101), *Sepia* spp (Sep m 1), *Seriola* spp (Ser d 1, Ser la 1), *Sergestes* spp (Ser lu 1), *Seriola* spp (Ser q 1, Ser ri 1),

*Sesamum* spp (Ses i 1, Ses i 1.0101, Ses i 2, Ses i 2.0101, Ses i 3, Ses i 3.0101, Ses i 4, Ses i 4.0101, Ses i 5, Ses i 5.0101, Ses i 6, Ses i 6.0101, Ses i 7, Ses i 7.0101, Ses i 8), *Shigella* spp (Shi bo GST, Shi dy GST), *Simulia* spp (Sim vi 1, Sim vi 2, Sim vi 3, Sim vi 4, Sim vi 70 kD), *Sinapis* spp (Sin a 1, Sin a 1.0101, Sin a 1.0104, Sin a 1.0105, Sin a 1.0106, Sin a 1.0107, Sin a 1.0108, Sin a 2, Sin a 2.0101, Sin a 3, Sin a 3.0101, Sin a 4, Sin a 4.0101), *Sinonovacula* spp (Sin c 1, Sin c 1.0101), *Solenopsis* spp (Sol g 2, Sol g 2.0101, Sol g 3, Sol g 3.0101, Sol g 4, Sol g 4.0101, Sol g 4.0201, Sol i 1, Sol i 1.0101, Sol i 2, Sol i 2.0101, Sol i 3, Sol i 3.0101, Sol i 4, Sol i 4.0101), *Solenocera* spp (Sol me 1), *Solenopsis* spp (Sol r 1, Sol r 2, Sol r 2.0101, Sol r 3, Sol r 3.0101, Sol s 2, Sol s 2.0101, Sol s 3, Sol s 3.0101, Sol s 4), *Solea* spp (Sol so 1, Sol so TPI), *Solanum* spp (Sola t 1, Sola t 1.0101, Sola t 2, Sola t 2.0101, Sola t 3, Sola t 3.0101, Sola t 3.0102, Sola t 4, Sola t 4.0101, Sola t 8, Sola t Glucanase), *Sorghum* spp (Sor b 1, Sor h 1, Sor h 1.0101, Sor h 12, Sor h 7), *Sparus* spp (Spa a 1), *Sphyrna* spp (Sph ti 1), *Spirulina* spp (Spi mx beta_Phycocyanin), *Spinacia* spp (Spi o 2, Spi o RuBisCO), *Squilla* spp (Squ ac 1, Squ ac 1.0101, Squ o 1, Squ o 1.0101), *Staphylococcus* spp (Sta a FBP, Sta a SEA, Sta a SEB, Sta a SEC, Sta a SED, Sta a SEE, Sta a TSST), *Stachybotrys* spp (Sta c 3, Sta c 3.0101, Sta c Cellulase, Sta c Hemolysin, Sta c SchS34, Sta c Stachyrase A), *Stemphylium* spp (Ste b 1, Ste c 1, Ste v 1), *Stolephorus* spp (Sto i 1), *Struthio* spp (Str c 1, Str c 2, Str c 3), *Streptococcus* spp (Str dy Streptokinase), *Streptomyces* spp (Str g Pronase), *Streptococcus* spp (Str pn PspC), *Strongylocentrotus* spp (Str pu 18 kD, Str pu Vitellogenin), *Streptococcus* spp (Str py SPEA, Str py SPEC, Str py Streptokinase), *Strongyloides* spp (Str st 45 kD), *Streptomyces* spp (Str v PAT), *Styela* spp (Sty p 1), *Suidasia* spp (Sui m 1, Sui m 13, Sui m 2, Sui m 3, Sui m 5, Sui m 5.01, Sui m 5.02, Sui m 5.03, Sui m 6, Sui m 7, Sui m 8, Sui m 9), *Sus* spp (Sus s ACTH, Sus s ALA, Sus s Amylase, Sus s BLG, Sus s Casein, Sus s Casein alphaS1, Sus s Casein alphaS2, Sus s Casein beta, Sus s Casein kappa, Sus s Gelatin, Sus s HG, Sus s Insulin, Sus s Lipase, Sus s Pepsin, Sus s Phosvitin, Sus s PRVB, Sus s PSA, Sus s TCTP), *Syntelopodeuma* spp (Syn y 7, Syn y 7.0101), *Syringa* spp (Syr v 1, Syr v 1.0101, Syr v 1.0102, Syr v 1.0103, Syr v 2, Syr v 3, Syr v 3.0101), *Tabanus* spp (Tab y 1, Tab y 1.0101, Tab y 2, Tab y 2.0101, Tab y 5, Tab y 5.0101), *Tadorna* spp (Tad ra 1), *Talaromyces* spp (Tal st 22, Tal st 3, Tal st 8), *Taraxacum* spp (Tar o 18 kD), *Taxodium* spp (Tax d 2), *Tegenaria* spp (Teg d Hemocyanin), *Teladorsagia* spp (Tel ci 3), *Thaumetopoea* spp (Tha p 1, Tha p 1.0101, Tha p 2, Tha p 2.0101), *Theragra* spp (The c 1), *Thermomyces* spp (The 1 Lipase, The sp Lipase, The sp Xylanase), *Thunnus* spp (Thu a 1, Thu a 1.0101, Thu a Collagen, Thu al 1, Thu at 1, Thu o 1, Thu o Collagen), *Thuja* spp (Thu oc 3, Thu p 1), *Thunnus* spp (Thu t 1, Thu to 1), *Thyrsites* spp (Thy at 1), *Thyrophygus* spp (Thy y 7, Thy y 7.0101), *Todarodes* spp (Tod p 1, Tod p 1.0101, Tod p 1.0102), *Toxoptera* spp (Tox c 7, Tox c 7.0101), *Toxocara* spp (Tox ca TES120, Tox ca TES26, Tox ca TES30), *Toxoplasma* spp (Tox g HSP70), *Trachypenaeus* spp (Tra c 1), *Trachinotus* spp (Tra ca 1), *Trachurus* spp (Tra j 1, Tra j Gelatin, Tra tr Gelatin), *Triticum* spp (Tri a 1, Tri a 10 kD, Tri a 12, Tri a 12.0101, Tri a 12.0102, Tri a 12.0103, Tri a 12.0104, Tri a 13, Tri a 14, Tri a 14.0101, Tri a 14.0201, Tri a 15, Tri a 15.0101, Tri a 18, Tri a 18.0101, Tri a 19, Tri a 19.0101, Tri a 2, Tri a 21, Tri a 21.0101, Tri a 23 kd, Tri a 25, Tri a 25.0101, Tri a 26, Tri a 26.0101, Tri a 27, Tri a 27.0101, Tri a 28, Tri a 28.0101, Tri a 29, Tri a 29.0101, Tri a 29.0201, Tri a 3, Tri a 30, Tri a 30.0101, Tri a 31, Tri a 31.0101, Tri a 32, Tri a 32.0101, Tri a 33, Tri a 33.0101, Tri a 34, Tri a 34.0101, Tri a 35, Tri a 35.0101, Tri a 36, Tri a 36.0101, Tri a 37, Tri a 37.0101, Tri a 4, Tri a 4.0101, Tri a 4.0201, Tri a 5, Tri a 7, Tri a aA_SI, Tri a alpha_Gliadin, Tri a bA, Tri a Bd36K, Tri a beta_Gliadin, Tri a Chitinase, Tri a CM16, Tri a DH, Tri a Endochitinase, Tri a gamma_Gliadin, Tri a Germin, Tri a Gliadin, Tri a GST, Tri a LMW Glu, Tri a LMW-GS B16, Tri a LMW-GS P42, Tri a LMW-GS P73, Tri a LTP2, Tri a omega2_Gliadin, Tri a Peroxidase, Tri a Peroxidase 1, Tri a SPI, Tri a TLP, Tri a Tritin, Tri a XI), *Tritirachium* spp (Tri al Proteinase K), *Tribolium* spp (Tri ca 17, Tri ca 17.0101, Tri ca 7, Tri ca 7.0101), *Trichostrongylus* spp (Tri co 3, Tri co 3.0101), *Trichophyton* spp (Tri eq 4), *Trigonella* spp (Tri fg 1, Tri fg 2, Tri fg 3, Tri fg 4), *Trichosanthes* spp (Tri k RIP), *Trichiurus* spp (Tri le 1), *Triticum* spp (Tri m Peroxidase), *Trichophyton* spp (Tri me 2, Tri me 4), *Trisetum* spp (Tri p 1, Tri p 5), *Trichinella* spp (Tri ps 3, Tri ps 3.0101), *Trichophyton* spp (Tri r 2, Tri r 2.0101, Tri r 4, Tri r 4.0101), *Trichoderma* spp (Tri rs Cellulase), *Triticum* spp (Tri s 14), *Trichophyton* spp (Tri sc 2, Tri sc 4, Tri so 2), *Trichinella* spp (Tri sp 3, Tri sp 3.0101, Tri sp 3.0102, Tri sp 3.0103, Tri sp 3.0104, Tri sp 3.0105, Tri sp 3.0106), *Trichophyton* spp (Tri t 1, Tri t 1.0101, Tri t 4, Tri t 4.0101), *Triticum* spp (Tri td 14, Tri td aA_TI), *Trichoderma* spp (Tri v Cellulase), *Trichophyton* spp (Tri ve 4), *Triatoma* spp (Tria p 1, Tria p 1.0101), *Triplochiton* spp (Trip s 1), *Turbo* spp (Tur c 1, Tur c PM), *Tyrophagus* spp (Tyr p 1, Tyr p 10, Tyr p 10.0101, Tyr p 10.0102, Tyr p 13, Tyr p 13.0101, Tyr p 2, Tyr p 2.0101, Tyr p 24, Tyr p 24.0101, Tyr p 3, Tyr p 3.0101, Tyr p 4, Tyr p 5, Tyr p 5.01, Tyr p 5.02, Tyr p 5.03, Tyr p 7, Tyr p alpha Tubulin), *Ulocladium* spp (Ulo a 1, Ulo at 1, Ulo b 1, Ulo c 1, Ulo co 1, Ulo cu 1, Ulo mu 1, Ulo ob 1, Ulo se 1, Ulo su 1, Ulo tu 1), *Uncia* spp (Unc u 1), *Urophycis* spp (Uro te 1), *Vaccinium* spp (Vac m 3), *Varroa* spp (Var j 13 kD), *Venerupis* spp (Ven ph 1, Ven ph 1.0101), *Vespula* spp (Ves f 1, Ves f 2, Ves f 5, Ves f 5.0101, Ves g 1, Ves g 2, Ves g 5, Ves g 5.0101, Ves m 1, Ves m 1.0101, Ves m 2, Ves m 2.0101, Ves m 5, Ves m 5.0101, Ves m MLT, Ves p 1, Ves p 2, Ves p 5, Ves p 5.0101, Ves s 1, Ves s 1.0101, Ves s 2, Ves s 5, Ves s 5.0101, Ves v 1, Ves v 1.0101, Ves v 2, Ves v 2.0101, Ves v 2.0201, Ves v 3, Ves v 3.0101, Ves v 5, Ves v 5.0101, Ves v 5-Pol a 5, Ves vi 5, Ves vi 5.0101), *Vespa* spp (Vesp c 1, Vesp c 1.0101, Vesp c 2, Vesp c 5, Vesp c 5.0101, Vesp c 5.0102, Vesp m 1, Vesp m 1.0101, Vesp m 5, Vesp m 5.0101, Vesp ma 1, Vesp ma 2, Vesp ma 5, Vesp ma MLT, Vesp v MLT), *Vigna* spp (Vig r 1, Vig r 1.0101, Vig r 17 kD, Vig r 5, Vig r 8S Globulin, Vig r Albumin, Vig r beta-Conglycinin), *Vitis* spp (Vit v 1, Vit v 1.0101, Vit v 4, Vit v 5, Vit v Glucanase, Vit v TLP), *Xiphias* spp (Xip g 1, Xip g 1.0101, Xip g 25 kD), *Zea* spp (Zea m 1, Zea m 1.0101, Zea m 11, Zea m 12, Zea m 12.0101, Zea m 12.0102, Zea m 12.0103, Zea m 12.0104, Zea m 12.0105, Zea m 13, Zea m 14, Zea m 14.0101, Zea m 14.0102, Zea m 2, Zea m 20S, Zea m 22, Zea m 25, Zea m 25.0101, Zea m 27 kD Zein, Zea m 3, Zea m 4, Zea m 5, Zea m 50 kD Zein, Zea m 7, Zea m Chitinase, Zea m G1, Zea m G2, Zea m PAO, Zea m Zml3), *Zeus* spp (Zeu fa 1), *Ziziphus* spp (Ziz m 1, Ziz m 1.0101), *Zoarces* spp (Zoa a ISP III), *Zygophyllum* spp (Zyg f 2)

In this context, the terms in brackets indicate the particular preferred allergens from the particular source.

Most preferably the antigen associated with allergy or allergic disease is preferably derived from a source selected from the list consisting of grass pollen (e.g. pollen of rye), tree pollen (e.g. pollen of hazel, birch, alder, ash), flower pollen, herb pollen (e.g. pollen of mugwort), dust mite (e.g. Der f 1, Der p 1, Eur m 1, Der m 1 Der f 2, Der p 2, Eur m 2, Tyr p 2, Lep d 2), mold (e.g. allergens of *Acremonium*,

*Aspergillus, Cladosporium, Fusarium, Mucor, Penicillium, Rhizopus, Stachybotrys, Trichoderma,* or *Alternaria*), animals (e.g Fel dl, Fel d 2, Fel d3, or Fel d4 of cats), food (e.g. allergens of fish (e.g. bass, cod, flounder), seafood (e.g. crab, lobster, shrimps), egg, wheat, nuts (e.g. peanuts, almonds, cashews, walnuts), soya, milk, etc.) or insect venom (e.g. allergens from the venom of wasps, bees, hornets, ants, mosquitos, or ticks).

c) Antigens Associated with Autoimmune Disease:

Antigens associated with autoimmune disease are preferably selected from autoantigens asscociated with autoimmune diseases selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barrd syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, *borrelia* arthritis), Mdnierd's disease (Morbus Mdnierd); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis *nodosa* (periarteiitis *nodosa*), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjdgren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis)

Particularly preferred in this context are autoantigens selected from:

myelin basic protein (MBP), proteolipid protein (PLP), and myelin oligodendrocyte glycoprotein (MOG), in each case associated with multiple sclerosis (MS);

CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Typ I;

interphotoreceptor retinoid-binding protein (IRBP) associated with autoimmune uveitis;

acetylcholine receptor AchR, and insulin-like growth factor-1 receptor (IGF-1R), in each case associated with Myasthenia gravis;

M-protein from beta-hemolytic streptocci (pseudo-autoantigen) associated with Rheumatic Fever;

Macrophage migration inhibitory factor associated with Arthritis;

Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjdgren's syndrome;

Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus;

oxLDL, beta(2)GPI, HSP60/65, and oxLDL/beta(2)GPI, in each case associated with Atherosclerosis;

cardiac beta(1)-adrenergic receptor associated with idiopathic dilated cardiomyopathy (DCM);

histidyl-tRNA synthetase (HisRS) associated with myositis; topoisomerase I associated with scleroderma disease.

Furthermore, in other embodiments, said antigen is associated with the respective autoimmune disease, like e.g. IL-17, heat shock proteins, and/or any idiotype pathogenic T cell or chemokine receptor which is expressed by immune cells involved in the autoimmune response in said autoimmune disease (such as any autoimmune diseases described herein).

d) Antigens Associated with a Cancer or Tumour Disease ("Tumour Antigens"):

"Tumour antigens" in this context are antigens which are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. Particular preferred tumour antigens are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTCi/m, B7H$_4$, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-All/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H$_1$, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Spl7, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR1, VEGFR-2/FLK-1, and WT1. Such tumour antigens preferably may be selected from the group consisting of p53, CA125, EGFR, Her2/neu, hTERT, PAP, MAGE-A1, MAGE-A3, Mesothelin, MUC-1, NY-ESO-1, GP100, MART-1, Tyrosinase, PSA, PSCA, PSMA VEGF, VEGFR1, VEGFR2, Ras, CEA or WT1, and more preferably from PAP, NY-ESO-1, MAGE-A3, WT1, and MUC-1.

In this context, and for certain embodiments of all aspects of the present invention, the antigen associated with a cancer or tumour disease, does not include (x) an idiotype immunoglobulin (an idiotype antibody or an idiotype B cell receptor); or (y) an idiotype T cell receptor, and optionally is not a fragment, variant and/or derivative of such antigen.

Furthermore, the at least one antigen, if provided as protein or peptide antigen is in certain embodiments not the model antigen Ovalbumine or a fragment of Ovalbumine, such as the Ovalbumine derived peptide SIINFEKL (SEQ ID NO: 116).

The at least one antigen in the inventive pharmaceutical composition can be provided as protein or peptide or can be encoded by a nucleic acid, e.g. a DNA (e.g. a plasmid DNA or viral DNA), or an RNA (e.g. an mRNA or a viral RNA). Preferably, the at least one antigen is provided as a protein or peptide, or a fragment, variant and/or derivative of said protein or peptide antigen. In certain embodiments, said protein or peptide antigen (or fragment, variant and/or derivative of said protein or peptide antigen) is comprised in, provided as or derived from a defined sample, for example a sample having a known number and or composition of components. For example, said protein or peptide antigen is not comprised in; or is not provided as; or is not derived from, in each case a mixture of (e.g. undefined) other components, such as a mixture being a preparation of inactivated or attenuated virus or pathogen (such as, in either case, any one describe herein). For example, the antigen used in any aspect of the present invention may be, or may be provided as, an isolated and/or purified protein or peptide antigen. As will be understood by the person of ordinary skill, an isolated (and/or purified) antigen includes such antigens that are present (or provided) in a (starting) composition that has less than about 40%, 30%, 20%, 10%, 5%, 2% or 1% non-desired or specified other components such as other proteins/peptides or impurities.

Protein or peptide antigens can, for example, be prepared as follows.

Protein or peptide antigens as described above, can be prepared using recombinant production methods, such as those described herein, or e.g. with the aid of molecular biology methods known to the person of ordinary skill. Such an antigen can be described, as applicable, as a "recombinant protein antigen" and/or a "recombinant peptide antigen".

Alternatively, a protein or peptide as described above (e.g fragments, domains, epitopes or protein antigens and/or peptide analogues) can be prepared using peptide synthesis methods such as those described herein, or e.g. with other methodologies known to the person of ordinary skill. Such an antigen can be described, as applicable, as a "synthetic protein antigen" and/or a "synthetic peptide antigen".

In case that the at least one antigen is provided as protein or peptide antigen (or a fragment, variant and/or derivative thereof), the peptide or protein antigen can be provided in a first alternative in a separate component of the inventive pharmaceutical composition. In this case the at least one protein or peptide antigen is not part of the polymeric carrier cargo complex or in other words: in this case the polymeric carrier cargo complex does not include the at least one antigen. In a second alternative the at least one protein or peptide antigen can be provided as component of the polymeric carrier cargo complex. In this case the peptide or protein antigen can be added to the polymeric carrier cargo complex during the polymerization step c) of the method of preparing of the polymeric carrier cargo complex as described herein. Thus, the peptide or protein antigen is integrated in the polymeric carrier cargo complex. Particularly preferred in this context is that the peptide or protein antigen bears at least one SH-moiety for polymerization with the other components of the polymeric carrier in the polymeric carrier cargo complex. Furthermore, in a further alternative a protein or peptide antigen is provided as component of the polymeric carrier of the polymeric carrier cargo complex and at least one additional protein or peptide antigen (the same or a different) is provided in a separate component of the inventive pharmaceutical composition which is not part of the polymeric carrier cargo complex.

Additionally, the at least one antigen (or a fragment, variant and/or derivative thereof) can be provided in the inventive pharmaceutical composition in the form of nucleic acids coding for the at least one antigen (or fragments, variants and/or derivatives thereof).

In this context, the nucleic acids coding for the at least one antigen (or fragments, variants and/or derivatives thereof) are defined as disclosed above for the nucleic acid cargo comprised in the polymeric carrier cargo complex used as an adjuvant in the inventive pharmaceutical composition. Therefore, also fragments, variants, derivatives and modifications of a nucleic acid as defined herein are explicitly encompassed.

The at least one antigen (or a fragment, variant and/or derivative thereof) if provided in the inventive pharmaceutical composition in the form of nucleic acids coding for the at least one antigen (or fragments, variants and/or derivatives thereof), can be prepared with all methods for nucleic acid synthesis known for a skilled person. Particularly preferred are methods for nucleic acid synthesis as defined herein.

Also in this case two alternatives exist. The first alternative provides the nucleic acid coding for the at least one antigen as part of the polymeric carrier cargo complex (e.g. as nucleic acid cargo molecule) and the second alternative provides the nucleic acid coding for the at least one antigen as separate component of the inventive pharmaceutical composition. Thus, in this case the nucleic acid coding for the at least one antigen is not part of the polymeric carrier cargo complex.

In a further embodiment of the present invention, the at least one antigen (or a fragment, variant and/or derivative thereof) coded by a nucleic acid can be provided as part of the (adjuvant) polymeric carrier cargo complex (e.g. as nucleic acid cargo coding for the at least one antigen) and additionally an antigen coded by a nucleic acid can be provided in a separate component which is not part of the polymeric carrier cargo complex.

The invention further provides the alternative that at least one antigen is provided as a nucleic acid (as part of the polymeric carrier cargo complex or not) and that at least one additional antigen is provided as protein or peptide antigen (as part of the polymeric carrier cargo complex or not).

As a further embodiment the at least one antigen if provided as protein or peptide or as a nucleic acid coding for the at least one antigen may further comprise or code for a signal peptide as defined herein.

As a further ingredient the pharmaceutical composition may comprise at least one additional pharmaceutically active component. A pharmaceutically active component in this connection is a compound that has a therapeutic effect to heal, ameliorate or prevent a particular indication, preferably tumour or cancer diseases, autoimmune disease, allergies or infectious diseases. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the pharmaceutical composition. If the pharmaceutical composition is provided in liquid form, the carrier will typically be pyrogen-free water; isotonic saline or buffered (aqueous) solutions, e.g phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person.

However, one or more compatible solid or liquid fillers or diluents or encapsulating compounds may be used as well for the pharmaceutical composition, which are suitable for administration to a patient to be treated. The term "compatible" as used here means that these constituents of the pharmaceutical composition are capable of being mixed with the polymeric carrier cargo complex as defined herein in such a manner that no interaction occurs which would substantially reduce the pharmaceutical effectiveness of the pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

According to a specific embodiment, the inventive pharmaceutical composition may comprise an (additional) adjuvant. In this context, an adjuvant may be understood as any compound, which is suitable to initiate or increase an immune response of the innate immune system, i.e. a non-specific immune response. With other words, when administered, the pharmaceutical composition typically elicits an innate immune response due to the adjuvant, optionally contained therein. Such an adjuvant may be selected from any adjuvant known to a skilled person and suitable for the present case, i.e. supporting the induction of an innate immune response in a mammal.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intraarticular, intra-nodal, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intraarticular, intra-nodal, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Particularly preferred is intradermal, subcutaneous and intramuscular injection. Sterile injectable forms of the pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as TWEEN®, Spans and other emulsifying agents or bioavailability enhancers which are commonly used in the manufacture of pharmaceutically acceptable solid, liquid, or other dosage forms may also be used for the purposes of formulation of the pharmaceutical composition.

The inventive pharmaceutical composition as defined herein may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the polymeric carrier cargo complex, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the pharmaceutical composition may be formulated in a suitable ointment, containing the polymeric carrier cargo complex suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

The inventive pharmaceutical composition typically comprises a "safe and effective amount" of the components of the pharmaceutical composition, particularly of the polymeric carrier cargo complex as defined herein or the nucleic acid as such. As used herein, a "safe and effective amount" means an amount of the polymeric carrier cargo complex as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment. A "safe and effective amount" of the components of the pharmaceutical composition, particularly of the polymeric carrier cargo complex or of the at least one antigen as defined herein, will furthermore vary in connection with the particular condition to be treated and also with the age and physical condition of the patient to be treated, the body weight, general health, sex, diet, time of administration, rate of excretion, drug combination, the activity of the polymeric carrier cargo complex or of the antigen, the severity of the condition, the duration of the treatment, the nature of the accompanying therapy, of the particular pharmaceutically acceptable carrier used, and similar factors, within the knowledge and experience of the accompanying doctor. The pharmaceutical composition may be used for human and also for veterinary medical purposes, preferably for human medical purposes, as a pharmaceutical composition in general or as a vaccine.

The inventive pharmaceutical composition can additionally contain one or more auxiliary substances in order to increase its immunogenicity or immunostimulatory capacity, if desired. A synergistic action of the (adjuvant) polymeric carrier cargo complex as defined herein and of an auxiliary substance, which may be optionally contained in the inventive pharmaceutical composition as defined herein, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the inventive pharmaceutical composition are emulsifiers, such as, for example, TWEEN®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The inventive pharmaceutical composition can also additionally or alternatively contain an immunostimulatory RNA, i.e. an RNA derived from an immunostimulatory RNA, which triggers or increases an (innate) immune response. Preferably, such an immunostimulatory RNA may be in general be as defined hereinbefore.

Another class of compounds, which may be added to the inventive pharmaceutical composition in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

In the context of the present invention, the nucleic acid cargo in the polymeric carrier cargo complex comprised in the inventive pharmaceutical composition is preferably as defined above. More preferably, the nucleic acid of the polymeric carrier cargo complex, preferably contained in the pharmaceutical composition, is typically an immunostimulatory nucleic acid as defined herein, e.g. a CpG-DNA or an immunostimulatory RNA (isRNA), preferably an isRNA. Alternatively or additionally, the nucleic acid of the polymeric carrier cargo complex, preferably contained in the pharmaceutical composition, is a coding nucleic acid sequence as defined herein, preferably a cDNA or an mRNA, more preferably encoding an adjuvant protein preferably as defined herein. In this context, the polymeric carrier cargo complex, typically initiates an innate immune response in the patient to be treated.

In a specific embodiment in this context, it is preferred that an adjuvant protein is a component of the polymeric carrier cargo complex and, preferably, of the polymeric carrier.

According to a further aspect, the present invention also provides kits, particularly kits of parts, comprising as components alone or in combination with optional further ingredients, and including (as a first component):

(A) a polymeric carrier cargo complex, comprising:
   a) (as a carrier) a polymeric carrier comprising disulfide-crosslinked cationic components, preferably formed by disulfide-crosslinked cationic components; and
   b) (as a cargo) at least one nucleic acid molecule, and
   (as a second component):
(B) at least one antigen that is selected from:
   (i) an antigen from a pathogen associated with infectious disease;
   (ii) an antigen associated with allergy or allergic disease;
   (iii) an antigen associated with autoimmune disease; or
   (iv) an antigen associated with a cancer or tumour disease, wherein in some embodiments the antigen associated with a cancer or tumour disease is another than an antigen comprising: (x) an idiotype immunoglobulin (e.g. an idiotype antibody or an idiotype B cell receptor); and/or (y) at least one idiotype T cell receptor,
   or a fragment, variant and/or derivative of said antigen;
in each case as defined anywhere herein, and optionally technical instructions with information on the administration and dosage of the polymeric carrier cargo complex and the at least one antigen. Such kits, preferably kits of parts, may be applied, e.g., for any of the applications or uses as defined herein. Such kits, when occurring as a kit of parts, may further contain each component of inventive pharmaceutical composition in a different part of the kit.

In certain embodiments of the kits of the present invention, the antigen is comprised in a vaccine.

The present invention furthermore provides several applications and uses of the inventive pharmaceutical composition (e.g. the adjuvanted vaccine) or of kits or kits of parts comprising same as defined anywhere herein.

In this context, the present invention also provides a method for transfecting and/or treating a cell, a tissue or an organism, thereby applying or administering the inventive pharmaceutical composition particularly for therapeutic purposes. In this context, typically after preparing the inventive pharmaceutical composition, the inventive pharmaceutical composition is preferably administered to a cell, a tissue or an organism, preferably using any of the administration modes as described herein. The method for transfecting and/or treating a cell may be carried out in vitro, in vivo or ex vivo.

Furthermore, the present invention provides the use of a pharmaceutical composition or of kits or kits of parts in each case as defined anywhere herein, in therapy and/or as a medicament, preferably as a vaccine such as an adjuvanted vaccine.

Also in certain embodiments of all aspects of the present invention, the at least one antigen is not selected from: (x) an idiotype immunoglobulin (an idiotype antibody or an idiotype B cell receptor); or (y) at least one idiotype T cell receptor; and optionally is not a fragment, variant and/or derivative of such antigen.

In this aspect of the present invention, particularly preferred is the use of the inventive pharmaceutical composition or of the kits or kits of parts comprising same as defined herein in the treatment of infectious diseases, allergies or allergic diseases, autoimmune diseases and cancer or tumour diseases, in each case as defined anywhere herein.

In this context, infectious diseases are preferably viral, bacterial or protozoological infectious diseases. Such infectious diseases, preferably (viral, bacterial or protozoological) infectious diseases, are typically selected from the list consisting of *Acinetobacter* infections, African sleeping sickness (African trypanosomiasis), AIDS (Acquired immunodeficiency syndrome), Amoebiasis, Anaplasmosis, Anthrax, Appendicitis, *Arcanobacterium haemolyticum* infections, Argentine hemorrhagic fever, Ascariasis, Aspergillosis, Astrovirus infections, Athlete's foot, Babesiosis, *Bacillus cereus* infections, Bacterial meningitis, Bacterial pneumonia, Bacterial vaginosis (BV), *Bacteroides* infections, Balantidiasis, *Baylisascaris* infections, Bilharziosis, BK virus infections, Black *piedra*, *Blastocystis hominis* infections, Blastomycosis, Bolivian hemorrhagic fever, *Borrelia* infectionss (Borreliosis), Botulism (and Infant botulism), Bovine tapeworm, Brazilian hemorrhagic fever, Brucellosis, *Burkholderia* infections, Buruli ulcer, Calicivirus infections (Norovirus and Sapovirus), Campylobacteriosis, Candidiasis (Candidosis), Canine tapeworm infections, Cat-scratch disease, Chagas Disease (American trypanosomiasis), Chancroid, Chickenpox, *Chlamydia* infections, *Chlamydia trachomatis* infections, *Chlamydophila pneumoniae* infections, Cholera, Chromoblastomycosis, Climatic bubo, Clonorchiasis, *Clostridium difficile* infections, Coccidioidomycosis, Cold, Colorado tick fever (CTF), Common cold (Acute viral rhinopharyngitis; Acute coryza), Condyloma *acuminata*, Conjunctivitis, Creutzfeldt-Jakob disease (CJD), Crimean-Congo hemorrhagic fever (CCHF), Cryptococcosis, Cryptosporidiosis, Cutaneous larva migrans (CLM), Cutaneous Leishmaniasis, Cyclosporiasis, Cysticercosis, Cytomegalovirus infections, Dengue fever, Dermatophytosis, Dientamoebiasis, Diphtheria, Diphyllobothriasis, Donavanosis, Dracunculiasis, Early summer meningoencephalitis (FSME), Ebola hemorrhagic fever, Echinococcosis, Ehrlichiosis, Enterobiasis (Pinworm infections), *Enterococcus* infections, Enterovirus infections, Epidemic typhus, Epiglottitis, Epstein-Barr Virus Infectious Mononucleosis, Erythema infectiosum (Fifth disease), Exanthem subitum, Fasciolopsiasis, Fasciolosis, Fatal familial insomnia (FFI), Fifth disease, Filariasis, Fish poisoning (Ciguatera), Fish tapeworm, Flu, Food poisoning by *Clostridium perfringens*, Fox tapeworm, Free-living amebic infections, *Fusobacterium* infections, Gas gangrene, Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infections, Group B streptococcal infections, *Haemophilus influenzae* infections, Hand foot and mouth disease (HFMD), Hantavirus Pulmonary Syndrome (HPS), *Helicobacter pylori* infections, Hemolytic-uremic syndrome (HUS), Hemorrhagic fever with renal syndrome (HFRS), Henipavirus infections, Hepatitis A, Hepatitis B, Hepatitis C, Hepatitis D, Hepatitis E, Herpes simplex, Herpes simplex type I, Herpes simplex type II, Herpes zoster, Histoplasmosis, Hollow warts, Hookworm infections, Human bocavirus infections, Human *ewingii* ehrlichiosis, Human granulocytic anaplasmosis (HGA), Human metapneumovirus infections, Human monocytic ehrlichiosis, Human papillomavirus (HPV) infections, Human parainfluenza virus infections, Hymenolepiasis, Influenza, Isosporiasis, Japanese encephalitis, Kawasaki disease, Keratitis, Kingella kingae infections, Kuru, Lambliasis (Giardiasis), Lassa fever, Legionellosis (Legionnaires' disease, Pontiac fever), Leishmaniasis, Leprosy, Leptospirosis, Lice, Listeriosis, Lyme borreliosis, Lyme disease, Lymphatic filariasis (Elephantiasis), Lymphocytic choriomeningitis, Malaria, Marburg hemorrhagic fever (MHF), Marburg virus, Measles, Melioidosis (Whitmore's disease), Meningitis, Meningococcal disease, Metagonimiasis, Microsporidiosis, Miniature tapeworm, Miscarriage (prostate inflammation), Molluscum contagiosum (MC), Mononucleosis, Mumps, Murine typhus (Endemic typhus), Mycetoma, *Mycoplasma hominis*, *Mycoplasma* pneumonia, Myiasis, Nappy/diaper dermatitis, Neonatal conjunctivitis (Ophthalmia neonatorum), Neonatal sepsis (Chorioamnionitis), Nocardiosis, Noma, Norwalk virus infections, Onchocerciasis (River blindness), Osteomyelitis, Otitis media, Paracoccidioidomycosis (South American blastomycosis), Paragonimiasis, Paratyphus, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Pfeiffer's glandular fever, Plague, Pneumococcal infections, *Pneumocystis* pneumonia (PCP), Pneumonia, Polio (childhood lameness), Poliomyelitis, Porcine tapeworm, *Prevotella* infections, Primary amoebic meningoencephalitis (PAM), Progressive multifocal leukoencephalopathy, Pseudo-croup, Psittacosis, Q fever, Rabbit fever, Rabies, Rat-bite fever, Reiter's syndrome, Respiratory syncytial virus infections (RSV), Rhinosporidiosis, Rhinovirus infections, Rickettsial infections, Rickettsialpox, Rift Valley fever (RVF), Rocky mountain spotted fever (RMSF), Rotavirus infections, Rubella, *Salmonella* paratyphus, *Salmonella* typhus, *Salmonellosis*, SARS (Severe Acute Respiratory Syndrome), Scabies, Scarlet fever, Schistosomiasis (Bilharziosis), Scrub typhus, Sepsis, Shigellosis (Bacillary dysentery), Shingles, Smallpox (Variola), Soft chancre, Sporotrichosis, Staphylococcal food poisoning, Staphylococcal infections, Strongyloidiasis, Syphilis, Taeniasis, Tetanus, Three-day fever, Tick-borne encephalitis, Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM) and Visceral Larva Migrans (VLM)), Toxoplasmosis, Trichinellosis, Trichomoniasis, Trichuriasis (Whipworm infections), Tripper, Trypanosomiasis (sleeping sickness), Tsutsugamushi disease, Tuberculosis, Tularemia, Typhus, Typhus fever, *Ureaplasma urealyticum* infections, Vaginitis (Colpitis), Variant Creutzfeldt-Jakob disease (vCJD, nvCJD), Venezuelan equine encephalitis, Venezuelan hemorrhagic fever, Viral pneumonia, Visceral Leishmaniosis, Warts, West Nile Fever, Western equine encephalitis, White *piedra* (Tinea blanca), Whooping cough, Yeast fungus spots, Yellow fever, *Yersinia pseudotuberculosis* infections, Yersiniosis, and Zygomycosis.

Allergies or allergic diseases are preferably selected from pollen allergy (allergy against grass pollen, tree pollen (e.g. pollen of hazel, birch, alder, ash), flower pollen, herb pollen (e.g. pollen of mugwort)), dust mite allergy, mold allergy (e.g. allergy against *Acremonium, Aspergillus, Cladosporium, Fusarium, Mucor, Penicillium, Rhizopus, Stachybotrys, Trichoderma,* or *Alternaria*), pet allergy (allergy against animals; e.g against cats, dogs, horses), food allergy (e.g. allergy against fish (e.g. bass, cod, flounder), seafood (e.g. crab, lobster, shrimps), egg, wheat, nuts (e.g. peanuts, almonds, cashews, walnuts), soya, milk, etc.) or insect bite allergy (allergy against insect venom, e.g. venom of wasps, bees, hornets, ants, mosquitos, or ticks).

According to another specific embodiment, diseases as defined herein comprise autoimmune diseases as defined in the following. Autoimmune diseases are preferably selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barrd syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, *borrelia* arthritis), Mdnierd's disease (Morbus Mdnierd); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis *nodosa* (periarteiitis *nodosa*), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjdgren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis).

Furthermore, cancer or tumor diseases are preferably selected from melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumors such as, for example, papilloma virus-induced carcinomas (e.g. cervical carcinoma=cervical cancer), adenocarcinomas, herpes virus-induced tumors (e.g. Burkitt's lymphoma, EBV-induced B-cell lymphoma), heptatitis B-induced tumors (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma (=oesophageal cancer), wart involvement, tumors of the small intestine, craniopharyngeomas, ovarian carcinoma, genital tumors, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumor, prostate cancer (=prostate tumors), etc.

In a further aspect, the present invention provides a polymeric carrier cargo complex as defined anywhere herein, such as one comprising:
 a) (as a carrier) a polymeric carrier comprising disulfide-crosslinked cationic components, preferably formed by disulfide-crosslinked cationic components; and
 b) (as a cargo) at least one nucleic acid molecule
for use in therapy in combination with at least one antigen, preferably a protein or peptide antigen or a fragment, variant and/or derivative thereof, in each case as defined anywhere herein, particularly in the treatment of infectious diseases, allergies or allergic diseases, autoimmune diseases and cancer or tumour diseases as defined above.

Additionally, the present invention provides at least one antigen, preferably a protein or peptide antigen or a fragment, variant and/or derivative thereof, in each case as defined anywhere herein, for use in therapy in combination with a polymeric carrier cargo complex as defined anywhere herein, such as one comprising:
 a) (as a carrier) a polymeric carrier comprising disulfide-crosslinked cationic components, preferably formed by disulfide-crosslinked cationic components, and
 b) (as a cargo) at least one nucleic acid molecule,
particularly in the treatment of infectious diseases, allergies or allergic diseases, autoimmune diseases and cancer or tumour diseases as defined above.

In certain embodiments of such aspects of the present invention, the antigen is comprised in a vaccine, such as a commercially available vaccine.

In this context, "in combination" means that the different components (the polymeric carrier cargo complex and the at least one antigen, or a fragment, variant and/or derivative thereof) can be provided together in the same composition, or can be formulated separately in different compositions, i.e. one composition comprising or representing the polymeric carrier cargo complex as defined herein, and one further composition comprising the at least one antigen, or a fragment, variant and/or derivative thereof as defined herein. If provided in different compositions the polymeric carrier cargo complex and the at least one antigen or a fragment, variant and/or derivative thereof may be administered separated in time (in a time-staggered manner) and/or may be administered at different administration sites and/or via different administration routes. This means that the polymeric carrier cargo complex may be administered e.g. prior, concurrent or subsequent to the at least one antigen, or fragment, variant and/or derivative thereof, or vice versa. Subsequent administration includes that each component used in the therapy is administered within about 48 hours, 24 hours, 12 hours, 8 hours, 6 hours, 4 hours, 2 hours, 1 hour, 30 mins, 15 mins or 5 mins of each other.

In a further aspect, the present invention provides a pharmaceutical package, including:
(A) a polymeric carrier cargo complex, comprising:
  a) (as a carrier) a polymeric carrier comprising disulfide-crosslinked cationic components, preferably formed by disulfide-crosslinked cationic components, and
  b) (as a cargo) at least one nucleic acid molecule, as defined anywhere herein;
and
(B) instructions describing the use of said polymeric carrier cargo complex in therapy in combination with at least one antigen or fragment, variant and/or derivative thereof as defined anywhere herein.

The pharmaceutical package may further comprise at least one antigen or fragment, variant and/or derivative thereof as defined anywhere herein.

Furthermore, the present invention provides in an additional embodiment a pharmaceutical package, including:
(A) at least one antigen or fragment, variant and/or derivative thereof, in each case as defined anywhere herein;
and
(B) instructions describing the use of said antigen or fragment, variant and/or derivative thereof in therapy in combination with a polymeric carrier cargo complex as defined anywhere herein.

The pharmaceutical package may further comprise a polymeric carrier cargo complex, comprising:
  a) (as a carrier) a polymeric carrier comprising disulfide-crosslinked cationic components, preferably formed by disulfide-crosslinked cationic components, and
  b) (as a cargo) at least one nucleic acid molecule, as defined anywhere herein.

In this context, the invention furthermore provides the use of the components included in the above defined pharmaceutical packages in the treatment of the particular disease (indication) selected from an infectious disease, an allergy or allergic disease, an autoimmune disease or a cancer or tumour disease as defined above. The respective disease may be one as described anywhere herein.

In the present invention, if not otherwise indicated, different features of alternatives and embodiments may be combined with each other, where suitable.

Taken together, in a preferred embodiment, the invention relates to
a pharmaceutical composition comprising
a polymeric carrier cargo complex and
at least one protein or peptide antigen
or a fragment, variant and/or derivative of said protein or peptide antigen;
wherein the polymeric carrier cargo complex comprises
  a polymeric carrier,
    preferably a polymeric carrier comprising disulfide-crosslinked cationic components, preferably formed by disulfide-crosslinked cationic components,
    more preferably one or more peptides according to formula (I) $(Arg)_l;(Lys)_m;(His);(Orn)_o;(Xaa)_x$ as defined above most preferably according to subformula (IA) or (IB) thereof as defined above,
  and at least one nucleic acid molecule,
    preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen.

In a further preferred embodiment, the invention relates to
a pharmaceutical composition comprising
a polymeric carrier cargo complex and
at least one protein or peptide antigen
or a fragment, variant and/or derivative of said protein or peptide antigen;
wherein the polymeric carrier cargo complex comprises
  a polymeric carrier,
    preferably a polymeric carrier comprising disulfide-crosslinked cationic components, preferably formed by disulfide-crosslinked cationic components,
    more preferably one or more peptides according to formula (I) $(Arg)_l;(Lys)_m;(His);(Orn)_o;(Orn)_o;(Xaa)_x$ as defined above, most preferably according to subformula (IA) or (IB) thereof as defined above,
  and at least one nucleic acid molecule,
    preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen, and wherein the protein or peptide antigen or the fragment, variant and/or derivative of said protein or peptide antigen is selected from:

an antigen from a pathogen associated with infectious disease, an antigen associated with allergy or allergic disease, an antigen associated with autoimmune disease, an antigen associated with a cancer or tumour disease.

In a further preferred embodiment, the invention relates to a pharmaceutical composition comprising a polymeric carrier cargo complex and at least one protein or peptide antigen or a fragment, variant and/or derivative of said protein or peptide antigen;

wherein the polymeric carrier cargo complex comprises a polymeric carrier, preferably a polymeric carrier comprising disulfide-crosslinked cationic components, preferably formed by disulfide-crosslinked cationic components, more preferably one or more peptides according to formula (I) $(Arg)_l;(Lys)_m;(His);(Orn)_o;(Orn)_o;(Xaa)_x$ as defined above, most preferably according to subformula (IA) or (IB) thereof as defined above, and at least one nucleic acid molecule, preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;

wherein the protein or peptide antigen or the fragment, variant and/or derivative of said protein or peptide antigen is selected from:

an antigen from a pathogen associated with infectious disease, an antigen associated with allergy or allergic disease, an antigen associated with autoimmune disease, an antigen associated with a cancer or tumour disease;

and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising a polymeric carrier cargo complex and at least one protein or peptide antigen or a fragment, variant and/or derivative of said protein or peptide antigen;

wherein the polymeric carrier cargo complex comprises a polymeric carrier, preferably a polymeric carrier comprising disulfide-crosslinked cationic components, preferably formed by disulfide-crosslinked cationic components, more preferably one or more peptides according to formula (I) $(Arg)_l;(Lys)_m;(His)_n;(Orn)_o;(Xaa)_x$ as defined above, most preferably according to subformula (IA) or (IB) thereof as defined above, and at least one nucleic acid molecule, preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;

wherein the protein or peptide antigen or the fragment, variant and/or derivative of said protein or peptide antigen is selected from an antigen from a pathogen associated with infectious disease, an antigen from a pathogen associated with infectious disease, an antigen associated with allergy or allergic disease, an antigen associated with autoimmune disease, an antigen associated with a cancer or tumour disease, preferably an antigen from a pathogen associated with infectious disease, more preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*,
more preferably an antigen from a pathogen selected from Rabies virus, Hepatitis B virus, human Papilloma virus (hPV);
and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier comprising disulfide-crosslinked cationic components, preferably formed by disulfide-crosslinked cationic components,
more preferably one or more peptides according to formula (I) $(Arg)_l;(Lys)_m;(His)_n;(Orn)_o;(Xaa)_x$ as defined above, most preferably according to subformula (IA) or (IB) thereof as defined above,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;
and wherein the protein or peptide antigen
or the fragment, variant and/or derivative of said protein or peptide antigen is selected from an antigen from a pathogen associated with infectious disease,
an antigen associated with allergy or allergic disease,
an antigen associated with autoimmune disease,
an antigen associated with a cancer or tumour disease,
preferably an antigen from a pathogen associated with infectious disease,
more preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*,
even more preferably an antigen from Rabies virus, most preferably an antigen from Rabies virus which is selected from the nucleoprotein (N), the phosphoprotein (P), the matrix protein (M), the glycoprotein (G), and the viral RNA polymerase (L);
and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier comprising disulfide-crosslinked cationic components, preferably formed by disulfide-crosslinked cationic components,
more preferably one or more peptides according to formula (I) $(Arg)_l;(Lys)_m;(His)_n;(Orn)_o;(Xaa)_x$ as defined above, most preferably according to subformula (IA) or (IB) thereof as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above,
or a nucleic acid molecule which encodes an antigen, more preferably a nucleic acid molecule which encodes an antigen which is the same antigen as the at least one protein or peptide antigen;
and wherein the protein or peptide antigen
or the fragment, variant and/or derivative of said protein or peptide antigen is selected from an antigen from a pathogen associated with infectious disease,
an antigen associated with allergy or allergic disease,
an antigen associated with autoimmune disease,
an antigen associated with a cancer or tumour disease,
preferably an antigen from a pathogen associated with infectious disease,
more preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*, even more preferably an antigen from Hepatitis B virus, most preferably an antigen from Hepatitis B virus which is selected from the Hepatitis B surface antigen (HBsAg), the Hepatitis B core antigen (HbcAg), the Hepatitis B virus DNA polymerase, the HBx protein, the preS2 middle surface protein, the large S protein, the virus protein VP1, the virus protein VP2, the virus protein VP3, and the virus protein VP4;

and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising a polymeric carrier cargo complex and at least one protein or peptide antigen or a fragment, variant and/or derivative of said protein or peptide antigen;

wherein the polymeric carrier cargo complex comprises
 a polymeric carrier,
  preferably a polymeric carrier comprising disulfide-crosslinked cationic components, preferably formed by disulfide-crosslinked cationic components,
   more preferably one or more peptides according to formula (I) $(Arg)_l;(Lys)_m;(His);(Orn)_o;(Orn)_o;(Xaa)_x$ as defined above, most preferably according to subformula (IA) or (IB) thereof as defined above,
  and at least one nucleic acid molecule,
   preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;

and wherein the protein or peptide antigen
 or the fragment, variant and/or derivative of said protein or peptide antigen is selected from an antigen from a pathogen associated with infectious disease, an antigen associated with allergy or allergic disease, an antigen associated with autoimmune disease, an antigen associated with a cancer or tumour disease, preferably an antigen from a pathogen associated with infectious disease, more preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*, even more preferably an antigen from Influenza virus, most preferably an antigen from Influenza virus which is selected from the Hemagglutinin (HA), the Neuraminidase (NA), the Nucleoprotein (NP), the M1 protein, the M2 protein, the NS1 protein, the NS2 protein (the NEP protein: nuclear export protein), the PA protein, the PB1 protein (polymerase basic 1 protein), the PB1-F2 protein and the PB2 protein of Influenza virus;

and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising a polymeric carrier cargo complex and at least one protein or peptide antigen or a fragment, variant and/or derivative of said protein or peptide antigen;

wherein the polymeric carrier cargo complex comprises
 a polymeric carrier,
  preferably a polymeric carrier comprising disulfide-crosslinked cationic components, preferably formed by disulfide-crosslinked cationic components,
   more preferably one or more peptides according to formula (I) $(Arg)_l;(Lys)_m;(His);(Orn)_o;(Orn)_o;(Xaa)_x$ as defined above, most preferably according to subformula (IA) or (IB) thereof as defined above,
  and at least one nucleic acid molecule,
   preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;

and wherein the protein or peptide antigen
 or the fragment, variant and/or derivative of said protein or peptide antigen is selected from an antigen from a pathogen associated with infectious disease, an antigen associated with allergy or allergic disease, an antigen associated with autoimmune disease, an antigen associated with a cancer or tumour disease,
preferably an antigen from a pathogen associated with infectious disease,
preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*,
more preferably an antigen from human Papilloma virus (hPV), even more preferably an antigen from human Papilloma virus (hPV) which is selected from the E1 protein, the E2 protein, the E3 protein, the E4 protein, the E5 protein, the E6 protein, the E7 protein, the E8 protein, the L1 protein, and the L2 protein;
and preferably wherein the protein or peptide antigen and/or the fragment, variant and/or derivative of said protein or peptide antigen is not included in the polymeric carrier cargo complex.

In a further preferred embodiment, the invention relates to
a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier comprising disulfide-crosslinked cationic components, preferably formed by disulfide-crosslinked cationic components,
more preferably one or more peptides according to formula (I) $(Arg)_l;(Lys)_m;(His);(Orn)_o;(Orn)_o;(Xaa)_x$ as defined above most according to subformula (IA) or (IB) thereof as defined above,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;
and wherein the protein or peptide antigen
or the fragment, variant and/or derivative of said protein or peptide antigen is selected from an antigen from a pathogen associated with infectious disease, an antigen associated with allergy or allergic disease, an antigen associated with autoimmune disease, an antigen associated with a cancer or tumour disease, preferably an antigen from a pathogen associated with infectious disease,
preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*,
more preferably an antigen from *Bacillus anthracis*, even more preferably an antigen from *Bacillus anthracis* which is selected from the protective antigen (PA), the edema factor (EF), the lethal factor (LF), and the S-layer homology proteins (SLH);
and preferably wherein the protein or peptide antigen and/or the fragment, variant and/or derivative of said protein or peptide antigen is not included in the polymeric carrier cargo complex.

In a further preferred embodiment, the invention relates to
a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier comprising disulfide-crosslinked cationic components, preferably formed by disulfide-crosslinked cationic components,
more preferably one or more peptides according to formula (I) $(Arg)_l;(Lys)_m;(His);(Orn)_o;(Xaa)_x$ as defined above most according to subformula (IA) or (IB) thereof as defined above,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122,
or a nucleic acid molecule which encodes an antigen, more preferably a nucleic acid molecule which encodes an antigen which is the same antigen as the at least one protein or peptide antigen;
and wherein the protein or peptide antigen
or the fragment, variant and/or derivative of said protein or peptide antigen is selected from an antigen from a pathogen associated with infectious disease,
an antigen associated with allergy or allergic disease,
an antigen associated with autoimmune disease,
an antigen associated with a cancer or tumour disease,
preferably an antigen from a pathogen associated with infectious disease, more preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*,
    even more preferably an antigen from Respiratory syncytial virus (RSV),
        most preferably an antigen from Respiratory syncytial virus (RSV) which is selected from the Fusion (F) protein, the nucleocapsid (N) protein, the phosphoprotein (P), the matrix (M) protein, the glycoprotein (G), the large protein (L; RNA polymerase), the non-structural protein 1 (NS1), the non-structural protein 2 (NS2), the small hydrophobic (SH) protein, the elongation factor M2-1, and the transcription regulation protein M2-2;
and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising a polymeric carrier cargo complex and at least one protein or peptide antigen or a fragment, variant and/or derivative of said protein or peptide antigen;

wherein the polymeric carrier cargo complex comprises
    a polymeric carrier,
        preferably a polymeric carrier comprising disulfide-crosslinked cationic components, preferably formed by disulfide-crosslinked cationic components,
            more preferably one or more peptides according to formula (I) $(Arg)_l;(Lys)_m;(His);(Orn)_o;(Xaa)_x$ as defined above most according to subformula (IA) or (IB) thereof as defined above,
    and at least one nucleic acid molecule,
        preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;

and wherein the protein or peptide antigen or the fragment, variant and/or derivative of said protein or peptide antigen is selected from an antigen from a pathogen associated with infectious disease, an antigen associated with allergy or allergic disease, an antigen associated with autoimmune disease, an antigen associated with a cancer or tumour disease,
preferably an antigen from a pathogen associated with infectious disease,
    more preferably an antigen from a pathogen selected from Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*,
        even more preferably an antigen from Herpes simplex virus (HSV),
            most preferably an antigen from Herpes simplex virus (HSV) which is selected from the Glycoprotein L (UL1), the Uracil-DNA glycosylase UL2, the UL3 protein, the UL4 protein, the DNA replication protein UL5, the Portal protein UL6, the Virion maturation protein UL7, the DNA helicase UL8, the Replication origin-binding protein UL9, the Glycoprotein M (UL10), the UL11 protein, the Alkaline exonuclease UL12, the Serine-threonine protein kinase UL13, the Tegument protein UL14, the Terminase (UL15), the Tegument protein UL16, the UL17 protein, the Capsid protein VP23 (UL18), the Major capsid protein VP5 (UL19), the Membrane protein UL20, the Tegument protein UL21, the Glycoprotein H (UL22), the Thymidine Kinase UL23, the UL24 protein, the UL25 protein, the Capsid protein P40 (UL26, VP24, VP22A), the Glycoprotein B (UL27), the ICP18.5 protein (UL28), the Major DNA-binding protein ICP8 (UL29), the DNA polymerase UL30, the Nuclear matrix protein UL31, the Envelope glycoprotein UL32, the UL33 protein, the Inner nuclear membrane protein UL34, the Capsid protein VP26 (UL35), the Large tegument protein UL36, the Capsid assembly protein UL37, the VP19C protein (UL38), the Ribonucleotide reductase (Large subunit) UL39, the Ribonucleotide reductase (Small subunit) UL40, the Tegument protein/Virion host shutoff VHS protein (UL41), the DNA polymerase processivity factor UL42, the Membrane protein UL43, the Glycoprotein C (UL44), the Membrane protein UL45, the Tegument proteins VP11/12 (UL46), the Tegument protein VP13/14 (UL47), the Virion maturation protein VP16 (UL48, Alpha-TIF), the Envelope protein UL49, the dUTP diphosphatase UL50, the Tegument protein UL51, the DNA helicase/primase complex protein UL52, the Glycoprotein K (UL53), the Transcriptional regulation protein IE63 (ICP27, UL54), the UL55 protein, the UL56 protein, the Viral replication protein ICP22 (IE68, US1), the US2 protein, the Serine/threonine-protein kinase US3, the Glycoprotein G (US4), the Glycoprotein J (US5), the Glycoprotein D (US6), the Glycoprotein I (US7), the Glycoprotein E (US8), the Tegument protein US9, the Capsid/Tegument protein US10, the Vmw21 protein (US11), the ICP47 protein (IE12, US12), the Major transcriptional activator ICP4 (IE175, RS1), the E3 ubiquitin ligase ICP0 (IE110), the Latency-related protein 1 (LRP1), the Latency-related protein 2 (LRP2), the Neurovirulence factor RL1 (ICP34.5), and
the Latency-associated transcript (LAT);
and preferably wherein the protein or peptide antigen and/or the fragment, variant and/or derivative of said protein or peptide antigen is not included in the polymeric carrier cargo complex.

In a further preferred embodiment, the invention relates to a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier comprising disulfide-crosslinked cationic components, preferably formed by disulfide-crosslinked cationic components,
more preferably one or more peptides according to formula (I) $(Arg)_l;(Lys)_m;(His);(Orn)_o;(Orn)_o;(Xaa)_x$ as defined above, most preferably according to subformula (IA) or (IB) thereof as defined above,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122,
or a nucleic acid molecule which encodes an antigen, more preferably a nucleic acid molecule which encodes an antigen which is the same antigen as the at least one protein or peptide antigen;
and wherein the protein or peptide antigen
or the fragment, variant and/or derivative of said protein or peptide antigen is selected from an antigen from a pathogen associated with infectious disease,
an antigen associated with allergy or allergic disease,
an antigen associated with autoimmune disease,
an antigen associated with a cancer or tumour disease,
preferably an antigen from a pathogen associated with infectious disease,
more preferably an antigen from a pathogen selected from Rabies virus, Hepatitis B virus, human Papilloma virus (hPV), *Bacillus anthracis*, Respiratory syncytial virus (RSV), Herpes simplex virus (HSV), and *Mycobacterium tuberculosis*, even more preferably an antigen from *Mycobacterium tuberculosis,*
most preferably an antigen from *Mycobacterium tuberculosis* which is selected from from the ESAT-6 protein, the ESX-1 protein, the CFP10 protein, the TB10.4 protein, the MPT63 protein, the MPT64 protein, the MPT83 protein, the MTB12 protein, the MTB8 protein, the AG85A protein, the AG85B protein, the Rpf-like proteins, the KATG protein, the PPE18 protein, the MTB32 protein, the MTB39 protein, the Crystallin, the HSP65 protein, the PST-S protein, and the HBHA protein, the 10 kDa filtrate antigen EsxB, the serine protease PepA, the fibronectin-binding protein D FbpD, the secreted protein MPT51, the periplasmic phosphate-binding lipoprotein PSTS1 (PBP-1), the periplasmic phosphate-binding lipoprotein PSTS3 (PBP-3, Phos-1), the PPE family protein PPE14, the PPE family protein PPE68, the protein MTB72F, the molecular chaperone DnaK, the cell surface lipoprotein MPT83, the lipoprotein P23, the Phosphate transport system permease protein PstA, the 14 kDa antigen, the fibronectin-binding protein C FbpC1, the Alanine dehydrogenase TB43, and the Glutamine synthetase 1;
and preferably wherein the protein or peptide antigen and/or the fragement, variant and/or derivative of said protein or peptide antigen is not included in the polymeric carrier cargo complex.

In a further preferred embodiment, the invention relates to a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier comprising disulfide-crosslinked cationic components, preferably formed by disulfide-crosslinked cationic components,
more preferably one or more peptides according to formula (I) $(Arg)_l;(Lys)_m;(His);(Orn)_o;(Orn)_o;(Xaa)_x$ as defined above most according to subformula (IA) or (IB) thereof as defined above,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122,
or a nucleic acid molecule which encodes an antigen, more preferably a nucleic acid molecule which encodes an antigen which is the same antigen as the at least one protein or peptide antigen;

and wherein the protein or peptide antigen
or the fragment, variant and/or derivative of said protein or peptide antigen is selected from an antigen from a pathogen associated with infectious disease,
an antigen associated with allergy or allergic disease,
an antigen associated with autoimmune disease,
an antigen associated with a cancer or tumour disease,
preferably a protein or peptide antigen which is associated with allergy or allergic disease and derived from a source selected from the list consisting of: grass pollen, tree pollen, flower pollen, herb pollen, dust mite, mold, animals, food, and insect venom, preferably tree pollen, flower pollen, herb pollen dust mite, food, and insect venom, most preferably an allergen as listed above,
and preferably wherein the protein or peptide antigen and/or the fragment, variant and/or derivative of said protein or peptide antigen is not included in the polymeric carrier cargo complex.

In a further preferred embodiment, the invention relates to
a pharmaceutical composition comprising
a polymeric carrier cargo complex and
at least one protein or peptide antigen
or a fragment, variant and/or derivative of said protein or peptide antigen;
wherein the polymeric carrier cargo complex comprises
a polymeric carrier,
preferably a polymeric carrier formed by disulfide-crosslinked cationic components,
more preferably one or more peptides according to formula (I) $(Arg)_l;(Lys)_m;(His);(Orn)_o;(Xaa)_x$ as defined above most according to subformula (IA) or (IB) thereof as defined above,
and at least one nucleic acid molecule,
preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen,
and wherein the protein or peptide antigen
or the fragment, variant and/or derivative of said protein or peptide antigen is selected from an antigen from a pathogen associated with infectious disease,
an antigen associated with allergy or allergic disease,
an antigen associated with autoimmune disease,
an antigen associated with a cancer or tumour disease,
preferably an antigen associated with autoimmune disease,
more preferably an antigen associated with multiple sclerosis (MS); diabetes Typ I; autoimmune uveitis; Myasthenia gravis; Rheumatic Fever; Arthritis; Sjdgren's syndrome; lupus erythematosus; Atherosclerosis; idiopathic dilated cardiomyopathy (DCM); myositis or scleroderma,
even more preferably an antigen selected from the group comprising myelin basic protein (MBP), proteolipid protein (PLP), and myelin oligodendrocyte glycoprotein (MOG), CD44, preproinsulin, proinsulin, insulin, glutamic acid decarboxylase (GAD65), tyrosine phosphatase-like insulinoma antigen 2 (IA2), zinc transporter ((ZnT8), and heat shock protein 60 (HSP60), interphotoreceptor retinoid-binding protein (IRBP), acetylcholine receptor AchR, and insulin-like growth factor-1 receptor (IGF-1R), M-protein from beta-hemolytic streptocci (pseudo-autoantigen), Macrophage migration inhibitory factor, Ro/La RNP complex, alpha- and beta-fodrin, islet cell autoantigen, poly (ADP)ribose polymerase (PARP), NuMA, NOR-90, Ro60 autoantigen, and p27 antigen, Ro60 autoantigen, low-density lipoproteins, Sm antigens of the U-1 small nuclear ribonucleoprotein complex (B/B', D1, D2, D3, E, F, G), and RNP ribonucleoproteins, oxLDL, beta(2) GPI, HSP60/65, and oxLDL/beta(2)GPI, cardiac beta(1)-adrenergic receptor, histidyl-tRNA synthetase (HisRS), topoisomerase I, IL-17; or heat shock proteins;
and preferably wherein the protein or peptide antigen and/or the fragment, variant and/or derivative of said protein or peptide antigen is not included in the polymeric carrier cargo complex.

Provided the antigen is associated with an autoimmune disease, it may be further preferred if the antigen is an immunoglobulin idiotype or a T cell receptor idiotype of a lymphoid cell, preferably of a B-cell or a T-cell. Such lymphoid cells, e.g. B-cells or T-cells may be responsible for destruction of body-cells, such as e.g. pancreatic beta-cells, if they are erroneously programmed to recognise and fight self-epitopes of the body. In this context, an immunoglobulin idiotype may be understood to be a peptide or protein having the particular molecular shape of the variable region of an immunoglobulin expressed by a particular type of B-cells. Such an idiotype may be used as antigen for eliciting an immune response directed against this particular type of B-cells, for example against malignant B-cells. A T cell receptor idiotype may be understood to be a peptide or protein having the particular molecular shape of the variable region of a T cell receptor expressed by a particular type of T-cells. Such an idiotype may be used as antigen for eliciting an immune response directed against this particular type of T-cells, for example against malignant T-cells. The inventive pharmaceutical composition may be used, for example, for vaccination against such mis-programmed lymphoid cells. E.g. treatment of a patient suffering from an autoimmune disease, such as e.g. Diabetes, Crohn's disease, Multiple sclerosis or the like, may occur by destruction of malfunctional lymphoid cells which attact the own body and subsequent vaccination with the inventive pharmaceutical composition.

In a further preferred embodiment, the invention relates to
a pharmaceutical composition comprising
a polymeric carrier cargo complex and
at least one protein or peptide antigen or a fragment, variant and/or derivative of said protein or peptide antigen;

wherein the polymeric carrier cargo complex comprises a polymeric carrier, preferably a polymeric carrier comprising disulfide-crosslinked cationic components, preferably formed by disulfide-crosslinked cationic components, more preferably one or more peptides according to formula (I) $(Arg)_l;(Lys)_m;(His);(Orn)_o;(Orn)_o;(Xaa)_x$ as defined above most according to sub-formula (IA) or (IB) thereof as defined above, and at least one nucleic acid molecule, preferably a nucleic acid molecule comprising, preferably consisting of a nucleic acid sequence according to formula (II) $G_lX_mG_n$, formula (III) $C_lX_mC_n$, formula (IV) $(N_uG_lX_mG_nN_v)_a$ or formula (V) $(N_uC_lX_mC_nN_v)_a$ as defined above, such as a nucleic acid molecule comprising or consisting of a nucleic acid sequence according to any one of SEQ ID NOs. 15-108 and 122 or a sequence which is at least 60%, preferably at least 70%, preferably at least 80%, more preferably at least 90%, and most preferably at least 95% identical to any one of SEQ ID NOs. 15-108 and 122, e.g. a nucleic acid molecule comprising or consisting of a nucleic acid sequence according to SEQ ID NO. 105 or 122 or a sequence which is at least 60%, preferably at least 70%, preferably at least 80%, more preferably at least 90%, and most preferably at least 95% identical to SEQ ID NO. 105 or 122, or a nucleic acid molecule which encodes an antigen, more preferably a nucleic acid molecule which encodes an antigen which is the same antigen as the at least one protein or peptide antigen;

and wherein the protein or peptide antigen or the fragment, variant and/or derivative of said protein or peptide antigen is selected from an antigen from a pathogen associated with infectious disease, an antigen associated with allergy or allergic disease, an antigen associated with autoimmune disease, an antigen associated with a cancer or tumour disease, preferably an antigen associated with a cancer or tumour disease, more preferably an antigen selected from p53, CA125, EGFR, Her2/neu, hTERT, PAP, MAGE-A1, MAGE-A3, Mesothelin, MUC-1, NY-ESO-1, GP100, MART-1, Tyrosinase, PSA, PSCA, PSMA VEGF, VEGFR1, VEGFR2, Ras, CEA and WT1;

and preferably wherein the protein or peptide antigen and/or the fragment, variant and/or derivative of said protein or peptide antigen is not included in the polymeric carrier cargo complex.

In each of these embodiments the polymeric carrier cargo complex is preferably for use as an adjuvant, wherein, more preferably, the at least one nucleic acid molecule is an immunostimulatory nucleic acid as defined herein, even more preferably the at least one nucleic acid molecule is RNA, most preferably an immunostimulatory RNA (isRNA). Particular preferred nucleic acid cargos in the context of the present invention are nucleic acid molecules comprising or consisting of a nucleic acid sequence according to SEQ ID NO. 105 or 122 or a nucleic acid sequence which is at least 60%, preferably at least 70%, preferably at least 80%, more preferably at least 90%, and most preferably at least 95% identical to SEQ ID NO. 105 or 122.

Further, in each of these embodiments, the polymeric carrier cargo complex may be a polymeric carrier cargo complex wherein the cationic components of the polymeric carrier and the nucleic acid molecule cargo comprised in said polymeric carrier cargo complex are provided in a N/P ratio in the range of 0.1-20, or in the range of 0.1-5, or in the range of 0.1-1, or in the range of 0.5-0.9.

In some embodiment, it may be preferred, provided the polymeric carrier cargo complex comprises a polymeric carrier, preferably a polymeric carrier formed by disulfide-crosslinked cationic components, and at least one nucleic acid molecule, that the pharmaceutical composition is not a composition comprising a polymeric carrier cargo complex formed by the disulfide-crosslinked cationic peptide $CR_{12}C$ as carrier and isRNA722A (SEQ ID No. 105) or isRNA722B (SEQ ID No. 122) as nucleic acid cargo to the protein vaccine Ovalbumine (OVA protein).

In some embodiment, it may be preferred, provided the polymeric carrier cargo complex comprises a polymeric carrier, preferably a polymeric carrier formed by disulfide-crosslinked cationic components, and at least one nucleic acid molecule, that the pharmaceutical composition is not a composition comprising a polymeric carrier cargo complex formed by the disulfide-crosslinked cationic peptide $CR_{12}C$ as carrier and isRNA722A (SEQ ID No. 105) or isRNA722B (SEQ ID No. 122) as nucleic acid cargo to the Ovalbumine-specific peptide vaccine SIINFEKL_(SEQ ID NO: 116).

Accordingly, in some embodiments, it may be preferred that the pharmaceutical composition is not a composition comprising a polymeric carrier cargo complex formed by the disulfide-crosslinked cationic peptide $CR_{12}C$ (SEQ ID No. 6) as carrier and isRNA722A (SEQ ID No. 105) or isRNA722B (SEQ ID No. 122) as nucleic acid cargo and an antigen which is Ovalbumin (OVA protein) (SEQ ID No. 117).

In some embodiments, it may be further preferred, provided that the pharmaceutical composition comprises a polymeric carrier cargo complex comprising a polymeric carrier formed by disulfide-crosslinked cationic components and at least one nucleic acid molecule, that the at least one antigen is not an antigen associated with a cancer or tumour disease, particularly lymphoma or a lymphoma associated disease, wherein said antigen is an immunoglobulin idiotype of a lymphoid blood cell or a T cell receptor idiotype of a lymphoid blood cell or a fragment, variant and/or derivative of such an immunoglobulin idiotype or T cell receptor idiotype.

In this context, an immunoglobulin idiotype may be understood to be a peptide or protein having the particular molecular shape of the variable region of an immunoglobulin expressed by a particular type of B-cells. Such an idiotype may be used as antigen for eliciting an immune response directed against this particular type of B-cells, for example against malignant B-cells. A T cell receptor idiotype may be understood to be a peptide or protein having the particular molecular shape of the variable region of a T cell receptor expressed by a particular type of T-cells. Such an idiotype may be used as antigen for eliciting an immune response directed against this particular type of T-cells, for example against malignant T-cells.

In some embodiments, it may be preferred, provided that the pharmaceutical composition comprises a polymeric carrier cargo complex comprising a polymeric carrier formed by disulfide-crosslinked cationic components and at least one nucleic acid molecule, that the at least one antigen associated with a cancer or tumour disease is not an antigen associated with lymphoma, preferably not B-cell lymphoma, T-cell lymphoma or Non-Hodgkin's lymphoma.

In some embodiments it may be preferred, provided that the pharmaceutical composition comprises a polymeric carrier cargo complex comprising a polymeric carrier formed by disulfide-crosslinked cationic components and at least one nucleic acid molecule, that the at least one antigen associated with a cancer or tumour disease is not an antigen derived from a malignant cell, preferably not from a malignant B cell or a malignant T cell.

In some further embodiments, it may be preferred that the pharmaceutical composition may comprise no further component than the components A) and B), preferably no other mRNA component (other than comprised by the components A), preferably the pharmaceutical compositon may not comprise any mRNA at all.

In some further embodiments, it may be preferred, provided the pharmaceutical composition comprises mRNA (other than nucleic acid of component A), the mRNA may not be a mRNA encoding a peptide or antigen according to B), further preferred the mRNA may not be a mRNA encoding Ovalbumin, PSMA, Luciferase or STEAP.

In some further embodiments, it may be preferred, provided the pharmaceutical composition contains a mRNA (other than nucleic acid of component A), particularly mRNA encoding a peptide or antigen according to B), and/or mRNA encoding Ovalbumin, PSMA, Luciferase or STEAP, the mRNA may not be complexed with protamin, preferably not in a ratio of 2:1 or 4:1 or between 2:1 and 4:1.

In some further embodiments, it may be preferred that the claimed pharmaceutical composition may not be used for treatment of pancreas carcinoma or non-small cell lung carcinoma.

In some further embodiments, it may be preferred, provided the pharmaceutical composition comprises mRNA (other than nucleic acid of component A), that the mRNA may not be a free mRNA.

In some further embodiments, it may be preferred, provided the pharmaceutical composition comprises mRNA (other than nucleic acid of component A), that the mRNA may not be complexed with protamine.

In some further embodiments, it may be preferred, provided the pharmaceutical composition comprises free mRNA, that the mRNA may not encode for a therapeutically active protein and may not encode for an antibody and may not encode for an antigen.

In some further embodiments, it may be preferred that with respect to component A) of the inventive pharmaceutical composition, that a) may not be protamine.

In some further embodiments, it may be preferred that with respect to component A) of the inventive pharmaceutical composition, that the carrier protein may not be protamine.

In some further embodiments, it may be preferred, provided that a) of component A) is protamine, a) is not present in a ratio of 1:2 or 1:4 or between 1:2 and 1:4, with respect to b) of component A).

In some further embodiments, it may be preferred, provided that the carrier protein of component A) is protamine, the carrier protein is not present in a ratio of 1:2 or 1:4 with respect to the nucleic acid of component A).

In some further embodiments, it may be preferred, that with respect to component A) the nucleic acid is not an mRNA.

In some further embodiments, it may be preferred, provided the nucleic acid of component A) is an mRNA, that the mRNA does not encode Ovalbumin, PSMA, Luciferase or STEAP.

In some further embodiments, it may be preferred, provided the nucleic acid, i.e. b), of the component A) is mRNA; that the mRNA is not a free mRNA, but is exclusively complexed with the carrier protein of a).

In some further embodiments, component (B) is not ovalbumin or a fragment of ovalbumin. Preferably, the pharmaceutical composition, the kit, or the pharmaceutical package according to the present invention does not comprise ovalbumin or a fragment of ovalbumin or a nucleic acid sequence coding for ovalbumin or coding for a fragment of ovalbumin.

FIGURES

The following Figures are intended to illustrate the invention further. They are not intended to limit the subject matter of the invention thereto.

FIG. 1: shows the raw correlation curve of polymeric carrier cargo complexes formed by the disulfide-crosslinked cationic peptides $CR_{12}C$ and $CR_7C$ as carrier after lyophilisation compared to complexes with non-polymerizing cationic peptides as carrier ($R_{12}$ and $R_7$) by dynamic light scattering using a Zetasizer Nano (Malvern Instruments, Malvern, UK). The hydrodynamic diameters were measured with fresh prepared complexes and with reconstituted complexes after lyophilisation The mass ratio of peptide:RNA was 1:2. As result it can be shown that the polymeric carrier cargo complexes comprising cystein-containing peptides as cationic components which lead to a polymerization of the polymeric carrier by disulfide bonds do not change in size in contrast to the complexes formed by non-polymerizing peptides which increase in size and therefore are not stable during the lyophilization step. Therefore complexes with polymerized peptides as polymeric carriers show advantageous properties for lyophilization.

Figure 2:
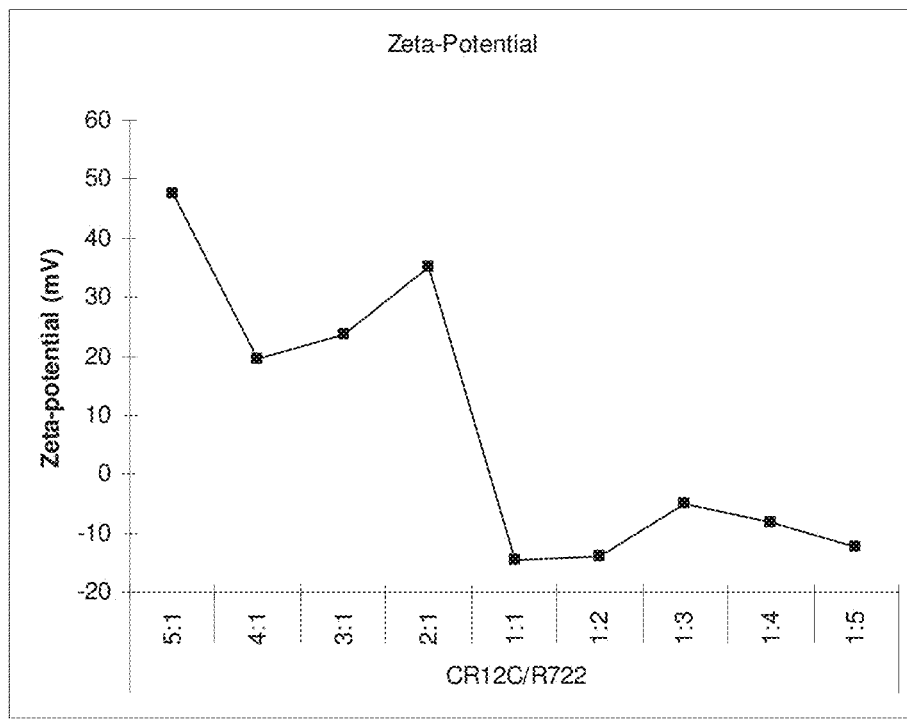

FIG. 2: shows the Zeta-potential of polymeric carrier cargo complexes formed by the disulfide-cross-linked cationic peptide $CR_{12}C$ and the R722 as nucleic acid cargo at different w/w ratios. As can be seen, the zeta potential changes from positive to negative when the w/w ratio is changed from excess peptide to a 1:1 ratio (peptide/RNA).

FIG. 3A: shows the secretion of hIFNa cytokine (in vitro) in hPBMCs after stimulation with polymeric carrier cargo complexes formed by the disulfide-crosslinked cationic peptide $CR_{12}C$ and the CpG 2216 as nucleic acid cargo in a mass ratio of 1:2.5 (w/w) ($CR_{12}C$/CpG 2216). As can be seen, the polymeric carrier cargo complexes lead to an increase of hIFNa cytokine release in hPBMCs compared to the nucleic acid cargo alone or the cationic peptide alone.

FIG. 3B: shows the secretion of hTNFa cytokine (in vitro) in hPBMCs after stimulation with polymeric carrier cargo complexes formed by the disulfide-crosslinked cationic peptide $CR_{12}C$ and the CpG 2216 as nucleic acid cargo in a mass ratio of 1:2.5 (w/w) ($CR_{12}C$/CpG 2216). As can be seen, the polymeric carrier cargo complexes do not lead to an increase in hTNFa cytokine release in hPBMCs compared to the nucleic acid cargo alone or the cationic peptide alone.

FIG. 4A: shows the secretion of hIFNa cytokine (in vitro) in hPBMCs after stimulation with polymeric carrier cargo complexes formed by the disulfide-crosslinked cationic peptide $CR_{12}C$ and the mRNA R491 coding for luciferase as nucleic acid cargo in a mass ratio of 1:2 (w/w) ($CR_{12}C$/

R491). As can be seen, the polymeric carrier cargo complexes lead to an increase of hIFNa cytokine release in hPBMCs compared to the nucleic acid cargo alone or the cationic peptide alone.

FIG. 4B: shows the secretion of hTNFa cytokine (in vitro) in hPBMCs after stimulation with polymeric carrier cargo complexes formed by the disulfide-crosslinked cationic peptide $CR_{12}C$ and the mRNA R491 coding for luciferase as nucleic acid cargo in a mass ratio of 1:2 (w/w) ($CR_{12}C$/R491). As can be seen, the polymeric carrier cargo complexes lead to an increase of hTNFa cytokine release in hPBMCs compared to the nucleic acid cargo alone or the cationic peptide alone.

FIG. 5A: shows the secretion of hIFNa cytokine (in vitro) in hPBMCs after stimulation with polymeric carrier cargo complexes formed by the disulfide-crosslinked cationic peptide $CR_{12}C$ and a short GU rich RNA oligonucleotide (short GU rich) as nucleic acid cargo in a mass ratio of 1:2.5 (w/w) ($CR_{12}C$/short GU rich). As can be seen, the polymeric carrier cargo complexes lead to an increase of hIFNa cytokine release in hPBMCs compared to the nucleic acid cargo alone or the cationic peptide alone.

FIG. 5B: shows the secretion of hTNFa cytokine (in vitro) in hPBMCs after stimulation with polymeric carrier cargo complexes formed by the disulfide-crosslinked cationic peptide $CR_{12}C$ and a short GU rich RNA oligonucleotide (short GU rich) as nucleic acid cargo in a mass ratio of 1:2.5 (w/w) ($CR_{12}C$/short GU rich). As can be seen, the polymeric carrier cargo complexes lead to an increase of hTNFa cytokine release in hPBMCs compared to the nucleic acid cargo alone or the cationic peptide alone.

FIG. 6A: shows the secretion of hIFNa cytokine (in vitro) in hPBMCs after stimulation with polymeric carrier cargo complexes formed by the disulfide-crosslinked cationic peptide $CR_7C$ and the long non-coding GU-rich isRNA R722 as nucleic acid cargo. As can be seen, the polymeric carrier cargo complexes ($CR_7C$/R722) lead to an increase of hIFNa cytokine release in hPBMCs compared to cargo complexes ($R_7$/R722) formed by the non-polymerized peptide $R_7$.

FIG. 6B: shows the secretion of hTNFa cytokine (in vitro) in hPBMCs after stimulation with polymeric carrier cargo complexes formed by the disulfide-crosslinked cationic peptide $CR_7C$ and the long non-coding GU-rich isRNA R722 as nucleic acid cargo. As can be seen, the polymeric carrier cargo complexes ($CR_7C$/R722) only leads to a weak increase of hTNFa cytokine release in hPBMCs compared to carrier cargo complexes ($R_7$/R722) formed by the non-polymerized peptide $R_7$.

FIG. 7A: shows the secretion of hIFNa cytokine (in vitro) in hPBMCs after stimulation with polymeric carrier cargo complexes formed by the disulfide-crosslinked cationic peptide $CR_9C$ and the long non-coding GU-rich isRNA R722 as nucleic acid cargo. As can be seen, the inventive polymeric carrier cargo complexes ($CR_9C$/R722) lead to an increase of hIFNa cytokine release in hPBMCs compared to carrier cargo complexes ($R_9$/R722) formed by the non-polymerized peptide $R_9$.

FIG. 7B: shows the secretion of hTNFa cytokine (in vitro) in hPBMCs after stimulation with polymeric carrier cargo complexes formed by the disulfide-crosslinked cationic peptide $CR_9C$ and the long non-coding GU-rich isRNA R722 as nucleic acid cargo. As can be seen, the polymeric carrier cargo complexes ($CR_9C$/R722) do not lead to an increase of hTNFa cytokine release in hPBMCs compared to carrier cargo complexes ($R_9$/R722) formed by the non-polymerized peptide $R_9$.

FIG. 8A: shows the secretion of hIFNa cytokine (in vitro) in hPBMCs after stimulation with polymeric carrier cargo complexes formed by the disulfide-crosslinked cationic peptide $CR_{12}C$ and the isRNA R722 as nucleic acid cargo at different w/w ratios. As can be seen, the polymeric carrier cargo complexes lead to an increase in hIFNa cytokine release in hPBMCs compared to the nucleic acid cargo alone or the cationic peptide alone.

FIG. 8B: shows the secretion of hTNFa cytokine (in vitro) in hPBMCs after stimulation with polymeric carrier cargo complexes formed by the disulfide-crosslinked cationic peptide $CR_{12}C$ and the isRNA R722 as nucleic acid cargo at different w/w ratios. As can be seen, the polymeric carrier cargo complexes lead to an increase in hTNFa cytokine release in hPBMCs compared to the nucleic acid cargo alone or the cationic peptide alone.

FIG. 9A: shows the secretion of hIFNa cytokine (in vitro) in hPBMCs after stimulation with polymeric carrier complexes formed by the cationic peptides $CH_6R4H_6C$, $CH_3R4H_3C$ and $CHK_7HC$ and the isRNA R722 as nucleic acid cargo at different N/P ratios. As can be seen, the polymeric carrier cargo complexes lead to an increase in hIFNa cytokine release in hPBMCs compared to the nucleic acid cargo alone or the cationic peptide alone.

FIG. 9B: shows the secretion of hTNFa cytokine (in vitro) in hPBMCs after stimulation with polymeric carrier complexes formed by the disulfide-crosslinked cationic peptides $CH_6R4H_6C$, $CH_3R4H_3C$ and $CHK_7HC$ and the isRNA R722 as nucleic acid cargo at different N/P ratios. As can be seen, the polymeric carrier cargo complexes lead to an increase in hTNFa cytokine release in hPBMCs compared to the nucleic acid cargo alone or the cationic peptide alone. Particularly polymeric cargo complexes with an N/P ratio greater or equal 1 result in TNFalpha secretion.

Figure 10:
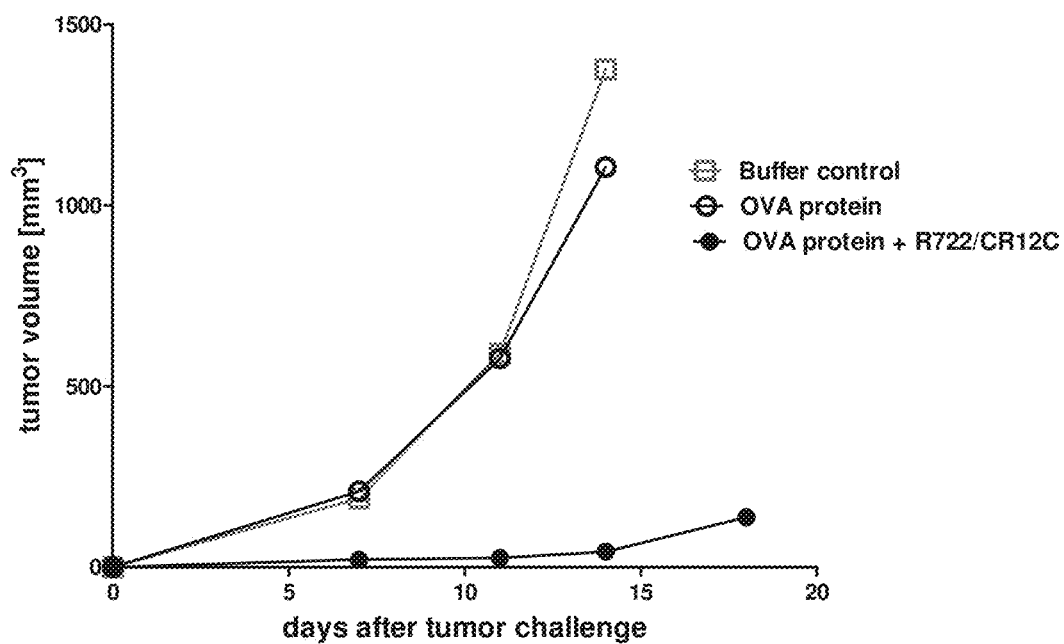

FIG. 10: shows the (in vivo) effect of the addition of the polymeric carrier cargo complex formed by the disulfide-crosslinked cationic peptide $CR_{12}C$ as carrier and the isRNA R722 as nucleic acid cargo to the protein antigen Ovalbumine (OVA protein) for the use as an adjuvant in tumour challenge experiments.

For this purpose 7 female C57BL/6 mice per group were vaccinated three times in two weeks with g 5 μg Ovalbumin protein combined with 45 μg $CR_{12}C$/R722 (1:2; w/w). For comparison mice were injected without the polymeric cargo complexes.

As can be seen, the polymeric carrier cargo complex extremely decelaterates the tumour growth compared to the protein antigen alone, which has no effect on tumor growth in comparison to the buffer control.

Figure 11:
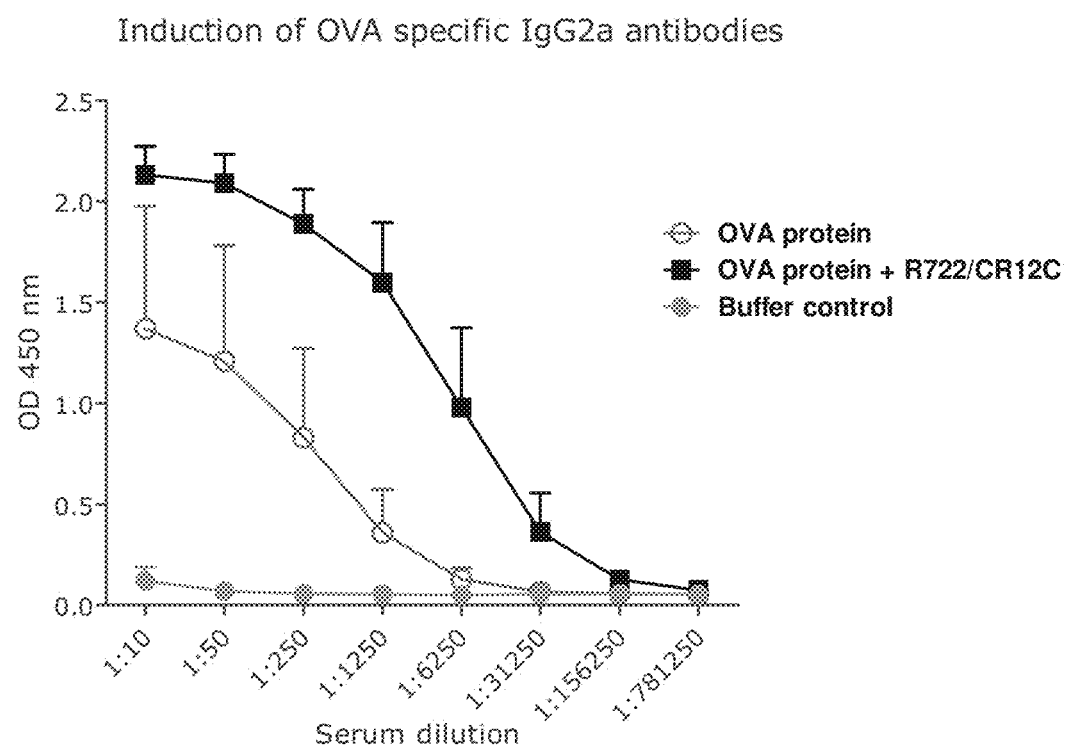

FIG. 11: shows the (in vivo) effect of the addition of the polymeric carrier cargo complex formed by the disulfide-crosslinked cationic peptide $CR_{12}C$ as carrier and the isRNA R722 as nucleic acid cargo to the protein antigen Ovalbumine (OVA protein) for the use as an adjuvant on the induction of Ovalbumine-specific IgG2a antibodies.

For this purpose 5 female C57BL/6 mice per group were vaccinated three times in two weeks with 5 μg Ovalbumin protein combined with 45 μg $CR_{12}C$/R722 (1:2; w/w). For comparison mice were injected without the polymeric cargo complexes.

As can be seen, the polymeric carrier cargo complex strongly increases the B-cell response, which proofs the beneficial adjuvant properties of the polymeric carrier cargo complexes, particularly in regard to the induction of a Th1-shifted immune response.

Figure 12:
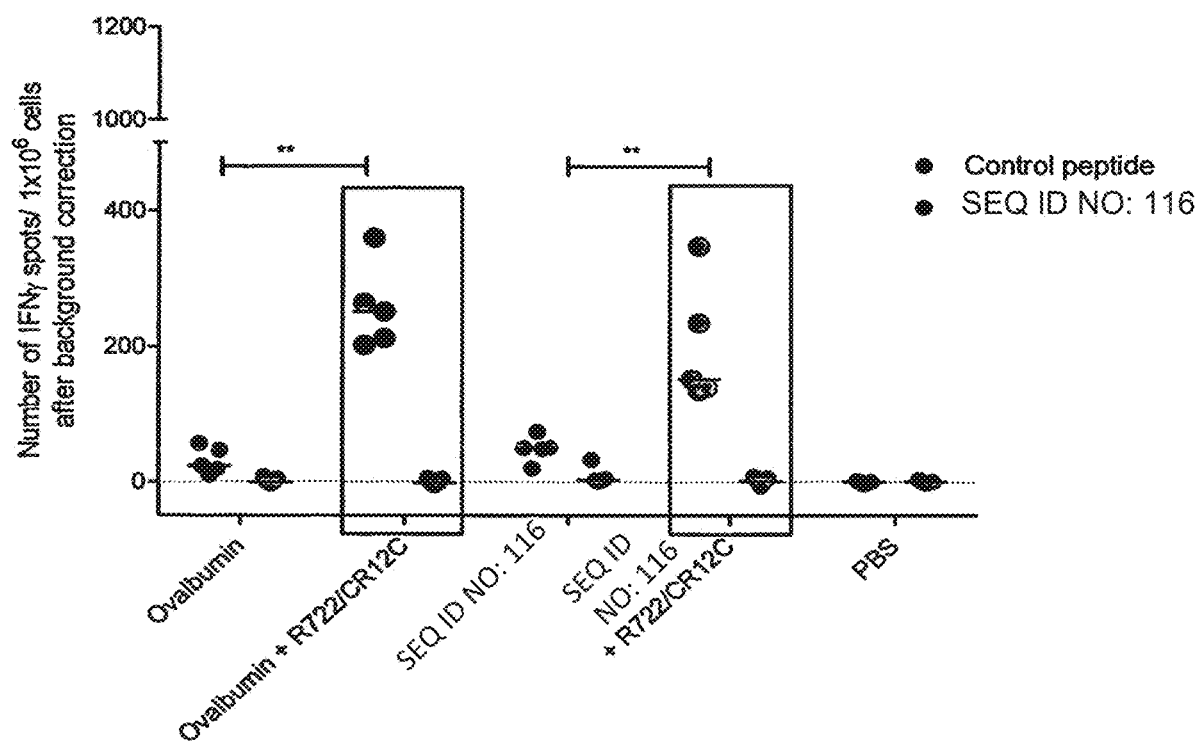

FIG. 12: shows IFN-γ secretion in splenocytes after stimulation with SEQ ID NO: 116. The (in vivo) effect of the addition of the polymeric carrier cargo complex formed by the disulfide-crosslinked cationic peptide $CR_{12}C$ as carrier and the isRNA R722 as nucleic acid cargo to the protein antigen Ovalbumine (OVA protein) or the Ovalbumine-specific peptide antigen SIINFEKL (SEQ ID NO: 116) for the use as an adjuvant on the induction of Ovalbumine-specific cytotoxic T cells is shown.

For this purpose 5 female C57BL/6 mice per group were vaccinated three times in two weeks with 5 µg Ovalbumin protein or 50 µg SIINFEKEL (SEQ ID NO: 116) peptide combined with 45 µg $CR_{12}C$/R722 (1:2; w/w). For comparison mice were injected without the polymeric cargo complexes.

As can be seen, the polymeric carrier cargo complex strongly increases the induction of Ovalbumin-specific cytotoxic T cells compared to the vaccination with protein or peptide alone, which further proofs the beneficial adjuvant properties of the polymeric carrier cargo complex, particularly in regard to the induction of a Th1-shifted immune response.

Figure 13:
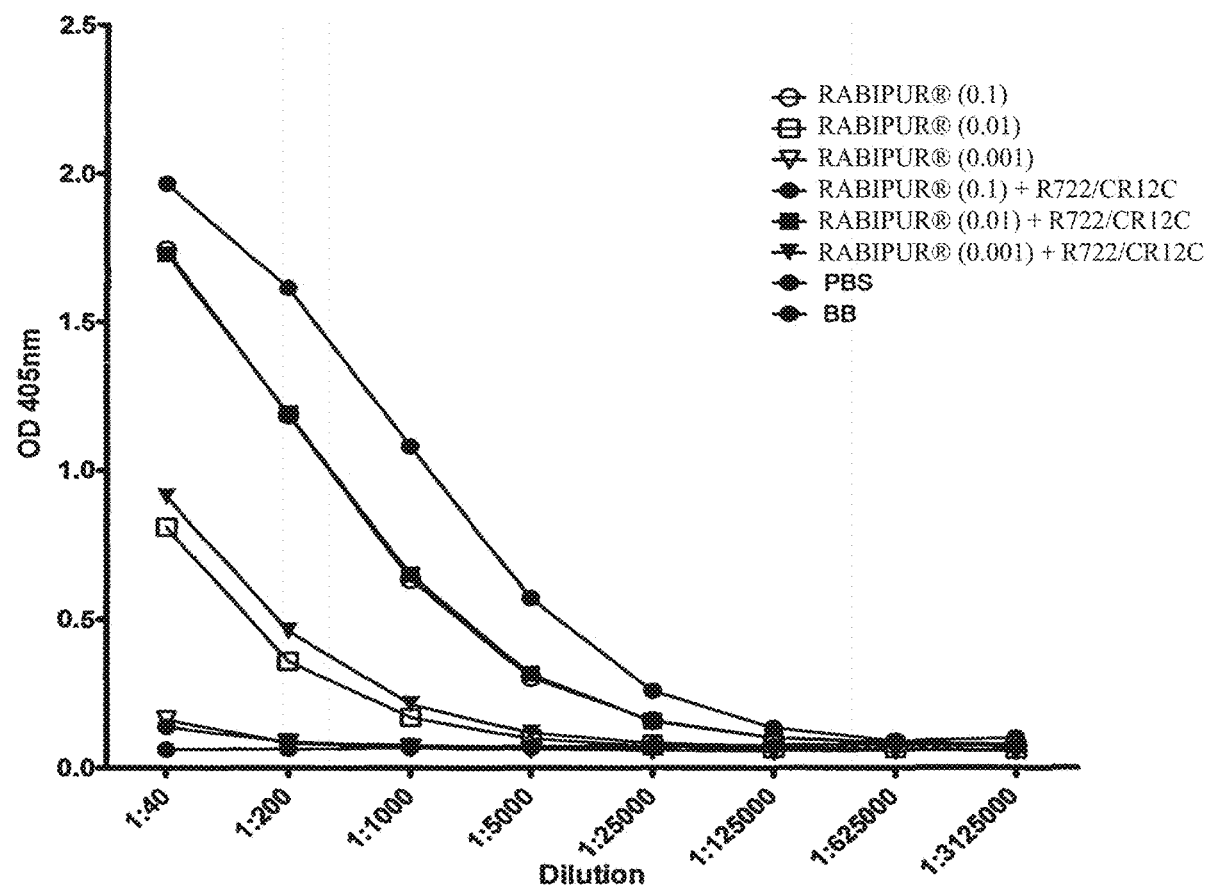

FIG. 13: shows the (in vivo) effect of the addition of the polymeric carrier cargo complex formed by the disulfide-crosslinked cationic peptide $CR_{12}C$ as carrier and the isRNA R722 as nucleic acid cargo to the vaccine RABIPUR® (comprising inactivated Rabies virus) for the use as an adjuvant on the induction of Rabies specific IgG antibodies (as represented by OD 405 nm).

For this purpose 8 female BALB/c mice were injected intramuscularly with the 0.1, 0.01, and the 0.001 fold human dose of RABIPUR® and 30 µg R722 and 8.1 µg $CR_{12}C$ (3.7:1 w/w). 21 days after the immunization blood samples were taken and analysed for total IgG antibodies directed against the Rabies virus.

As can be seen, the polymeric carrier cargo complex strongly increases the induction of Rabies-specific IgG antibodies compared to the vaccination with RABIPUR® alone, which further proofs the beneficial adjuvant properties of the polymeric carrier cargo complex.

Figure 14:
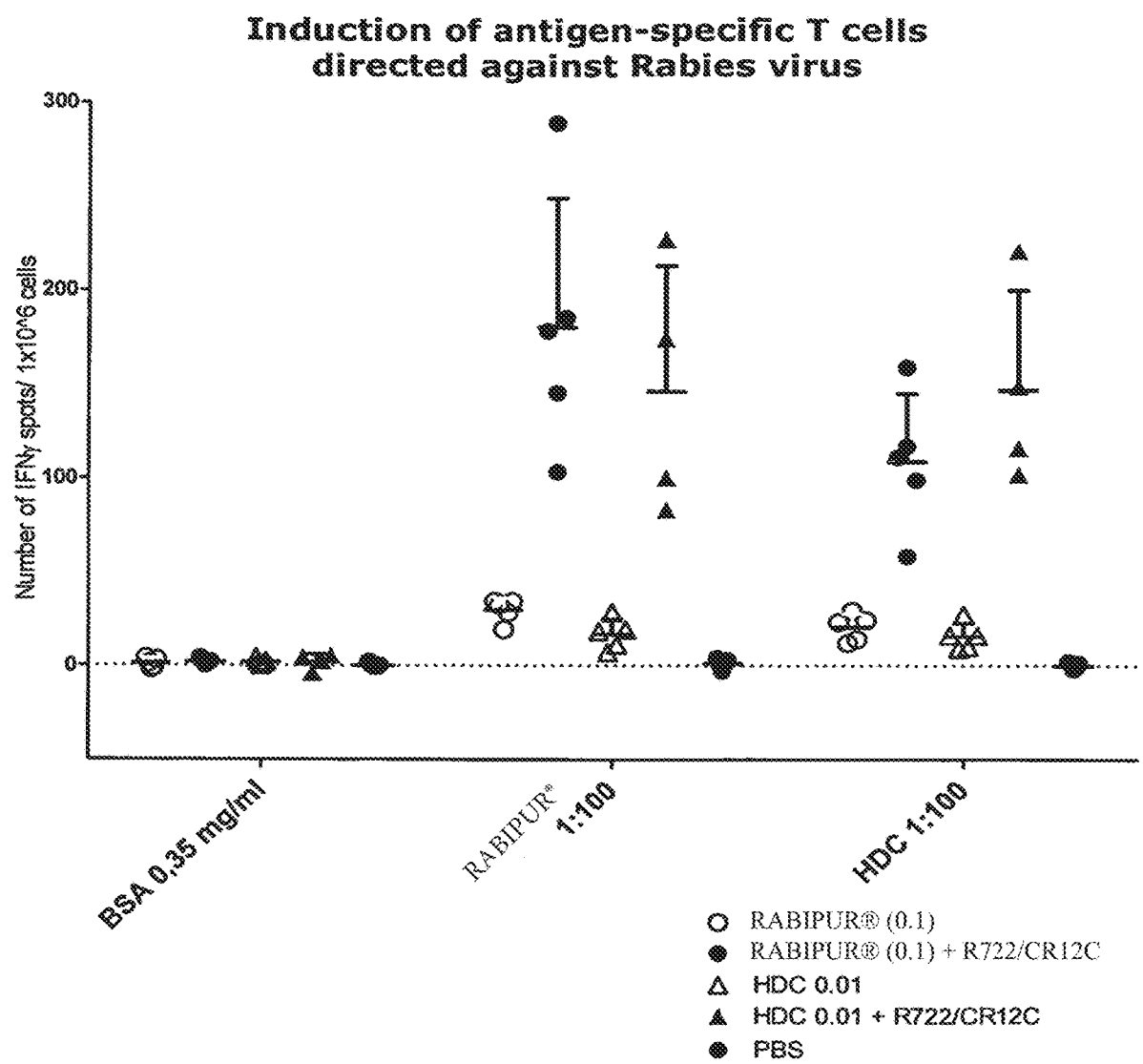

FIG. 14: shows the (in vivo) effect of the addition of the polymeric carrier cargo complex formed by the disulfide-crosslinked cationic peptide $CR_{12}C$ as carrier and the isRNA R722 as nucleic acid cargo to the vaccine RABIPUR® or HDC (comprising inactivated Rabies virus) for the use as an adjuvant on the induction of Rabies specific cytotoxic T cells (as represented by number of spots in the ELISPOT assay).

For this purpose 5 female BALB/c mice were injected intramuscularly with the 0.01 fold human dose of RABIPUR® or HDC and 30 µg R722 and 8.1 µg $CR_{12}C$ (3.7:1 w/w). 5 days after the immunization the mice were sacrificed, the spleens were removed and the splenocytes were isolated.

As can be seen, the polymeric carrier cargo complex strongly increases the induction of Rabies-specific cytotoxic T cells compared to the vaccination with RABIPUR® or HDC alone, which further proofs the beneficial adjuvant properties of the polymeric carrier cargo complex, particularly in regards to the induction of a Th1-shifted immune response.

Figure 15:
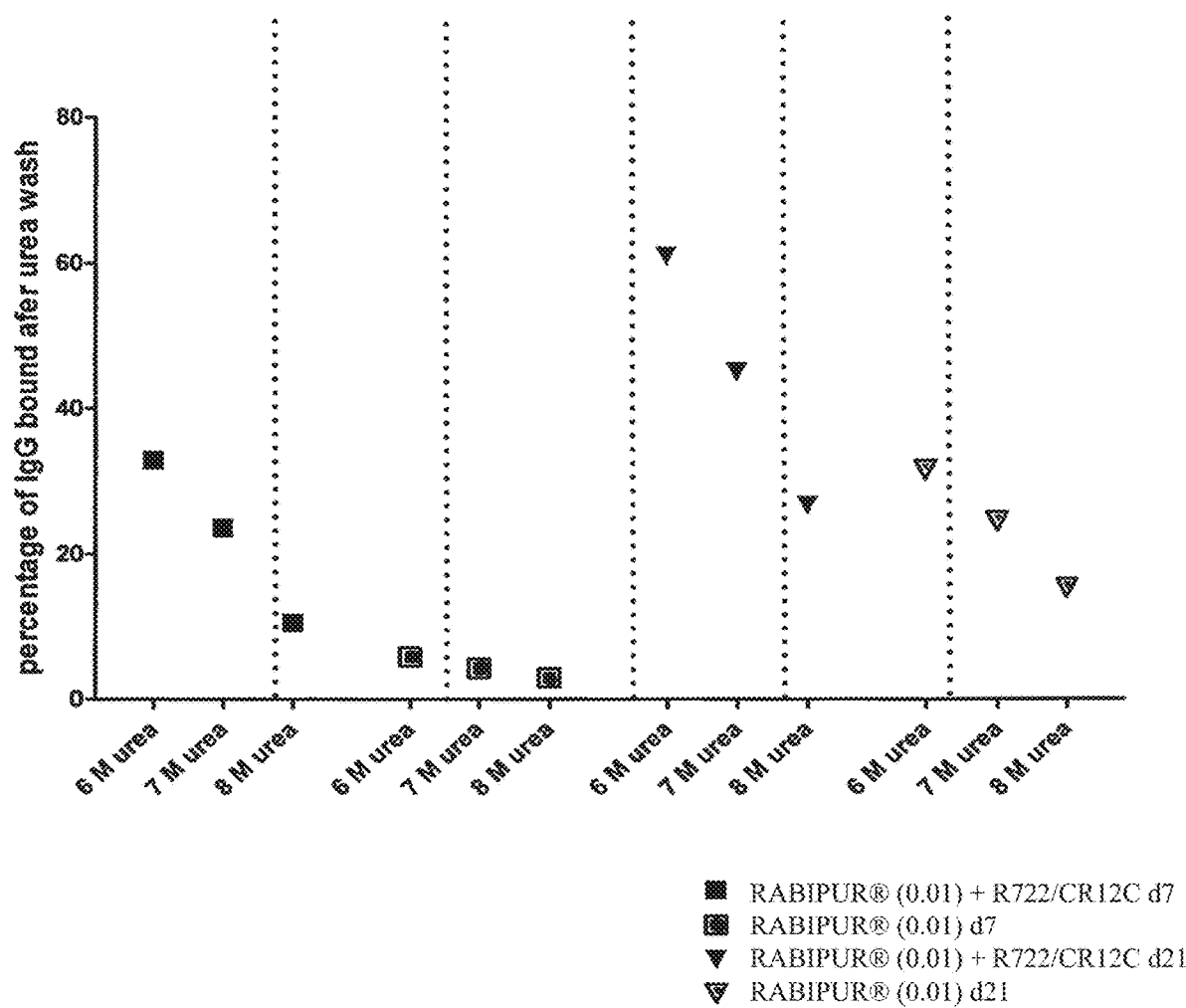

FIG. 15: shows the (in vivo) effect of the addition of the polymeric carrier cargo complex formed by the disulfide-crosslinked cationic peptide CR12C as carrier and the isRNA R722 as nucleic acid cargo to the vaccine RABIPUR® (comprising inactivated Rabies virus) for the use as an adjuvant on the induction of Rabies specific IgG antibodies. Furthermore it shows the effect of the polymeric carrier cargo complex on the induction of antibodies with high affinity to the antigen (as represented by % of bound IgG).

For this purpose 8 female BALB/c mice were injected intramuscularly with the 0.01 fold human dose of RABIPUR® and 30 µg R722 and 8.1 µg $CR_{12}C$ (3.7:1 w/w). 7 and 21 days after the immunization blood samples were taken and analysed for total IgG antibodies directed against the Rabies virus. To examine the affinity of the generated antibodies directed against the Rabies virus, during the performance of the ELISA the bound antibodies were washed with an increasing concentration of urea.

As can be seen, the polymeric carrier cargo complex strongly increases the induction of Rabies-specific IgG antibodies with high affinity to the antigen compared to the vaccination with RABIPUR® alone, which further proofs the beneficial adjuvant properties of the polymeric carrier cargo complex, particularly in regards to the induction of antibodies with high affinity.

Figure 16:
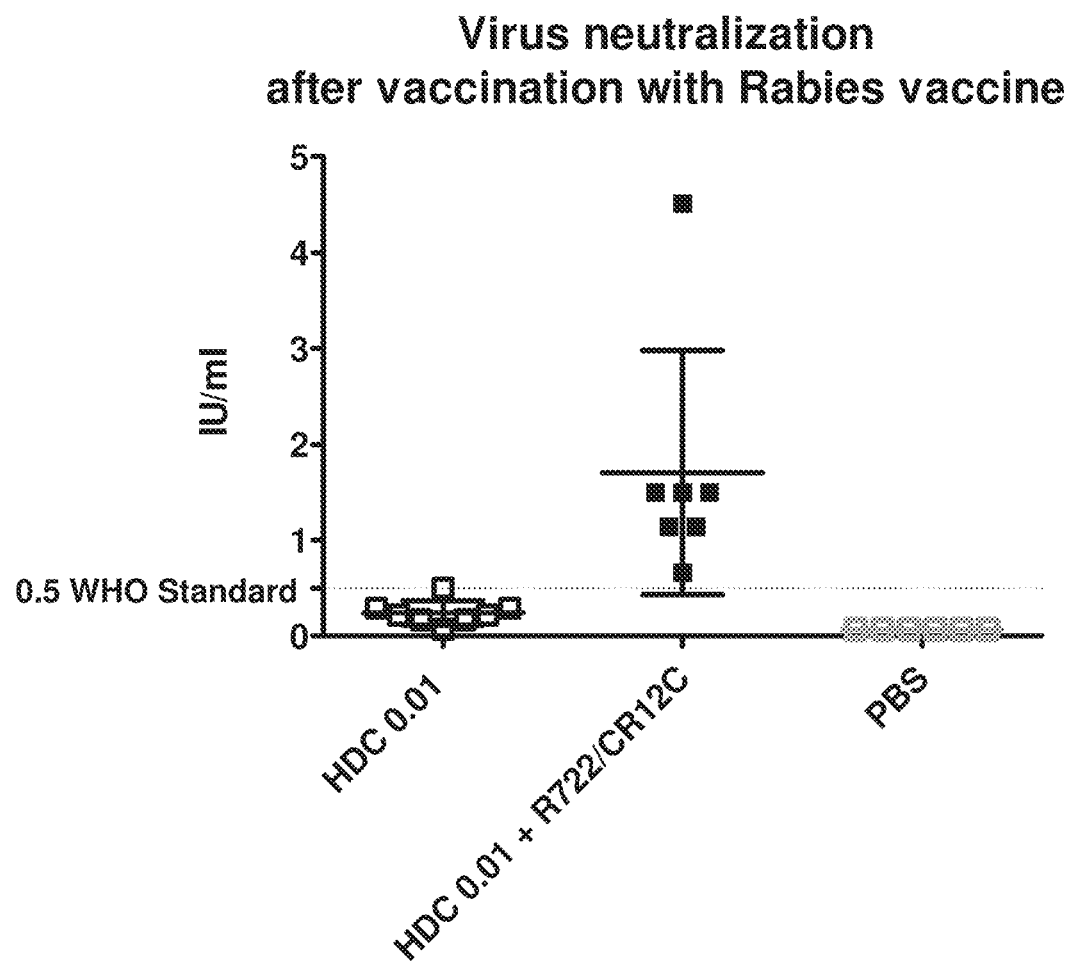

FIG. 16: shows the (in vivo) effect of the addition of the polymeric carrier cargo complex formed by the disulfide-crosslinked cationic peptide $CR_{12}C$ as carrier and the isRNA R722 as nucleic acid cargo to the vaccine HDC (comprising inactivated Rabies virus) for the use as an adjuvant on the induction of Rabies virus neutralizing antibodies (as represented by IU/ml).

For this purpose 8 female BALB/c mice were injected intramuscularly with the 0.01 fold human dose of HDC and 30 µg R722 and 15 µg $CR_{12}C$ (2:1 w/w). 21 days after the immunization blood samples were taken and virus neutralization was analysed.

As can be seen, the polymeric carrier cargo complex strongly increases the neutralizing antibody titer compared to the vaccination with HDC alone, which further proofs the beneficial adjuvant properties of the polymeric carrier cargo complex.

Figure 17:
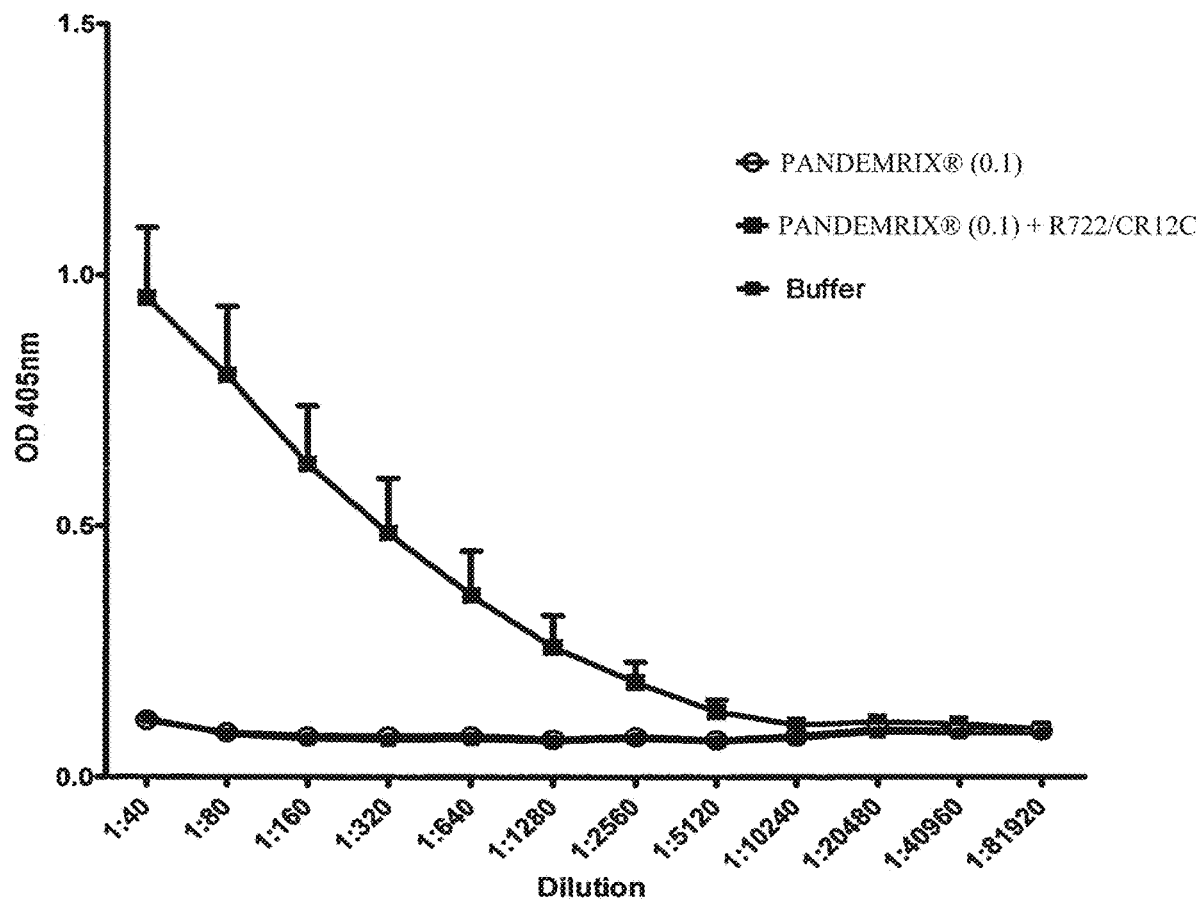

FIG. 17: shows the (in vivo) effect of the addition of the polymeric carrier cargo complex formed by the disulfide-crosslinked cationic peptide $CR_{12}C$ as carrier and the isRNA R722 as nucleic acid cargo to the swine flu vaccine PANDEMRIX® (comprising inactivated H1N1 influenza virus) for the use as an adjuvant on the induction of H1N1 influenza specific IgG2a antibodies.

For this purpose 5 female BALB/c mice were injected intramuscularly with 0.1 µg PANDEMRIX® and 30 µg R722 and 15 µg $CR_{12}C$ (2:1 w/w). 14 days after the immunization blood samples were taken and analysed for induction of IgG2a antibodies directed against H1N1 influenza virus (as represented by OD 405 nm).

As can be seen, the polymeric carrier cargo complex strongly increases the induction of Influenza-specific IgG2a antibodies compared to the vaccination with PANDEMRIX® alone, which further proofs the beneficial adjuvant properties of the polymeric carrier cargo complex, particularly in regards to the induction of a Th1-shifted immune response.

Figure 18:
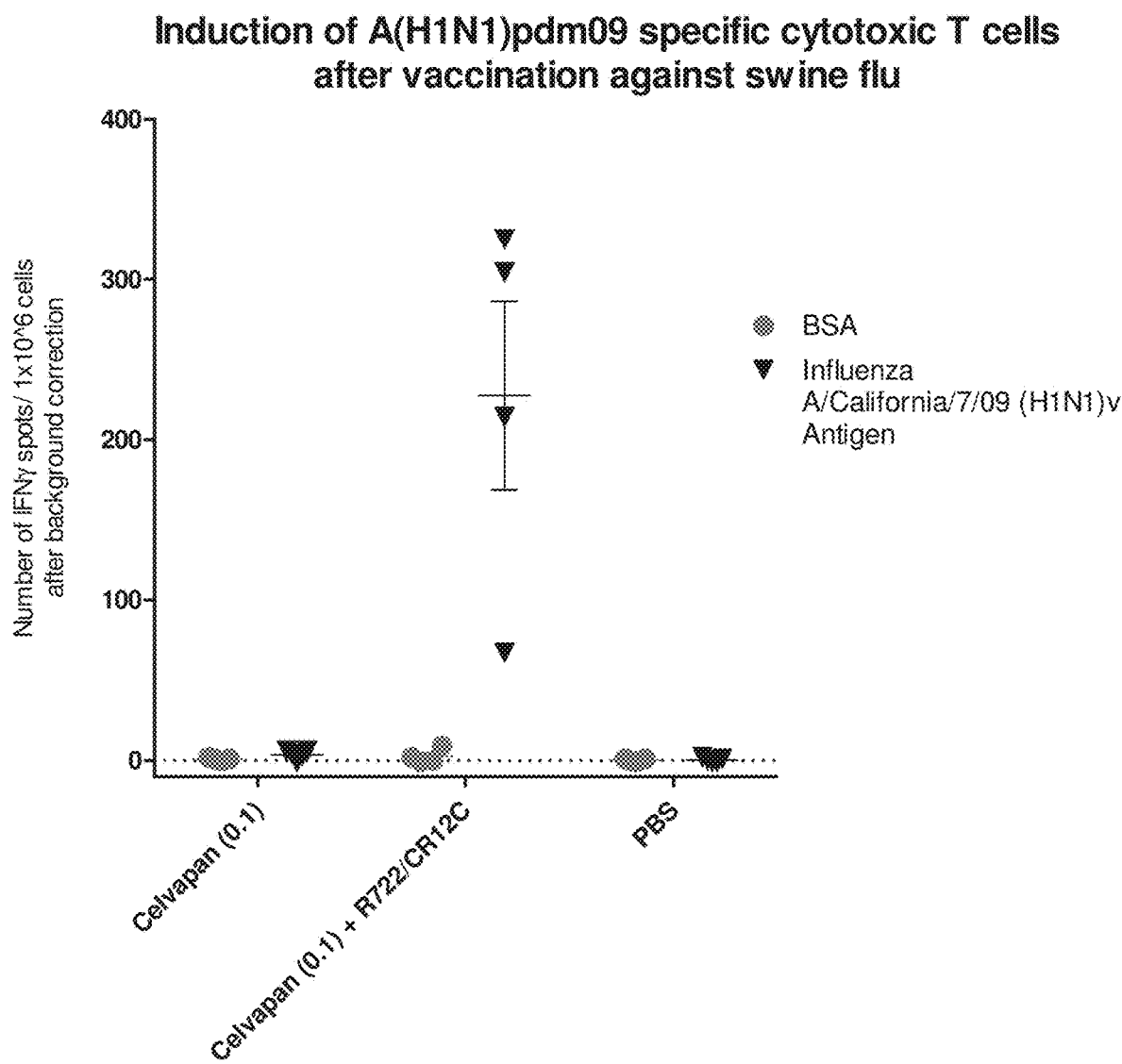

FIG. 18: shows the (in vivo) effect of the addition of the polymeric carrier cargo complex formed by the disulfide-crosslinked cationic peptide $CR_{12}C$ as carrier and the isRNA R722 as nucleic acid cargo to the A(H1N1)pdm09influenza vaccine CELVAPAN® (comprising inactivated A(H1N1) pdm09influenza virus) for the use as an adjuvant on the induction of A(H1N1)pdm09specific cytotoxic T cells (as represented by number of spots in the ELISPOT assay).

For this purpose 5 female BALB/c mice were injected intramuscularly with the 0.1 µg CELVAPAN® and 15

µg R722 and 7.5 µg $CR_{12}C$ (2:1 w/w). 6 days after the immunization the mice were sacrificed, the spleens were removed and the splenocytes were isolated.

As can be seen, the polymeric carrier cargo complex strongly increases the induction of A(H1N1)pdm09-specific cytotoxic T cells compared to the vaccination with CELVAPAN® alone, which further proofs the beneficial adjuvant properties of the polymeric carrier cargo complex, particularly in regards to the induction of a Th1-shifted immune response.

FIG. 19: shows the (in vivo) effect of the addition of the polymeric carrier cargo complex formed by the disulfide-crosslinked cationic peptide $CR_{12}C$ as carrier and the isRNA R722 as nucleic acid cargo to the seasonal influenza vaccine BEGRIVAC® (comprising inactivated seasonal influenza virus strains as recommended by the WHO) for the use as an adjuvant on the induction of influenza specific IgG2a antibodies (as represented by OD 405 nm).

For this purpose 8 female BALB/c mice were injected intramuscularly with 0.1 μg BEGRIVAC® and 30 μg R722 and 15 μg $CR_{12}C$ (2:1 w/w). 28 days after the immunization blood samples were taken and analysed for IgG2a antibodies directed against influenza virus.

As can be seen, the polymeric carrier cargo complex strongly increases the induction of Influenza-specific IgG2a antibodies compared to the vaccination with BEGRIVAC® alone, which further proofs the beneficial adjuvant properties of the polymeric carrier cargo complex, particularly in regards to the induction of a Th1-shifted immune response.

FIG. 20: shows the (in vivo) effect of the addition of the polymeric carrier cargo complex formed by the disulfide-crosslinked cationic peptide $CR_{12}C$ as carrier and the isRNA R722 as nucleic acid cargo to the Hepatitis B vaccine ENGERIX®-B (comprising recombinant Hepatitis B Surface Antigen (HBsAg)) for the use as an adjuvant on the induction of HBsAG specific antibodies (as represented by fluorescence).

For this purpose 8 female BALB/c mice were injected intramuscularly with 0.5 μg ENGERIX®-B and 6.25 μg R722 and 1.7 μg $CR_{12}C$ (3.7:1 w/w). 28 days after the immunization blood samples were taken and analysed for IgG2a antibodies directed against the HBsAGg As can be seen, the polymeric carrier cargo complex strongly increases the induction of HBsAg-specific IgG2a antibodies compared to the vaccination with ENGERIX®-B alone, which further proofs the beneficial adjuvant properties of the polymeric carrier cargo complex, particularly in regards to the induction of a Th1-shifted immune response.

FIG. 21: shows the (in vivo) effect of the addition of the polymeric carrier cargo complex formed by the disulfide-crosslinked cationic peptide $CR_{12}C$ as carrier and the isRNA R722 as nucleic acid cargo to a human papilloma virus 16 (HPV16) derived peptide for the use as an adjuvant on the induction of HPV16 E7 specific cytotoxic T cells (as represented by number of spots in the ELISPOT assay).

For this purpose 5 female C57BL/6 mice were injected intradermally with 100 μg of the HPV16 E7 derived peptide E7aa43-77 and 50 μg R722 and 25 μg $CR_{12}C$ (2:1 w/w). 8 days after the immunization the mice were sacrificed, the spleens were removed and the splenocytes were isolated.

As can be seen, the polymeric carrier cargo complex strongly increases the induction of HPV16 E7-specific cytotoxic T cells compared to the vaccination with the peptide alone, which further proofs the beneficial adjuvant properties of the polymeric carrier cargo complex, particularly in regards to the induction of a Th1-shifted immune response.

FIG. 22: shows the (in vivo) effect of the addition of the polymeric carrier cargo complex formed by the disulfide-crosslinked cationic peptide $CR_{12}C$ as carrier and the isRNA R722 as nucleic acid cargo to a human papilloma virus 16 (HPV16) derived peptide for the use as an adjuvant on the induction of HPV16 E7 specific cytotoxic T cells (as represented by number of spots in the ELISPOT assay).

For this purpose 5 female C57BL/6 mice were injected intradermally with 100 μg of the HPV16 E7 derived peptide E7aa43-77 and 50 μg R722 and 25 μg $CR_{12}C$ (2:1 w/w). Furthermore mice were injected with the polymeric carrier cargo complex additionally comprising the antigenic peptide E7aa43-77. Seven days after the immunization the mice were sacrificed, the spleens were removed and the splenocytes were isolated.

As can be seen, the polymeric carrier cargo complex strongly increases the induction of HPV16 E7-specific cytotoxic T cells compared to the vaccination with the peptide alone. Furthermore the results show that the inclusion of the antigenic peptide in the polymeric carrier cargo complex further improves the induction of HPV16 E7-specific cytotoxic T cells. Therefore also this experiment proofs the beneficial adjuvant properties of the polymeric carrier cargo complex, particularly in regards to the induction of a Th1-shifted immune response.

FIG. 23: shows the (in vivo) effect of the addition of the polymeric carrier cargo complex formed by the disulfide-crosslinked cationic peptide $CR_{12}C$ as carrier and the isRNA R722 as nucleic acid cargo to the human NY-ESO-1 protein for the use as an adjuvant on the induction of NY-ESO-1 specific cytotoxic T cells (as represented by number of spots in the ELISPOT assay).

For this purpose 5 female C57BL/6 mice were injected intramuscularly with 5 μg NY-ESO-1 protein and 30 μg R722 and 15 μg $CR_{12}C$ (2:1 w/w) 2 times within 15 days. 7 days after the last immunization the mice were sacrificed, the spleens were removed and the splenocytes were isolated.

As can be seen, the polymeric carrier cargo complex strongly increases the induction of NY-ESO-1-specific cytotoxic T cells compared to the vaccination with the protein alone, which further proofs the beneficial adjuvant properties of the polymeric carrier cargo complex, particularly in regards to the induction of a Th1-shifted immune response.

FIG. 24: shows the survival of rabies challenged mice. The (in vivo) effect of the addition of the polymeric carrier cargo complex formed by the disulfide-crosslinked cationic peptide $CR_{12}C$ as carrier and the isRNA R722 as nucleic acid cargo to the vaccine RABIPUR® (comprising inactivated Rabies virus) for the use as an adjuvant for the enhancement of protection against lethal virus challenge infection is shown.

For this purpose 8 female BALB/c mice were injected intramuscularly with the 0.001 fold human dose of RABIPUR® and 3 μg R722 and 0.81 μg $CR_{12}C$ (3.7:1 w/w). 37 days after vaccination the mice were infected with a lethal dose of rabies virus of challenge virus strain (CVS) using a 25-fold $LD_{50}$ (lethal doses 50%).

As can be seen, the polymeric carrier cargo complex strongly increases the survival of mice against lethal Rabies virus infection compared to vaccination with RABIPUR® alone, which further proofs the beneficial adjuvant properties of the polymeric carrier cargo complex.

Figure 25C:
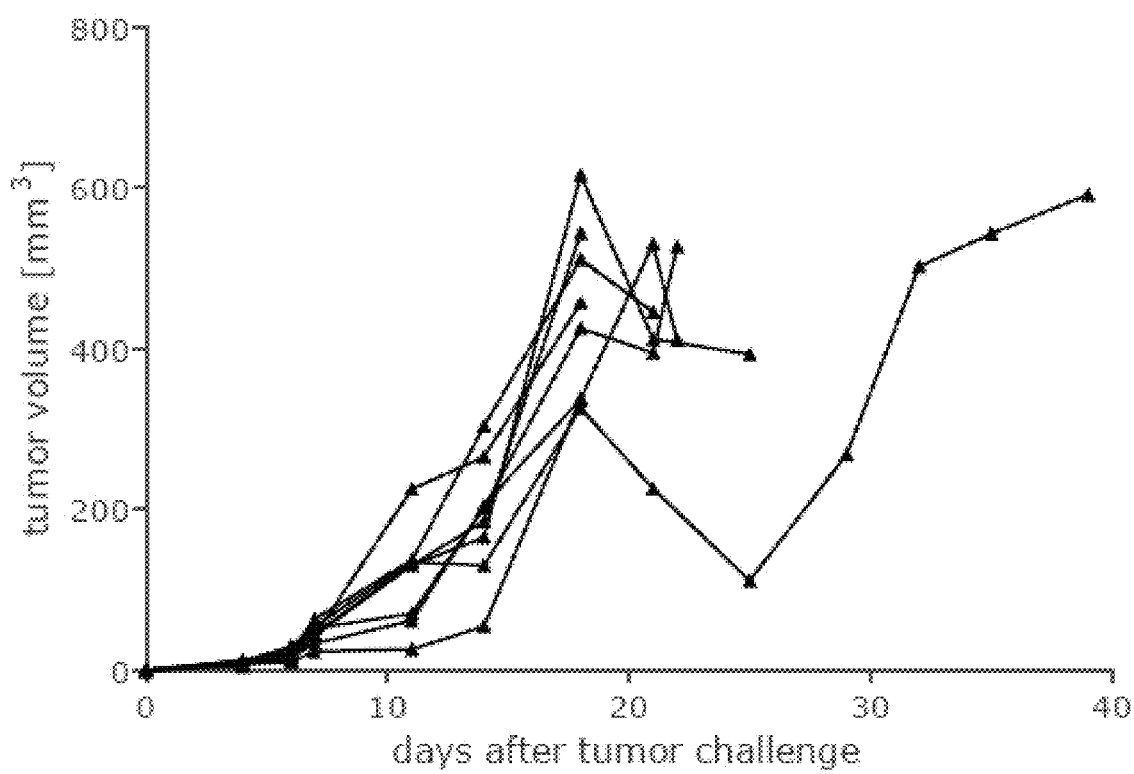

FIGS. 25A-C: show the (in vivo) effect of the addition of the polymeric carrier cargo complex formed by the disulfide-crosslinked cationic peptide $CR_{12}C$ as carrier and the isRNA R722 as nucleic acid cargo to the human papilloma virus 16 (HPV16) derived long-chain peptide E7aa43-77 for the use as an adjuvant in tumour challenge experiments.

For this purpose, 8 C57BL/6 mice per group were challenged on day 1 with $1 \times 10^5$ TC-1 cells which express the HPV E6 and E7 protein. Vaccination started on day 7 after tumor challenge (median tumor volume 31-48 $mm^3$). Mice were intradermally vaccinated 5 times (on day 8, 12, 15, 19 and 22) with 5 μg (FIG. 25A) or 50 μg (FIG. 25B) E7 peptide combined with 50 μg $CR_{12}C$/R722 (1:2; w/w). For comparison, mice were injected with the polymeric cargo complexes alone (FIG. 25C).

As can be seen, the polymeric carrier cargo complex combined with HPV-16 derived E7 peptide E7aa43-77 even impairs the growth of tumours compared to the polymeric carrier cargo complex alone.

Figure 26:
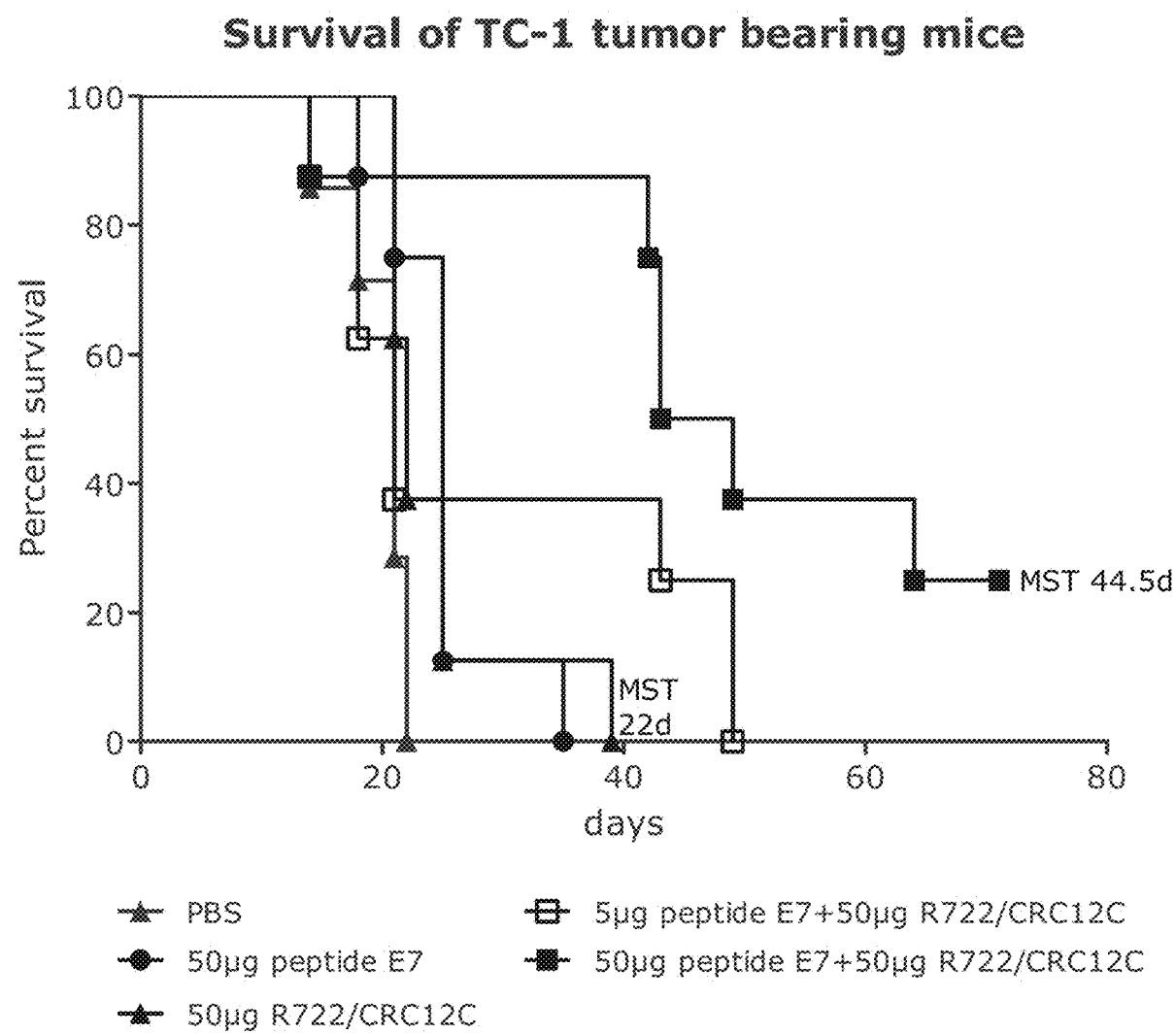

FIG. 26: shows the (in vivo) effect of the addition of the polymeric carrier cargo complex formed by the disulfide-crosslinked cationic peptide $CR_{12}C$ as carrier and the isRNA R722 as nucleic acid cargo to the human papilloma virus 16 (HPV16) derived E7 peptide E7aa43-77 for the use as an adjuvant in tumour challenge experiments.

For this purpose, 8 C57BL/6 mice per group were challenged on day 1 with $1 \times 10^5$ TC-1 cells. Vaccination started on day 7 after tumor challenge (median tumor volume 31-48 $mm^3$). Mice were intradermally vaccinated 5 times (on day 8, 12, 15, 19 and 22) with 5 g or 50 μg E7 peptide E7aa43-77 combined with 50 μg $CR_{12}C$/R722 (1:2; w/w). For comparison, mice were injected with the E7 peptide or the polymeric cargo complexes alone. Injection with PBS buffer served as negative control.

As can be seen, the polymeric carrier cargo complex combined with HPV-16 derived E7 peptide strongly enhances the survival of tumor bearing mice (Mean survival time of 44.5 days for 50 μg E7 peptide+50 μg polymeric carrier cargo complex; mean survival time of 22 days 5 μg E7 peptide+50 μg polymeric carrier cargo complex) compared to the E7 peptide or 50 polymeric carrier cargo complex alone.

Figure 27:
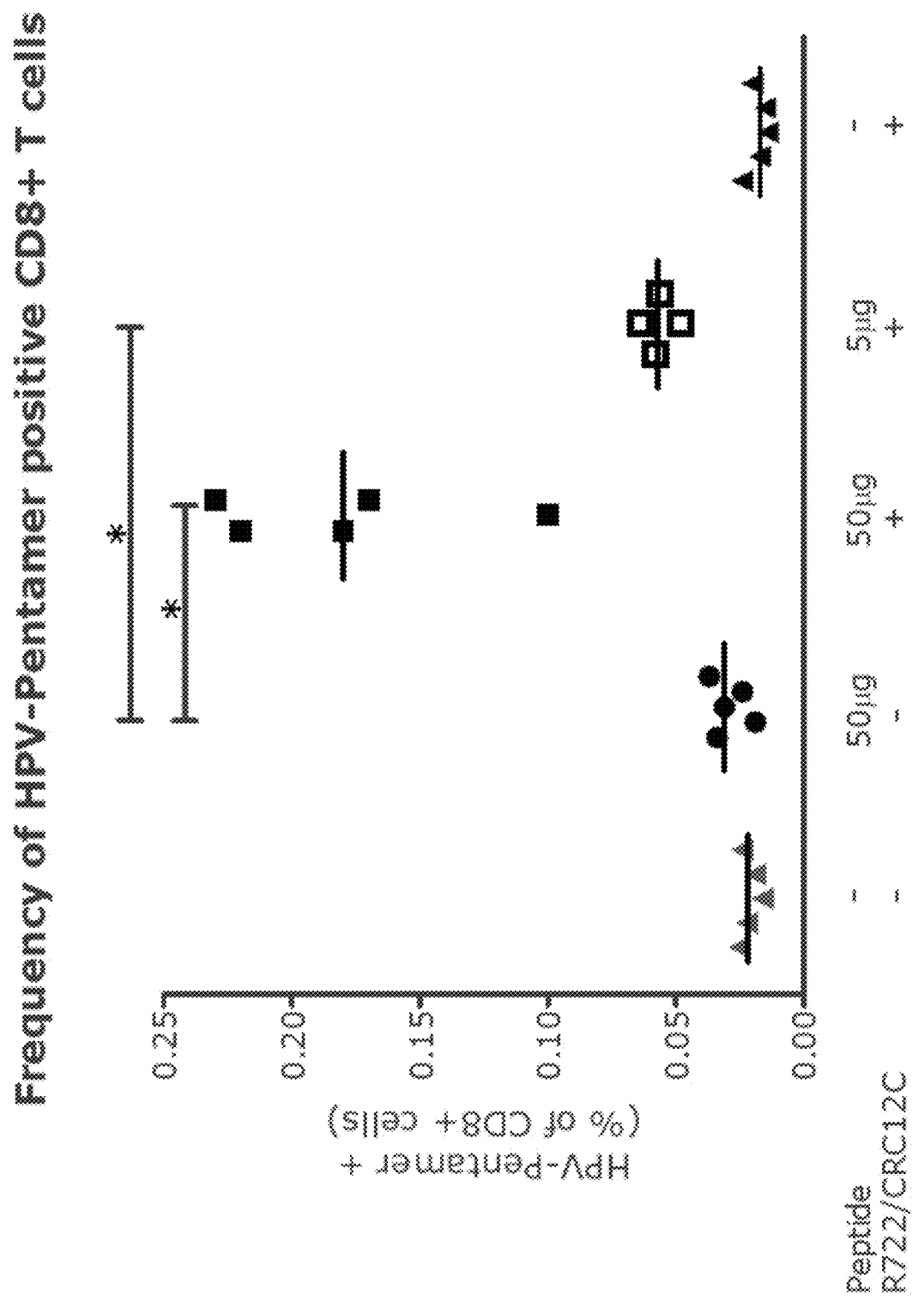

FIG. 27: shows the (in vivo) effect of the addition of the polymeric carrier cargo complex formed by the disulfide-crosslinked cationic peptide $CR_{12}C$ as carrier and the isRNA R722 as nucleic acid cargo to the human papilloma virus 16 (HPV16) derived E7 peptide E7aa43-77 for the use as an adjuvant in tumour challenge experiments.

For this purpose, 13 C57BL/6 mice per group were intradermally vaccinated once per week for four weeks with the polymeric carrier cargo complex formed by the disulfide-crosslinked cationic peptide $CR_{12}C$ as carrier and the isRNA R722 as nucleic acid cargo and the E7 peptide as indicated in the Figure. Eight weeks after the fourth vaccination, 5 mice/group were sacrificed, splenocytes were isolated and the frequency of antigen-specific $CD8^+$ T cells was determined by HPV-pentamer staining and flow cytometry according to example 13.

As can be seen, the polymeric carrier cargo complex combined with the HPV-16 derived E7 peptide E7aa43-77 results in a statistically significant increase of antigen-specific $CD8^+$ T cells compared to mice vaccinated with 50 μg of the E7 peptide alone (p=0.0007 for 5 μg E7 peptide and p=0.0002 50 μg E7 peptide; statistical differences between groups were assessed by unpaired t-test). Thus, the combination of the polymeric carrier cargo complex combined with the HPV-16 derived E7 peptide induces a potent memory $CD8^+$ T cell response.

Figure 28:
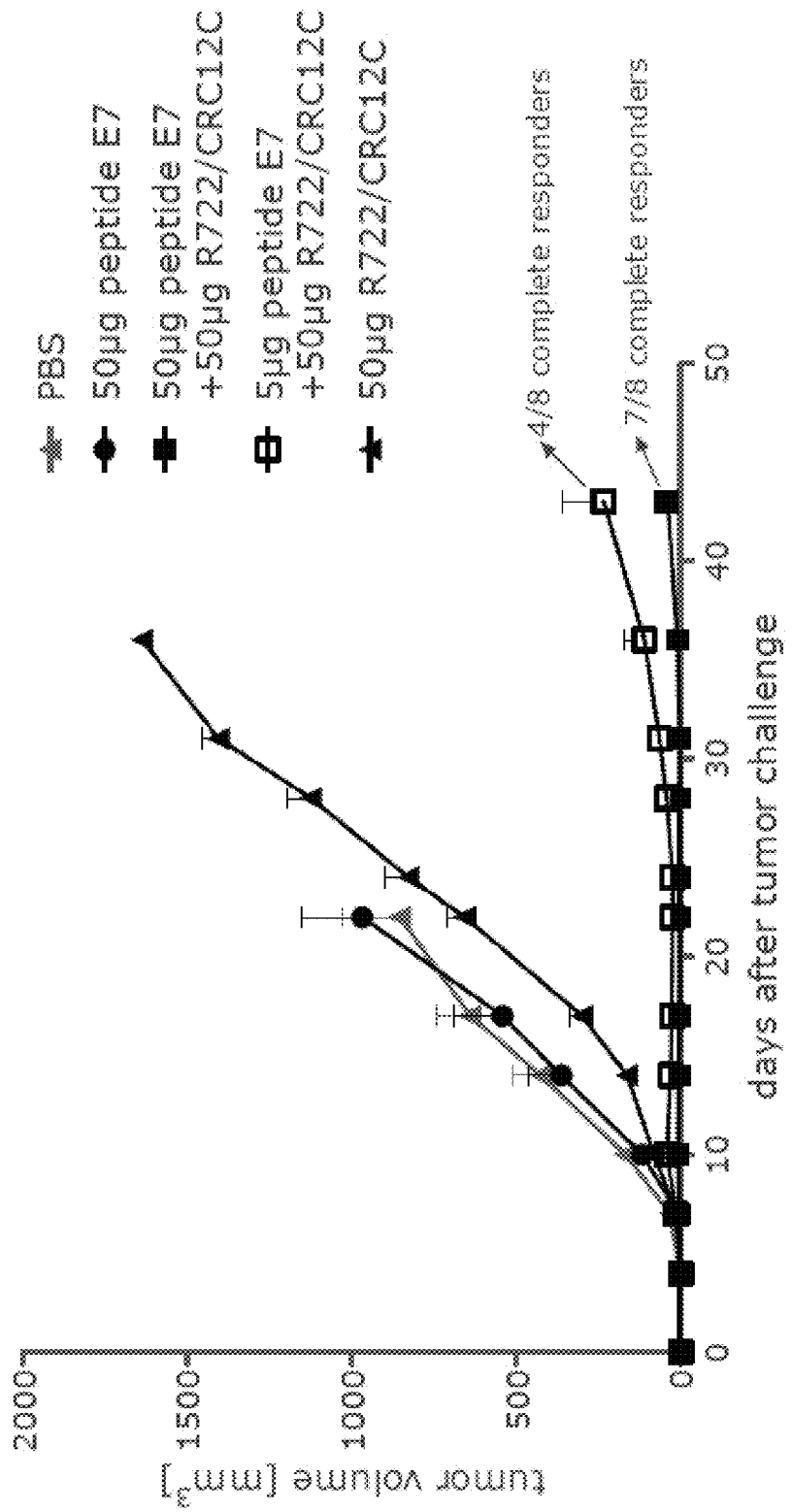

FIG. 28: shows the (in vivo) effect of the addition of the polymeric carrier cargo complex formed by the disulfide-crosslinked cationic peptide $CR_{12}C$ as carrier and the isRNA R722 as nucleic acid cargo to the human papilloma virus 16 (HPV16) derived E7 peptide E7aa43-77 for the use as an adjuvant in tumour challenge experiments.

For this purpose, 13 C57BL/6 mice per group were intradermally vaccinated once per week for four weeks with the polymeric carrier cargo complex formed by the disulfide-crosslinked cationic peptide $CR_{12}C$ as carrier and the isRNA R722 as nucleic acid cargo and the E7 peptide as indicated in the Figure. Eight weeks after the fourth vaccination 8 mice/group were challenged with $1 \times 10^5$ TC-1 tumor cells and tumor growth was monitored.

As can be seen, the polymeric carrier cargo complex combined with the HPV-16 derived E7 peptide E7aa43-77 results in a drastic delay of tumor growth (4 complete responses for 5 μg E7 peptide+50 μg of 50 μg polymeric carrier cargo complex; 7 complete responders for 50 μg E7 peptide+50 μg of 50 μg polymeric carrier cargo complex). Thus, the combination of the polymeric carrier cargo complex combined with the HPV-16 derived E7 peptide induces a potent memory $CD8^+$ T cell response.

Figure 29A:
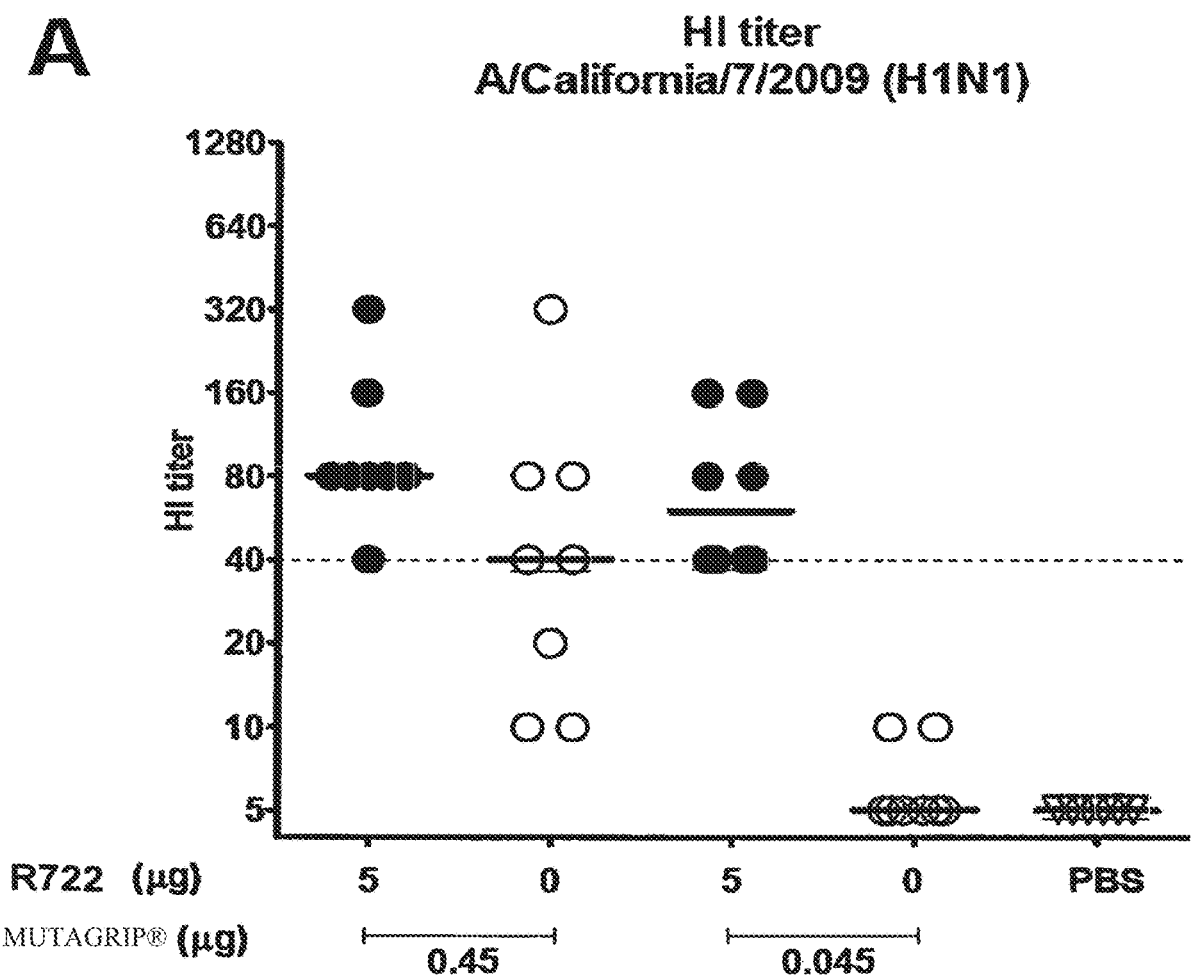
Figure 29B:
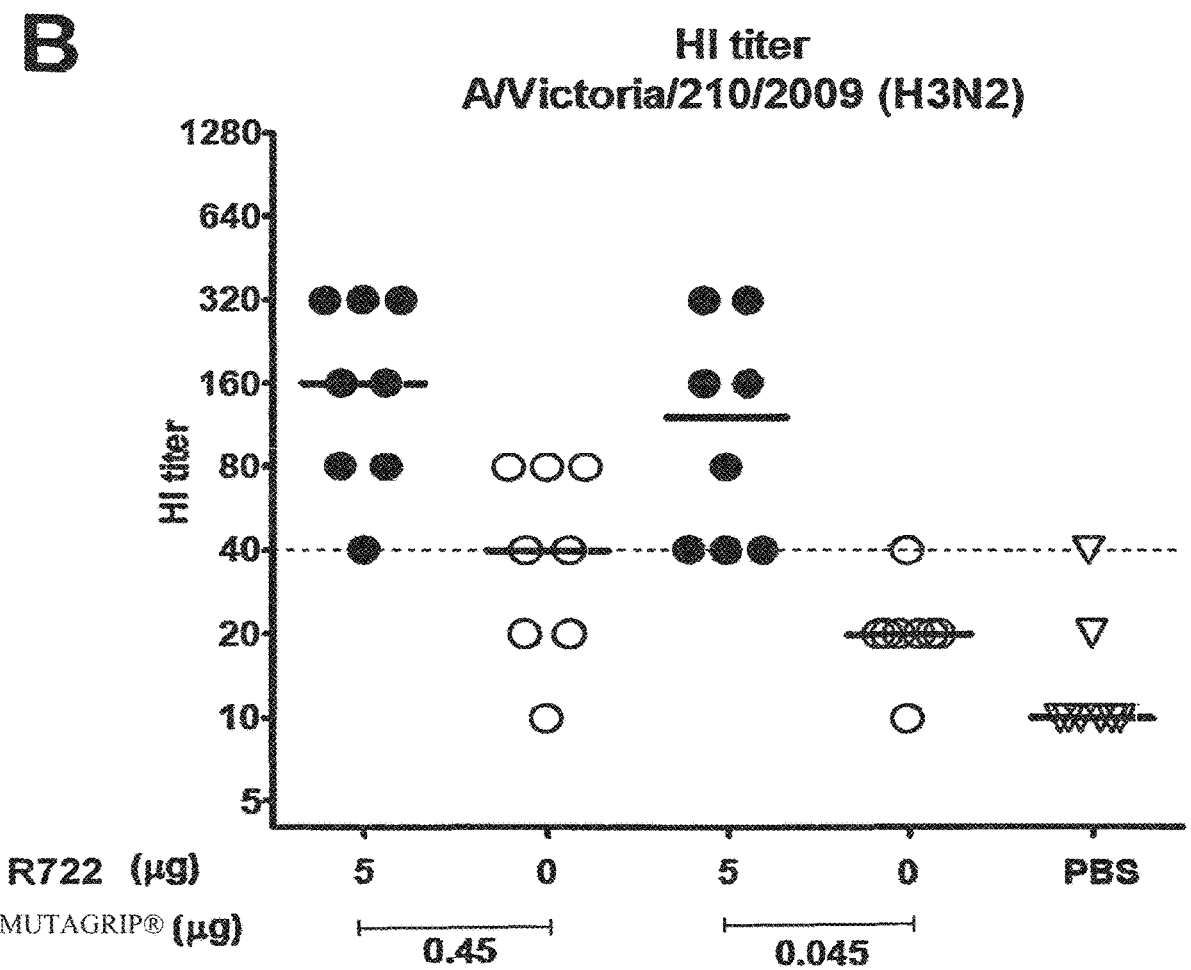

FIGS. 29A-B: show the (in vivo) effect of the addition of the polymeric carrier cargo complex formed by the disulfide-crosslinked cationic peptide $CR_{12}C$ as carrier and the isRNA R722 as nucleic acid cargo to the seasonal influenza vaccine MUTAGRIP® (comprising inactivated seasonal influenza virus strains as recommended by the WHO) for the use as an adjuvant on the induction of influenza specific hemagglutinin inhibition (HI) titers (as represented by HI titer).

For this purpose, 8 female BALB/c mice were injected intramuscularly with 0.45 μg or 0.045 μg MUTAGRIP® and 5 μg R722+1.35 μg $CR_{12}C$ (3.7:1, w/w). 21 days after the immunization blood samples were taken and HI titers were determined in the sera. The HI titer is widely used as a surrogate parameter of influenza vaccine efficacy with a HI titer of ≥1:40 commonly defined as the protective limit in humans.

As can be seen, the polymeric carrier cargo complex strongly increases the induction of influenza A H1N1-specific HI titers (FIG. 29A) and H3N2-specific HI titers (FIG. 29B) compared to the vaccination with MUTAGRIP® alone, which further demonstrates the beneficial adjuvant properties of the polymeric carrier cargo complex.

Figure 30:
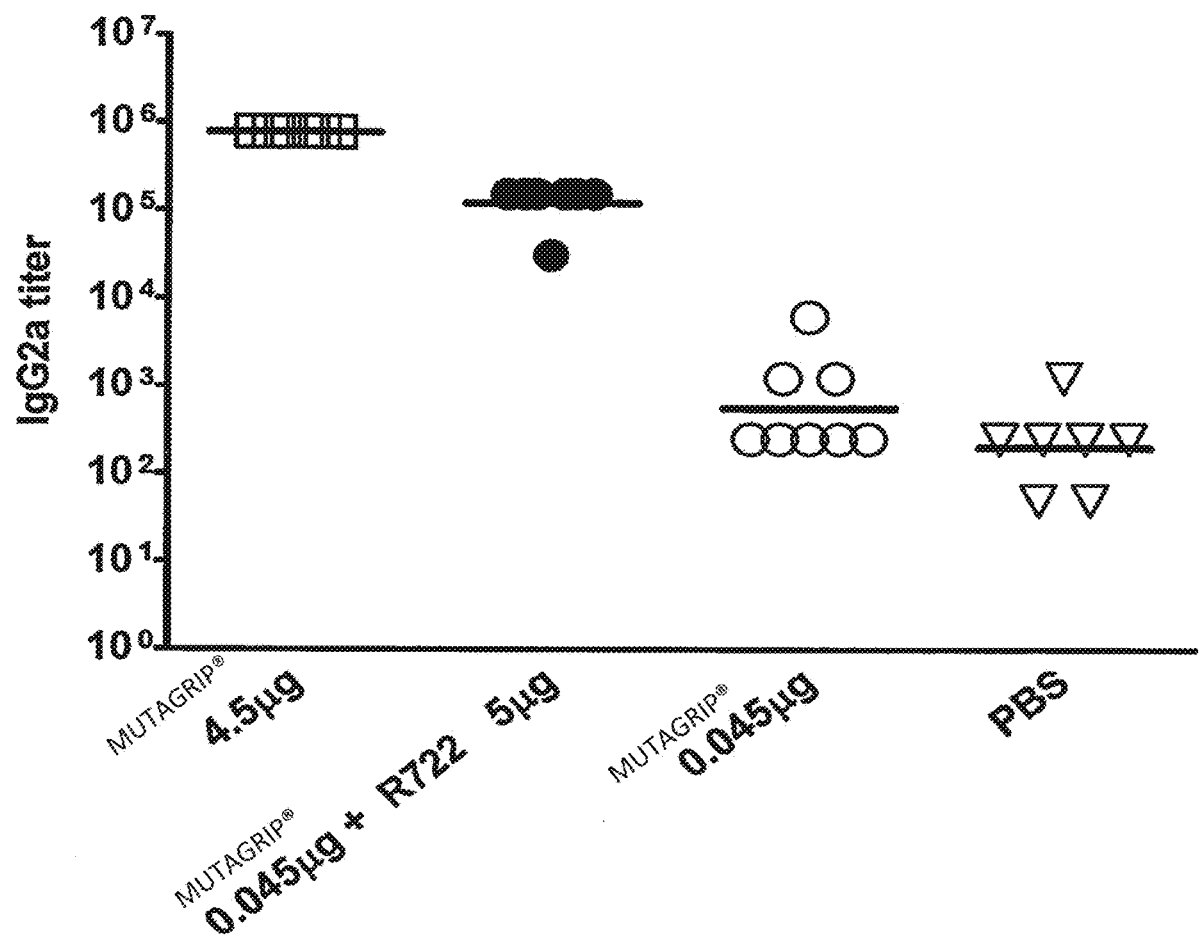

FIG. 30: shows the (in vivo) effect of the addition of the polymeric carrier cargo complex formed by the disulfide-crosslinked cationic peptide $CR_{12}C$ as carrier and the isRNA R722 as nucleic acid cargo to the seasonal influenza vaccine MUTAGRIP® (comprising inactivated seasonal influenza virus strains as recommended by the WHO) for the use as an adjuvant on the induction of influenza specific IgG2a antibodies (as represented by IgG2a titer).

For this purpose, 8 female BALB/c mice were injected intramuscularly with 4.5 μg or 0.045 μg MUTAGRIP® and 5 μg R722+1.35 μg $CR_{12}C$ (3.7:1 w/w). 21 days after the immunization blood samples were taken and analysed for IgG2a antibodies directed against influenza A H1N1 virus.

As can be seen, the polymeric carrier cargo complex strongly increases the induction of influenza A H1N1-specific IgG2a antibodies compared to the vaccination with MUTAGRIP® alone, which further demonstrates the beneficial adjuvant properties of the polymeric carrier cargo complex, particularly in regards to dose-sparing of the seasonal influenza vaccine.

EXAMPLES

The following examples are intended to illustrate the invention further. They are not intended to limit the subject matter of the invention thereto.

1. Reagents:

Cationic Peptides as Cationic Component of the Polymeric Carrier:

$R_7$:
(SEQ ID NO. 109)
Arg-Arg-Arg-Arg-Arg-Arg-Arg ($Arg_7$)

$CR_7C$:
(SEQ ID NO. 1)
Cys-Arg-Arg-Arg-Arg-Arg-Arg-Arg-Cys (Cys$Arg_7$Cys)

$R_9$:
(SEQ ID NO. 110)
Arg-Arg-Arg-Arg-Arg-Arg-Arg-Arg-Arg ($Arg_9$)

$R_{12}$:
(SEQ ID NO. 111)
Arg-Arg-Arg-Arg-Arg-Arg-Arg-Arg-Arg-Arg-Arg-Arg ($Arg_{12}$)

$CR_9C$:
(SEQ ID NO. 2)
Cys-Arg-Arg-Arg-Arg-Arg-Arg-Arg-Arg-Arg-Cys (Cys-$Arg_9$-Cys)

$CR_{12}C$:
(SEQ ID NO. 6)
Cys-Arg-Arg-Arg-Arg-Arg-Arg-Arg-Arg-Arg-Arg-Arg-Arg-Cys (Cys-$Arg_{12}$-Cys)

Nucleic Acids as Cargo of the Polymeric Carrier Cargo Complex:

R1180: mRNA coding for luciferase
(SEQ ID NO. 112)
GGGAGAAAGCUUGAGGAUGGAGGACGCCAAGAACAUCAAGAAGGGCCCGG

CGCCCUUCUACCCGCUGGAGGACGGGACCGCCGGCGAGCAGCUCCACAAG

GCCAUGAAGCGGUACGCCCUGGUGCCGGGCACGAUCGCCUUCACCGACGC

CCACAUCGAGGUCGACAUCACCUACGCGGAGUACUUCGAGAUGAGCGUGC

GCCUGGCCGAGGCCAUGAAGCGGUACGGCCUGAACACCAACCACCGGAUC

GUGGUGUGCUCGGAGAACAGCCUGCAGUUCUUCAUGCCGGUGCUGGGCGC

CCUCUUCAUCGGCGUGGCCGUCGCCCCGGCGAACGACAUCUACAACGAGC

GGGAGCUGCUGAACAGCAUGGGGAUCAGCCAGCCGACCGUGGUGUUCGUG

AGCAAGAAGGGCCUGCAGAAGAUCCUGAACGUGCAGAAGAAGCUGCCCAU

CAUCCAGAAGAUCAUCAUCAUGGACAGCAAGACCGACUACCAGGGCUUCC

AGUCGAUGUACACGUUCGUGACCAGCCACCUCCCGCCGGGCUUCAACGAG

UACGACUUCGUCCCGGAGAGCUUCGACCGGGACAAGACCAUCGCCCUGAU

CAUGAACAGCAGCGGCAGCACCGGCCUGCCGAAGGGGGUGGCCCUGCCGC

ACCGGACCGCCUGCGUGCGCUUCUCGCACGCCCGGGACCCCAUCUUCGGC

AACCAGAUCAUCCCGGACACCGCCAUCCUGAGCGUGGUGCCGUUCCACCA

CGGCUUCGGCAUGUUCACGACCCUGGGCUACCUCAUCUGCGGCUUCCGGG

UGGUCCUGAUGUACCGGUUCGAGGAGGAGCUGUUCCUGCGGAGCCUGCAG

GACUACAAGAUCCAGAGCGCGCUGCUCGUGCCGACCCUGUUCAGCUUCUU

CGCCAAGAGCACCCUGAUCGACAAGUACGACCUGUCGAACCUGCACGAGA

UCGCCAGCGGGGCGCCCCGCUGAGCAAGGAGGUGGGCGAGGCCGUGGCC

AAGCGGUUCCACCUCCCGGGCAUCCGCCAGGGCUACGGCCUGACCGAGAC

CACGAGCGCGAUCCUGAUCACCCCCGAGGGGGACGACAAGCCGGGCGCCG

UGGGCAAGGUGGUCCCGUUCUUCGAGGCCAAGGUGGUGGACCUGGACACC

GGCAAGACCCUGGGCGUGAACCAGCGGGGCGAGCUGUGCGUGCGGGGGCC

GAUGAUCAUGAGCGGCUACGUGAACAACCCGGAGGCCACCAACGCCCUCA

UCGACAAGGACGGCUGGCUGCACAGCGGCGACAUCGCCUACUGGGACGAG

GACGAGCACUUCUUCAUCGUCGACCGGCUGAAGUCGCUGAUCAAGUACAA

GGGCUACCAGGUGGCGCCGGCCGAGCUGGAGAGCAUCCUGCUCCAGCACC

CCAACAUCUUCGACGCCGGCGUGGCCGGGCUGCCGGACGACGACGCCGGC

GAGCUGCCGGCCGCGGUGGUGGUGCUGGAGCACGGCAAGACCAUGACGGA

GAAGGAGAUCGUCGACUACGUGGCCAGCCAGGUGACCACCGCCAAGAAGC

UGCGGGGCGGCGUGGUGUUCGUGGACGAGGUCCCGAAGGGCCUGACCGGG

AAGCUCGACGCCCGGAAGAUCCGCGAGAUCCUGAUCAAGGCCAAGAAGGG

CGGCAAGAUCGCCGUGUAAGACUAGUUAUAAGACUGACUAGCCCGAUGGG

CCUCCCAACGGGCCCUCCUCCCCUCCUUGCACCGAGAUUAAUAAAAAAAA

AAAAAAAAAAAAAAAAAAAAAAAAAAAAAAAAAAAAAAAAAAAAAAAA

AAAAAAUAUUCCCCCCCCCCCCCCCCCCCCCCCCCCCCCCUCUAG (R1180)

R722A: long non-coding isGU-rich RNA
(SEQ ID NO. 105)

R722B: long non-coding isGU-rich RNA
(SEQ ID NO. 122)

R491: mRNA coding for luciferase
(SEQ ID NO. 113)
GGGAGAAAGCUUGAGGAUGGAGGACGCCAAGAACAUCAAGAAGGGCCCGG

CGCCCUUCUACCCGCUGGAGGACGGGACCGCCGGCGAGCAGCUCCACAAG

GCCAUGAAGCGGUACGCCCUGGUGCCGGGCACGAUCGCCUUCACCGACGC

CCACAUCGAGGUCGACAUCACCUACGCGGAGUACUUCGAGAUGAGCGUGC

GCCUGGCCGAGGCCAUGAAGCGGUACGGCCUGAACACCAACCACCGGAUC

GUGGUGUGCUCGGAGAACAGCCUGCAGUUCUUCAUGCCGGUGCUGGGCGC

CCUCUUCAUCGGCGUGGCCGUCGCCCCGGCGAACGACAUCUACAACGAGC

GGGAGCUGCUGAACAGCAUGGGGAUCAGCCAGCCGACCGUGGUGUUCGUG

-continued

AGCAAGAAGGGCCUGCAGAAGAUCCUGAACGUGCAGAAGAAGCUGCCCAU

CAUCCAGAAGAUCAUCAUCAUGGACAGCAAGACCGACUACCAGGGCUUCC

AGUCGAUGUACACGUUCGUGACCAGCCACCUCCCGCCGGGCUUCAACGAG

UACGACUUCGUCCCGGAGAGCUUCGACCGGGACAAGACCAUCGCCCUGAU

CAUGAACAGCAGCGGCAGCACCGGCCUGCCGAAGGGGUGGCCCUGCCGC

ACCGGACCGCCUGCGUGCGCUUCUCGCACGCCCGGGACCCCAUCUUCGGC

AACCAGAUCAUCCCGGACACCGCCAUCCUGAGCGUGGUGCCGUUCCACCA

CGGCUUCGGCAUGUUCACGACCCUGGGCUACCUCAUCUGCGGCUUCCGGG

UGGUCCUGAUGUACCGGUUCGAGGAGGAGCUGUUCCUGCGGAGCCUGCAG

GACUACAAGAUCCAGAGCGCGCUGCUCGUGCCGACCCUGUUCAGCUUCUU

CGCCAAGAGCACCCUGAUCGACAAGUACGACCUGUCGAACCUGCACGAGA

UCGCCAGCGGGGCGCCCCGCUGAGCAAGGAGGUGGGCGAGGCCGUGGCC

AAGCGGUUCCACCUCCCGGGCAUCCGCCAGGGCUACGGCCUGACCGAGAC

CACGAGCGCGAUCCUGAUCACCCCCGAGGGGACGACAAGCCGGGCGCCG

UGGGCAAGGUGGUCCCGUUCUUCGAGGCCAAGGUGGUGGACCUGGACACC

GGCAAGACCCUGGGCGUGAACCAGCGGGGCGAGCUGUGCGUGCGGGGGCC

GAUGAUCAUGACGCGGCUACGUGAACAACCCGGAGGCCACCAACGCCCUCA

UCGACAAGGACGGCUGGCUGCACAGCGGCGACAUCGCCUACUGGGACGAG

GACGAGCACUUCUUCAUCGUCGACCGGCUGAAGUCGCUGAUCAAGUACAA

GGGCUACCAGGUGGCGCCGGCCGAGCUGGAGAGCAUCCUGCUCCAGCACC

CCAACAUCUUCGACGCCGGCGUGGCCGGGCUGCCGGACGACGACGCCGGC

GAGCUGCCGGCCGCGGUGGUGGUGCUGGAGCACGGCAAGACCAUGACGGA

GAAGGAGAUCGUCGACUACGUGGCCAGCCAGGUGACCACCGCCAAGAAGC

UGCGGGCGGCGUGGUGUUCGUGGACGAGGUCCCGAAGGGCCUGACCGGG

AAGCUCGACGCCCGGAAGAUCCGCGAGAUCCUGAUCAAGGCCAAGAAGGG

CGGCAAGAUCGCCGUGUAAGACUAGUUAUAAGACUGACUAGCCCGAUGGG

CCUCCCAACGGGCCCUCCUCCCCUCCUUGCACCGAGAUUAAUAAAAAAAA

AAAAAAAAAAAAAAAAAAAAAAAAAAAAAAAAAAAAAAAAAAAAAAAAA

AAAAAAUAUUCCCCCCCCCCCCCCCCCCCCCCCCCCCUCUAGACAAU

UGGAAUU (R491)

CpG 2216: CpG oligonucleotide
(SEQ ID NO. 114)
GGGGGACGATCGTCGGGGGG

ShortGU rich: GU-rich RNA oligonucleotide
(SEQ ID NO. 115)
GGUUUUUUUUUUUUUUUGGG

Experiments indicating the use of nucleic acid cargo R722 have been performed with the sequences R722A and/or R722B.

Antigens and Epitopes:

Ovalbumine-derived peptide
(SEQ ID NO. 116)
SIINFEKL

Ovalbumine:
(SEQ ID NO. 117)

-continued

MGSIGAASMEFCFDVFKELKVHHANENIFYCPIAIMSALAMVYLGAKDST

RTQINKVVRFDKLPGFGDSIEAQCGTSVNVHSSLRDILNQITKPNDVYSF

SLASRLYAEERYPILPEYLQCVKELYRGGLEPINFQTAADQARELINSWV

ESQTNGIIRNVLQPSSVDSQTAMVLVNAIVFKGLWEKAFKDEDTQAMPFR

VTEQESKPVQMMYQIGLFRVASMASEKMKILELPFASGTMSMLVLLPDEV

SGLEQLESIINFEKLTEWTSSNVMEERKIKVYLPRMKMEEKYNLTSVLMA

MGITDVFSSSANLSGISSAESLKISQAVHAAHAEINEAGREVVGSAEAGV

DAASVSEEFRADHPFLFCIKHIATNAVLFFGRCVSP

HPV16 E7 aa43-77:
(SEQ ID NO. 118)
GQAEPDRAHYNIVTFCCKCDSTLRLCVQSTHVDIR

HPV16 E7 aa48-57:
(SEQ ID NO. 119)
DRAHYNIVTF

HPV16 E7 aa49-57 (H-2 Db):
(SEQ ID NO. 120)
RAHYNIVTF

NY-ESO-1:
(SEQ ID NO. 121)
MQAEGRGTGGSTGDADGPGGPGIPDGPGGNAGGPGEAGATGGRGPRGAGA

ARASGPGGGAPRGPHGGAASGLNGCCRCGARGPESRLLEFYLAMPFATPM

EAELARRSLAQDAPPLPVPGVLLKEFTVSGNILTIRLTAADHRQLQLSIS

SCLQQLSLLMWITQCFLPVFLAQPPSGQRR

2. Preparation of Nucleic Acid Sequences:

For the present examples nucleic acid sequences as indicated in example 1 were prepared and used for formation of the polymerized polymeric carrier cargo complexes or for non-polymerized carrier cargo complexes for comparison. These polymeric carrier cargo complexes were used for in vitro and in vivo transaction, for in vitro immunostimulation and for particle characterizations.

According to a first preparation, the DNA sequences, coding for the corresponding RNA sequences R1180, R722 and R491 sequences were prepared. The sequences of the corresponding RNAs are shown in the sequence listing (SEQ ID NOs: 112, 105, and 113).

The short GU rich sequences and the CpG 2216 oligonucleotides were prepared by automatic solid-phase synthesis by means of phosphoramidite chemistry. The sequences are shown in the sequence listing (SEQ ID NOs: 115 and 114).

In Vitro Transcription:

The respective DNA plasmids prepared according to Example 2 for R1180, R722 and R491 were transcribed in vitro using T7-Polymerase (T7-Opti mRNA Kit, CureVac, Tuibingen, Germany) following the manufactures instructions. Subsequently the mRNA was purified using PUREMESSENGER®, RNA production process (CureVac, Tubingen, Germany).

3. Synthesis of Polymeric Carrier Cargo Complexes:

The nucleic acid sequences defined above in Example 1 were mixed with the cationic components as defined in Example 1. Therefore, the indicated amount of nucleic acid sequence was mixed with the respective cationic component in mass ratios as indicated, thereby forming a complex. If polymerizing cationic components were used according to the present invention polymerization of the cationic components took place simultaneously to complexation of the nucleic acid cargo. Afterwards the resulting solution was adjusted with water to a final volume of 50 µl and incubated for 30 min at room temperature. The different ratios of cationic component/nucleic acid used in the experiments are shown in Table 1.

TABLE 1

| Sample (cationic peptide/nucleic acid) | Mass ratio | N/P ratio | Molar ratio |
|---|---|---|---|
| CR$_{12}$C/R1180 | 1:2 | 0.9 | 44:1 |
| CR$_{12}$C/R1180 | 2:1 | 3.6 | 185:1 |
| R$_{12}$/R1180 | 1:2 | 0.7 | 48:1 |
| R$_{12}$/R1180 | 2:1 | 2.5 | 146:1 |
| CR$_9$C/R1180 | 2:1 | 0.9 | 55:1 |
| R$_9$/R1180 | 2:1 | 1.1 | 65:1 |
| CR$_7$C | 1:2 | 0.8 | 70:1 |
| R$_7$ | 1:2 | 1.0 | 85:1 |
| CR$_{12}$C/CpG | 1:2, 5 | 4.9 | 8:1 |
| CR$_{12}$C/R491 | 1:2 | 0.9 | 150:1 |
| CR$_{12}$C/short GU-rich | 1:2, 5 | 4.9 | 8:1 |
| CR$_{12}$C/R722 | 5:1 | 9.6 | 444:1 |
| CR$_{12}$C/R722 | 4:1 | 7.6 | 355:1 |
| CR$_{12}$C/R722 | 3:1 | 5.7 | 266:1 |
| CR$_{12}$C/R722 | 2:1 | 3.8 | 177:1 |
| CR$_{12}$C/R722 | 1:1 | 1.9 | 88:1 |
| CR$_{12}$C/R722 | 1:2 | 0.9 | 44:1 |
| CR$_{12}$C/R722 | 1:3 | 0.6 | 29:1 |
| CR$_{12}$C/R722 | 1:4 | 0.5 | 22:1 |
| CR$_{12}$C/R722 | 1:5 | 0.4 | 17:1 |

N/P ratio = is a measure of the ionic charge of the cationic component of the polymeric carrier or of the polymeric carrier as such. In the case that the cationic properties of the cationic component are provided by nitrogen atoms the N/P ratio is the ratio of basic nitrogen atoms to phosphate residues, considering that nitrogen atoms confer to positive charges and phosphate of the phosphate backbone of the nucleic acid confers to the negative charge.
N/P is preferably calculated by the following formula:

$$N/P = \frac{pmol\,[RNA] * ratio * cationic\,AS}{\mu g\,RNA * 3 * 1000}$$

As an example the RNA R722 according to SEQ ID NO: 122 was applied, which has a molecular weight of 186 kDa. Therefore 1 µg R722 RNA confers to 5.38 pmol RNA.

4. Cytokine Stimulation in hPBMCs:

HPBMC cells from peripheral blood of healthy donors were isolated using a Ficoll gradient and washed subsequently with 1×PBS (phophate-buffered saline). The cells were then seeded on 96-well microtiter plates (200×10$^3$/well). The hPBMC cells were incubated for 24 h with 10 µl of the polymeric carrier cargo complex from Example 3 containing the indicated amount of nucleic acid in X-VIVO 15 Medium (BioWhittaker). The immunostimulatory effect was measured by detecting the cytokine production of the hPBMCs (Tumour necrose factor alpha and Interferon alpha). Therefore, ELISA microtiter plates (Nunc MAX-ISORB™) were incubated over night (o/n) with binding buffer (0.02% NaN$_3$, 15 mM Na$_2$CO$_3$, 15 mM NaHCO$_3$, pH 9.7), additionally containing a specific cytokine antibody. Cells were then blocked with 1×PBS, containing 1% BSA (bovine serum albumin). The cell supernatant was added and incubated for 4 h at 37° C. Subsequently, the microtiter plate was washed with 1×PBS, containing 0.05% TWEEN®-20 and then incubated with a Biotin-labelled secondary antibody (BD Pharmingen, Heidelberg, Germany). Streptavidin-coupled horseraddish peroxidase was added to the plate. Then, the plate was again washed with 1×PBS, containing 0.05% TWEEN®-20 and ABTS (2,2'-azino-bis(3-ethyl-benzthiazoline-6-sulfonic acid) was added as a substrate. The amount of cytokine was determined by measuring the absorption at 405 nm (OD 405) using a standard curve with recombinant cytokines (BD Pharmingen, Heidelberg, Germany) with the Sunrise ELISA-Reader from Tecan (Crailsheim, Germany). The respective results are shown in FIG. 3-9.

5. Zetapotential Measurements:

The Zeta potential of the polymeric carrier cargo complexes was evaluated by the laser Doppler electrophoresis method using a Zetasizer Nano (Malvern Instruments, Malvern, UK). The measurement was performed at 25° C. and a scattering angle of 173° was used. The results are shown in FIG. 2.

6. Stability of Complexes after Lyophilization

The hydrodynamic diameters of polymeric carrier cargo complexes as prepared above were measured by dynamic light scattering using a Zetasizer Nano (Malvern Instruments, Malvern, UK) according to the manufacturer's instructions. The measurements were performed at 25° C. in buffer analysed by a cumulant method to obtain the hydrodynamic diameters and polydispersity indices of the polymeric carrier cargo complexes. Polymeric carrier cargo complexes were formed as indicated in Example 3 and the hydrodynamic diameters were measured with fresh prepared complexes and with reconstituted complexes after lyophilization. The respective results of the experiment are shown in FIG. 1.

7. Immunization Experiments:

a) Immunization with Ovalbumine or SIINFEKL (SEO ID NO: 116):

For immunization the vaccines Ovalbumine protein (OVA) (5 µg) or Ovalbumin-specific peptide SIINFEKL (SEO ID NO: 116) (50 µg) were combined with the polymeric cargo complexes R722/CR$_{12}$C (in a ratio of 2:1 w/w) (30 µg R722/15 µg CR$_{12}$C) as adjuvant and injected intradermally into female C57BL/6 mice (7 mice per group for tumour challenge and 5 mice per group for detection of an immune response). The vaccination was repeated 2 times in 2 weeks. For comparison mice were injected alone with the antigens.

b) Immunization with Rabies Vaccine:

For immunization the vaccine RABIPUR® or HDC (both comprise inactivated Rabies virus) (0.1, 0.01 and 0.001 fold human dose) was combined with the polymeric cargo complexes R722/CR$_{12}$C (in a ratio of 3.7:1 w/w) (30 µg R722/8.1 µg CR$_{12}$C) as adjuvant and injected intramuscularly into female Balb/c mice (5 or 8 mice per group; as indicated). For comparison mice were injected with RABIPUR® or HDC alone.

c) Immunization with Influenza A(H1N1)Pdm09 (Swine Flu) Vaccine:

For immunization the vaccine PANDEMRIX® or CELVAPAN® (both comprise inactivated A(H1N1)pdm09 influenza virus) (0.1 µg/dose) was combined with the polymeric cargo complexes R722/CR$_{12}$C (in a ratio of 2:1 w/w) (15 µg R722/7.5 µg CR$_{12}$C for CELVAPAN® and 30 µg R722/15 µg CR$_{12}$C for PANDEMRIX®) as adjuvant and injected intramuscularly into female Balb/c mice (5 mice per group). For comparison mice were injected with PANDEMRIX® or CELVAPAN® alone.

d) Immunization with Seasonal Influenza Vaccine:

For immunization the seasonal influenza vaccine BEGRIVAC® (comprises inactivated influenza virus strains as recommended by the WHO; season 2009/2010) (0.1 µg/dose) was combined with the polymeric cargo complexes R722/CR$_{12}$C (in a ratio of 2:1 w/w) (30 µg R722/15 µg CR$_{12}$C) as adjuvant and injected intramuscularly into female Balb/c mice (8 mice per group). For comparison mice were injected with BEGRIVAC® alone.

e) Immunization with Hepatitis B Vaccine:

For immunization the Hepatitis B vaccine ENGERIX®-B (comprises recombinant Hepatitis B surface antigen) (0.5 g/dose) was combined with the polymeric cargo complexes R722/CR$_{12}$C (in a ratio of 3.7:1 w/w) (6.25 µg R722/1.7 µg CR$_{12}$C) as adjuvant and injected intramuscularly into female Balb/c mice (8 mice per group). For comparison mice were injected with ENGERIX®-B alone.

f) Immunization with Human Papilloma Virus 16 (HPV16) E7-Derived Peptide:

For immunization the HPV16-derived peptide E7 aa43-77 (100 g/dose) was combined with the polymeric cargo complexes R722/CR$_{12}$C (in a ratio of 2:1 w/w) (50 µg R722/25 µg CR$_{12}$C) as adjuvant and injected intradermally into female C57BL/6 mice (5 mice per group). For comparison mice were injected with peptide alone.

Figure 22:
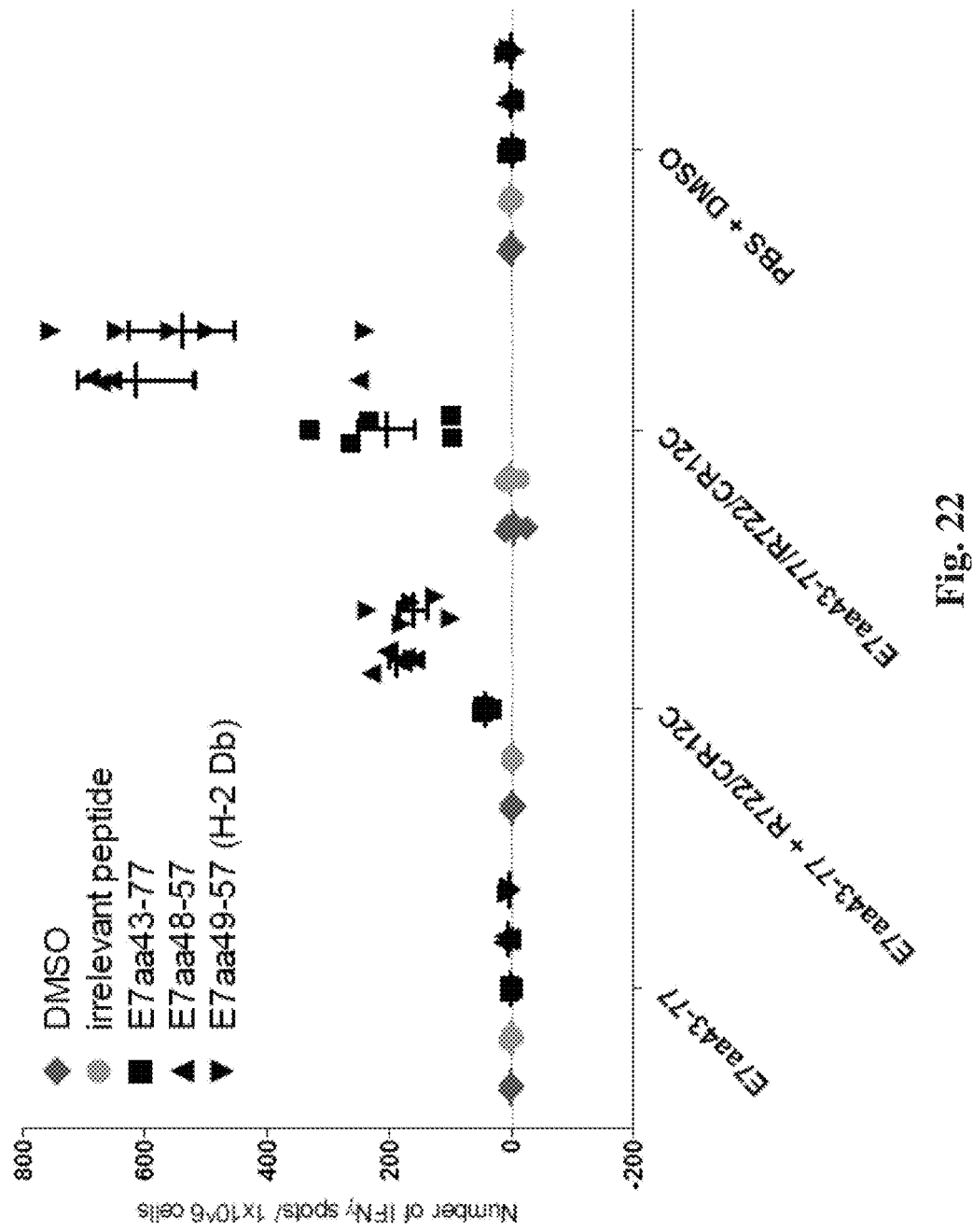

In a further experiment (FIG. 22) the HPV-derived peptide E7 aa43-77 (100 µg/dose) was combined with the polymeric cargo complexes R722/CR$_{12}$C (in a ratio of 2:1 w/w) (50 µg R722/25 µg CR$_{12}$C) during the polymerization step c) of the method of preparing the polymeric carrier cargo complexed as defined above. Therefore the HPV-derived peptide is part of the polymeric carrier cargo complex and is indicated as E7 aa43-77/R722/CR$_{12}$C. For comparison in this further experiment, mice were injected with peptide alone (E7 aa43-77) and the inventive pharmaceutical composition comprising the E7 aa43-77 peptide as antigen and the polymeric carrier cargo complex as adjuvant, wherein the polymeric carrier cargo complex does not comprise the antigen (E7 aa43-77+R722/CR$_{12}$C).

g) Immunization with NY-ESO-1 Protein:

For immunization the tumour antigen NY-ESO-1 protein (5 µg/dose) was combined with the polymeric cargo complexes R722/CR$_{12}$C (in a ratio of 2:1 w/w) (30 µg R722 15 µg CR$_{12}$C) as adjuvant and injected 2 times within 15 days intramuscularly into female C57BL/6 mice (5 mice per group). For comparison mice were injected with protein alone.

Figure 19:
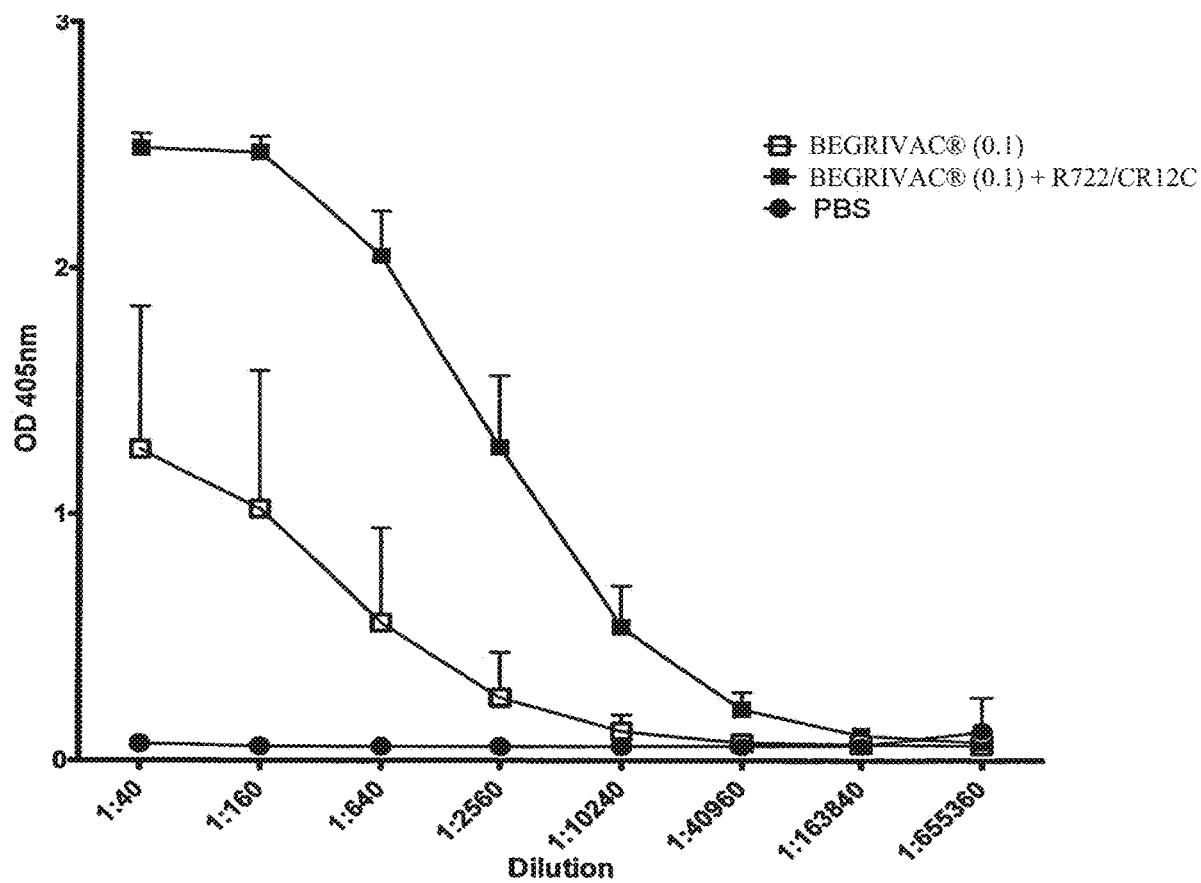

8. Detection of an Antigen-Specific Immune Response (B-Cell Immune Response):

a) Detection of Antibodies Directed Against Ovalbumine:

Detection of an antigen specific immune response (B-cell immune response) was carried out by detecting antigen specific antibodies. Therefore, blood samples were taken from vaccinated mice 5 days after the last vaccination and sera were prepared. MAXISORB™ ELISA plates (Nalgene Nunc International) were coated with *Gallus gallus* ovalbumine protein. After blocking with 1×PBS containing 0.05% TWEEN®-20 and 1% BSA the plates were incubated with diluted mouse serum. Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured. The results of this induction of antibodies upon vaccination with an inventive pharmaceutical composition are shown in FIG. 11.

b) Detection of Antibodies Directed Against Rabies Virus:

Detection of an antigen specific immune response (B-cell immune response) was carried out by detecting Rabies virus specific total IgG antibodies. Therefore, blood samples were taken from vaccinated mice 7 and 21 days after vaccination and sera were prepared. MAXISORB™ ELISA plates (Nalgene Nunc International) were coated with the commercially available rabies vaccine containing inactivated virus (HDC; 1:10000). After blocking with 1×PBS containing 0.05% TWEEN®-20 and 1% BSA the plates were incubated with diluted mouse serum. Subsequently a Horseradish peroxidase-coupled secondary antibody (Anti-mouse-IgG Pharmingen) was added. After washing, the plate was developed using ABTS and subsequently the conversion of the ABTS substrate (2,2'-azino-bis(3-ethyl-benzthiazoline-6-sulfonic acid) was measured. The results of this induction of antibodies upon vaccination with an inventive pharmaceutical composition are shown in FIG. 13.

c) Determination of the Affinity of Antibodies Directed Against Rabies Virus:

Detection of the total IgG antibodies directed against Rabies virus was carried out as disclosed under b) with the differences that mouse sera were only tested at a dilution of 1:40. Furthermore after incubation with the mouse serum the plates were washed with an increasing concentration of urea (6, 7 and 8 M urea). By washing with urea only antibodies with a high affinity to the antigen can be detected. The results of this induction of antibodies upon vaccination with an inventive pharmaceutical composition are shown in FIG. 15.

d) Detection of Antibodies Directed Against A(H1N1) Pdm09 Influenza Virus (Swine Flu):

Detection of an antigen specific immune response (B-cell immune response) was carried out by detecting A(H1N1) pdm09 influenza virus specific IgG2a antibodies. Therefore, blood samples were taken from vaccinated mice 14 days after vaccination and sera were prepared. MAXISORB™ ELISA plates (Nalgene Nunc International) were coated with Influenza A/California/7/09 A(H1N1)pdm09 inactivated virus (NIBSC, UK) (at 1 µg/ml). After blocking with 1 xPBS containing 0.05% TWEEN®-20 and 1% BSA the plates were incubated with diluted mouse serum. Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured to determine the induction of IgG2a antibodies. The results of this induction of antibodies upon vaccination with an inventive pharmaceutical composition are shown in FIG. 17.

e) Detection of Antibodies Directed Against Seasonal Influenza Virus Strains:

Detection of an antigen specific immune response (B-cell immune response) was carried out by detecting influenza virus specific IgG2a antibodies. Therefore, blood samples were taken from vaccinated mice 28 days after vaccination and sera were prepared. MAXISORB™ ELISA plates (Nalgene Nunc International) were coated with INFLUVAC® 2009/10 vaccine (at 5 µg/ml) containing the same viral Influenza antigens as the Influenza vaccine used for vaccination. After blocking with 1×PBS containing 0.05% TWEEN®-20 and 1% BSA the plates were incubated with diluted mouse serum. Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured to determine the induction of IgG2a antibodies. The results of this induction of antibodies upon vaccination with an inventive pharmaceutical composition are shown in FIG. 19.

f) Detection of Antibodies Directed Against Hepatitis B Surface Antigen (HBsAg):

Detection of an antigen specific immune response (B-cell immune response) was carried out by detecting HBsAG specific IgG2a antibodies. Therefore, blood samples were taken from vaccinated mice 28 days after vaccination and sera were prepared. MAXISORB™ ELISA plates (Nalgene Nunc International) were coated with recombinant Hepatitis B Surface Antigen (HBsAG) (Aldevron, USA) (1 µg/ml).

Figure 20:
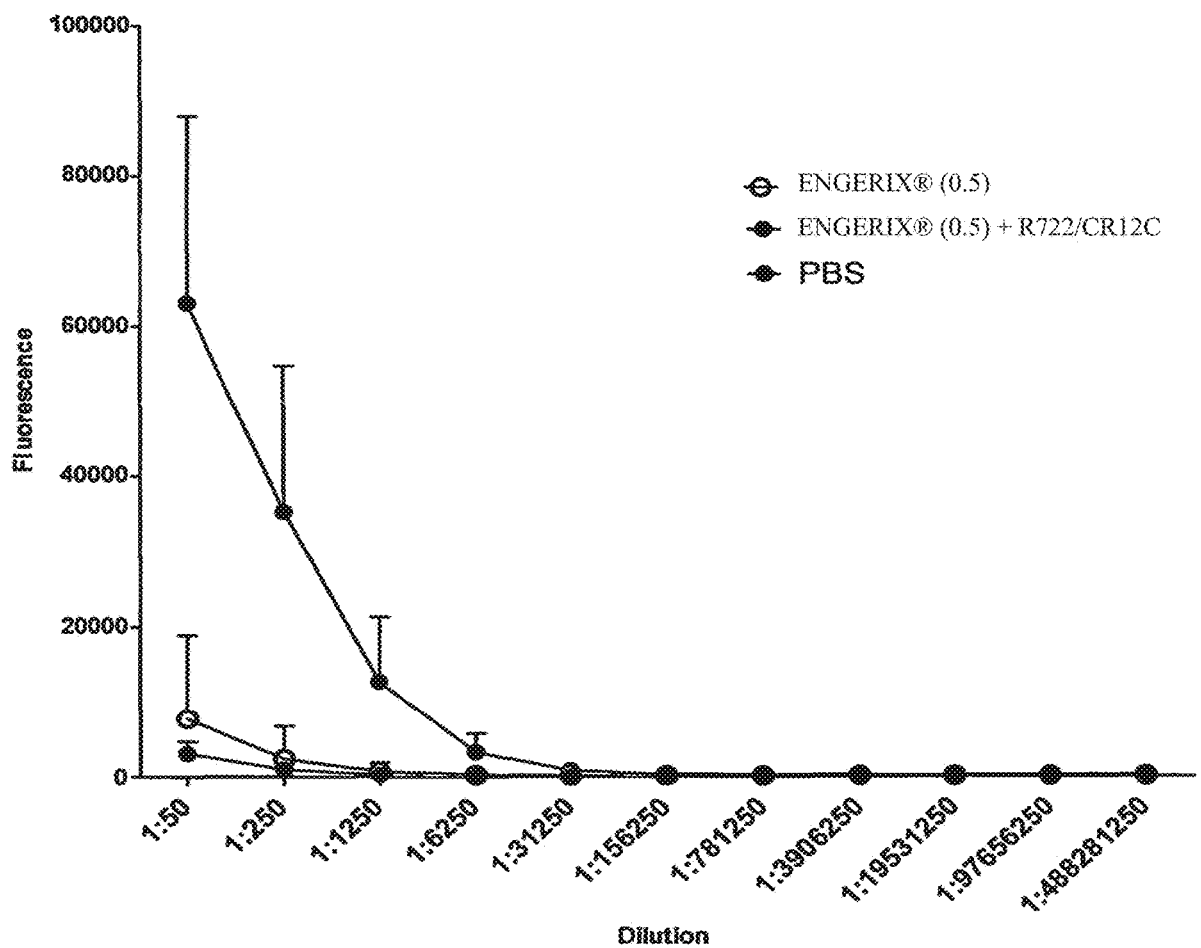

After blocking with 1×PBS containing 0.05% TWEEN®-20 and 1% BSA the plates were incubated with diluted mouse serum. Subsequently a biotin-coupled secondary antibody (Anti-mouse-IgG2a Pharmingen) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured to determine the induction of IgG2a antibodies. The results of this induction of antibodies upon vaccination with an inventive pharmaceutical composition are shown in FIG. 20.

Figure 21:
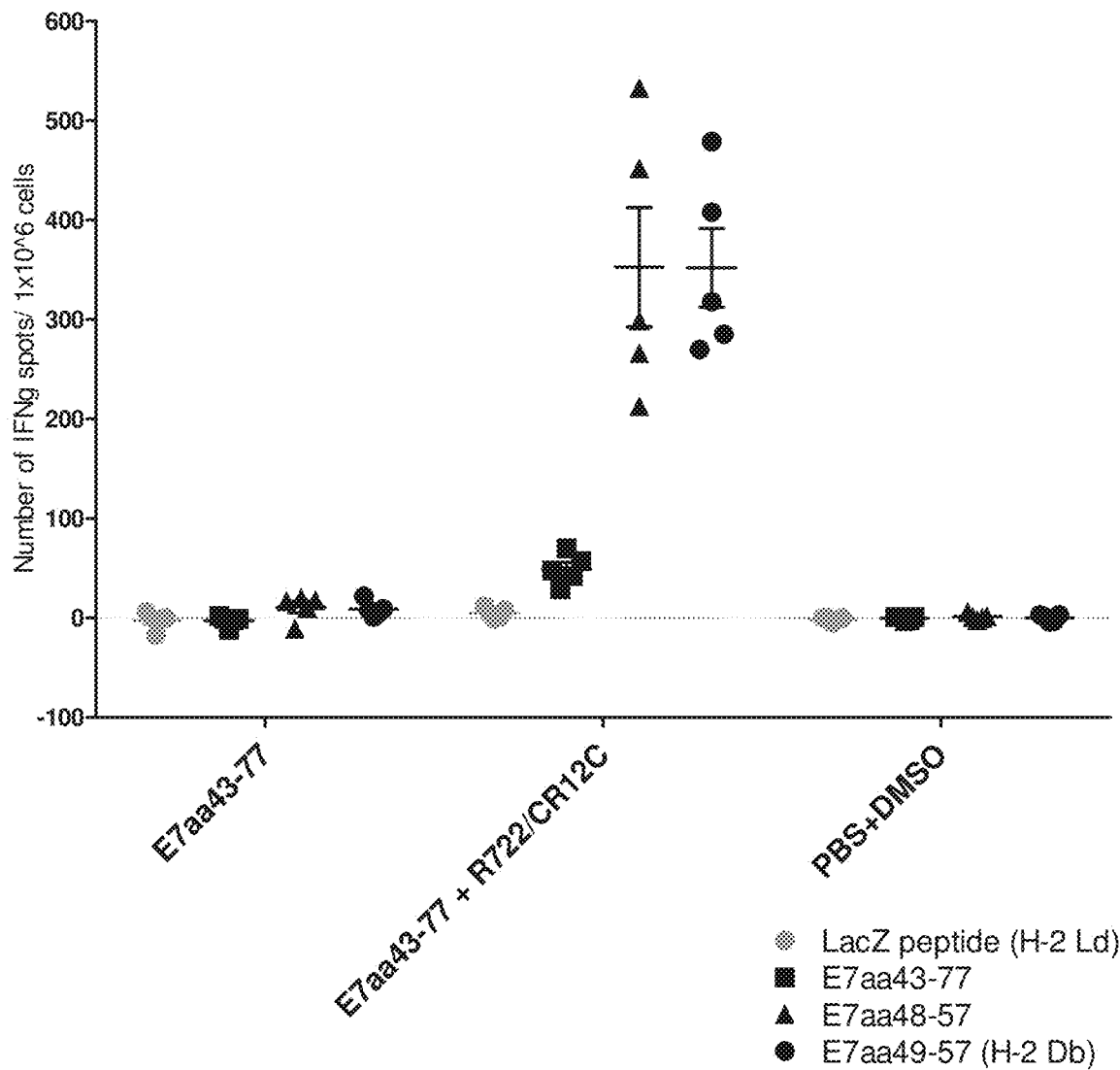
Figure 23:
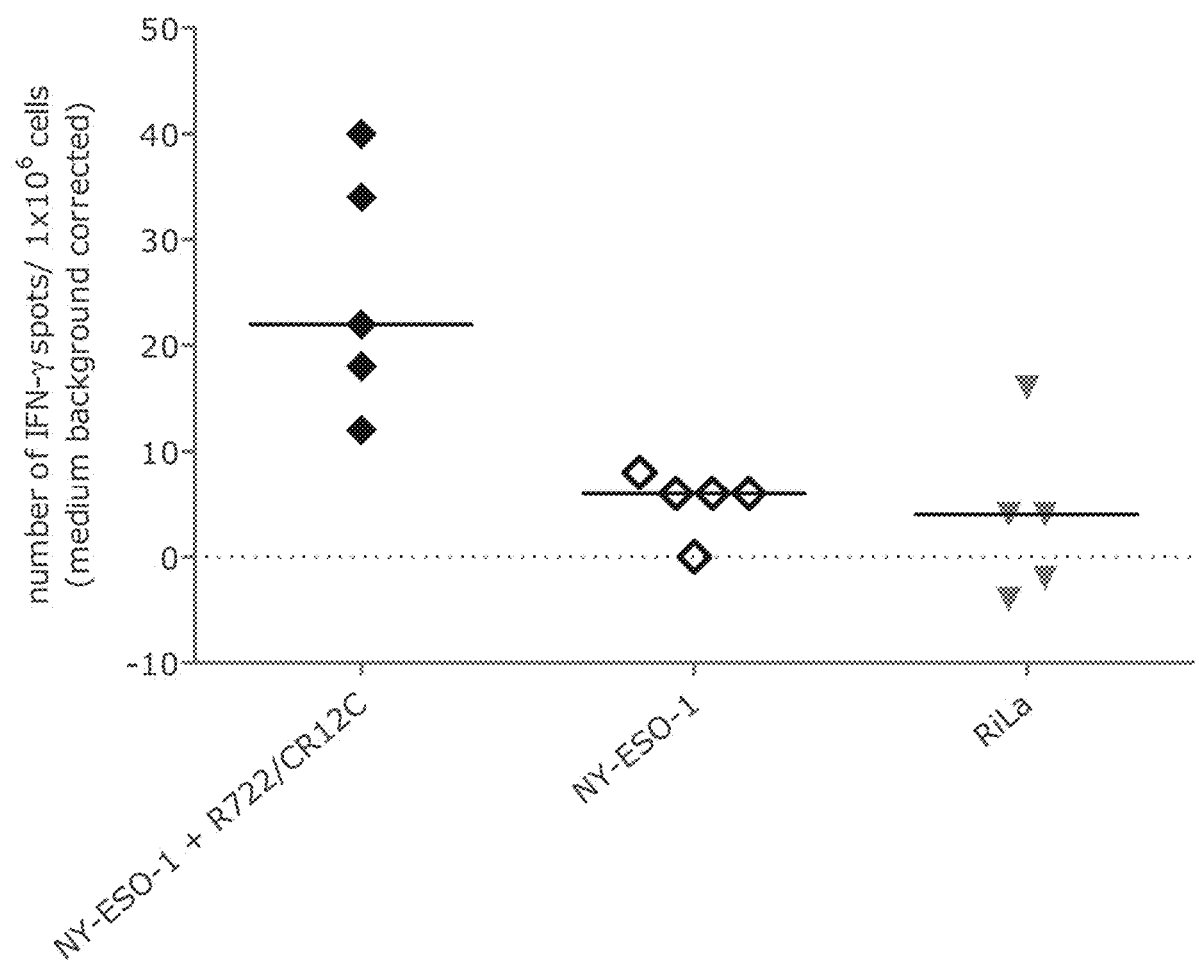

9. Detection of an Antigen Specific Cellular Immune Response by ELISPOT:

a) Detection of Cytotoxic T Cell Response Directed Against Ovalbumine:

5 days after the last vaccination mice were sacrificed, the spleens were removed and the splenocytes were isolated. For detection of INFgamma a coat multiscreen plate (Millipore) was incubated overnight with coating buffer (0.1 M Carbonat-Bicarbonat Buffer pH 9.6, 10.59 g/l $Na_2CO_3$, 8.4 g/l $NaHCO_3$) comprising antibody against INFγ (BD Pharmingen, Heidelberg, Germany). The next day $1×10^6$ cells/well were added and re-stimulated with 1 µg/well of relevant peptide (SIINFEKL (SEQ ID NO: 116) of ovalbumin); irrelevant peptide (Connexin=control peptide) or buffer without peptide. Afterwards the cells are incubated for 24 h at 37° C. The next day the plates were washed 3 times with PBS, once with water and once with PBS/0.05% TWEEN®-20 and afterwards incubated with a biotin-coupled secondary antibody for 11-24 h at 4° C. Then the plates were washed with PBS/0.05% TWEEN®-20 and incubated for 2 h at room temperature with alkaline phosphatase coupled to streptavidin in blocking buffer. After washing with PBS/0.05% TWEEN®-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction. The results of this induction of specific cytotoxic T-cells upon vaccination with an inventive pharmaceutical composition are shown in FIG. 12.

b) Detection of a Cytotoxic T Cell Response Directed Against Rabies Virus:

5 days after vaccination mice were sacrificed, the spleens were removed and the splenocytes were isolated. For detection of INFgamma a coat multiscreen plate (Millipore) was incubated overnight with coating buffer (0.1 M Carbonat-Bicarbonat Buffer pH 9.6, 10.59 g/l $Na_2CO_3$, 8.4 g/l $NaHCO_3$) comprising antibody against INF□ (BD Pharmingen, Heidelberg, Germany). The next day $5×10^5$ cells/well were added and re-stimulated with inactivated Rabies virus (RABIPUR® 1:100 or HDC 1:100)) or buffer without peptide (BSA). Afterwards the cells are incubated for 24 h at 37° C. The next day the plates were washed 3 times with PBS, for 5 minutes with water and once with PBS/0.05% TWEEN®-20 and afterwards incubated with a biotin-coupled secondary antibody for 11-24 h at 4° C. Then the plates were washed with PBS/0.05% TWEEN®-20 and incubated for 2 h at room temperature with alkaline phosphatase coupled to streptavidin in blocking buffer. After washing with PBS/0.05% TWEEN®-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction. The results of this induction of specific cytotoxic T-cells upon vaccination with an inventive pharmaceutical composition are shown in FIG. 14.

c) Detection of a Cytotoxic T Cell Response Directed Against Swine Flu (a(H1N1)Pdm09):

6 days after vaccination mice were sacrificed, the spleens were removed and the splenocytes were isolated. For detection of INFgamma a coat multiscreen plate (Millipore) was incubated overnight with coating buffer (0.1 M Carbonat-Bicarbonat Buffer pH 9.6, 10.59 g/l $Na_2CO_3$, 8.4 g/l $NaHCO_3$) comprising antibody against INF□ (BD Pharmingen, Heidelberg, Germany). The next day $5×10^5$ cells/well were added and re-stimulated with Influenza A/California/7/09 A(H1N1)pdm09 inactivated virus (NIBSC, UK) (10 µg/ml?) or buffer without peptide (BSA). Afterwards the cells are incubated for 24 h at 37° C. The next day the plates were washed 3 times with PBS, for 5 minutes with water and once with PBS/0.05% TWEEN®-20 and afterwards incubated with a biotin-coupled secondary antibody for 11-24 h at 4° C. Then the plates were washed with PBS/0.05% TWEEN®-20 and incubated for 2 h at room temperature with alkaline phosphatase coupled to streptavidin in blocking buffer. After washing with PBS/0.05% TWEEN®-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction. The results of this induction of specific cytotoxic T-cells upon vaccination with an inventive pharmaceutical composition are shown in FIG. 18.

d) Detection of a Cytotoxic T Cell Response Directed Against E7 Protein of Human Papilloma Virus 16 (HPV16):

8 days after vaccination mice were sacrificed, the spleens were removed and the splenocytes were isolated. For detection of INFgamma a coat multiscreen plate (Millipore) was incubated overnight with coating buffer (0.1 M Carbonat-Bicarbonat Buffer pH 9.6, 10.59 g/l $Na_2CO_3$, 8.4 g/l $NaHCO_3$) comprising antibody against INF□ (BD Pharmingen, Heidelberg, Germany). The next day $5×10^5$ cells/well were added and re-stimulated with different E7 derived peptides (E7 aa43-77, E748-57, E7 aa49-57) (1 µg/ml), an irrelevant peptide (LacZ peptide H-2 Ld) or buffer without peptide (DMSO). Afterwards the cells are incubated for 24 h at 37° C. The next day the plates were washed 3 times with PBS, for 5 minutes with water and once with PBS/0.05% TWEEN®-20 and afterwards incubated with a biotin-coupled secondary antibody for 11-24 h at 4° C. Then the plates were washed with PBS/0.05% TWEEN®-20 and incubated for 2 h at room temperature with alkaline phosphatase coupled to streptavidin in blocking buffer. After washing with PBS/0.05% TWEEN®-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction. The results of this induction of specific cytotoxic T-cells upon vaccination with an inventive pharmaceutical composition including a peptide antigen from a pathogen associated with infectious disease are shown in FIG. 21 for the E7aa43-77 peptide antigen not included in the polymeric cargo complex, and additionally for the E7aa43-77 peptide antigen when included in the polymeric cargo complex in FIG. 22.

e) Detection of a Cytotoxic T Cell Response Directed Against the Tumour Antigen NY-ESO-1:

7 days after vaccination mice were sacrificed, the spleens were removed and the splenocytes were isolated. For detection of INFgamma a coat multiscreen plate (Millipore) was incubated overnight with coating buffer (0.1 M Carbonat-Bicarbonat Buffer pH 9.6, 10.59 g/l $Na_2CO_3$, 8.4 g/l $NaHCO_3$) comprising antibody against INF☐ (BD Pharmingen, Heidelberg, Germany). The next day $1\times10^6$ cells/well were added and re-stimulated with an epitope library of NY-ESO-1 comprising predicted MHC I and MHC II epitopes. Afterwards the cells are incubated for 24 h at 37° C. The next day the plates were washed 3 times with PBS, once with water and once with PBS/0.05% TWEEN®-20 and afterwards incubated with a biotin-coupled secondary antibody for 11-24 h at 4° C. Then the plates were washed with PBS/0.05% TWEEN®-20 and incubated for 2 h at room temperature with alkaline phosphatase coupled to streptavidin in blocking buffer. After washing with PBS/0.05% TWEEN®-20 the substrate (5-Bromo-4-Cloro-3-Indolyl Phosphate/Nitro Blue Tetrazolium Liquid Substrate System from Sigma Aldrich, Taufkirchen, Germany) was added to the plate and the conversion of the substrate could be detected visually. The reaction was then stopped by washing the plates with water. The dried plates were then read out by an ELISPOT plate reader. For visualization of the spot levels the numbers were corrected by background subtraction. The results of this induction of specific cytotoxic T-cells upon vaccination with an inventive pharmaceutical composition including at least one tumour antigen are shown in FIG. 23.

10. Tumour Challenge:

One week after the last vaccination $1\times10^6$ E.G7-OVA cells (tumour cells which stably express ovalbumine) were implanted subcutaneously in the vaccinated mice. Tumour growth was monitored by measuring the tumour size in 3 dimensions using a calliper. The results of the induction of an anti-tumoural response upon vaccination with an inventive pharmaceutical composition are shown in FIG. 10.

11. Virus Neutralization Test:

Detection of the virus neutralizing antibody response (specific B-cell immune response) was carried out by the mean of virus neutralisation assay. Therefore, blood samples were taken from vaccinated mice 21 days after vaccination and sera were prepared. These sera were used in fluorescent antibody virus neutralisation (FAVN) test using the cell culture adapted challenge virus strain (CVS) of rabies virus as recommended by the OIE (World Organisation for Animal Health) and first described in Cliquet F., Aubert M. & Sagne L. (1998); J. Immunol. Methods, 212, 79-87. Shortly, heat inactivated sera will be tested as quadruplicates in serial two-fold dilutions as quadruplicates for there potential to neutralise 100 $TCID_{50}$ (tissue culture infectious doses 50%) of CVS in 50 µl of volume. Therefore sera dilutions are incubated with virus for 1 hour at 37° C. (in humid incubator with 5% $CO_2$) and subsequently trypsinized BHK-21 cells are added ($4\times10^5$ cells/ml; 50 µl per well). Infected cell cultures are incubated for 48 hours in humid incubator at 37° C. and 5% $CO_2$. Infection of cells is analysed after fixation of cells using 80% acetone at room temperature using FITC anti-rabies conjugate. Plates were washed twice using PBS and excess of PBS was removed. Cell cultures are scored positive or negative for the presence of rabies virus. Negative scored cells in sera treated wells represent neutralization of rabies virus. Each FAVN tests includes WHO or OIE standard serum (positive reference serum) that serves as reference for standardisation of the assay. Neutralization activity of test sera is calculated with reference to the standard serum and displayed as International Units/ml (IU/ml). The results of this experiment are shown in FIG. 16.

Figure 24:
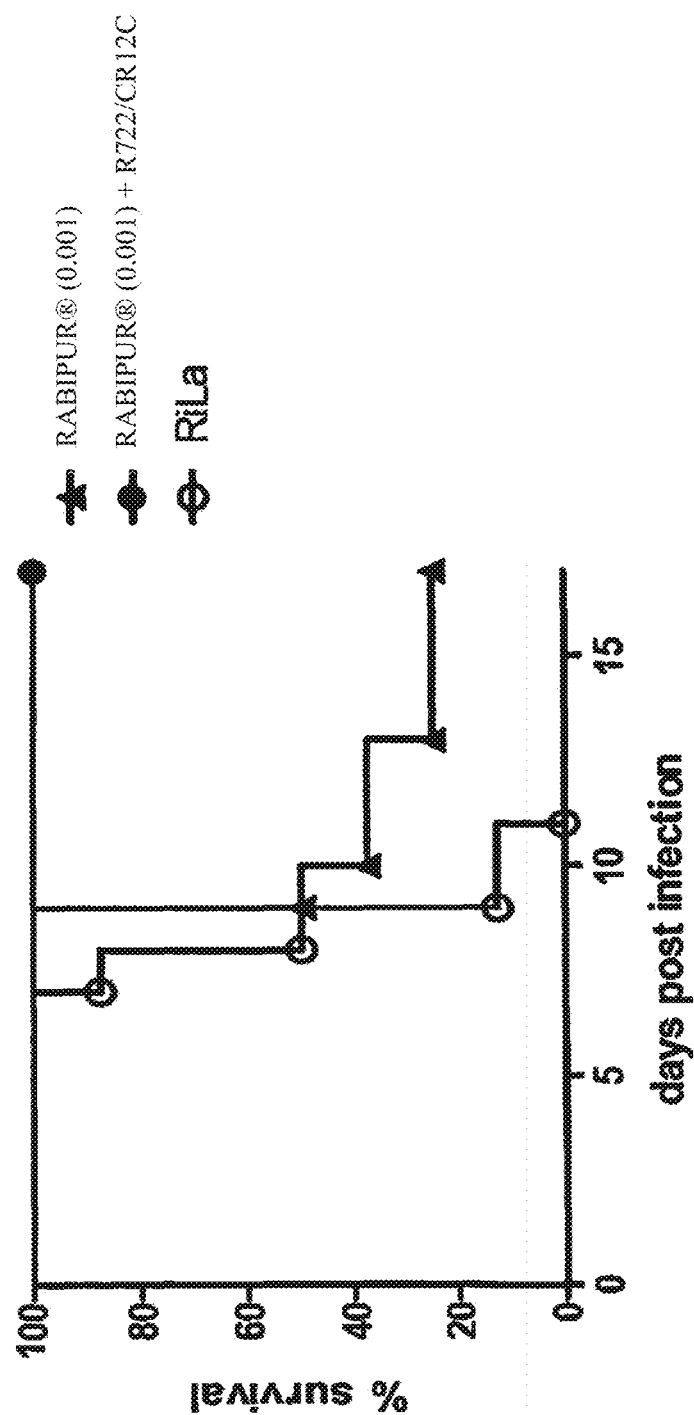

12. Rabies Virus Challenge Infection of Mice:

37 days after single intramuscular immunization of mice using 0.001 fold human dose of RABIPUR® and 3 µg R722 and 0.81 µg $CR_{12}C$ (3.7:1 w/w) all mice in the experiment were infected using 25-fold $LD_{50}$ of CVS strain of Rabies virus intracranially (i.c.). Mice were monitored for specific symptoms of Rabies disease and body weight development. The results of this experiment are shown in FIG. 24.

13. Tumour Challenge with TC-1 Cells (Measurement of Tumour Growth and Animal Survival in a Therapeutic Setting):

Eight C57BL/6 mice per group were challenged on day 1 with $1\times10^5$ TC-1 cells which express the HPV E6 and E7 protein. Vaccination started on day 7 after tumor challenge (median tumor volume 31-48 mm³). Mice were intradermally vaccinated 5 times (on day 8, 12, 15, 19 and 22) with 5 µg or 50 µg E7 peptide combined with 50 µg $CR_{12}C$/R722 (1:2; w/w). For comparison, mice were injected with the polymeric cargo complexes alone.

The polymeric carrier cargo complex combined with HPV-16 derived E7 peptide E7aa43-77 even impairs the growth of tumours compared to the polymeric carrier cargo complex alone (FIG. 25).

The polymeric carrier cargo complex combined with HPV-16 derived E7 peptide strongly enhances the survival of tumor bearing mice (Mean survival time of 44.5 days for 50 µg E7 peptide+50 µg polymeric carrier cargo complex; mean survival time of 22 days for 5 µg E7 peptide+50 µg polymeric carrier cargo complex) compared to the E7 peptide or 50 polymeric carrier cargo complex alone (FIG. 26).

14. Tumour Challenge with TC-1 Cells (Induction of a T Cell Memory Response):

Thirteen C57BL/6 mice per group were intradermally vaccinated once per week for four weeks (on days 0, 7, 14 and 21) with the polymeric carrier cargo complex formed by the disulfide-crosslinked cationic peptide CR12C as carrier and the isRNA R722 as nucleic acid cargo and the E7 peptide.

Eight weeks after the fourth vaccination, 5 mice/group were sacrificed, splenocytes were isolated and the frequency of antigen-specific $CD8^+$ T cells was determined by HPV-pentamer staining and flow cytometry according to example 15.

The polymeric carrier cargo complex combined with the HPV-16 derived E7 peptide E7aa43-77 results in a statistically significant increase of antigen-specific $CD8^+$ T cells compared to mice vaccinated with 50 µg of the E7 peptide alone (p=0.0007 for 5 µg E7 peptide and p=0.0002 50 µg E7 peptide; statistical differences between groups were assessed by unpaired t-test). Thus, the combination of the polymeric carrier cargo complex combined with the HPV-16 derived E7 peptide induces a potent memory $CD8^+$ T cell response (FIG. 27).

Eight weeks after the fourth vaccination 8 mice/group were challenged with $1\times10^5$ TC-1 tumor cells and tumor growth was monitored.

The polymeric carrier cargo complex combined with the HPV-16 derived E7 peptide E7aa43-77 results in a drastic delay of tumor growth (4 complete responses for 5 µg E7 peptide+50 µg of 50 µg polymeric carrier cargo complex; 7 complete responders for 50 µg E7 peptide+50 µg of 50 µg polymeric carrier cargo complex). Thus, the combination of the polymeric carrier cargo complex combined with the HPV-16 derived E7 peptide induces a potent memory CD8$^+$ T cell response (FIG. 28).

15. Detection of Antigen Specific Cellular Immune Responses by Pentamer Staining:

Freshly isolated splenocytes were seeded into 96-well plates (2×10$^6$ cells/well) and stained with Fc-Block (1:100, anti-CD16/CD32; BD Biosciences). After a 20 minute incubation, the H-2Db-RAHYNIVTF-Pentamer (HPV 16 E7 49-57)-Pentamer-PE (10 µl/well) was added and cells were incubated for an additional 30 minutes at 4° C. After washing cells were stained with the following antibodies: CD19-FITC (1:200), CD8-PerCP-Cy5.5 (1:200), KLRG1-PECy7 (1:200), CD44-APC (1:100), CD127-eFluor450 (1:100) (eBioscience) and CD3-APC-Cy7 (1:200) (BD Biosciences). Aqua Dye was used to distinguish live/dead cells (Invitrogen). Cells were collected using a Canto II flow cytometer (Beckton Dickinson). Flow cytometry data were analysed using FlowJo software (Tree Star, Inc.). Statistical analysis was performed using GraphPad Prism software, Version 5.01. Statistical differences between groups were assessed by unpaired t test with Welch's correction.

16. Immunization with Seasonal Influenza and Detection of Antibodies:

For immunization the seasonal influenza vaccine MUTAGRIP® (comprises inactivated influenza virus strains as recommended by the WHO; season 2011/2012) (4.5, 0.45 and 0.045 µg) was combined with the polymeric cargo complexes R722/CR$_{12}$C (in a ratio of 3.7:1 w/w) (5 µg R722/1.35 µg CR$_{12}$C) as adjuvant and injected intramuscularly into female Balb/c mice (8 mice per group). For comparison mice were injected with MUTAGRIP® alone.

Detection of an antigen specific immune response (B-cell immune response) was carried out by detecting influenza virus hemagglutinin inhibition (HI) titers. Therefore, blood samples were taken from vaccinated mice 21 days after vaccination and sera were heat inactivated, incubated with kaolin, and pre-adsorbed to chicken red blood cells. For the HI assay, 50 µl of 2-fold dilutions of pre-treated sera were incubated with inactivated influenza A/California/7/2009 H1N1 or influenza A/Victoria/210/2009 H3N2 (both NIBSC) and 50 µl 0.5% chicken red blood cells were added. The results of this induction of HI titers upon vaccination with an inventive pharmaceutical composition are shown in FIG. 29.

Detection of an antigen specific immune response (B-cell immune response) was carried out by detecting influenza virus specific IgG2a antibodies. Therefore, blood samples were taken from vaccinated mice 21 days after vaccination and sera were prepared. MAXISORB™ ELISA plates (Nalgene Nunc International) were coated with inactivated influenza A/California/7/2009 H1N1 (NIBSC, Potters Bar, UK) at 1 µg/ml. After blocking with 1×PBS containing 0.05% TWEEN®-20 and 1% BSA the plates were incubated with diluted mouse serum. Subsequently, a biotin-coupled secondary antibody (Anti-mouse-IgG2a Pharmingen) was added. After washing, the plate was incubated with Horse-radish peroxidase-streptavidin and subsequently the conversion of the ABTS substrate (2,2'-azino-bis(3-ethyl-benzthiazoline-6-sulfonic acid) was measured to determine the induction of IgG2a antibodies. The results of this induction of antibodies upon vaccination with an inventive pharmaceutical composition are shown in FIG. 30.

The invention claimed is:

1. A method of inducing an immune response to an antigen, the method comprising administering to a subject in need thereof a pharmaceutical composition comprising:
   (A) a polymeric carrier cargo complex, comprising:
      a) a polymeric carrier comprising disulfide-crosslinked cationic peptides, as a carrier; and
      b) at least one immunostimulatory RNA (isRNA) molecule as a cargo,
      wherein the cationic components and the isRNA molecule of the polymeric carrier cargo complex are provided in a nitrogen to phosphor atoms (N/P) ratio in the range of 0.1-0.9,
   and
   (B) at least one protein or peptide antigen that is selected from the group consisting of:
      a) an antigen from a pathogen associated with infectious disease;
      b) an antigen associated with allergy or allergic disease;
      c) an antigen associated with autoimmune disease; and
      d) an antigen associated with a cancer or tumour disease,
   wherein said pharmaceutical composition lacks an mRNA component,
   wherein the cationic peptides each comprise a sequence selected from the group consisting of $CR_{7-20}C$ (SEQ ID NOs: 1-14),
   wherein the at least one protein or peptide antigen is a separate component of the pharmaceutical composition from the polymeric carrier cargo complex.

2. The method of claim 1, wherein said immunostimulatory RNA comprises a sequence that is at least 90% identical to the sequence of SEQ ID NO: 105.

3. The method of claim 2, wherein said immunostimulatory RNA comprises a sequence that is at least 95% identical to the sequence of SEQ ID NO: 105.

4. The method of claim 3, wherein said immunostimulatory RNA comprises the sequence of SEQ ID NO: 105.

5. The method of claim 1, wherein the immune response is an adaptive immune response.

6. The method of claim 1, wherein the immune response is a B-cell immune response.

7. The method of claim 1, wherein the immune response is a cytotoxic T-cell immune response.

8. The method of claim 1, wherein the immune response is a Th1-shifted immune response.

9. The method of claim 1, wherein the cationic peptides each comprise the sequence $CR_{12}C$ (SEQ ID NO: 6).

10. The method of claim 1, wherein the at least one protein or peptide antigen comprises an antigen from a pathogen associated with infectious disease or an antigen associated with a cancer or tumour disease.

11. The method of claim 9, wherein the antigen associated with a cancer or tumour disease comprises a human tumour antigen or an antigenic fragment thereof.

12. The method of claim 1, wherein the immune response comprises the induction of the cytokine IFN-alpha.

13. The method of claim 1, wherein component (B) is not covalently linked to component (A).

14. The method of claim 1, wherein said protein or peptide antigen is from a pathogen selected from the list consisting of: Rabies virus, Hepatitis B virus, human Papilloma virus (hPV), *Bacillus anthracis*, Respiratory syncytial virus (RSV), Herpes simplex virus (HSV), Influenza virus and *Mycobacterium tuberculosis*.

15. The method of claim 1, wherein said protein or peptide antigen is selected from the list consisting of:
   The Hemagglutinin (HA), the Neuraminidase (NA), the Nucleoprotein (NP), the M1 protein, the M2 protein, the NS1 protein, the NS2 protein (the NEP protein: nuclear export protein), the PA protein, the PB1 protein (polymerase basic 1 protein), the PB 1-F2 protein and the PB2 protein of Influenza virus;

The nucleoprotein (N), the phosphoprotein (P), the matrix protein (M), the glycoprotein (G), and the viral RNA polymerase (L), in each case of Rabies virus;

the Hepatitis B surface antigen (HBsAg), the Hepatitis B core antigen (HbcAg), the Hepatitis B virus DNA polymerase, the HBx protein, the preS2 middle surface protein, the large S protein, the virus protein VP1, the virus protein VP2, the virus protein VP3, and the virus protein VP4, in each case of Hepatitis B virus;

the E1 protein, the E2 protein, the E3 protein, the E4 protein, the E5 protein, the E6 protein, the E7 protein, the E8 protein, the L1 protein, and the L2 protein, in each case of human Papilloma virus (hPV);

the protective antigen (PA), the edema factor (EF), the lethal factor (LF), and the S-layer homology proteins (SLH), in each case of *Bacillus anthracis;* the Fusion (F) protein, the nucleocapsid (N) protein, the phosphoprotein (P), the matrix (M) protein, the glycoprotein (G), the large protein (L; RNA polymerase), the non-structural protein 1 (NS1), the non-structural protein 2 (NS2), the small hydrophobic (SH) protein, the elongation factor M2-1, and the transcription regulation protein M2-2, in each case of respiratory syncytial virus (RSV);

the Glycoprotein L (UL1), the Uracil-DNA glycosylase UL2, the UL3 protein, the UL4 protein, the DNA replication protein UL5, the Portal protein UL6, the Virion maturation protein UL7, the DNA helicase UL8, the Replication origin-binding protein UL9, the Glycoprotein M (UL10), the UL11 protein, the Alkaline exonuclease UL12, the Serine-threonine protein kinase UL13, the Tegument protein UL14, the Terminase (UL15), the Tegument protein UL16, the UL17 protein, the Capsid protein VP23 (UL18), the Major capsid protein VP5 (UL19), the Membrane protein UL20, the Tegument protein UL21, the Glycoprotein H (UL22), the Thymidine Kinase UL23, the UL24 protein, the UL25 protein, the Capsid protein P40 (UL26, VP24, VP22A), the Glycoprotein B (UL27), the ICP18.5 protein (UL28), the Major DNA-binding protein ICP8 (UL29), the DNA polymerase UL30, the Nuclear matrix protein UL31, the Envelope glycoprotein UL32, the UL33 protein, the Inner nuclear membrane protein UL34, the Capsid protein VP26 (UL35), the Large tegument protein UL36, the Capsid assembly protein UL37, the VP19C protein (UL38), the Ribonucleotide reductase (Large subunit) UL39, the Ribonucleotide reductase (Small subunit) UL40, the Tegument protein/Virion host shutoff VHS protein (UL41), the DNA polymerase processivity factor UL42, the Membrane protein UL43, the Glycoprotein C (UL44), the Membrane protein UL45, the Tegument proteins VP11/12 (UL46), the Tegument protein VP13/14 (UL47), the Virion maturation protein VP16 (UL48, Alpha-TIF), the Envelope protein UL49, the dUTP diphosphatase UL50, the Tegument protein UL51, the DNA helicase/primase complex protein UL52, the Glycoprotein K (UL53), the Transcriptional regulation protein IE63 (ICP27, UL54), the UL55 protein, the UL56 protein, the Viral replication protein ICP22 (IE68, US1), the US2 protein, the Serine/threonine-protein kinase US3, the Glycoprotein G (US4), the Glycoprotein J (US5), the Glycoprotein D (US6), the Glycoprotein I (US7), the Glycoprotein E (US8), the Tegument protein US9, the Capsid/Tegument protein US10, the Vmw21 protein (US11), the ICP47 protein (IE12, US12), the Major transcriptional activator ICP4 (IE175, RS1), the E3 ubiquitin ligase ICP0 (IE110), the Latency-related protein 1 (LRP1), the Latency-related protein 2 (LRP2), the Neurovirulence factor RL1 (ICP34.5), and the Latency-associated transcript (LAT), in each case of Herpes simplex virus (HSV); or the ESAT-6 protein, the ESX-1 protein, the CFP10 protein, the TB 10.4 protein, the MPT63 protein, the MPT64 protein, the MPT83 protein, the MTB12 protein, the MTB8 protein, the AG85A protein, the AG85B protein, the Rpf-like proteins, the KATG protein, the PPE18 protein, the MTB32 protein, the MTB39 protein, the Crystallin, the HSP65 protein, the PST-S protein, and the HBHA protein, the 10 kDa filtrate antigen EsxB, the serine protease PepA, the fibronectin-binding protein D FbpD, the secreted protein MPT51, the periplasmic phosphate-binding lipoprotein PSTS1 (PBP-1), the periplasmic phosphate-binding lipoprotein PSTS3 (PBP-3, Phos-1), the PPE family protein PPE14, the PPE family protein PPE68, the protein MTB72F, the molecular chaperone DnaK, the cell surface lipoprotein MPT83, the lipoprotein P23, the Phosphate transport system permease protein PstA, the 14 kDa antigen, the fibronectin-binding protein C FbpC1, the Alanine dehydrogenase TB43, and the Glutamine synthetase 1, in each case of *Mycobacterium tuberculosis.*

16. The method of claim 1, wherein said protein or peptide antigen is associated with allergy or allergic disease and is derived from a source selected from the list consisting of: grass pollen, tree pollen, flower pollen, herb pollen, dust mite, mold, animals, food, and insect venom.

17. The method of claim 1, wherein said protein or peptide antigen is associated with autoimmune disease and is selected from the list consisting of:

myelin basic protein (MBP), proteolipid protein (PLP), and myelin oligodendrocyte glycoprotein (MOG), in each case associated with multiple sclerosis (MS);

CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Typ I;

interphotoreceptor retinoid-binding protein (IRBP) associated with autoimmune uveitis;

acetylcholine receptor AchR, and insulin-like growth factor-1 receptor (IGF-1R), in each case associated with Myasthenia gravis;

M-protein from beta-hemolytic streptocci (pseudo-autoantigen) associated with Rheumatic Fever;

Macrophage migration inhibitory factor associated with Arthritis;

Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjögren's syndrome;

Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus;

oxLDL, beta(2)GPI, HSP60/65, and oxLDL/beta(2)GPI, in each case associated with Atherosclerosis;

cardiac beta(1)-adrenergic receptor associated with idiopathic dilated cardiomyopathy (DCM);

histidyl-tRNA synthetase (HisRS) associated with myositis;

topoisomerase I associated with scleroderma;
IL-17; or
heat shock proteins.

18. The method of claim 1, wherein said protein or peptide antigen is associated with a cancer or tumour disease and is selected from the list consisting of: p53, CA125, EGFR, Her2/neu, hTERT, PAP, MAGE-A1, MAGE-A3, Mesothelin, MUC-1, NY-ESO-1, GP100, MART-1, Tyrosinase, PSA, PSCA, PSMA VEGF, VEGFR1, VEGFR2, Ras, CEA and WT1.

19. The method of claim 1, wherein said polymeric carrier cargo complex is an adjuvant, which enhanced an immune response in the subject.

20. The method of claim 1, wherein the cationic components and the isRNA molecule of the polymeric carrier cargo complex are provided in a nitrogen to phosphor atoms (N/P) ratio in the range of 0.5-0.9.

* * * * *